United States Patent [19]

Nakamura et al.

[11] Patent Number: 5,939,532
[45] Date of Patent: *Aug. 17, 1999

[54] HUMANIZED ANTIBODIES TO GANGLIOSIDE GM$_2$

[75] Inventors: Kazuyasu Nakamura; Masamichi Koike, both of Tokyo, Japan; Kenya Shitara, San Diego, Calif.; Nobuo Hanai, Kanagawa, Japan; Yoshihisa Kuwana, Tokyo, Japan; Mamoru Hasegawa, Kanagawa, Japan

[73] Assignee: Kyowa Hakko Kogyo Co., Ltd, Tokyo, Japan

[ * ] Notice: This patent is subject to a terminal disclaimer.

[21] Appl. No.: 08/483,528

[22] Filed: Jun. 7, 1995

Related U.S. Application Data

[63] Continuation-in-part of application No. 08/116,778, Sep. 7, 1993, Pat. No. 5,830,470.

[51] Int. Cl.$^6$ .............................. C12P 21/08; C12P 21/06; C07K 16/00; C12N 5/00
[52] U.S. Cl. .................................. 530/387.3; 530/387.5; 530/388.1; 435/328; 435/329; 435/69.3; 424/141.1
[58] Field of Search .............................. 530/388.1, 387.3, 530/387.5; 424/141.1; 435/328, 329, 69.3

[56] References Cited

FOREIGN PATENT DOCUMENTS

| | | |
|---|---|---|
| 314 161 | 5/1989 | European Pat. Off. . |
| 533 199 | 3/1993 | European Pat. Off. . |

OTHER PUBLICATIONS

Baker et al (Cancer Research vol. 51 pp. 144–149), Jan. 1991.
Liu et al (Gene vol. 54 No. 1 pp. 33–40), Jul. 1987.
Lobuglio et al (Proc. Natl. Acad. Sci. USA vol. 86 pp. 4220–4224), 1989.
Morrison et al (Proc. Natl. Acad. Sci. USA vol. 81 pp. 6851–6855), 1984.
Jones et al (Nature vol. 231 pp. 522–525), 1986.
Hakimi et al (Journal of Immunology vol. 147(4) pp. 1352–1359), 1991.
Mueller et al (Journal of Immunology vol. 144(4) pp. 1382–1386), 1990.
Kenneth R.H. Editor Monoclonal Antibodies Plenum Press New York pp. 275–291, 1980.
Hakomori et al (Cancer Research vol. 45 pp. 2405–2414), 1985.
Tai et al (PNAS USA vol. 50 pp. 5392–5396), 1983.
Miyake et al (Cancer Research vol. 48 pp. 6154–6160), 1988.

Miyaji et al (Cytotechnology vol. 3 pp. 133–140), 1990.
Kuwana et al (Biochem & Biophysical Research Communications vol. 149(3) pp. 960–968, 1987.
Hamer et al (Cell vol. 17 pp. 737–747), 1979.
Page et al (Bio/Technology vol. 9 pp. 64–68), 1991.
Saul et al (Journal of Biological Chemistry vol. 253(2) pp. 585–597, 1978.
Epp et al (Eur. J. Biochem. vol. 45, pp. 513–524), 1974.
Emery et al (Expert Opinion on Investigational Drugs vol. 3(3) pp. 241–251, Mar. 1994.
Livingston, "Approaches to Augmenting the Immunogenicity of Melanoma Gangliosides: From Whole Melanoma Cells to Ganglioside–KLH Conjugate Vaccines", Immunological Reviews 145:147–166 (1995).
Harris (Tibtech vol. 11 pp. 42–44), 1993.
Osband et al (Immunology Today vol. 111 No. 6 pp. 193–195), 1990.
Oi & Morrison (Biotechniques vol. 4 pp. 214–221), 1986.
Morrison & Oi (Advances in Immunology vol. 44 pp. 65–92), 1989.
Reichmann et al (Nature vol. 332 pp. 323–327), 1988.
Hakamori et al (Monoclonal Antibod. & Functional Cell Lines, Plenum Press pp. 67–100), 1985.
Ire et al (The Lancet pp. 786–787), Apr. 8, 1989.
Natoli et al (Cancer Research vol. 46 pp. 4116–4120), 1986.
Freedman et al (J. Biol. Chem 264(21) pp. 12122–12155), 1984.
Miyaki et al (Cancer Research vol. 46 pp. 4116–4120), 1986.

*Primary Examiner*—Anthony C. Caputa
*Assistant Examiner*—Mark Navarro
*Attorney, Agent, or Firm*—Nixon & Vanderhye, P.C.

[57] ABSTRACT

Chimeric human antibody expression vectors are constructed by inserting the antibody heavy chain variable region-encoding cDNA and antibody light chain variable region-encoding cDNA isolated from hybridomas producing a mouse or rat monoclonal antibody reacting with the ganglioside GM$_2$ respectively into an expression vector for use in animal cells which contains the human antibody heavy chain constant region- or human antibody light chain constant region-encoding cDNA. The expression vectors are introduced into animal cells and the transformant thus obtained is cultured for the production of a chimeric human antibody reacting with the ganglioside GM$_2$. In contrast to mouse monoclonal antibodies, the chimeric human antibodies of the invention will not cause anti-mouse immunoglobulin antibody production in the patient's body but shows a prolonged blood half-life, with a reduced frequency of adverse effects, so that it can be expected to be superior to mouse monoclonal antibodies in the efficacy in the treatment of human cancer, for instance.

2 Claims, 106 Drawing Sheets

XbaI
Klenow fragment
XhoI linker pCCTCGAGG
            GGAGCTCCp

EcoRI
SacI
Klenow fragment

HindIII
Klenow fragment

ApaI
Klenow fragment

ClaI
Klenow fragment
XhoI linker pCCTCGAGG
           GGAGCTCCp

SmaI
EcoRI linker pGGAATTCC
             CCTTAAGGp

EcoRI
Klenow fragment
HindIII linker pCAAGCTTG
              GTTCGAACp

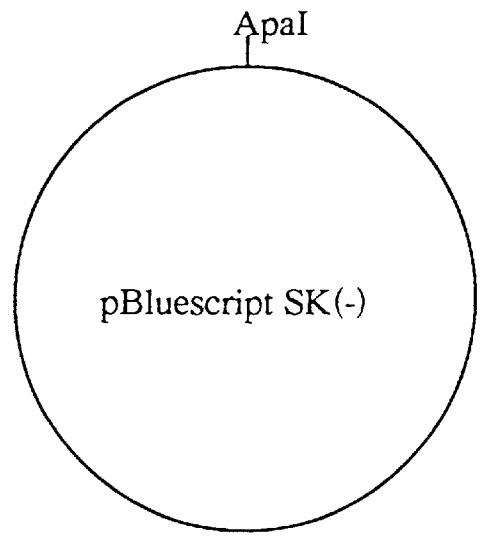
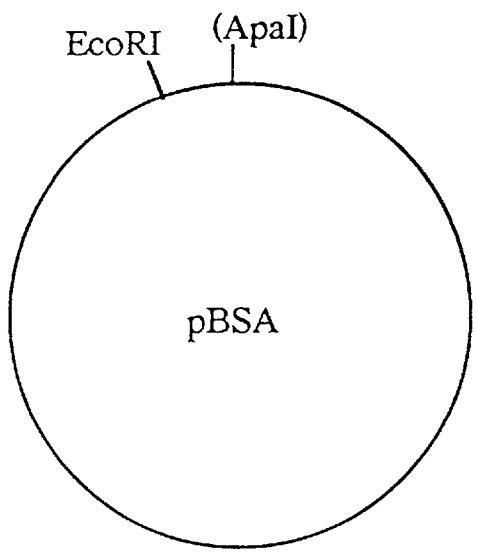
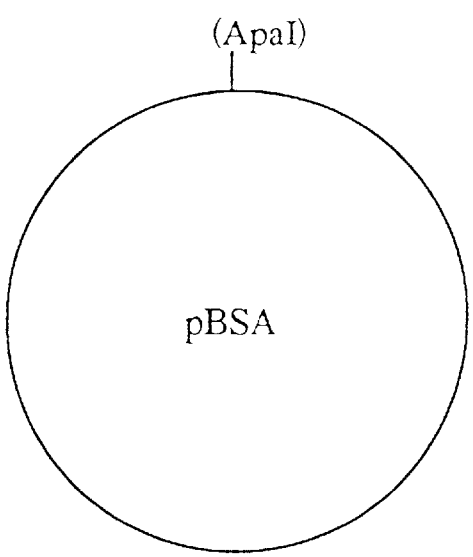
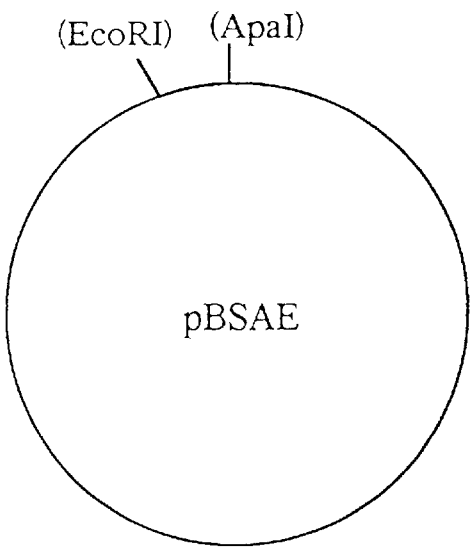
FIG. 64
FIG. 65

SEQUENCE LISTING (1) GENERAL INFORMATION:

(iii) NUMBER OF SEQUENCES: 103

(2) INFORMATION FOR SEQ ID NO:1:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: sig_peptide
        (B) LOCATION: -19..-1
        (C) IDENTIFICATION METHOD:
            BY SIMILARITY WITH KNOWN SEQUENCE OR TO AN
            ESTABLISHED CONSENSUS (ix) FEATURE:
        (A) NAME/KEY: domain
        (B) LOCATION: 31..35
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 1"

(ix) FEATURE:
        (A) NAME/KEY: domain
        (B) LOCATION: 50..66
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 2"

(ix) FEATURE:
        (A) NAME/KEY: domain
        (B) LOCATION: 99..109
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 3"

(xi) SEQUENCE DESCRIPTION: SEQ ID NO:1:

```
CTCCACAGTC CCTGAAGACA CTGACTCTAA CC ATG GGA TGG AGC TGG ATC TTT         53
                                   Met Gly Trp Ser Trp Ile Phe
                                       -15

CTC TTC CTC CTG TCA GGA ACT GCA GGT GTC CTC TCT GAG GTC CAG CTG        101
Leu Phe Leu Leu Ser Gly Thr Ala Gly Val Leu Ser Glu Val Gln Leu
        -10                  -5                   1

CAG CAG TCT GGA CCT GAG CTG GTG AAG CCT GGG GCT TCA GTG AAG ATA        149
Gln Gln Ser Gly Pro Glu Leu Val Lys Pro Gly Ala Ser Val Lys Ile
  5                  10                  15                  20

TCC TGC AAG GCT TCT GGA TAC ACA TTC ACT GAC TAC AAC ATG GAC TGG        197
Ser Cys Lys Ala Ser Gly Tyr Thr Phe Thr Asp Tyr Asn Met Asp Trp
                 25                  30                  35
```

| | | |
|---|---|---|
| GTG AAG CAG AGC CAT GGA AAG AGC CTT GAG TGG ATT GGA TAT ATT TAT<br>Val Lys Gln Ser His Gly Lys Ser Leu Glu Trp Ile Gly Tyr Ile Tyr<br>                  40                            45                          50 | 245 |
| CCT AAC AAT GGT GGT ACT GGC TAC AAC CAG AAG TTC AAG AGC AAG GCC<br>Pro Asn Asn Gly Gly Thr Gly Tyr Asn Gln Lys Phe Lys Ser Lys Ala<br>         55                            60                            65 | 293 |
| ACA TTG ACT GTA GAC AAG TCC TCC AGC ACA GCC TAC ATG GAG CTC CAC<br>Thr Leu Thr Val Asp Lys Ser Ser Ser Thr Ala Tyr Met Glu Leu His<br>   70                           75                          80 | 341 |
| AGC CTG ACA TCT GAG GAC TCT GCA GTC TAT TAC TGT GCA ACC TAC GGT<br>Ser Leu Thr Ser Glu Asp Ser Ala Val Tyr Tyr Cys Ala Thr Tyr Gly<br>85                       90                          95                     100 | 389 |
| CAT TAC TAC GGC TAC ATG TTT GCT TAC TGG GGC CAA GGG ACT CTG GTC<br>His Tyr Tyr Gly Tyr Met Phe Ala Tyr Trp Gly Gln Gly Thr Leu Val<br>                  105                         110                        115 | 437 |
| ACT GTC TCT GCA<br>Thr Val Ser Ala<br>          120 | 449 |

(2) INFORMATION FOR SEQ ID NO:2:

(i) SEQUENCE CHARACTERISTICS:
        (A) LENGTH: 393 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: sig_peptide
        (B) LOCATION: -22..-1
        (C) IDENTIFICATION METHOD:
            BY SIMILARITY WITH KNOWN SEQUENCE TO TO AN
            ESTABLISHED CONSENSUS (ix) FEATURE:
        (A) NAME/KEY: domain
        (B) LOCATION: 24..33
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 1"

(ix) FEATURE:
        (A) NAME/KEY: domain
        (B) LOCATION: 49..55
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 2"

(ix) FEATURE:
        (A) NAME/KEY: domain
        (B) LOCATION: 88..96
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 3"

(xi) SEQUENCE DESCRIPTION: SEQ ID NO:2:

| | | |
|---|---|---|
| GACAAA ATG CAT TTT CAA GTG CAG ATT TTC AGC TTC CTG CTA ATC AGT<br>        Met His Phe Gln Val Gln Ile Phe Ser Phe Leu Leu Ile Ser<br>             -20                         -15                         -10 | 48 |
| GCC TCA GTC ATA ATG TCC AGA GGA CAA ATT GTT CTC ACC CAG TCT CCA<br>Ala Ser Val Ile Met Ser Arg Gly Gln Ile Val Leu Thr Gln Ser Pro<br>         -5                            1                          5 | 96 |
| GCA ATC ATG TCT GCA TCT CCA GGG GAG AAG GTC ACC ATA ACC TGC AGT<br>Ala Ile Met Ser Ala Ser Pro Gly Glu Lys Val Thr Ile Thr Cys Ser<br>      10                          15                          20 | 144 |

-continued

| | | |
|---|---|---|
| GCC AGC TCA AGT GTA AGT TAC ATG CAC TGG TTC CAG CAG AAG CCA GGC<br>Ala Ser Ser Ser Val Ser Tyr Met His Trp Phe Gln Gln Lys Pro Gly<br>25                        30                         35                       40 | | 192 |
| ACT TCT CCC AAA CTC TGG ATT TAT AGC ACA TCC AAC CTG GCT TCT GGA<br>Thr Ser Pro Lys Leu Trp Ile Tyr Ser Thr Ser Asn Leu Ala Ser Gly<br>                  45                       50                       55 | | 240 |
| GTC CCT GCT CGC TTC AGT GGC AGT GGA TCT GGG ACC TCT TAC TCT CTC<br>Val Pro Ala Arg Phe Ser Gly Ser Gly Ser Gly Thr Ser Tyr Ser Leu<br>              60                      65                        70 | | 288 |
| ACA ATC AGC CGA ATG GAG GCT GAA GAT GCT GCC ACT TAT TAC TGC CAG<br>Thr Ile Ser Arg Met Glu Ala Glu Asp Ala Ala Thr Tyr Tyr Cys Gln<br>        75                       80                       85 | | 336 |
| CAA AGG AGT AGT TAC CCG TAC ACG TTC GGA GGG GGG ACC AAG CTG GAA<br>Gln Arg Ser Ser Tyr Pro Tyr Thr Phe Gly Gly Gly Thr Lys Leu Glu<br>90                       95                       100 | | 384 |
| ATA AAA CGG<br>Ile Lys Arg<br>105 | | 393 |

(2) INFORMATION FOR SEQ ID NO:3:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: sig_peptide
        (B) LOCATION: -19..-1
        (C) IDENTIFICATION METHOD:
            BY SIMILARITY WITH KNOWN SEQUENCE OR TO AN
            ESTABLISHED CONSENSUS (ix) FEATURE:
        (A) NAME/KEY: domain
        (B) LOCATION: 31..35
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 1"

(ix) FEATURE:
        (A) NAME/KEY: domain
        (B) LOCATION: 55..66
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 2"

(ix) FEATURE:
        (A) NAME/KEY: domain
        (B) LOCATION: 99..107
        (C) IDENTIFICATION METHOD: BY SIMILARITY
            WITH KNOWN SEQUENCE OR TO AN ESTABLISEHD
            CONSENSUS
        (D) OTHER INFORMATION: /product= "HYPERVARIABLE REGION 3"

(xi) SEQUENCE DESCRIPTION: SEQ ID NO:3:

| | |
|---|---|
| CTCCACAGTC CCTGAAGACA CTGACTCTAA CC ATG GGA TGG AGC TGG ATC TTT<br>                                                              Met Gly Trp Ser Trp Ile Phe<br>                                                                                -15 | 53 |
| CTC TTC CTC CTG TCA GGA ACT GCA GGT GTC CTC TCT GAG GTC CAG CTG<br>Leu Phe Leu Leu Ser Gly Thr Ala Gly Val Leu Ser Glu Val Gln Leu<br>        -10                        -5                               1 | 101 |
| CAG CAG TCT GGA CCT GAG CTG GTG AAG CCT GGG GCT TCA GTG AAG ATA<br>Gln Gln Ser Gly Pro Glu Leu Val Lys Pro Gly Ala Ser Val Lys Ile<br>     5                        10                       15                       20 | 149 |

```
TCC TGC AAG GCT TCT GGA TAC ACA TTC ACT GAC TAC AAC ATG GAC TGG      197
Ser Cys Lys Ala Ser Gly Tyr Thr Phe Thr Asp Tyr Asn Met Asp Trp
            25                  30                  35

GTG AAG CAG AGC CAT GGA AAG AGC CTT GAG TGG ATT GGA TAT ATT TAT      245
Val Lys Gln Ser His Gly Lys Ser Leu Glu Trp Ile Gly Tyr Ile Tyr
                40                  45                  50

CCT AAC AAT GGT GGT ACT GGC TAC AAC CAG AAG TTC AAG AGC AAG GCC      293
Pro Asn Asn Gly Gly Thr Gly Tyr Asn Gln Lys Phe Lys Ser Lys Ala
                55                  60                  65

ACA TTG ACT GTA GAC AAG TCC TCC AGC ACA GCC TAC ATG GAG CTC CAC      341
Thr Leu Thr Val Asp Lys Ser Ser Ser Thr Ala Tyr Met Glu Leu His
        70                  75                  80

AGC CTG ACA TCT GAG GAC TCT GCA GTC TAT TAC TGT GCA AGA GCG GGG      389
Ser Leu Thr Ser Glu Asp Ser Ala Val Tyr Tyr Cys Ala Arg Ala Gly
 85                 90                  95                 100

AGG TAT TAC TAC GCC TGG GAC TGG GGC CAA GGG ACT CTG GTC ACT GTC      437
Arg Tyr Tyr Tyr Ala Trp Asp Trp Gly Gln Gly Thr Leu Val Thr Val
                105                 110                 115

TCT GCA                                                              443
Ser Ala
```

(2) INFORMATION FOR SEQ ID NO:4:

(i) SEQUENCE CHARACTERISTICS:
        (A) LENGTH: 405 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: sig_peptide
        (B) LOCATION: 10..66
        (C) IDENTIFICATION METHOD:
            BY SIMILARITY WITH KNOWN SEQUENCE OR TO AN
            ESTABLISHED CONSENSUS (ix) FEATURE:
        (A) NAME/KEY: domain
        (B) LOCATION: 157..171
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 1"

(ix) FEATURE:
        (A) NAME/KEY: domain
        (B) LOCATION: 214..261
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 2"

(ix) FEATURE:
        (A) NAME/KEY: domain
        (B) LOCATION: 358..369
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 3"

(xi) SEQUENCE DESCRIPTION: SEQ ID NO:4:

```
CATCACAGC ATG GCT GTC CTG GTG CTG TTG CTC TGC CTG GTG ACA TTT        48
          Met Ala Val Leu Val Leu Leu Leu Cys Leu Val Thr Phe
                    -15                 -10

CCA AGC TGT GTC CTG TCC CAA GTG CAG CTG AAG GAG TCA GGA CCT GGT      96
Pro Ser Cys Val Leu Ser Gln Val Gln Leu Lys Glu Ser Gly Pro Gly
         -5                   1               5                 10

CTG GTG CAG CCC TCA CAG ACC CTG TCC CTC ACC TGC ACT GTC TCT GGG     144
```

```
Leu Val Gln Pro Ser Gln Thr Leu Ser Leu Thr Cys Thr Val Ser Gly
            15                  20                  25

TTC TCA TTA ACC AGC TAT ACT GTA AGC TGG GTT CGC CAG CCT CCA GGA          192
Phe Ser Leu Thr Ser Tyr Thr Val Ser Trp Val Arg Gln Pro Pro Gly
            30                  35                  40

AAG GGT CTG GAG TGG ATT GCA GCA ATA TCA AGT GGT GGA AGC ACA TAT          240
Lys Gly Leu Glu Trp Ile Ala Ala Ile Ser Ser Gly Gly Ser Thr Tyr
            45                  50                  55

TAT AAT TCA GCT CTC AAA TCA CGA CTG AGC ATC AGC AGG GAC ACC TCC          288
Tyr Asn Ser Ala Leu Lys Ser Arg Leu Ser Ile Ser Arg Asp Thr Ser
        60                  85                  70

AAG AGC CAA GTT TTC TTA AAA ATG AAC AGT CTG CAA ACT GAA GAC ACA          336
Lys Ser Gln Val Phe Leu Lys Met Asn Ser Leu Gln Thr Glu Asp Thr
 75                 80                  85                  90

GCC ATG TAC TTC TGT GCC CCT TCT GAG GGG GCC TGG GGC CAA GGA GTC          384
Ala Met Tyr Phe Cys Ala Pro Ser Glu Gly Ala Trp Gly Gln Gly Val
                95                  100                 105

ATG GTC ACA GTC TCC TCA GAG                                               405
Met Val Thr Val Ser Ser Glu
            110
```

(2) INFORMATION FOR SEQ ID NO:5:

(i) SEQUENCE CHARACTERISTICS:
  (A) LENGTH: 402 base pairs
  (B) TYPE: nucleic acid
  (C) STRANDEDNESS: double
  (D) TOPOLOGY: linear (ii) MOLECULE TYPE: cDNA to mRNA (ix) FEATURE:
  (A) NAME/KEY: sig_peptide
  (B) LOCATION: 19..78
  (C) IDENTIFICATION METHOD:
   BY SIMILARITY WITH KNOWN SEQUENCE OR TO AN
   ESTABLISHED CONSENSUS (ix) FEATURE:
  (A) NAME/KEY: domain
  (B) LOCATION: 148..180
  (C) IDENTIFICATION METHOD: BY SIMILARITY
   WITH KNOWN SEQUENCE OR TO AN ESTABILSHED
   CONSENSUS
  (D) OTHER INFORMATION: /product= "HYPERVARIABLE REGION 1"

(ix) FEATURE:
  (A) NAME/KEY: domain
  (B) LOCATION: 226..246
  (C) IDENTIFICATION METHOD: BY SIMILARITY
   WITH KNOWN SEQUENCE OR TO AN ESTABLISHED
   CONSENSUS
  (D) OTHER INFORMATION: /product= "HYPERVARIABLE REGION 2"

(ix) FEATURE:
  (A) NAME/KEY: domain
  (B) LOCATION: 343..369
  (C) IDENTIFICATION METHOD: BY SIMILARITY
   WITH KNOWN SEQUENCE OR TO AN ESTABLISHED
   CONSENSUS
  (D) OTHER INFORMATION: /product= "HYPERVARIABLE REGION 3"

(xi) SEQUENCE DESCRIPTION: SEQ ID NO:5:

```
ACAGGACACA GGTCAGTC ATG ATG GCT CCA GTC CAG CTC TTA GGG CTG CTG          51
                    Met Met Ala Pro Val Gln Leu Leu Gly Leu Leu
                    -20             -15                 -10

CTG ATT TGG CTC CCA GCC ATG AGA TGT GAC ATC CAG ATG ACC CAG TCT          99
Leu Ile Trp Leu Pro Ala Met Arg Cys Asp Ile Gln Met Thr Gln Ser
            -5                   1                  5

CCT TCA TTC CTG TCT GCA TCT GTG GGA GAC AGA GTC ACT ATC AAC TGC          147
```

```
Pro Ser Phe Leu Ser Ala Ser Val Gly Asp Arg Val Thr Ile Asn Cys
        10                  15                  20

AAA GCA AGT CAG AAT ATT AAC AAG TAC TTA AAC TGG TAT CAG CAA AAG         195
Lys Ala Ser Gln Asn Ile Asn Lys Tyr Leu Asn Trp Tyr Gln Gln Lys
        25                  30                  35

CTT GGA GAA GCT CCC AAA CGC CTG ATA TAT AAT ACA AAC AAT TTG CAA         243
Leu Gly Glu Ala Pro Lys Arg Leu Ile Tyr Asn Thr Asn Asn Leu Gln
 40              45                  50                      55

ACG GGC ATT CCA TCA AGG TTC AGT GGC AGT GGA TCT GGT ACA GAT TAC         291
Thr Gly Ile Pro Ser Arg Phe Ser Gly Ser Gly Ser Gly Thr Asp Tyr
                 60                  65                  70

ACA CTC ACC ATC AGC AGC CTG CAG CCT GAA GAT TTT GCC ACA TAT TTC         339
Thr Leu Thr Ile Ser Ser Leu Gln Pro Glu Asp Phe Ala Thr Tyr Phe
                 75                  80                  85

TGC TTG CAG CAT AAT AGT TTT CCG AAC ACG TTT GGA GCT GGG ACC AAG         387
Cys Leu Gln His Asn Ser Phe Pro Asn Thr Phe Gly Ala Gly Thr Lys
             90                  95                 100

CTG GAG CTG AAA CGG                                                     402
Leu Glu Leu Lys Arg
        105

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAC TAC AAC ATG GAC                                                      15
Asp Tyr Asn Met Asp
 1               5

(2) INFORMATION FOR SEQ ID NO:7:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TAT ATT TAT CCT AAC AAT GGT GGT ACT GGC TAC AAC CAG AAG TTC AAG          48
Tyr Ile Tyr Pro Asn Asn Gly Gly Thr Gly Tyr Asn Gln Lys Phe Lys
 1               5                  10                  15

AGC                                                                      51
Ser (2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TAC GGT CAT TAC TAC GGC TAC ATG TTT GCT TAC                              33
Tyr Gly His Tyr Tyr Gly Tyr Met Phe Ala Tyr
 1               5                  10
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA(genomic)

(xi) SEQUENCE DESCRIPTION: SEQ ID NO:9:

```
AGT GCC AGC TCA AGT GTA AGT TAC ATG CAC                              30
Ser Ala Ser Ser Ser Val Ser Tyr Met His
 1               5                  10
```

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
AGC ACA TCC AAC CTG GCT TCT                                          21
Ser Thr Ser Asn Leu Ala Ser
 1               5
```

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
CAG CAA AGG AGT AGT TAC CCG TAC ACG                                  27
Gln Gln Arg Ser Ser Tyr Pro Tyr Thr
 1               5
```

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:12:

```
GTC ACT GTC TCT GCA GCC TCC ACC AAG GGC C                            31
Val Thr Val Ser Ala Ala Ser Thr Lys Gly
 1               5                  10
```

(2) INFORMATION FOR SEQ ID NO:13:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:13:

```
C ACG TTC GGA GGG GGG ACC AAG CTG GAA ATA AAA CGA ACT GTG GCT    46
  Thr Phe Gly Gly Gly Thr Lys Leu Glu Ile Lys Arg Thr Val Ala
  1               5                   10                  15

GCA CC                                                            51
Ala
```

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:14:

```
CAA GGA GTC ATG GTC ACA GTC TCG AGC GCC TCC ACC AAG GGC           42
Gln Gly Val Met Val Thr Val Ser Ser Ala Ser Thr Lys Gly
1               5                   10

C                                                                 43
```

(2) INFORMATION FOR SEQ ID NO:15:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:15:

```
C ACG TTT GGA GCT GGT ACC AAG CTT GAG CTC AAA CGA ACT GTG GCT    46
  Thr Phe Gly Ala Gly Thr Lys Leu Glu Leu Lys Arg Thr Val Ala
  1               5                   10                  15

GCA CC                                                            51
Ala
```

(2) INFORMATION FOR SEQ ID NO:16:

(i) SEQUENCE CHARACTERISTICS:
        (A) LENGTH: 812 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: HYBRIDOMA KM50

(ix) FEATURE:
        (A) NAME/KEY: TATA_signal
        (B) LOCATION: 261..267

(xi) SEQUENCE DESCRIPTION: SEQ ID NO:16:

```
AAAGTCAGAC AACTTTGTAG AGTAGGTTCT ATCAATCCTA CTGCAATCCA ACATCACTGA    60

GGACAAATGT TTATACTGAG GAACCTGGTC TTGTGTGATA CGTACTTTCT GTGGGAAGCA   120

GATACGCACT CTCATGTGGC TCCTGAATTT CCCATCACAG AATGATACAT CTTGAGTCCT   180

AAAATTTAAG TACACCATCA GTGTCAGCAC CTGGTGAGGA AATGCAAATC TCTCCTGGAT   240

CCACCCAACC TTGGGTTGAA AAGCCAAAGC TGGGCCTGGG TACTCACTGG TGTGCAGCC    299

ATG GAC AGG CTT ACT TCC TCA TTC CTA CTG CTG ATG GTC CCT GCA          344
Met Asp Arg Leu Thr Ser Ser Phe Leu Leu Leu Met Val Pro Ala
```

```
                -15              -10              -5
TGTGAGTACC AAAGCTTCCT AAGTGATGAA CTGTTCTATC CTCACCTGTT CAAACCTGAC        404

CTCCTCCCCT TTGATTTCTC CACAG AT GTC CTG TCT CAG GTT ACT CTG AAA          455
                               Tyr Val Leu Ser Gln Val Thr Leu Lys
                                                 1                5

GAA TCT GGC CCT GGG ATA TTG CAG CCC TCC CAG ACC CTC AGT CTG ACT         503
Glu Ser Gly Pro Gly Ile Leu Gln Pro Ser Gln Thr Leu Ser Leu Thr
             10                  15                  20

TGC TCT TTC TCT GGG TTT TCA CTG AGC ACT TAT GGT ATG TGT GTG GGC         551
Cys Ser Phe Ser Gly Phe Ser Leu Ser Thr Tyr Gly Met Cys Val Gly
         25                  30                  35

TGG ATT CGT CAG TCT TCA GGG AAG GGT CTG GAG TGG CTG GCA AAC GTT         599
Trp Ile Arg Gln Ser Ser Gly Lys Gly Leu Glu Trp Leu Ala Asn Val
     40                  45                  50

TGG TGG AGT GAT GCT AAG TAC TAC AAT CCA TCT CTG AAA AAC CGG CTC         647
Trp Trp Ser Asp Ala Lys Tyr Tyr Asn Pro Ser Leu Lys Asn Arg Leu
 55                  60                  65

ACA ATC TCC AAG GAC ACC TCC AAC AAC CAA GCA TTC CTC AAG ATC ACC         695
Thr Ile Ser Lys Asp Thr Ser Asn Asn Gln Ala Phe Leu Lys Ile Thr
 70                  75                  80                  85

AAT ATG GAC ACT GCA GAT ACT GCC ATA TAC TAC TGT GCT GGG AGA GGG         743
Asn Met Asp Thr Ala Asp Thr Ala Ile Tyr Tyr Cys Ala Gly Arg Gly
             90                  95                 100

GCT ACG GAG GGT ATA GTG AGC TTT GAT TAC TGG GGC CAC GGA GTC ATG         791
Ala Thr Glu Gly Ile Val Ser Phe Asp Tyr Trp Gly His Gly Val Met
                105                 110                 115

GTC ACA GTC TCC TCA GGTAAG                                              812
Val Thr Val Ser Ser
         120

(2) INFORMATION FOR SEQ ID NO:17:

(i) SEQUENCE CHARACTERISTICS:
        (A) LENGTH: 46 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:17:

AGCTGAATTC GGGCCCGATA TCAAGCTTGT CGACTCTAGA GGTACC                       46

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:18:

GATGAAGACA GATATCGCAG CCACAGTTC                                          29

(2) INFORMATION FOR SEQ ID NO:19:

(i) SEQUENCE CHARACTERISTICS:
        (A) LENGTH: 408 base pairs
        (B) TYPE: nucleic acid
        (C) STRANDEDNESS: double
        (D) TOPOLOGY: linear (ii) MOLECULE TYPE: cDNA to mRNA
```

(vi) ORIGINAL SOURCE:
            (B) STRAIN: HYBRIDOMA KM-641

(ix) FEATURE:
            (A) NAME/KEY: sig_peptide
            (B) LOCATION: 25..84
            (C) IDENTIFICATION METHOD:
                BY SIMILARITY WITH KNOWN SEQUENCE OR TO AN
                ESTABLISHED CONSENSUS (xi) SEQUENCE DESCRIPTION: SEQ ID NO:19:

AATTCGGCAC GAGTCAGCCT GGAC ATG ATG TCC TCT GCT CAG TTC CTT GGT         51
                          Met Met Ser Ser Ala Gln Phe Leu Gly
                              -20                 -15

CTC CTG TTG CTC TGT TTT CAA GGT ACC AGA TGT GAT ATC CAG ATG ACA         99
Leu Leu Leu Leu Cys Phe Gln Gly Thr Arg Cys Asp Ile Gln Met Thr
            -10              -5              1               5

CAG ACT GCA TCC TCC CTG CCT GCC TCT CTG GGA GAC AGA GTC ACC ATC        147
Gln Thr Ala Ser Ser Leu Pro Ala Ser Leu Gly Asp Arg Val Thr Ile
                10                  15                  20

AGT TGC AGT GCA AGT CAG GAC ATT AGT AAT TAT TTA AAC TGG TAT CAA        195
Ser Cys Ser Ala Ser Gln Asp Ile Ser Asn Tyr Leu Asn Trp Tyr Gln
                25                  30                  35

CAG AAA CCA GAT GGA ACT GTT AAA CTC CTG ATC TTT TAC TCA TCA AAT        243
Gln Lys Pro Asp Gly Thr Val Lys Leu Leu Ile Phe Tyr Ser Ser Asn
                40                  45                  50

TTA CAC TCG GGA GTC CCA TCA AGG TTC AGT GGC GGT GGG TCC GGG ACA        291
Leu His Ser Gly Val Pro Ser Arg Phe Ser Gly Gly Gly Ser Gly Thr
        55                  60                  65

GAT TAT TCT CTC ACC ATC AGC AAC CTG GAG CCT GAA GAT ATT GCC ACT        339
Asp Tyr Ser Leu Thr Ile Ser Asn Leu Glu Pro Glu Asp Ile Ala Thr
70                  75                  80                  85

TAC TTT TGT CAT CAG TAT AGT AAG CTT CCG TGG ACG TCC GGT GGA GGC        387
Tyr Phe Cys His Gln Tyr Ser Lys Leu Pro Trp Thr Ser Gly Gly Gly
                90                  95                 100

ACC AAG CTG GAA ATC AAA CGG                                            408
Thr Lys Leu Glu Ile Lys Arg
            105

(2) INFORMATION FOR SEQ ID NO:20:

(i) SEQUENCE CHARACTERISTICS:
            (A) LENGTH: 403 base pairs
            (B) TYPE: nucleic acid
            (C) STRANDEDNESS: double
            (D) TOPOLOGY: linear (ii) MOLECULE TYPE: cDNA to mRNA (vi) ORIGINAL SOURCE:
            (B) STRAIN: HYBRIDOMA KM-641

(ix) FEATURE:
            (A) NAME/KEY: sig_peptide
            (B) LOCATION: 14..43
            (C) IDENTIFICATION METHOD:
                BY SIMILARITY WITH KNOWN SEQUENCE OR TO AN
                ESTABLISHED CONSENSUS (xi) SEQUENCE DESCRIPTION: SEQ ID NO:20:

AATTCGGCAC GAG CTT GTC CTT GTT TTC AAA GGT GTT CAG TGT GAA GTG          49
               Leu Val Leu Val Phe Lys Gly Val Gln Cys Glu Val
               -10             -5                  1

ACG CTG GTG GAG TCT GGG GGA GAC TTT GTG AAA CCT GGA GGG TCC CTG         97
Thr Leu Val Glu Ser Gly Gly Asp Phe Val Lys Pro Gly Gly Ser Leu
            5                   10                  15

```
AAA GTC TCC TGT GCA GCC TCT GGA TTC GCT TTC AGT CAT TAT GCC ATG      145
Lys Val Ser Cys Ala Ala Ser Gly Phe Ala Phe Ser His Tyr Ala Met
 20                  25                  30

TCT TGG GTT CGC CAG ACT CCG GCG AAG AGG CTG GAA TGG GTC GCA TAT      193
Ser Trp Val Arg Gln Thr Pro Ala Lys Arg Leu Glu Trp Val Ala Tyr
 35                  40                  45                  50

ATT AGT AGT GGT GGT AGT GGC ACC TAC TAT TCA GAC AGT GTA AAG GGC      241
Ile Ser Ser Gly Gly Ser Gly Thr Tyr Tyr Ser Asp Ser Val Lys Gly
                 55                  60                  65

CGA TTC ACC ATT TCC AGA GAC AAT GCC AAG AAC ACC CTG TAC CTG CAA      289
Arg Phe Thr Ile Ser Arg Asp Asn Ala Lys Asn Thr Leu Tyr Leu Gln
             70                  75                  80

ATG CGC AGT CTG AGG TCT GAG GAC TCG GCC ATG TAT TTC TGT ACA AGA      337
Met Arg Ser Leu Arg Ser Glu Asp Ser Ala Met Tyr Phe Cys Thr Arg
         85                  90                  95

GTT AAA CTG GGA ACC TAC TAC TTT GAC TCC TGG GGC CAA GGC ACC ACT      385
Val Lys Leu Gly Thr Tyr Tyr Phe Asp Ser Trp Gly Gln Gly Thr Thr
100                 105                 110

CTC ACT GTC TCC TCA GCT                                              403
Leu Thr Val Ser Ser Ala
115                 120

(2) INFORMATION FOR SEQ ID NO:21:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:21:

AATTCACC ATG GAG TTT GGG CTC AGC TGG CTT TTT                          35
         Met Glu Phe Gly Leu Ser Trp Leu Phe
          1               5

(2) INFORMATION FOR SEQ ID NO:22:

(i) SEQUENCE CHARACTERISTICS:
        (A) LENGTH: 43 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:22:

CAA GGT ACC ACG TTA ACT GTC TCC TCA GCC TCC ACC AAG GGC               42
Gln Gly Thr Thr Leu Thr Val Ser Ser Ala Ser Thr Lys Gly
 1               5                  10

C                                                                     43

(2) INFORMATION FOR SEQ ID NO:23:

(i) SEQUENCE CHARACTERISTICS:
        (A) LENGTH: 80 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:23:

GGCCGCACCA TGGGATGGAG CTGGATCTTT CTCTTCCTCC TGTCAGGAAC TGCTGGTGTC     60

CTCTCTCAGG TCCAACTGCA                                                 80
```

(2) INFORMATION FOR SEQ ID NO:24:

(i) SEQUENCE CHARACTERISTICS:
        (A) LENGTH: 59 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:24:

```
GGAGAGCGGT CCAGGTCTTG TGAGGCCTAG CCAGACCCTG AGCCTGACCT GCACCGTGT        59
```

(2) INFORMATION FOR SEQ ID NO:25:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:25:

```
CCGGATTCAC CTTCAGCGAC TACAACATGG ACTGGGTGAG ACAGCCACCT GGACGAGGTC        60
```

(2) INFORMATION FOR SEQ ID NO:26:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:26:

```
TCGAGTGGAT TGGATATATT TATCCTAACA ATGGTGGTAC TGGCTACAAC CAGAAGTTCA        60

AGAGCAGAGT GACAATGCTG G                                                  81
```

(2) INFORMATION FOR SEQ ID NO:27:

(i) SEQUENCE CHARACTERISTICS:
        (A) LENGTH: 61 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:27:

```
TCGACACCAG CAAGAACCAG TTCAGCCTGA GACTCAGCAG CGTGACAGCC GCCGACACCG        60

C                                                                        61
```

(2) INFORMATION FOR SEQ ID NO:28:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:28:

```
GGTCTATTAT TGTGCGCGCT ACGGTCATTA CTACGGCTAC ATGTTTGCTT ACTGGGGTCA        60
```

(2) INFORMATION FOR SEQ ID NO:29:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:29:

```
CACCGTCACA GTCTCCTCAG CCTCCACCAA GGGCC                              35
```

(2) INFORMATION FOR SEQ ID NO:30:

(i) SEQUENCE CHARACTERISTICS:
        (A) LENGTH: 77 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:30:

```
AATTCACCAT GCATTTTCAA GTGCAGATTT TCAGCTTCCT GCTAATCAGT GCCTCAGTCA   60

TAATGTCCAG AGGAGAT                                                  77
```

(2) INFORMATION FOR SEQ ID NO:31:

(i) SEQUENCE CHARACTERISTICS:
        (A) LENGTH: 62 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:31:

```
ATCCAGCTGA CCCAGAGCCC AAGCAGCCTG AGCGCTAGCG TGGGTGACAG AGTGACCATG   60

AC                                                                  62
```

(2) INFORMATION FOR SEQ ID NO:32:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:32:

```
GTGCAGTGCC AGCTCAAGTG TAAGTTACAT GCACTGGTAT CAGCAGAAGC CAGGTAAGGC   60

TCCAA                                                               65
```

(2) INFORMATION FOR SEQ ID NO:33:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:33:

```
AGCTTCTGAT CTACAGCACA TCCAACCTGG CTTCTGGTGT GCCAT                        45

(2) INFORMATION FOR SEQ ID NO:34:

(i) SEQUENCE CHARACTERISTICS:
        (A) LENGTH: 76 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:34:

CTAGATTCAG CGGTAGCGGT AGCGGTACAG ACTTCACCTT CACCATCAGC AGCCTCCAGC        60

CAGAGGACAT CGCTAC                                                        76

(2) INFORMATION FOR SEQ ID NO:35:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:35:

GTACTACTGC CAGCAAAGGA GTAGTTACCC GTACACGTTC GGCGGGGGGA CCAAGGTGGA        60

AATCAAACGT ACGGTGGCTG CACC                                               84

(2) INFORMATION FOR SEQ ID NO:36:

(i) SEQUENCE CHARACTERISTICS:
        (A) LENGTH: 442 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GGCCGCACC ATG GGA TGG AGC TGG ATC TTT CTC TTC CTC CTG TCA GGA            48
           Met Gly Trp Ser Trp Ile Phe Leu Phe Leu Leu Ser Gly
           -19             -15                 -10

ACT GCT GGT GTC CTC TCT CAG GTC CAA CTG CAG GAG AGC GGT CCA GGT          96
Thr Ala Gly Val Leu Ser Gln Val Gln Leu Gln Glu Ser Gly Pro Gly
     -5                   1               5                  10

CTT GTG AGG CCT AGC CAG ACC CTG AGC CTG ACC TGC ACC GTG TCC GGA         144
Leu Val Arg Pro Ser Gln Thr Leu Ser Leu Thr Cys Thr Val Ser Gly
             15                  20                  25

TTC ACC TTC AGC GAC TAC AAC ATG GAC TGG GTG AGA CAG CCA CCT GGA         192
Phe Thr Phe Ser Asp Tyr Asn Met Asp Trp Val Arg Gln Pro Pro Gly
                 30                  35                  40

CGA GGT CTC GAG TGG ATT GGA TAT ATT TAT CCT AAC AAT GGT GGT ACT         240
Arg Gly Leu Glu Trp Ile Gly Tyr Ile Tyr Pro Asn Asn Gly Gly Thr
                     45                  50                  55

GGC TAC AAC CAG AAG TTC AAG AGC AGA GTG ACA ATG CTG GTC GAC ACC         288
Gly Tyr Asn Gln Lys Phe Lys Ser Arg Val Thr Met Leu Val Asp Thr
         60                  65                  70

AGC AAG AAC CAG TTC AGC CTG AGA CTC AGC AGC GTG ACA GCC GCC GAC         336
Ser Lys Asn Gln Phe Ser Leu Arg Leu Ser Ser Val Thr Ala Ala Asp
    75                  80                  85                  90

ACC GCG GTC TAT TAT TGT GCG CGC TAC GGT CAT TAC TAC GGC TAC ATG         384
Thr Ala Val Tyr Tyr Cys Ala Arg Tyr Gly His Tyr Tyr Gly Tyr Met
```

```
                95                100               105
TTT GCT TAC TGG GGT CAA GGT ACC ACC GTC ACA GTC TCC TCA GCC TCC       432
Phe Ala Tyr Trp Gly Gln Gly Thr Thr Val Thr Val Ser Ser Ala Ser
            110                 115                 120

ACC AAG GGC C                                                         442
Thr Lys Gly
        125
```

(2) INFORMATION FOR SEQ ID NO:37:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

```
AATTCACC ATG CAT TTT CAA GTG CAG ATT TTC AGC TTC CTG CTA ATC AGT       50
         Met His Phe Gln Val Gln Ile Phe Ser Phe Leu Leu Ile Ser
         -22     -20                 -15                 -10

GCC TCA GTC ATA ATG TCC AGA GGA GAT ATC CAG CTG ACC CAG AGC CCA        98
Ala Ser Val Ile Met Ser Arg Gly Asp Ile Gln Leu Thr Gln Ser Pro
            -5              1                 5

AGC AGC CTG AGC GCT AGC GTG GGT GAC AGA GTG ACC ATC ACG TGC AGT       146
Ser Ser Leu Ser Ala Ser Val Gly Asp Arg Val Thr Ile Thr Cys Ser
        10                  15                  20

GCC AGC TCA AGT GTA AGT TAC ATG CAC TGG TAT CAG CAG AAG CCA GGT       194
Ala Ser Ser Ser Val Ser Tyr Met His Trp Tyr Gln Gln Lys Pro Gly
25              30                  35                      40

AAG GCT CCA AAG CTT CTG ATC TAC AGC ACA TCC AAC CTG GCT TCT GGT       242
Lys Ala Pro Lys Leu Leu Ile Tyr Ser Thr Ser Asn Leu Ala Ser Gly
            45                  50                  55

GTG CCA TCT AGA TTC AGC GGT AGC GGT AGC GGT ACA GAC TTC ACC TTC       290
Val Pro Ser Arg Phe Ser Gly Ser Gly Ser Gly Thr Asp Phe Thr Phe
            60                  65                  70

ACC ATC AGC AGC CTC CAG CCA GAG GAC ATC GCT ACG TAC TAC TGC CAG       338
Thr Ile Ser Ser Leu Gln Pro Glu Asp Ile Ala Thr Tyr Tyr Cys Gln
        75                  80                  85

CAA AGG AGT AGT TAC CCG TAC ACG TTC GGC GGG GGG ACC AAG GTG GAA       386
Gln Arg Ser Ser Tyr Pro Tyr Thr Phe Gly Gly Gly Thr Lys Val Glu
        90                  95                 100

ATC AAA CGT ACG GTG GCT GCA CC                                        409
Ile Lys Arg Thr Val Ala Ala
105             110
```

(2) INFORMATION FOR SEQ ID NO:38:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:38:

```
CACTCAGTGT TAACTGAGGA GCAGGTGAAT TC                                    32
```

(2) INFORMATION FOR SEQ ID NO:39:

(i) SEQUENCE CHARACTERISTICS:
        (A) LENGTH: 40 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:39:

AGCTGAATTC ACCTGCTCCT CAGTTAACAC TGAGTGGTAC                              40

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:40:

AATTCGTACG GTGGCTGCAC C                                                  21

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:41:

GGTGCAGCCA CCGTACG                                                       17

(2) INFORMATION FOR SEQ ID NO:42:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:42:

CTCGCGACTA GTGGGCCCGC GGCCGC                                             26

(2) INFORMATION FOR SEQ ID NO:43:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:43:

AGCTGCGGCC GCGGGCCCAC TAGTCGCGAG GTAC                                    34

(2) INFORMATION FOR SEQ ID NO:44:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:44:

GTGGCGGCCG CTTGGGCCCG                                           20

(2) INFORMATION FOR SEQ ID NO:45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:45:

CGGGCCCAAG CGGCCGCCAC                                           20

(2) INFORMATION FOR SEQ ID NO:46:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:46:

CATGAATTCT TCGTACGGTT CGATAAATCG ATACCG                         36

(2) INFORMATION FOR SEQ ID NO:47:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:47:

CGGTATCGAT TTATCGAACC GTACGAAGAA TTCATGAGCT                     40

(2) INFORMATION FOR SEQ ID NO:48:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:48:

CACGTTCGGA GGGGGGACCA AGCTGGAAAT AAAAC                          35

(2) INFORMATION FOR SEQ ID NO:49:

(i) SEQUENCE CHARACTERISTICS:
            (A) LENGTH: 35 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:49:

GTACGTTTTA TTTCCAGCTT GGTCCCCCCT CCGAA                              35

(2) INFORMATION FOR SEQ ID NO:50:

(i) SEQUENCE CHARACTERISTICS:
        (A) LENGTH: 61 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:50:

TCGACACCAG CAAGAACACA GCCTACCTGA GACTCAGCAG CGTGACAGCC GCCGACACCG    60
C                                                                  61

(2) INFORMATION FOR SEQ ID NO:51:

(i) SEQUENCE CHARACTERISTICS:
        (A) LENGTH: 59 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:51:

CCGGATACAC ATTCACTGAC TACAACATGG ACTGGGTGAG ACAGAGCCAT GACGAGGTC    59

(2) INFORMATION FOR SEQ ID NO:52:

(i) SEQUENCE CHARACTERISTICS:
        (A) LENGTH: 442 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(vi) ORIGINAL SOURCE:
        (A) ORGANISM: Homo sapiens and mouse (ix) FEATURE:
        (A) NAME/KEY: sig_peptide
        (B) LOCATION: -19..-1
        (C) IDENTIFICATION METHOD: by similarity with known sequence
            or to an established consensu (ix) FEATURE:
        (A) NAME/KEY: domain
        (B) LOCATION: 31..35
        (C) IDENTIFICATION METHOD: by similarity with known sequence
            or to an established consensu
        (D) OTHER INFORMATION: /product= "CDR1"

(ix) FEATURE:
        (A) NAME/KEY: domain
        (B) LOCATION: 50..66
        (C) IDENTIFICATION METHOD: by similarity with known sequence
            or to an established consensu
        (D) OTHER INFORMATION: /product= "CDR2"

(ix) FEATURE:
  (A) NAME/KEY: domain
  (B) LOCATION: 99..109
  (C) IDENTIFICATION METHOD: by similarity with known sequence or to an established consensu
  (D) OTHER INFORMATION: /product= "CDR3"

(xi) SEQUENCE DESCRIPTION: SEQ ID NO:52:

```
GGCCGCACC ATG GGA TGG AGC TGG ATC TTT CTC TTC CTC CTG TCA GGA        48
          Met Gly Trp Ser Trp Ile Phe Leu Phe Leu Leu Ser Gly
          -19                 -15                 -10

ACT GCT GGT GTC CTC TCT CAG GTC CAA CTG CAG GAG AGC GGT CCA GGT      96
Thr Ala Gly Val Leu Ser Gln Val Gln Leu Gln Glu Ser Gly Pro Gly
        -5                  1               5                  10

CTT GTG AGG CCT AGC CAG ACC CTG AGC CTG ACC TGC ACC GTG TCC GGA     144
Leu Val Arg Pro Ser Gln Thr Leu Ser Leu Thr Cys Thr Val Ser Gly
                15                  20                  25

TTC ACC TTC AGC GAC TAC AAC ATG GAC TGG GTG AGA CAG CCA CCT GGA     192
Phe Thr Phe Ser Asp Tyr Asn Met Asp Trp Val Arg Gln Pro Pro Gly
            30                  35                  40

CGA GGT CTC GAG TGG ATT GGA TAT ATT TAT CCT AAC AAT GGT GGT ACT     240
Arg Gly Leu Glu Trp Ile Gly Tyr Ile Tyr Pro Asn Asn Gly Gly Thr
        45                  50                  55

GGC TAC AAC CAG AAG TTC AAG AGC AGA GTG ACA ATG CTG GTC GAC ACC     288
Gly Tyr Asn Gln Lys Phe Lys Ser Arg Val Thr Met Leu Val Asp Thr
    60                  65                  70

AGC AAG AAC ACA GCC TAC CTG AGA CTC AGC AGC GTG ACA GCC GCC GAC     336
Ser Lys Asn Thr Ala Tyr Leu Arg Leu Ser Ser Val Thr Ala Ala Asp
75                  80                  85                  90

ACC GCG GTC TAT TAT TGT GCA ACC TAC GGT CAT TAC TAC GGC TAC ATG     384
Thr Ala Val Tyr Tyr Cys Ala Thr Tyr Gly His Tyr Tyr Gly Tyr Met
                95                  100                 105

TTT GCT TAC TGG GGT CAA GGT ACC ACC GTC ACA GTC TCC TCA GCC TCC     432
Phe Ala Tyr Trp Gly Gln Gly Thr Thr Val Thr Val Ser Ser Ala Ser
            110                 115                 120

ACC AAG GGC C                                                       442
Thr Lys Gly
        125
```

(2) INFORMATION FOR SEQ ID NO:53:

(i) SEQUENCE CHARACTERISTICS:
    (A) LENGTH: 442 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc = "synthetic DNA"

(vi) ORIGINAL SOURCE:
    (A) ORGANISM: Homo sapiens and mouse (ix) FEATURE:
    (A) NAME/KEY: sig_peptide
    (B) LOCATION: -19..-1
    (C) IDENTIFICATION METHOD: by similarity with known sequence or to an established consensu (ix) FEATURE:
    (A) NAME/KEY: domain
    (B) LOCATION: 31..35
    (C) IDENTIFICATION METHOD: by similarity with known sequence or to an established consensu
    (D) OTHER INFORMATION: /product= "CDR1"

(ix) FEATURE:
    (A) NAME/KEY: domain
    (B) LOCATION: 50..66

(C) IDENTIFICATION METHOD: by similarity with known sequence
            or to an established consensu
        (D) OTHER INFORMATION: /product= "CDR2"

(ix) FEATURE:
         (A) NAME/KEY: domain
         (B) LOCATION: 99..109
         (C) IDENTIFICATION METHOD: by similarity with known sequence
             or to an established consensu
         (D) OTHER INFORMATION: /product= "CDR3"

(xi) SEQUENCE DESCRIPTION: SEQ ID NO:53:

```
GGCCGCACC ATG GGA TGG AGC TGG ATC TTT CTC TTC CTC CTG TCA GGA            48
          Met Gly Trp Ser Trp Ile Phe Leu Phe Leu Leu Ser Gly
          -19                 -15                 -10

ACT GCT GGT GTC CTC TCT CAG GTC CAA CTG CAG GAG AGC GGT CCA GGT          96
Thr Ala Gly Val Leu Ser Gln Val Gln Leu Gln Glu Ser Gly Pro Gly
     -5                   1                5                  10

CTT GTG AGG CCT AGC CAG ACC CTG AGC CTG ACC TGC ACC GTG TCC GGA         144
Leu Val Arg Pro Ser Gln Thr Leu Ser Leu Thr Cys Thr Val Ser Gly
                 15                  20                  25

TAC ACA TTC ACT GAC TAC AAC ATG GAC TGG GTG AGA CAG AGC CAT GGA         192
Tyr Thr Phe Thr Asp Tyr Asn Met Asp Trp Val Arg Gln Ser His Gly
             30                  35                  40

CGA GGT CTC GAG TGG ATT GGA TAT ATT TAT CCT AAC AAT GGT GGT ACT         240
Arg Gly Leu Glu Trp Ile Gly Tyr Ile Tyr Pro Asn Asn Gly Gly Thr
         45                  50                  55

GGC TAC AAC CAG AAG TTC AAG AGC AGA GTG ACA ATG CTG GTC GAC ACC         288
Gly Tyr Asn Gln Lys Phe Lys Ser Arg Val Thr Met Leu Val Asp Thr
     60                  65                  70

AGC AAG AAC CAG TTC AGC CTG AGA CTC AGC AGC GTG ACA GCC GCC GAC         336
Ser Lys Asn Gln Phe Ser Leu Arg Leu Ser Ser Val Thr Ala Ala Asp
 75                  80                  85                  90

ACC GCG GTC TAT TAT TGT GCA ACC TAC GGT CAT TAC TAC GGC TAC ATG         384
Thr Ala Val Tyr Tyr Cys Ala Thr Tyr Gly His Tyr Tyr Gly Tyr Met
                 95                  100                 105

TTT GCT TAC TGG GGT CAA GGT ACC ACC GTC ACA GTC TCC TCA GCC TCC         432
Phe Ala Tyr Trp Gly Gln Gly Thr Thr Val Thr Val Ser Ser Ala Ser
                 110                 115                 120

ACC AAG GGC C                                                           442
Thr Lys Gly
        125
```

(2) INFORMATION FOR SEQ ID NO:54:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:54:

```
CAGGAAACAG CTATGACGCG GCCGCCACCA TGGGATGGAG CTGGATCTTT CTCTTCCTCC       60

TGTCAGGAAC TGCAGGTGTC CTCTCTGAGG TGCAGCTGGT                            100
```

(2) INFORMATION FOR SEQ ID NO:55:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "synthetic DNA"

(xi) SEQUENCE DESCRIPTION: SEQ ID NO:55:

AGTCAGTGAA GGTGTATCCG AAGCCTTGC AGGAGACCTT CACTGAGGCC CCAGGCTTCT     60

TCACCTCTGC TCCAGACTGC ACCAGCTGCA CCTCAGAGAG                        100

(2) INFORMATION FOR SEQ ID NO:56:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:56:

CGGATACACC TTCACTGACT ACAACATGGA CTGGGTGCGA CAGGCCCCTG ACAAGGGCT     60

CGAGTGGATG GGATATATTT ATCCTAACAA TGGTGGTACT                        100

(2) INFORMATION FOR SEQ ID NO:57:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:57:

AGCTCCATGT AGGCTGTGCT CGTGGATGTG TCTACGGTAA TGGTGACCTT GCTCTTGAAC     60

TTCTGGTTGT AGCCAGTACC ACCATTGTTA GGAT                                94

(2) INFORMATION FOR SEQ ID NO:58:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:58:

AGCACAGCCT ACATGGAGCT GCACAGCCTG AGATCTGAGG ACACGGCCGT GTATTACTGT     60

GCGACCTACG GTCATTACTA CGGCTACATG TTTGCT                              96

(2) INFORMATION FOR SEQ ID NO:59:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:59:

GTTTTCCCAG TCACGACGGG CCCTTGGTGG AGGCTGAGGA GACGGTGACC AGGGTTCCCT     60

GGCCCCAGTA AGCAAACATG TAGCCGTAGT                                     90

(2) INFORMATION FOR SEQ ID NO:60:

(i) SEQUENCE CHARACTERISTICS:
        (A) LENGTH: 432 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(vi) ORIGINAL SOURCE:
        (A) ORGANISM: Homo sapiens and mouse (ix) FEATURE:
        (A) NAME/KEY: sig_peptide
        (B) LOCATION: -19..-1
        (C) IDENTIFICATION METHOD: by similarity with known sequence
            or to an established consensu (ix) FEATURE:
        (A) NAME/KEY: domain
        (B) LOCATION: 31..35
        (C) IDENTIFICATION METHOD: by similarity with known sequence
            or to an established consensu
        (D) OTHER INFORMATION: /product= "CDR1"

(ix) FEATURE:
        (A) NAME/KEY: domain
        (B) LOCATION: 50..66
        (C) IDENTIFICATION METHOD: by similarity with known sequence
            or to an established consensu
        (D) OTHER INFORMATION: /product= "CDR2"

(ix) FEATURE:
        (A) NAME/KEY: domain
        (B) LOCATION: 99..109
        (C) IDENTIFICATION METHOD: by similarity with known sequence
            or to an established consensu
        (D) OTHER INFORMATION: /product= "CDR3"

(xi) SEQUENCE DESCRIPTION: SEQ ID NO:60:

```
ATG GGA TGG AGC TGG ATC TTT CTC TTC CTC CTG TCA GGA ACT GCA GGT        48
Met Gly Trp Ser Trp Ile Phe Leu Phe Leu Leu Ser Gly Thr Ala Gly
-19             -15                 -10                 -5

GTC CTC TCT GAG GTG CAG CTG GTG CAG TCT GGA GCA GAG GTG AAG AAG        96
Val Leu Ser Glu Val Gln Leu Val Gln Ser Gly Ala Glu Val Lys Lys
             1               5                  10

CCT GGG GCC TCA GTG AAG GTC TCC TGC AAG GCT TCC GGA TAC ACC TTC       144
Pro Gly Ala Ser Val Lys Val Ser Cys Lys Ala Ser Gly Tyr Thr Phe
 15                  20                  25

ACT GAC TAC AAC ATG GAC TGG GTG CGA CAG GCC CCT GGA CAA GGG CTC       192
Thr Asp Tyr Asn Met Asp Trp Val Arg Gln Ala Pro Gly Gln Gly Leu
 30                  35                  40                  45

GAG TGG ATG GGA TAT ATT TAT CCT AAC AAT GGT GGT ACT GGC TAC AAC       240
Glu Trp Met Gly Tyr Ile Tyr Pro Asn Asn Gly Gly Thr Gly Tyr Asn
                 50                  55                  60

CAG AAG TTC AAG AGC AAG GTC ACC ATT ACC GTA GAC ACA TCC ACG AGC       288
Gln Lys Phe Lys Ser Lys Val Thr Ile Thr Val Asp Thr Ser Thr Ser
                 65                  70                  75

ACA GCC TAC ATG GAG CTG CAC AGC CTG AGA TCT GAG GAC ACG GCC GTG       336
Thr Ala Tyr Met Glu Leu His Ser Leu Arg Ser Glu Asp Thr Ala Val
             80                  85                  90

TAT TAC TGT GCG ACC TAC GGT CAT TAC TAC GGC TAC ATG TTT GCT TAC       384
Tyr Tyr Cys Ala Thr Tyr Gly His Tyr Tyr Gly Tyr Met Phe Ala Tyr
             95                 100                 105

TGG GGC CAG GGA ACC CTG GTC ACC GTC TCC TCA GCC TCC ACC AAG GGC       432
Trp Gly Gln Gly Thr Leu Val Thr Val Ser Ser Ala Ser Thr Lys Gly
110                 115                 120                 125
```

(2) INFORMATION FOR SEQ ID NO:61:

(i) SEQUENCE CHARACTERISTICS:
        (A) LENGTH: 68 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:61:

```
GTACTACTGC CAGCAAAGGA GTAGTTACCC GTACACGTTC GGCGGGGGGA CCAAGGTGGA      60

AATCAAAC                                                              68
```

(2) INFORMATION FOR SEQ ID NO:62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:62:

```
ACTCTGTCAC CTGGGCTAGC GCTCA                                           25
```

(2) INFORMATION FOR SEQ ID NO:63:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:63:

```
TGAGCGCTAG CCCAGGTGAC AGAGT                                           25
```

(2) INFORMATION FOR SEQ ID NO:64:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(vi) ORIGINAL SOURCE:
        (A) ORGANISM: Homo sapiens and mouse (ix) FEATURE:
        (A) NAME/KEY: sig_peptide
        (B) LOCATION: -22..-1
        (C) IDENTIFICATION METHOD: by similarity with known sequence
            or to an established consensu (ix) FEATURE:
        (A) NAME/KEY: domain
        (B) LOCATION: 24..33
        (C) IDENTIFICATION METHOD: by similarity with known sequence
            or to an established consensu
        (D) OTHER INFORMATION: /product= "CDR1"

(ix) FEATURE:

(A) NAME/KEY: domain
                    (B) LOCATION: 49..55
                    (C) IDENTIFICATION METHOD: by similarity with known sequence
                        or to an established consensu
                    (D) OTHER INFORMATION: /product= "CDR2"

(ix) FEATURE:
                    (A) NAME/KEY: domain
                    (B) LOCATION: 88..96
                    (C) IDENTIFICATION METHOD: by similarity with known sequence
                        or to an established consensu
                    (D) OTHER INFORMATION: /product= "CDR3"

(xi) SEQUENCE DESCRIPTION: SEQ ID NO:64:

```
ATG CAT TTT CAA GTG CAG ATT TTC AGC TTC CTG CTA ATC AGT GCC TCA        48
Met His Phe Gln Val Gln Ile Phe Ser Phe Leu Leu Ile Ser Ala Ser
-22         -20                 -15                 -10

GTC ATA ATG TCC AGA GGA GAT ATC CAG CTG ACC CAG AGC CCA AGC AGC        96
Val Ile Met Ser Arg Gly Asp Ile Gln Leu Thr Gln Ser Pro Ser Ser
        -5                   1               5                  10

CTG AGC GCT AGC CCA GGT GAC AGA GTG ACC ATC ACG TGC AGT GCC AGC       144
Leu Ser Ala Ser Pro Gly Asp Arg Val Thr Ile Thr Cys Ser Ala Ser
                15                  20                  25

TCA AGT GTA AGT TAC ATG CAC TGG TAT CAG CAG AAG CCA GGT AAG GCT       192
Ser Ser Val Ser Tyr Met His Trp Tyr Gln Gln Lys Pro Gly Lys Ala
            30                  35                  40

CCA AAG CTT CTG ATC TAC AGC ACA TCC AAC CTG GCT TCT GGT GTG CCA       240
Pro Lys Leu Leu Ile Tyr Ser Thr Ser Asn Leu Ala Ser Gly Val Pro
        45                  50                  55

TCT AGA TTC AGC GGT AGC GGT AGC GGT ACA GAC TTC ACC TTC ACC ATC       288
Ser Arg Phe Ser Gly Ser Gly Ser Gly Thr Asp Phe Thr Phe Thr Ile
    60                  65                  70

AGC AGC CTC CAG CCA GAG GAC ATC GCT ACG TAC TAC TGC CAG CAA AGG       336
Ser Ser Leu Gln Pro Glu Asp Ile Ala Thr Tyr Tyr Cys Gln Gln Arg
75                  80                  85                  90

AGT AGT TAC CCG TAC ACG TTC GGC GGG GGG ACC AAG GTG GAA ATC AAA       384
Ser Ser Tyr Pro Tyr Thr Phe Gly Gly Gly Thr Lys Val Glu Ile Lys
                95                 100                 105

CGT ACG                                                                390
Arg Thr
```

(2) INFORMATION FOR SEQ ID NO:65:

(i) SEQUENCE CHARACTERISTICS:
                    (A) LENGTH: 25 base pairs
                    (B) TYPE: nucleic acid
                    (C) STRANDEDNESS: single
                    (D) TOPOLOGY: linear (ii) MOLECULE TYPE: other nucleic acid
                    (A) DESCRIPTION: /desc = "synthetic DNA"

(xi) SEQUENCE DESCRIPTION: SEQ ID NO:65:

GTGCTGTAGA TCCAAAGCTT TGGAG                                            25

(2) INFORMATION FOR SEQ ID NO:66:

(i) SEQUENCE CHARACTERISTICS:
                    (A) LENGTH: 25 base pairs
                    (B) TYPE: nucleic acid
                    (C) STRANDEDNESS: single
                    (D) TOPOLOGY: linear (ii) MOLECULE TYPE: other nucleic acid
                    (A) DESCRIPTION: /desc = "synthetic DNA"

(xi) SEQUENCE DESCRIPTION: SEQ ID NO:66:

(2) INFORMATION FOR SEQ ID NO:67:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(vi) ORIGINAL SOURCE:
        (A) ORGANISM: Homo sapiens and mouse (ix) FEATURE:
        (A) NAME/KEY: sig_peptide
        (B) LOCATION: -22..-1
        (C) IDENTIFICATION METHOD: by similarity with known sequence
            or to an established consensu (ix) FEATURE:
        (A) NAME/KEY: domain
        (B) LOCATION: 24..33
        (C) IDENTIFICATION METHOD: by similarity with known sequence
            or to an established consensu
        (D) OTHER INFORMATION: /product= "CDR1"

(ix) FEATURE:
        (A) NAME/KEY: domain
        (B) LOCATION: 49..55
        (C) IDENTIFICATION METHOD: by similarity with known sequence
            or to an established consensu
        (D) OTHER INFORMATION: /product= "CDR2"

(ix) FEATURE:
        (A) NAME/KEY: domain
        (B) LOCATION: 88..96
        (C) IDENTIFICATION METHOD: by similarity with known sequence
            or to an established consensu
        (D) OTHER INFORMATION: /product= "CDR3"

(xi) SEQUENCE DESCRIPTION: SEQ ID NO:67:

```
CTCCAAAGCT TTGGATCTAC AGCAC                                              25

ATG CAT TTT CAA GTG CAG ATT TTC AGC TTC CTG CTA ATC AGT GCC TCA          48
Met His Phe Gln Val Gln Ile Phe Ser Phe Leu Leu Ile Ser Ala Ser
-22         -20                 -15                 -10

GTC ATA ATG TCC AGA GGA GAT ATC CAG CTG ACC CAG AGC CCA AGC AGC          96
Val Ile Met Ser Arg Gly Asp Ile Gln Leu Thr Gln Ser Pro Ser Ser
    -5                   1                   5                   10

CTG AGC GCT AGC GTG GGT GAC AGA GTG ACC ATC ACG TGC AGT GCC AGC         144
Leu Ser Ala Ser Val Gly Asp Arg Val Thr Ile Thr Cys Ser Ala Ser
                15                  20                  25

TCA AGT GTA AGT TAC ATG CAC TGG TAT CAG CAG AAG CCA GGT AAG GCT         192
Ser Ser Val Ser Tyr Met His Trp Tyr Gln Gln Lys Pro Gly Lys Ala
            30                  35                  40

CCA AAG CTT TGG ATC TAC AGC ACA TCC AAC CTG GCT TCT GGT GTG CCA         240
Pro Lys Leu Trp Ile Tyr Ser Thr Ser Asn Leu Ala Ser Gly Val Pro
        45                  50                  55

TCT AGA TTC AGC GGT AGC GGT AGC GGT ACA GAC TTC ACC TTC ACC ATC         288
Ser Arg Phe Ser Gly Ser Gly Ser Gly Thr Asp Phe Thr Phe Thr Ile
    60                  65                  70

AGC AGC CTC CAG CCA GAG GAC ATC GCT ACG TAC TAC TGC CAG CAA AGG         336
Ser Ser Leu Gln Pro Glu Asp Ile Ala Thr Tyr Tyr Cys Gln Gln Arg
75                  80                  85                  90

AGT AGT TAC CCG TAC ACG TTC GGC GGG GGG ACC AAG GTG GAA ATC AAA         384
Ser Ser Tyr Pro Tyr Thr Phe Gly Gly Gly Thr Lys Val Glu Ile Lys
                95                  100                 105

CGT ACG                                                                 390
Arg Thr
```

(2) INFORMATION FOR SEQ ID NO:68:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:68:

ACGTAGCAGC ATCTTCAGCC TGGAG                                                  25

(2) INFORMATION FOR SEQ ID NO:69:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:69:

CTCCAGGCTG AAGATGCTGC TACGT                                                  25

(2) INFORMATION FOR SEQ ID NO:70:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(vi) ORIGINAL SOURCE:
        (A) ORGANISM: Homo sapiens and mouse (ix) FEATURE:
        (A) NAME/KEY: sig_peptide
        (B) LOCATION: -22..-1
        (C) IDENTIFICATION METHOD: by similarity with known sequence
            or to an established consensu (ix) FEATURE:
        (A) NAME/KEY: domain
        (B) LOCATION: 24..33
        (C) IDENTIFICATION METHOD: by similarity with known sequence
            or to an established consensu
        (D) OTHER INFORMATION: /product= "CDR1"

(ix) FEATURE:
        (A) NAME/KEY: domain
        (B) LOCATION: 49..55
        (C) IDENTIFICATION METHOD: by similarity with known sequence
            or to an established consensu
        (D) OTHER INFORMATION: /product= "CDR2"

(ix) FEATURE:
        (A) NAME/KEY: domain
        (B) LOCATION: 88..96
        (C) IDENTIFICATION METHOD: by similarity with known sequence
            or to an established consensu
        (D) OTHER INFORMATION: /product= "CDR3"

(xi) SEQUENCE DESCRIPTION: SEQ ID NO:70:

```
ATG CAT TTT CAA GTG CAG ATT TTC AGC TTC CTG CTA ATC AGT GCC TCA      48
Met His Phe Gln Val Gln Ile Phe Ser Phe Leu Leu Ile Ser Ala Ser
-22     -20                 -15                 -10
```

```
GTC ATA ATG TCC AGA GGA GAT ATC CAG CTG ACC CAG AGC CCA AGC AGC        96
Val Ile Met Ser Arg Gly Asp Ile Gln Leu Thr Gln Ser Pro Ser Ser
 -5               1               5                      10

CTG AGC GCT AGC GTG GGT GAC AGA GTG ACC ATC ACG TGC AGT GCC AGC       144
Leu Ser Ala Ser Val Gly Asp Arg Val Thr Ile Thr Cys Ser Ala Ser
             15                  20                  25

TCA AGT GTA AGT TAC ATG CAC TGG TAT CAG CAG AAG CCA GGT AAG GCT       192
Ser Ser Val Ser Tyr Met His Trp Tyr Gln Gln Lys Pro Gly Lys Ala
                 30              35                  40

CCA AAG CTT CTG ATC TAC AGC ACA TCC AAC CTG GCT TCT GGT GTG CCA       240
Pro Lys Leu Leu Ile Tyr Ser Thr Ser Asn Leu Ala Ser Gly Val Pro
             45                  50                  55

TCT AGA TTC AGC GGT AGC GGT AGC GGT ACA GAC TTC ACC TTC ACC ATC       288
Ser Arg Phe Ser Gly Ser Gly Ser Gly Thr Asp Phe Thr Phe Thr Ile
     60              65                  70

AGC AGC CTC CAG GCT GAA GAT GCT GCT ACG TAC TAC TGC CAG CAA AGG       336
Ser Ser Leu Gln Ala Glu Asp Ala Ala Thr Tyr Tyr Cys Gln Gln Arg
 75              80                  85                  90

AGT AGT TAC CCG TAC ACG TTC GGC GGG GGG ACC AAG GTG GAA ATC AAA       384
Ser Ser Tyr Pro Tyr Thr Phe Gly Gly Gly Thr Lys Val Glu Ile Lys
                 95                 100                 105

CGT ACG                                                                390
Arg Thr (2) INFORMATION FOR SEQ ID NO:71:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:71:

ATGGTGAAAG AGTAAGATGT ACCGC                                            25

(2) INFORMATION FOR SEQ ID NO:72:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:72:

GCGGTACATC TTACTCTTTC ACCAT                                            25

(2) INFORMATION FOR SEQ ID NO:73:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(vi) ORIGINAL SOURCE:
        (A) ORGANISM: Homo sapiens and mouse (ix) FEATURE:
```

(A) NAME/KEY: sig_peptide
        (B) LOCATION: -22..-1
        (C) IDENTIFICATION METHOD: by similarity with known sequence
            or to an established consensu (ix) FEATURE:
        (A) NAME/KEY: domain
        (B) LOCATION: 24..33
        (C) IDENTIFICATION METHOD: by similarity with known sequence
            or to an established consensu
        (D) OTHER INFORMATION: /product= "CDR1"

(ix) FEATURE:
        (A) NAME/KEY: domain
        (B) LOCATION: 49..55
        (C) IDENTIFICATION METHOD: by similarity with known sequence
            or to an established consensu
        (D) OTHER INFORMATION: /product= "CDR2"

(ix) FEATURE:
        (A) NAME/KEY: domain
        (B) LOCATION: 88..96
        (C) IDENTIFICATION METHOD: by similarity with known sequence
            or to an established consensu
        (D) OTHER INFORMATION: /product= "CDR3"

(xi) SEQUENCE DESCRIPTION: SEQ ID NO:73:

```
ATG CAT TTT CAA GTG CAG ATT TTC AGC TTC CTG CTA ATC AGT GCC TCA        48
Met His Phe Gln Val Gln Ile Phe Ser Phe Leu Leu Ile Ser Ala Ser
-22         -20             -15             -10

GTC ATA ATG TCC AGA GGA GAT ATC CAG CTG ACC CAG AGC CCA AGC AGC        96
Val Ile Met Ser Arg Gly Asp Ile Gln Leu Thr Gln Ser Pro Ser Ser
    -5              1               5                      10

CTG AGC GCT AGC CCA GGT GAC AGA GTG ACC ATC ACG TGC AGT GCC AGC       144
Leu Ser Ala Ser Pro Gly Asp Arg Val Thr Ile Thr Cys Ser Ala Ser
                15              20                  25

TCA AGT GTA AGT TAC ATG CAC TGG TAT CAG CAG AAG CCA GGT AAG GCT       192
Ser Ser Val Ser Tyr Met His Trp Tyr Gln Gln Lys Pro Gly Lys Ala
            30              35              40

CCA AAG CTT TGG ATC TAC AGC ACA TCC AAC CTG GCT TCT GGT GTG CCA       240
Pro Lys Leu Trp Ile Tyr Ser Thr Ser Asn Leu Ala Ser Gly Val Pro
        45              50              55

TCT AGA TTC AGC GGT AGC GGT AGC GGT ACA TCT TAC TCT TTC ACC ATC       288
Ser Arg Phe Ser Gly Ser Gly Ser Gly Thr Ser Tyr Ser Phe Thr Ile
    60              65              70

AGC AGC CTC CAG CCA GAG GAC ATC GCT ACG TAC TAC TGC CAG CAA AGG       336
Ser Ser Leu Gln Pro Glu Asp Ile Ala Thr Tyr Tyr Cys Gln Gln Arg
75              80              85                  90

AGT AGT TAC CCG TAC ACG TTC GGC GGG GGG ACC AAG GTG GAA ATC AAA       384
Ser Ser Tyr Pro Tyr Thr Phe Gly Gly Gly Thr Lys Val Glu Ile Lys
                95              100             105

CGT ACG                                                                390
Arg Thr
```

(2) INFORMATION FOR SEQ ID NO:74:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:74:

TCTGGCTCCA TTCGGCTGAT GGTGAAAGAG TAAGATGTAC        40

5,939,532

137

138

-continued (2) INFORMATION FOR SEQ ID NO:75:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
       (A) DESCRIPTION: /desc = "synthetic DNA"

(xi) SEQUENCE DESCRIPTION: SEQ ID NO:75:

```
GTACATCTTA CTCTTTCACC ATCAGCCGAA TGGAGCCAGA                              40
```

(2) INFORMATION FOR SEQ ID NO:76:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (ii) MOLECULE TYPE: other nucleic acid
       (A) DESCRIPTION: /desc = "synthetic DNA"

(vi) ORIGINAL SOURCE:
       (A) ORGANISM: Homo sapiens and mouse (ix) FEATURE:
       (A) NAME/KEY: sig_peptide
       (B) LOCATION: -22..-1
       (C) IDENTIFICATION METHOD: by similarity with known sequence
          or to an established consensu (ix) FEATURE:
       (A) NAME/KEY: domain
       (B) LOCATION: 24..33
       (C) IDENTIFICATION METHOD: by similarity with known sequence
          or to an established consensu
       (D) OTHER INFORMATION: /product= "CDR1"

(ix) FEATURE:
       (A) NAME/KEY: domain
       (B) LOCATION: 49..55
       (C) IDENTIFICATION METHOD: by similarity with known sequence
          or to an established consensu
       (D) OTHER INFORMATION: /product= "CDR2"

(ix) FEATURE:
       (A) NAME/KEY: domain
       (B) LOCATION: 88..96
       (C) IDENTIFICATION METHOD: by similarity with known sequence
          or to an established consensu
       (D) OTHER INFORMATION: /product= "CDR3"

(xi) SEQUENCE DESCRIPTION: SEQ ID NO:76:

```
ATG CAT TTT CAA GTG CAG ATT TTC AGC TTC CTG CTA ATC AGT GCC TCA         48
Met His Phe Gln Val Gln Ile Phe Ser Phe Leu Leu Ile Ser Ala Ser
-22     -20             -15                 -10

GTC ATA ATG TCC AGA GGA GAT ATC CAG CTG ACC CAG AGC CCA AGC AGC         96
Val Ile Met Ser Arg Gly Asp Ile Gln Leu Thr Gln Ser Pro Ser Ser
    -5                   1               5                  10

CTG AGC GCT AGC CCA GGT GAC AGA GTG ACC ATC ACG TGC AGT GCC AGC        144
Leu Ser Ala Ser Pro Gly Asp Arg Val Thr Ile Thr Cys Ser Ala Ser
                    15                  20                  25

TCA AGT GTA AGT TAC ATG CAC TGG TAT CAG CAG AAG CCA GGT AAG GCT        192
Ser Ser Val Ser Tyr Met His Trp Tyr Gln Gln Lys Pro Gly Lys Ala
                30                  35                  40

CCA AAG CTT TGG ATC TAC AGC ACA TCC AAC CTG GCT TCT GGT GTG CCA        240
Pro Lys Leu Trp Ile Tyr Ser Thr Ser Asn Leu Ala Ser Gly Val Pro
                45                  50                  55

TCT AGA TTC AGC GGT AGC GGT AGC GGT ACA TCT TAC TCT TTC ACC ATC        288
```

```
Ser Arg Phe Ser Gly Ser Gly Ser Gly Thr Ser Tyr Ser Phe Thr Ile
    60              65                  70

AGC CGA ATG GAG CCA GAG GAC ATC GCT ACG TAC TAC TGC CAG CAA AGG         336
Ser Arg Met Glu Pro Glu Asp Ile Ala Thr Tyr Tyr Cys Gln Gln Arg
75              80                  85                  90

AGT AGT TAC CCG TAC ACG TTC GGC GGG GGG ACC AAG GTG GAA ATC AAA         384
Ser Ser Tyr Pro Tyr Thr Phe Gly Gly Gly Thr Lys Val Glu Ile Lys
                95                  100                 105

CGT ACG                                                                 390
Arg Thr
```

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:77:

```
TTCTGCTGGA ACCAGTGCAT                                                    20
```

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:78:

```
ATGCACTGGT TCCAGCAGAA                                                    20
```

(2) INFORMATION FOR SEQ ID NO:79:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(vi) ORIGINAL SOURCE:
        (A) ORGANISM: Homo sapiens and mouse (ix) FEATURE:
        (A) NAME/KEY: sig_peptide
        (B) LOCATION: -22..-1
        (C) IDENTIFICATION METHOD: by similarity with known sequence
            or to an established consensu (ix) FEATURE:
        (A) NAME/KEY: domain
        (B) LOCATION: 24..33
        (C) IDENTIFICATION METHOD: by similarity with known sequence
            or to an established consensu
        (D) OTHER INFORMATION: /product= "CDR1"

(ix) FEATURE:
        (A) NAME/KEY: domain
        (B) LOCATION: 49..55
        (C) IDENTIFICATION METHOD: by similarity with known sequence
            or to an established consensu
        (D) OTHER INFORMATION: /product= "CDR2"

(ix) FEATURE:
   (A) NAME/KEY: domain
   (B) LOCATION: 88..96
   (C) IDENTIFICATION METHOD: by similarity with known sequence
      or to an established consensu
   (D) OTHER INFORMATION: /product= "CDR3"

(xi) SEQUENCE DESCRIPTION: SEQ ID NO:79:

| ATG | CAT | TTT | CAA | GTG | CAG | ATT | TTC | AGC | TTC | CTG | CTA | ATC | AGT | GCC | TCA | 48 |
| Met | His | Phe | Gln | Val | Gln | Ile | Phe | Ser | Phe | Leu | Leu | Ile | Ser | Ala | Ser | |
| -22 | | -20 | | | | -15 | | | | | -10 | | | | | |

| GTC | ATA | ATG | TCC | AGA | GGA | GAT | ATC | CAG | CTG | ACC | CAG | AGC | CCA | AGC | AGC | 96 |
| Val | Ile | Met | Ser | Arg | Gly | Asp | Ile | Gln | Leu | Thr | Gln | Ser | Pro | Ser | Ser | |
| | -5 | | | | | 1 | | | | 5 | | | | | 10 | |

| CTG | AGC | GCT | AGC | CCA | GGT | GAC | AGA | GTG | ACC | ATC | ACG | TGC | AGT | GCC | AGC | 144 |
| Leu | Ser | Ala | Ser | Pro | Gly | Asp | Arg | Val | Thr | Ile | Thr | Cys | Ser | Ala | Ser | |
| | | | | 15 | | | | | 20 | | | | | 25 | | |

| TCA | AGT | GTA | AGT | TAC | ATG | CAC | TGG | TTC | CAG | CAG | AAG | CCA | GGT | AAG | GCT | 192 |
| Ser | Ser | Val | Ser | Tyr | Met | His | Trp | Phe | Gln | Gln | Lys | Pro | Gly | Lys | Ala | |
| | | | 30 | | | | | 35 | | | | | 40 | | | |

| CCA | AAG | CTT | TGG | ATC | TAC | AGC | ACA | TCC | AAC | CTG | GCT | TCT | GGT | GTG | CCA | 240 |
| Pro | Lys | Leu | Trp | Ile | Tyr | Ser | Thr | Ser | Asn | Leu | Ala | Ser | Gly | Val | Pro | |
| | | | 45 | | | | 50 | | | | | 55 | | | | |

| TCT | AGA | TTC | AGC | GGT | AGC | GGT | AGC | GGT | ACA | TCT | TAC | TCT | TTC | ACC | ATC | 288 |
| Ser | Arg | Phe | Ser | Gly | Ser | Gly | Ser | Gly | Thr | Ser | Tyr | Ser | Phe | Thr | Ile | |
| | 60 | | | | | 65 | | | | | 70 | | | | | |

| AGC | AGC | CTC | CAG | CCA | GAG | GAC | ATC | GCT | ACG | TAC | TAC | TGC | CAG | CAA | AGG | 336 |
| Ser | Ser | Leu | Gln | Pro | Glu | Asp | Ile | Ala | Thr | Tyr | Tyr | Cys | Gln | Gln | Arg | |
| 75 | | | | | 80 | | | | | 85 | | | | | 90 | |

| AGT | AGT | TAC | CCG | TAC | ACG | TTC | GGC | GGG | GGG | ACC | AAG | GTG | GAA | ATC | AAA | 384 |
| Ser | Ser | Tyr | Pro | Tyr | Thr | Phe | Gly | Gly | Gly | Thr | Lys | Val | Glu | Ile | Lys | |
| | | | 95 | | | | | 100 | | | | | 105 | | | |

| CGT | ACG | 390 |
| Arg | Thr | |

(2) INFORMATION FOR SEQ ID NO:80:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:80:

TGGAGTCGGC TGATGGTGAG AGAGT                               25

(2) INFORMATION FOR SEQ ID NO:81:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:81:

ACTCTCTCAC CATCAGCCGA CTCCA                               25

(2) INFORMATION FOR SEQ ID NO:82:

```
        (i) SEQUENCE CHARACTERISTICS:
            (A) LENGTH: 390 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "synthetic DNA"

(vi) ORIGINAL SOURCE:
            (A) ORGANISM: Homo sapiens and mouse (ix) FEATURE:
            (A) NAME/KEY: sig_peptide
            (B) LOCATION: -22..-1
            (C) IDENTIFICATION METHOD: by similarity with known sequence
                or to an established consensu (ix) FEATURE:
            (A) NAME/KEY: domain
            (B) LOCATION: 24..33
            (C) IDENTIFICATION METHOD: by similarity with known sequence
                or to an established consensu
            (D) OTHER INFORMATION: /product= "CDR1"

(ix) FEATURE:
            (A) NAME/KEY: domain
            (B) LOCATION: 49..55
            (C) IDENTIFICATION METHOD: by similarity with known sequence
                or to an established consensu
            (D) OTHER INFORMATION: /product= "CDR2"

(ix) FEATURE:
            (A) NAME/KEY: domain
            (B) LOCATION: 88..96
            (C) IDENTIFICATION METHOD: by similarity with known sequence
                or to an established consensu
            (D) OTHER INFORMATION: /product= "CDR3"

(xi) SEQUENCE DESCRIPTION: SEQ ID NO:82:

ATG CAT TTT CAA GTG CAG ATT TTC AGC TTC CTG CTA ATC AGT GCC TCA          48
Met His Phe Gln Val Gln Ile Phe Ser Phe Leu Leu Ile Ser Ala Ser
-22     -20                 -15                 -10

GTC ATA ATG TCC AGA GGA GAT ATC CAG CTG ACC CAG AGC CCA AGC AGC          96
Val Ile Met Ser Arg Gly Asp Ile Gln Leu Thr Gln Ser Pro Ser Ser
    -5                  1                   5                  10

CTG AGC GCT AGC CCA GGT GAC AGA GTG ACC ATC ACG TGC AGT GCC AGC         144
Leu Ser Ala Ser Pro Gly Asp Arg Val Thr Ile Thr Cys Ser Ala Ser
                    15                  20                  25

TCA AGT GTA AGT TAC ATG CAC TGG TAT CAG CAG AAG CCA GGT AAG GCT         192
Ser Ser Val Ser Tyr Met His Trp Tyr Gln Gln Lys Pro Gly Lys Ala
                30                  35                  40

CCA AAG CTT TGG ATC TAC AGC ACA TCC AAC CTG GCT TCT GGT GTG CCA         240
Pro Lys Leu Trp Ile Tyr Ser Thr Ser Asn Leu Ala Ser Gly Val Pro
            45                  50                  55

TCT AGA TTC AGC GGT AGC GGT AGC GGT ACA TCT TAC TCT CTC ACC ATC         288
Ser Arg Phe Ser Gly Ser Gly Ser Gly Thr Ser Tyr Ser Leu Thr Ile
        60                  65                  70

AGC CGA CTC CAG CCA GAG GAC ATC GCT ACG TAC TAC TGC CAG CAA AGG         336
Ser Arg Leu Gln Pro Glu Asp Ile Ala Thr Tyr Tyr Cys Gln Gln Arg
75                  80                  85                  90

AGT AGT TAC CCG TAC ACG TTC GGC GGG GGG ACC AAG GTG GAA ATC AAA         384
Ser Ser Tyr Pro Tyr Thr Phe Gly Gly Gly Thr Lys Val Glu Ile Lys
                95                  100                 105

CGT ACG                                                                 390
Arg Thr (2) INFORMATION FOR SEQ ID NO:83:

(i) SEQUENCE CHARACTERISTICS:
```

(A) LENGTH: 390 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "synthetic DNA"

(vi) ORIGINAL SOURCE:
            (A) ORGANISM: Homo sapiens and mouse (ix) FEATURE:
            (A) NAME/KEY: sig_peptide
            (B) LOCATION: -22..-1
            (C) IDENTIFICATION METHOD: by similarity with known sequence
                or to an established consensu (ix) FEATURE:
            (A) NAME/KEY: domain
            (B) LOCATION: 24..33
            (C) IDENTIFICATION METHOD: by similarity with known sequence
                or to an established consensu
            (D) OTHER INFORMATION: /product= "CDR1"

(ix) FEATURE:
            (A) NAME/KEY: domain
            (B) LOCATION: 49..55
            (C) IDENTIFICATION METHOD: by similarity with known sequence
                or to an established consensu
            (D) OTHER INFORMATION: /product= "CDR2"

(ix) FEATURE:
            (A) NAME/KEY: domain
            (B) LOCATION: 88..96
            (C) IDENTIFICATION METHOD: by similarity with known sequence
                or to an established consensu
            (D) OTHER INFORMATION: /product= "CDR3"

(xi) SEQUENCE DESCRIPTION: SEQ ID NO:83:

```
ATG CAT TTT CAA GTG CAG ATT TTC AGC TTC CTG CTA ATC AGT GCC TCA         48
Met His Phe Gln Val Gln Ile Phe Ser Phe Leu Leu Ile Ser Ala Ser
-22         -20                 -15                 -10

GTC ATA ATG TCC AGA GGA GAT ATC CAG CTG ACC CAG AGC CCA AGC AGC         96
Val Ile Met Ser Arg Gly Asp Ile Gln Leu Thr Gln Ser Pro Ser Ser
        -5                   1                   5                  10

CTG AGC GCT AGC CCA GGT GAC AGA GTG ACC ATC ACG TGC AGT GCC AGC        144
Leu Ser Ala Ser Pro Gly Asp Arg Val Thr Ile Thr Cys Ser Ala Ser
                15                  20                  25

TCA AGT GTA AGT TAC ATG CAC TGG TTC CAG CAG AAG CCA GGT AAG GCT        192
Ser Ser Val Ser Tyr Met His Trp Phe Gln Gln Lys Pro Gly Lys Ala
        30                  35                  40

CCA AAG CTT TGG ATC TAC AGC ACA TCC AAC CTG GCT TCT GGT GTG CCA        240
Pro Lys Leu Trp Ile Tyr Ser Thr Ser Asn Leu Ala Ser Gly Val Pro
                45                  50                  55

TCT AGA TTC AGC GGT AGC GGT AGC GGT ACA TCT TAC TCT CTC ACC ATC        288
Ser Arg Phe Ser Gly Ser Gly Ser Gly Thr Ser Tyr Ser Leu Thr Ile
        60                  65                  70

AGC CGA CTC CAG CCA GAG GAC ATC GCT ACG TAC TAC TGC CAG CAA AGG        336
Ser Arg Leu Gln Pro Glu Asp Ile Ala Thr Tyr Tyr Cys Gln Gln Arg
75                  80                  85                  90

AGT AGT TAC CCG TAC ACG TTC GGC GGG GGG ACC AAG GTG GAA ATC AAA        384
Ser Ser Tyr Pro Tyr Thr Phe Gly Gly Gly Thr Lys Val Glu Ile Lys
                95                 100                 105

CGT ACG                                                                390
Arg Thr
```

(2) INFORMATION FOR SEQ ID NO:84:

(i) SEQUENCE CHARACTERISTICS:
            (A) LENGTH: 94 base pairs (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:84:

CAGGAAACAG CTATGACGAA TTCCACCATG CATTTTCAAG TGCAGATTTT CAGCTTCCTG      60

CTAATCAGTG CCTCAGTCAT AATGTCCAGA GGAG                                  94

(2) INFORMATION FOR SEQ ID NO:85:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:85:

ACAAGTGATG GTGACTCTGT CTCCTGGAGA TGCAGACATG GAGGATGGAG ACTGGGTCAG      60

CTGGATGTCT CCTCTGGACA TTATGACT                                        88

(2) INFORMATION FOR SEQ ID NO:86:

(i) SEQUENCE CHARACTERISTICS:
            (A) LENGTH: 92 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:86:

ACAGAGTCAC CATCACTTGT AGTGCAAGTT CAAGTGTAAG TTACATGCAC TGGTTTCAGC      60

AGAAACCAGG GAAATCACCT AAGCTCTGGA TC                                   92

(2) INFORMATION FOR SEQ ID NO:87:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:87:

AAGATGTACC GCTACCGCTA CCGCTGAATC TAGATGGCAC ACCAGAAGCT AAATTTGAAG      60

TTGAGTAGAT CCAGAGCTTA GGTGATT                                         87

(2) INFORMATION FOR SEQ ID NO:88:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:88:

```
TAGCGGTAGC GGTACATCTT ACTCTCTCAC CATCAGCAGC ATGCAGCCTG AAGATTTTGC    60

AACTTATTAC TGTCAGCAAA GGAGTAGTT                                     89
```

(2) INFORMATION FOR SEQ ID NO:89:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:89:

```
GTTTTCCCAG TCACGACCGT ACGTTTGATT TCCAGCTTGG TCCCCTGGCC GAACGTGTAC    60

GGGTAACTAC TCCTTTGCTG ACAG                                          84
```

(2) INFORMATION FOR SEQ ID NO:90:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(vi) ORIGINAL SOURCE:
        (A) ORGANISM: Homo sapiens and mouse (ix) FEATURE:
        (A) NAME/KEY: sig_peptide
        (B) LOCATION: -22..-1
        (C) IDENTIFICATION METHOD: by similarity with known sequence
            or to an established consensu (ix) FEATURE:
        (A) NAME/KEY: domain
        (B) LOCATION: 24..33
        (C) IDENTIFICATION METHOD: by similarity with known sequence
            or to an established consensu
        (D) OTHER INFORMATION: /product= "CDR1"

(ix) FEATURE:
        (A) NAME/KEY: domain
        (B) LOCATION: 49..55
        (C) IDENTIFICATION METHOD: by similarity with known sequence
            or to an established consensu
        (D) OTHER INFORMATION: /product= "CDR2"

(ix) FEATURE:
        (A) NAME/KEY: domain
        (B) LOCATION: 88..96
        (C) IDENTIFICATION METHOD: by similarity with known sequence
            or to an established consensu
        (D) OTHER INFORMATION: /product= "CDR3"

(xi) SEQUENCE DESCRIPTION: SEQ ID NO:90:

```
ATG CAT TTT CAA GTG CAG ATT TTC AGC TTC CTG CTA ATC AGT GCC TCA     48
Met His Phe Gln Val Gln Ile Phe Ser Phe Leu Leu Ile Ser Ala Ser
-22     -20             -15             -10

GTC ATA ATG TCC AGA GGA GAC ATC CAG CTG ACC CAG TCT CCA TCC TCC     96
Val Ile Met Ser Arg Gly Asp Ile Gln Leu Thr Gln Ser Pro Ser Ser
    -5                   1               5                  10

ATG TCT GCA TCT CCA GGA GAC AGA GTC ACC ATC ACT TGT AGT GCA AGT    144
Met Ser Ala Ser Pro Gly Asp Arg Val Thr Ile Thr Cys Ser Ala Ser
                15                  20                  25

TCA AGT GTA AGT TAC ATG CAC TGG TTT CAG CAG AAA CCA GGG AAA TCA    192
```

```
Ser Ser Val Ser Tyr Met His Trp Phe Gln Gln Lys Pro Gly Lys Ser
         30              35                  40

CCT AAG CTC TGG ATC TAC TCA ACT TCA AAT TTA GCT TCT GGT GTG CCA         240
Pro Lys Leu Trp Ile Tyr Ser Thr Ser Asn Leu Ala Ser Gly Val Pro
         45              50                  55

TCT AGA TTC AGC GGT AGC GGT AGC GGT ACA TCT TAC TCT CTC ACC ATC         288
Ser Arg Phe Ser Gly Ser Gly Ser Gly Thr Ser Tyr Ser Leu Thr Ile
         60              65                  70

AGC AGC ATG CAG CCT GAA GAT TTT GCA ACT TAT TAC TGT CAG CAA AGG         336
Ser Ser Met Gln Pro Glu Asp Phe Ala Thr Tyr Tyr Cys Gln Gln Arg
75              80                  85                  90

AGT AGT TAC CCG TAC ACG TTC GGC CAG GGG ACC AAG CTG GAA ATC AAA         384
Ser Ser Tyr Pro Tyr Thr Phe Gly Gln Gly Thr Lys Leu Glu Ile Lys
             95                 100                 105

CGT ACG                                                                 390
Arg Thr
```

(2) INFORMATION FOR SEQ ID NO:91:

(i) SEQUENCE CHARACTERISTICS:
        (A) LENGTH: 139 amino acids
        (B) TYPE: amino acid
        (D) TOPOLOGY: linear (ii) MOLECULE TYPE: protein (ix) FEATURE:
        (A) NAME/KEY: sig_peptide
        (B) LOCATION: -19..-1
        (C) IDENTIFICATION METHOD:
            BY SIMILARITY WITH KNOWN SEQUENCE OR TO AN
            ESTABLISHED CONSENSUS (ix) FEATURE:
        (A) NAME/KEY: domain
        (B) LOCATION: 31..35
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 1"

(ix) FEATURE:
        (A) NAME/KEY: domain
        (B) LOCATION: 50..66
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 2"

(ix) FEATURE:
        (A) NAME/KEY: domain
        (B) LOCATION: 99..109
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 3"

(xi) SEQUENCE DESCRIPTION: SEQ ID NO:91:

```
                              Met Gly Trp Ser Trp Ile Phe
                                              -15

Leu Phe Leu Leu Ser Gly Thr Ala Gly Val Leu Ser Glu Val Gln Leu
        -10                 -5                   1

Gln Gln Ser Gly Pro Glu Leu Val Lys Pro Gly Ala Ser Val Lys Ile
 5               10                  15                  20

Ser Cys Lys Ala Ser Gly Tyr Thr Phe Thr Asp Tyr Asn Met Asp Trp
             25                  30                  35

Val Lys Gln Ser His Gly Lys Ser Leu Glu Trp Ile Gly Tyr Ile Tyr
         40                  45                  50
```

```
Pro Asn Asn Gly Gly Thr Gly Tyr Asn Gln Lys Phe Lys Ser Lys Ala
        55                  60                  65

Thr Leu Thr Val Asp Lys Ser Ser Thr Ala Tyr Met Glu Leu His
        70                  75                  80

Ser Leu Thr Ser Glu Asp Ser Ala Val Tyr Tyr Cys Ala Thr Tyr Gly
85                  90                  95                  100

His Tyr Tyr Gly Tyr Met Phe Ala Tyr Trp Gly Gln Gly Thr Leu Val
                105                 110                 115

Thr Val Ser Ala
        120

(2) INFORMATION FOR SEQ ID NO:92:

(i) SEQUENCE CHARACTERISTICS:
        (A) LENGTH: 129 amino acids
        (B) TYPE: amino acid
        (D) TOPOLOGY: linear (ii) MOLECULE TYPE: protein (ix) FEATURE:
        (A) NAME/KEY: sig_peptide
        (B) LOCATION: -22..-1
        (C) IDENTIFICATION METHOD:
            BY SIMILARITY WITH KNOWN SEQUENCE TO TO AN
            ESTABLISHED CONSENSUS (ix) FEATURE:
        (A) NAME/KEY: domain
        (B) LOCATION: 24..33
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 1"

(ix) FEATURE:
        (A) NAME/KEY: domain
        (B) LOCATION: 49..55
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 2"

(ix) FEATURE:
        (A) NAME/KEY: domain
        (B) LOCATION: 88..96
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 3"

(xi) SEQUENCE DESCRIPTION: SEQ ID NO:92:

Met His Phe Gln Val Gln Ile Phe Ser Phe Leu Leu Ile Ser
                -20                 -15                 -10

Ala Ser Val Ile Met Ser Arg Gly Gln Ile Val Leu Thr Gln Ser Pro
        -5                  1                   5

Ala Ile Met Ser Ala Ser Pro Gly Glu Lys Val Thr Ile Thr Cys Ser
        10                  15                  20

Ala Ser Ser Ser Val Ser Tyr Met His Trp Phe Gln Gln Lys Pro Gly
25                  30                  35                  40

Thr Ser Pro Lys Leu Trp Ile Tyr Ser Thr Ser Asn Leu Ala Ser Gly
                45                  50                  55

Val Pro Ala Arg Phe Ser Gly Ser Gly Ser Gly Thr Ser Tyr Ser Leu
                60                  65                  70

Thr Ile Ser Arg Met Glu Ala Glu Asp Ala Ala Thr Tyr Tyr Cys Gln
            75                  80                  85

Gln Arg Ser Ser Tyr Pro Tyr Thr Phe Gly Gly Gly Thr Lys Leu Glu
```

```
                    90              95             100
Ile Lys Arg
105
```

(2) INFORMATION FOR SEQ ID NO:93:

(i) SEQUENCE CHARACTERISTICS:
        (A) LENGTH: 137 amino acids
        (B) TYPE: amino acids
        (D) TOPOLOGY: linear (ii) MOLECULE TYPE: protein (ix) FEATURE:
        (A) NAME/KEY: sig_peptide
        (B) LOCATION: -19..-1
        (C) IDENTIFICATION METHOD:
            BY SIMILARITY WITH KNOWN SEQUENCE OR TO AN
            ESTABLISHED CONSENSUS (ix) FEATURE:
        (A) NAME/KEY: domain
        (B) LOCATION: 31..35
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 1"

(ix) FEATURE:
        (A) NAME/KEY: domain
        (B) LOCATION: 55..66
        (C) IDENTIFICATION METHOD: BY SIMILARITY
            WITH KNOWN SEQUENCE OR TO AN ESTABLISHED
            CONSENSUS
        (D) OTHER INFORMATION: /product= "HYPERVARIABLE REGION 2"

(ix) FEATURE:
        (A) NAME/KEY: domain
        (B) LOCATION: 99..107
        (C) IDENTIFICATION METHOD: BY SIMILARITY
            WITH KNOWN SEQUENCE OR TO AN ESTABLISEHD
            CONSENSUS
        (D) OTHER INFORMATION: /product= "HYPERVARIABLE REGION 3"

(xi) SEQUENCE DESCRIPTION: SEQ ID NO:93:

```
                                    Met Gly Trp Ser Trp Ile Phe
                                                        -15
Leu Phe Leu Leu Ser Gly Thr Ala Gly Val Leu Ser Glu Val Gln Leu
        -10                  -5                   1
Gln Gln Ser Gly Pro Glu Leu Val Lys Pro Gly Ala Ser Val Lys Ile
 5               10              15                       20
Ser Cys Lys Ala Ser Gly Tyr Thr Phe Thr Asp Tyr Asn Met Asp Trp
                 25              30                  35
Val Lys Gln Ser His Gly Lys Ser Leu Glu Trp Ile Gly Tyr Ile Tyr
             40              45                  50
Pro Asn Asn Gly Gly Thr Gly Tyr Asn Gln Lys Phe Lys Ser Lys Ala
             55              60              65
Thr Leu Thr Val Asp Lys Ser Ser Thr Ala Tyr Met Glu Leu His
     70              75              80
Ser Leu Thr Ser Glu Asp Ser Ala Val Tyr Tyr Cys Ala Arg Ala Gly
 85              90              95                      100
Arg Tyr Tyr Tyr Ala Trp Asp Trp Gly Gln Gly Thr Leu Val Thr Val
             105             110             115
Ser Ala
```

(2) INFORMATION FOR SEQ ID NO:94:

```
        (i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:94:

Asp Tyr Asn Met Asp
 1               5

(2) INFORMATION FOR SEQ ID NO:95:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (xi) SEQUENCE DESCRIPTION: SEQ ID NO:95:

Tyr Ile Tyr Pro Asn Asn Gly Gly Thr Gly Tyr Asn Gln Lys Phe Lys
 1               5                  10                  15
Ser (2) INFORMATION FOR SEQ ID NO:96:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (xi) SEQUENCE DESCRIPTION: SEQ ID NO:96:

Tyr Gly His Tyr Tyr Gly Tyr Met Phe Ala Tyr
 1               5                  10

(2) INFORMATION FOR SEQ ID NO:97:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:97:

Ser Ala Ser Ser Ser Val Ser Tyr Met His
 1               5                  10

(2) INFORMATION FOR SEQ ID NO:98:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:98:

Ser Thr Ser Asn Leu Ala Ser
 1               5

(2) INFORMATION FOR SEQ ID NO:99:

(i) SEQUENCE CHARACTERISTICS:
            (A) LENGTH: 9 amino acids
            (B) TYPE: amino acids
```

(D) TOPOLOGY: linear (ii) MOLECULE TYPE: peptide (xi) SEQUENCE DESCRIPTION: SEQ ID NO:99:

Gln Gln Arg Ser Ser Tyr Pro Tyr Thr
 1               5

(2) INFORMATION FOR SEQ ID NO:100:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:100:

Met Gly Trp Ser Trp Ile Phe Leu Phe Leu Leu Ser Gly
        -19             -15                 -10

Thr Ala Gly Val Leu Ser Gln Val Gln Leu Gln Glu Ser Gly Pro Gly
 -5                   1               5                   10

Leu Val Arg Pro Ser Gln Thr Leu Ser Leu Thr Cys Thr Val Ser Gly
             15                  20                  25

Phe Thr Phe Ser Asp Tyr Asn Met Asp Trp Val Arg Gln Pro Pro Gly
             30                  35                  40

Arg Gly Leu Glu Trp Ile Gly Tyr Ile Tyr Pro Asn Asn Gly Gly Thr
             45                  50                  55

Gly Tyr Asn Gln Lys Phe Lys Ser Arg Val Thr Met Leu Val Asp Thr
             60                  65                  70

Ser Lys Asn Gln Phe Ser Leu Arg Leu Ser Ser Val Thr Ala Ala Asp
 75                  80                  85                  90

Thr Ala Val Tyr Tyr Cys Ala Arg Tyr Gly His Tyr Tyr Gly Tyr Met
                 95                 100                 105

Phe Ala Tyr Trp Gly Gln Gly Thr Thr Val Thr Val Ser Ser Ala Ser
            110                 115                 120

Thr Lys Gly
        125

(2) INFORMATION FOR SEQ ID NO:101:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:101:

Met His Phe Gln Val Gln Ile Phe Ser Phe Leu Leu Ile Ser
        -22     -20                 -15                 -10

Ala Ser Val Ile Met Ser Arg Gly Asp Ile Gln Leu Thr Gln Ser Pro
                 -5              1               5

Ser Ser Leu Ser Ala Ser Val Gly Asp Arg Val Thr Ile Thr Cys Ser
         10              15                  20

Ala Ser Ser Ser Val Ser Tyr Met His Trp Tyr Gln Gln Lys Pro Gly
 25                  30                  35                  40

Lys Ala Pro Lys Leu Leu Ile Tyr Ser Thr Ser Asn Leu Ala Ser Gly
             45                  50                  55

Val Pro Ser Arg Phe Ser Gly Ser Gly Ser Gly Thr Asp Phe Thr Phe
             60                  65                  70

```
Thr Ile Ser Ser Leu Gln Pro Glu Asp Ile Ala Thr Tyr Tyr Cys Gln
        75              80              85

Gln Arg Ser Ser Tyr Pro Tyr Thr Phe Gly Gly Gly Thr Lys Val Glu
        90              95              100

Ile Lys Arg Thr Val Ala Ala
105             110
```

(2) INFORMATION FOR SEQ ID NO:102:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:102:

AAACGAACTG TGGCTGCACC ATCTGTC                           27

(2) INFORMATION FOR SEQ ID NO:103:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:103:

AAACGAACTG TGGCTGCACC ATCTGTC                           27

HUMANIZED ANTIBODIES TO GANGLIOSIDE GM$_2$

This is a continuation-in-part of application Ser. No. 08/116,778, filed Sep. 7, 1993, now U.S. Pat. No. 5,830,470, the contents of which are incorporated herein by reference.

FIELD OF THE INVENTION

The present invention relates to humanized antibodies reacting with the ganglioside GM$_2$. The humanized antibodies do not cause production of anti-mouse immunoglobulins in the patient's body as compared with mouse monoclonal antibodies, hence the incidence of adverse effects possibly caused by them is much lower, their blood half-lives are longer and, further, their anti-tumor effector effect is greater. Therefore, the humanized antibodies are expected to produce improved therapeutic effects as compared with mouse monoclonal antibodies.

BACKGROUND OF THE INVENTION

When administered to humans, mouse antibodies are generally recognized as foreign matters, inducing production of anti-mouse immunoglobulin antibodies in the human body. It is known that the former antibodies react with the latter antibodies to produce adverse effects [J. Clin. Oncol., 2, 881 (1984); Blood, 65, 1349 (1985); J. Natl. Cancer Inst., 80, 932 (1988); Proc. Natl. Acad. Sci. U.S.A., 82, 1242 (1985)] and that the mouse antibodies undergo rapid clearance [J. Nucl. Med., 26, 1011 (1985); Blood, 65, 1349 (1985); J. Natl. Cancer Inst., 80, 937 (1988)], thus showing only a reduced efficacy [J. Immunol., 135, 1530 (1985); Cancer Res., 46, 6489 (1986)]. Attempts have been made to solve these problems by deriving, from mouse monoclonal antibodies, chimeric human antibodies or CDR (complementarity determining region)-transplanted antibodies (reshaped antibodies) using gene engineering technique. In a human chimeric antibody, the variable regions thereof are of mouse origin and the constant regions thereof are of human origin [Proc. Natl. Acad. Sci. U.S.A., 81, 6851 (1984)] and it is reported that when administered to humans, said antibody causes litte human anti-mouse immunoglobulin antibody production, its blood half-life being 6-fold longer [Proc. Natl. Acad. Sci. U.S.A., 86, 4220 (1989)]. The CDR-transplanted antibodies are antibodies resulting from replacement of the CDRs in a human antibody alone with the CDRs from an animal other than the human [Nature, 321, 522 (1986)] and, in an experiment with monkeys, such antibodies showed reduced immunogenicity and 4- to 5-fold higher serum half-lives as compared with mouse antibodies [J. Immunol., 147, 1352 (1991)].

As regards the cytocidal activity of antibodies, it is reported that the Fc region of a human antibody is more potent in activating human complement and human effector cells than the Fc region of a mouse antibody. Thus, for instance, a chimeric antibody derived from a mouse monoclonal antibody to the ganglioside GD$_2$ and containing a human antibody Fc region enhances the human effector cell-mediated antitumor effect [J. Immunol., 144, 1382 (1990)]. Similar results are reported for CDR-transplanted antibodies [Nature, 332, 323 (1988)]. Such results indicate that, for clinical use, humanized monoclonal antibodies are preferred to mouse monoclonal antibodies.

The antibody classes include IgA, IgM, IgG, IgD and IgE and, in mice, the class IgG includes four subclasses, namely IgG$_1$, IgG$_2$a, IgG$_2$b and IgG$_3$ (in humans, IgG$_1$, IgG$_2$, IgG$_3$ and IgG$_4$). When antigens are administered to animals, the antibodies produced mostly belong to the classes IgM or IgG. IgG molecules have a molecular weight of about 160,000 daltons and a dimeric structure and are relatively easy to handle. IgM molecules are large with a molecular weight of about 900,000 daltons and occur in the form of a complicated pentameric structure coupled with the joining (J) chain, hence they have the following drawbacks: they are difficult to purify; they tend to agglutinate, hence are difficult to store; they are readily inactivated by partial decomposition in the presence of a protease, hence it is difficult to prepare Fab fragments; and they lose their binding activity in many instances upon chemical modification, for example chemical binding of an anticancer agent or a toxin [J. W. Goding: Monoclonal Antibodies: Principles and Practice, Academic Press, 1986]. As to which are superior in therapeutic effect against cancer, IgG class monoclonal antibodies or IgM class monoclonal antibodies, reference may be made to a detailed study made by Bernstein et al. using an IgG class monoclonal antibody and an IgM class monoclonal antibody to the lymphocyte Thy-1 antigen [Monoclonal Antibodies, edited by R. H. Kennet, T. J. Mckearn and K. B. Bechtol, Plenum Press, 1980, p. 275]. According to the reference, an IgG class monoclonal antibody and an IgM class monoclonal antibody comparable in terms of reactivity to Thy-1 antigen-positive lymphocytes, were compared in terms of antitumor effect. While the IgM monoclonal antibody was superior in in vitro complement-dependent antitumor effect, the IgG class monoclonal antibody showed a significant antitumor effect in in vivo antitumor effect in cancer-bearing mice, with no antitumor effect being observed with the IgM class monoclonal antibody. It was further revealed that, as compared with the IgG class monoclonal antibody, the IgM class monoclonal antibody showed a very short half-life in the blood after administration, in an isotope-labeled form, to mice. These results indicate that the monoclonal antibodies to be used clinically in humans should preferably be of the IgG class.

Gangliosides, a class of glycolipids, are constituents of animal cell membranes. These molecules are composed of a carbohydrate chain, which constitutes a hydrophilic side chain, and sphingosine and a fatty acid, which constitute hydrophobic side chains. It is known that the ganglioside species expressed and the amount thereof differ between cell species, organ species, and animal species, among others. Furthermore, it has been reported that the ganglioside expressed changed quantitatively and qualitatively during the process of cancer development [Cancer Res., 45, 2405 (1985)]. For example, expression of the gangliosides GD$_2$, GD$_3$ and GM$_2$ has been reported in neuroblastoma, lung small cell carcinoma, and melanoma, which are highly malignant neural ectodermal tumors [J. Exp. Med., 155, 1133 (1982); J. Biol. Chem., 257, 12752 (1982); Cancer Res., 47, 225 (1987); ibid., 47, 1098 (1987); ibid., 45, 2642 (1985); Proc. Natl. Acad. Sci. U.S.A., 80, 5392 (1983)].

GM$_2$, one of the gangliosides that are sialic acid residue containing glycolipids, occurs only in trace amounts in normal cells but is found in increased amounts in cancer cells in lung small cell carcinoma, melanoma, neuroblastoma, etc. Monoclonal antibodies to GM$_2$ are considered to be useful in the treatment of such cancers [Lancet, 4, 786 (1989)]. However, those monoclonal antibodies to GM$_2$ that have so far been reported are of the human IgM class or of the rat IgM, mouse IgM or mouse IgG class [Cancer Res., 46, 4116 (1986); Proc. Natl. Acad. Sci. U.S.A., 79, 7629 (1982); Cancer Res., 48, 6154 (1988); J. Biol. Chem., 264, 12122 (1989)].

Anti-ganglioside GM$_2$ monoclonal antibodies, if produced in the form of humanized antibodies, for example chimeric human antibodies or CDR-transplanted antibodies, which are not expected to induce anti-mouse immunoglobulin antibody production in the patient's body, produce reduced adverse effects and show a prolonged blood half-life and an enhanced antitumor effector effect. These antibodies are thus expected to be superior in therapeutic effect to the corresponding mouse monoclonal antibodies.

SUMMARY OF THE INVENTION

It is an object of the present invention to provide humanized antibodies to the ganglioside $GM_2$ (hereinafter, "humanized anti-$GM_2$ antibodies") which are useful in the treatment of cancers of neural ectodermal origin, among others.

The present inventors prepared the antibody heavy chain (hereinafter, "H chain") variable region (hereinafter "$V_H$") cDNA and light chain (hereinafter, "L chain") variable region (hereinafter, "$V_L$") cDNAs from mRNAs isolated from the hybridomas KM750 and KM796, described in EP-A-0 508 472. These hybridomas produce $IgG_3$ class mouse monoclonal antibodies to the ganglioside $GM_2$. $V_H$ and $V_L$ cDNAs were also prepared from mRNAs isolated from the hybridoma KM603, which produces an IgM class rat monoclonal antibody to the ganglioside $GM_2$. Chimeric human antibody expression vectors were constructed by inserting the cDNA into an expression vector containing human antibody H chain constant region (hereinafter, "$C_H$") or human antibody L chain constant region (hereinafter, "$C_L$") encoding sequences. Such vectors were then introduced into animal cells to effect the production of anti-ganglioside $GM_2$ chimeric human antibodies. Among the chimeric antibodies produced, the anti-ganglioside $GM_2$ chimeric human antibody, KM966, was found to react with the ganglioside $GM_2$ and show cytocidal activity. The H chain variable region of KM966 contains an amino acid sequence segment as defined by SEQ ID NO:91 and includes the 1st to 120th amino acids of that sequence and the L chain variable region of KM966 contains an amino acid sequence segment as defined by SEQ ID NO:92 and includes the 1st to 107th amino acids of said sequence. The present invention is based, at least in part, on these findings.

The present invention thus relates to a humanized antibody reacting with the ganglioside $GM_2$.

Figure 26A:
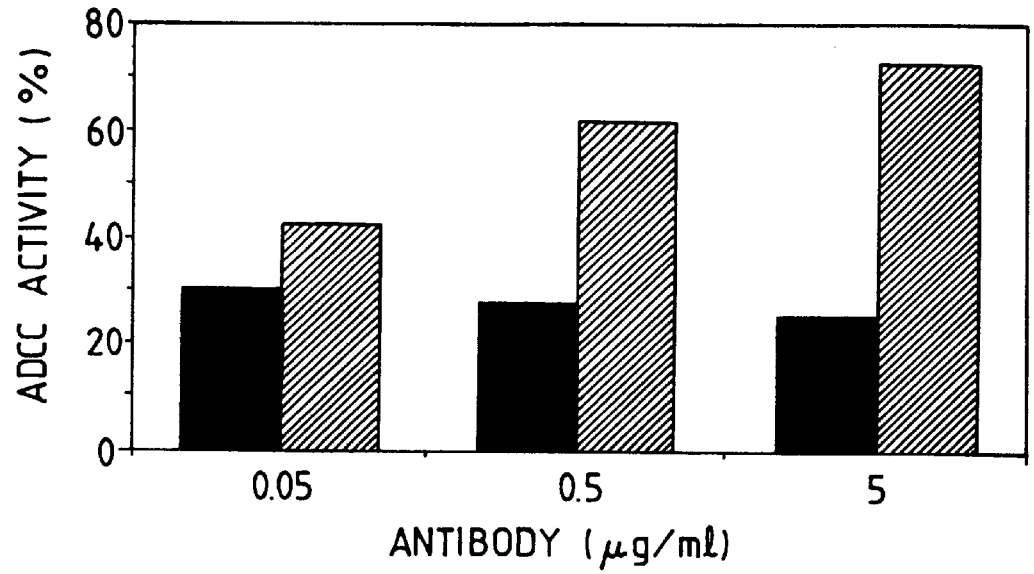
Figure 26B:
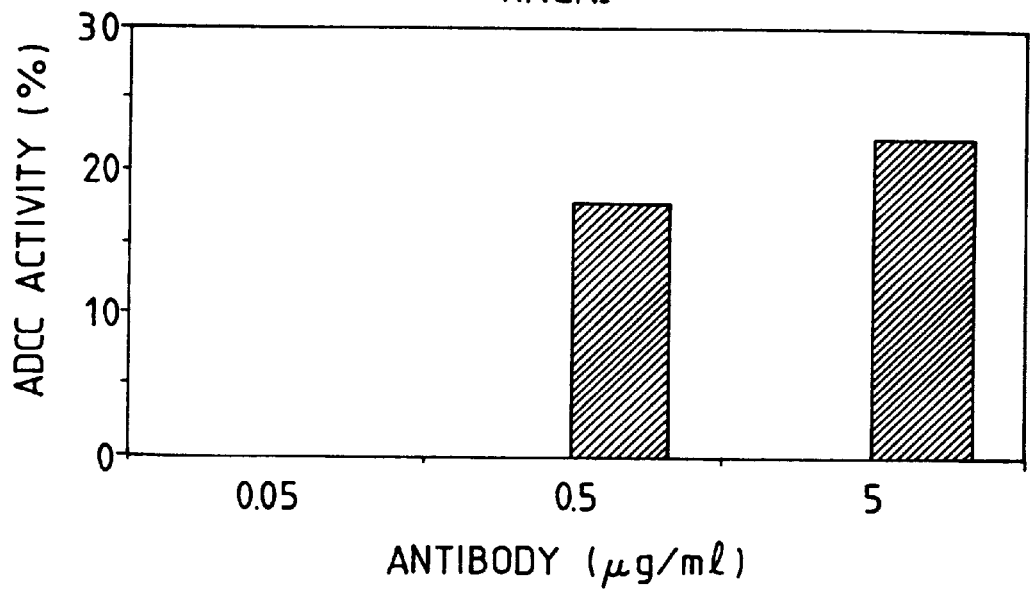

FIG. 26 graphically shows the ADCC activities of KM966 against the human lung large cell carcinoma cell line PC-13 and human neuroblastoma cell line NAGAI. The ordinate indicates the cytotoxicity and the abscissa the concentration of the antibody added. The solid bars indicate the ADCC activities of KM-696 and the shaded bars the ADCC activities of KM966.

Figure 27A:
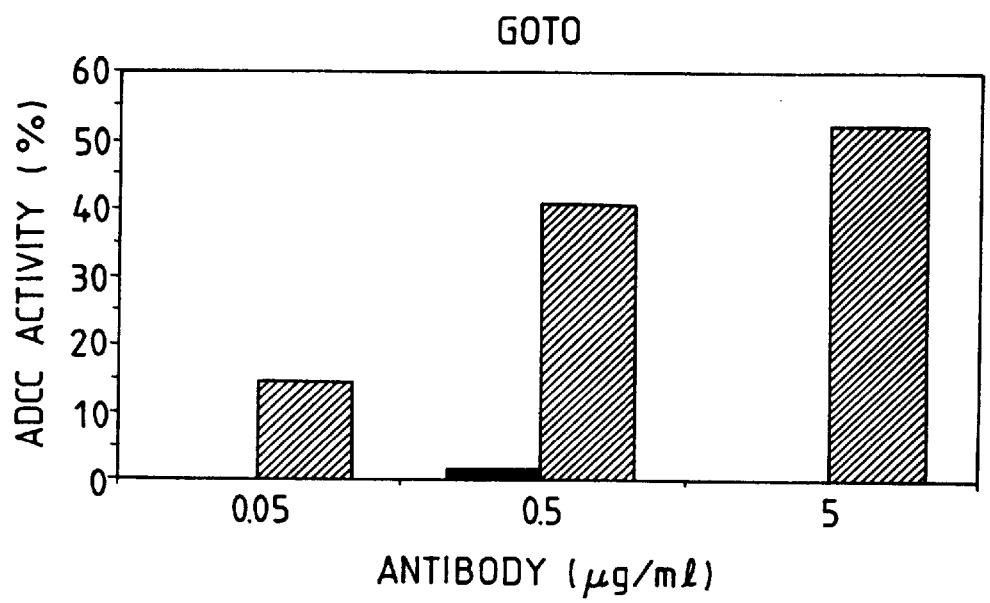
Figure 27B:
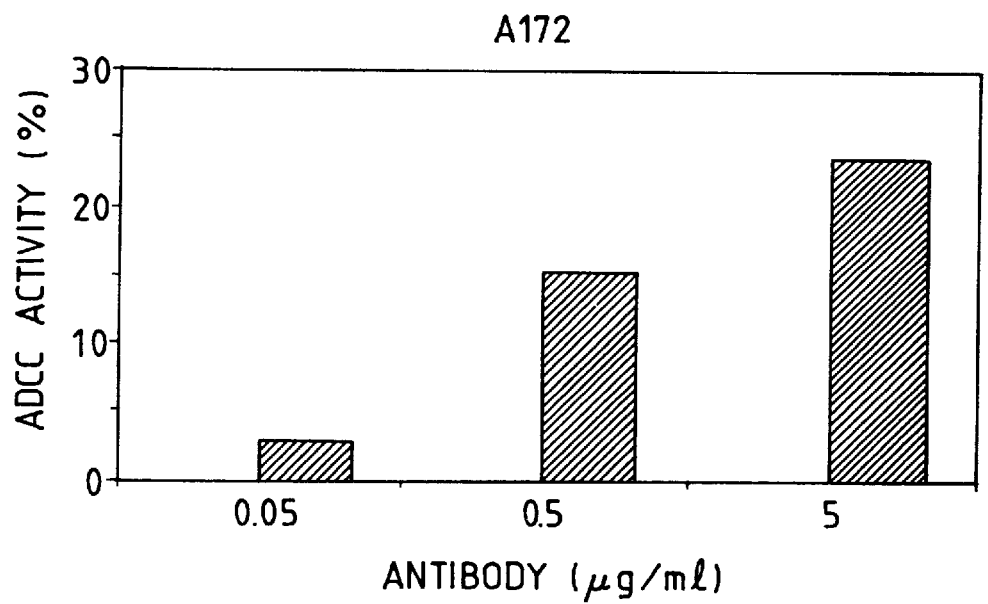

FIG. 27 graphically shows the ADCC activities of KM966 against the human neuroblastoma cell line GOTO and human brain tumor cell line A172. The ordinate indicates the cytotoxicity and the abscissa the concentration of the antibody added. The solid bars indicate the ADCC activities of KM-696 and the shaded bars the ADCC activities of KM966.

Figure 28:
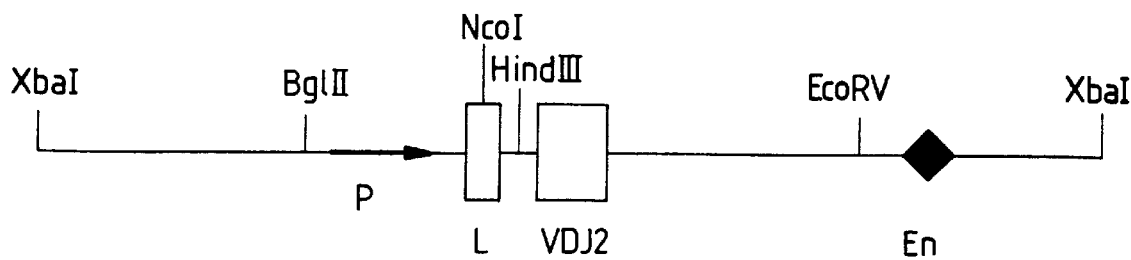

FIG. 28 shows a restriction enzyme cleavage map of a 9.3 kb XbaI fragment of the KM50 cell chromosomal DNA.

Figure 29:
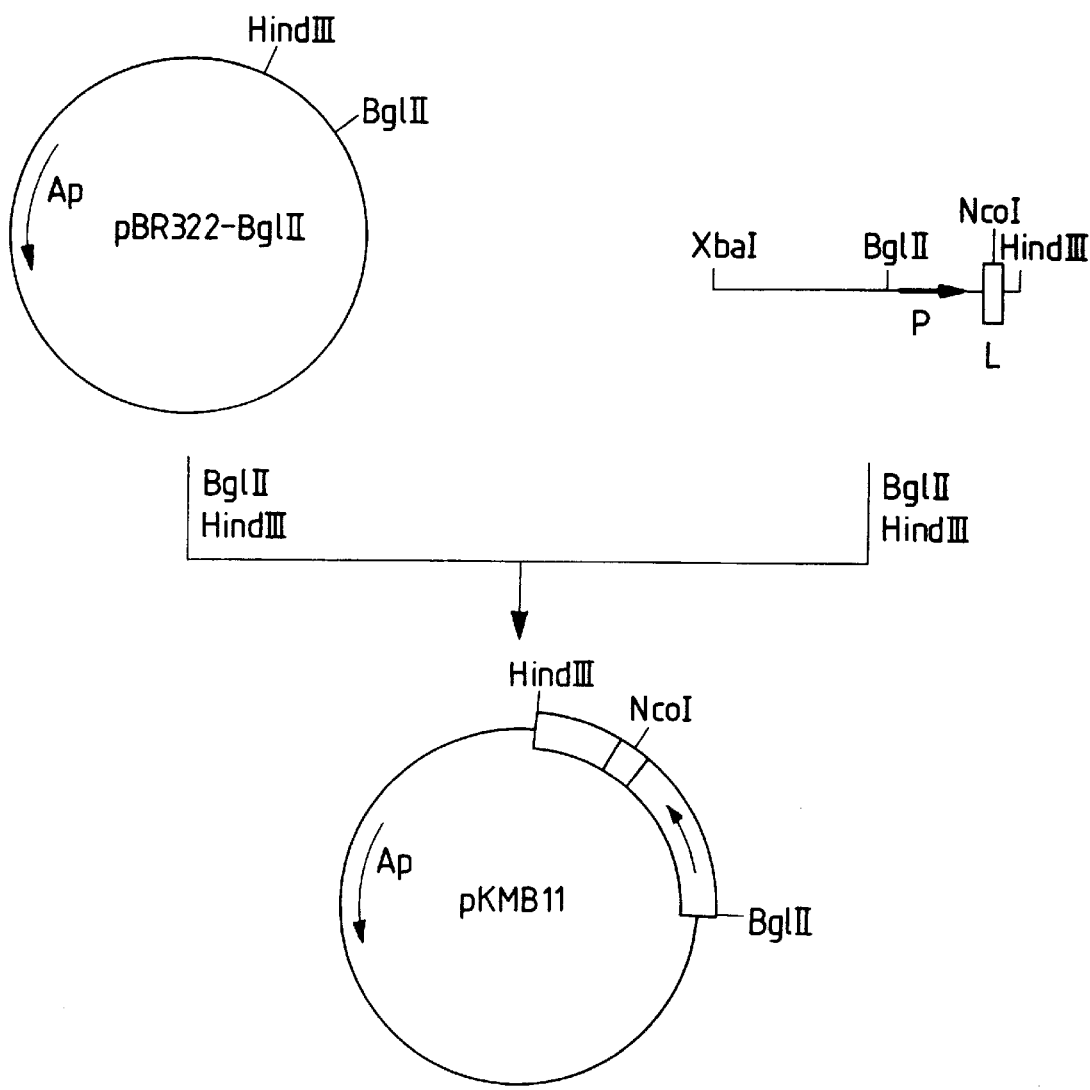

FIG. 29 shows a construction scheme for a plasmid, pKMB11.

Figure 30:
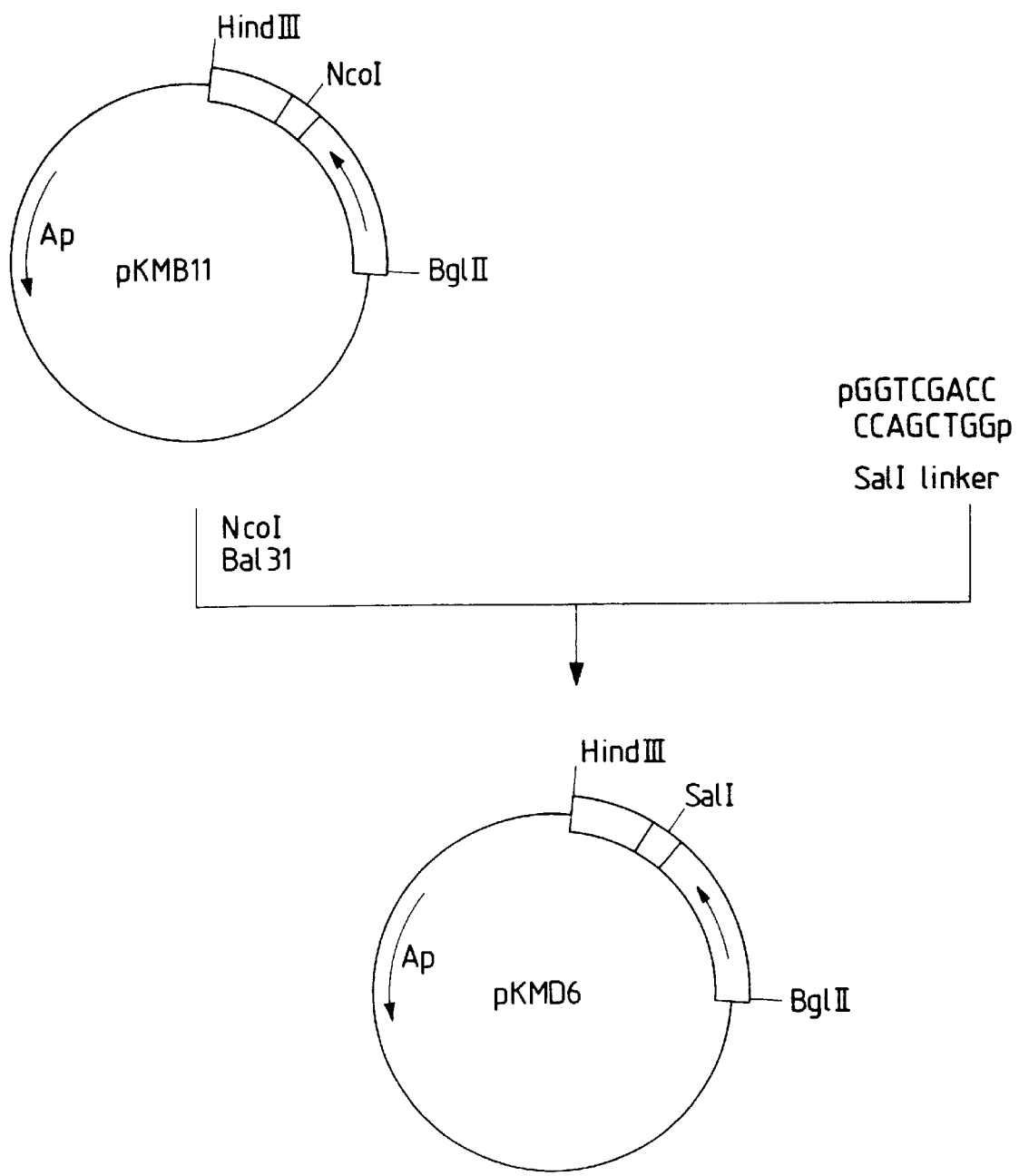

FIG. 30 shows a construction scheme for a plasmid, pKMD6.

Figure 31:
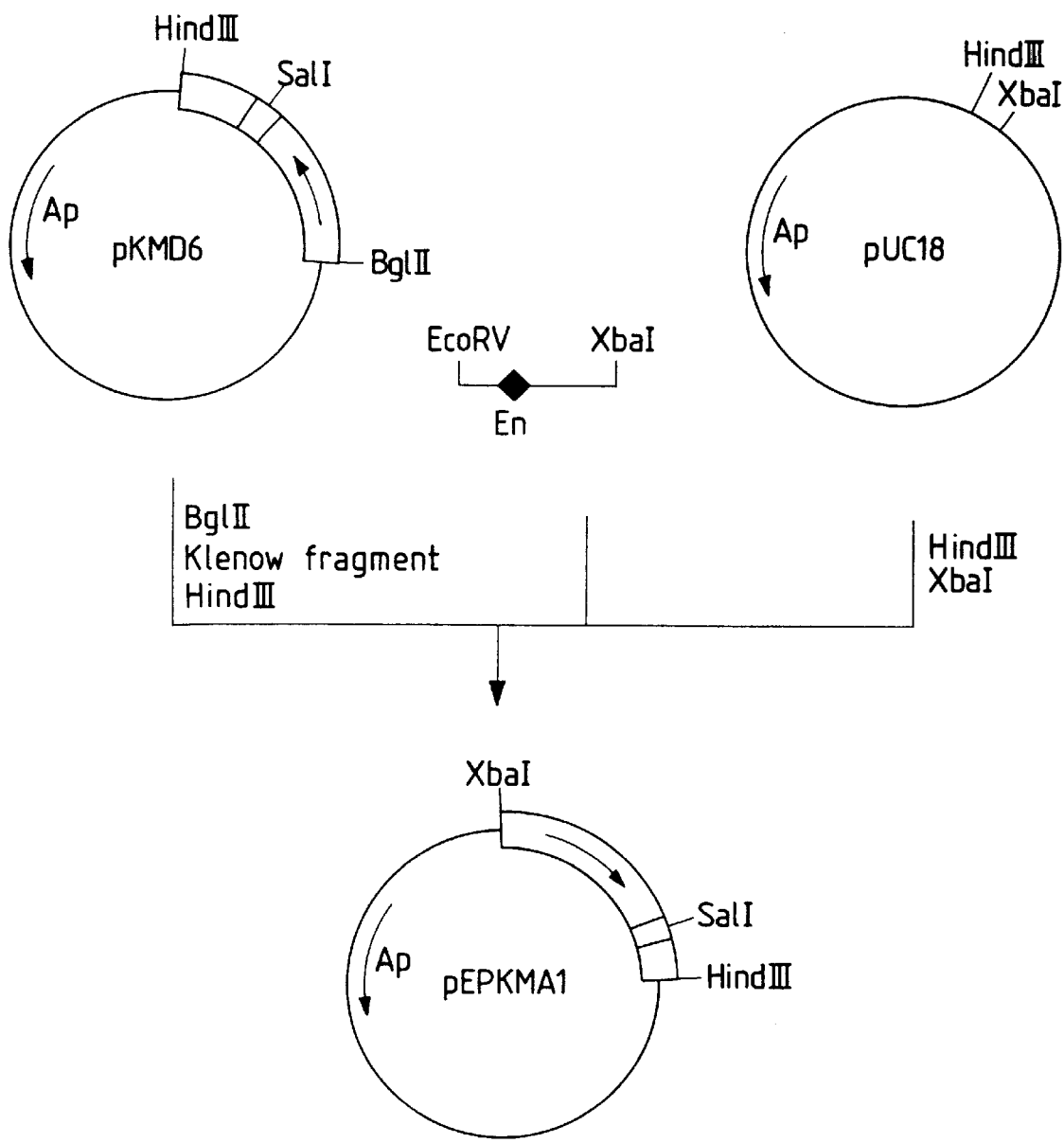

FIG. 31 shows a construction scheme for a plasmid, pEPKMA1.

Figure 32:
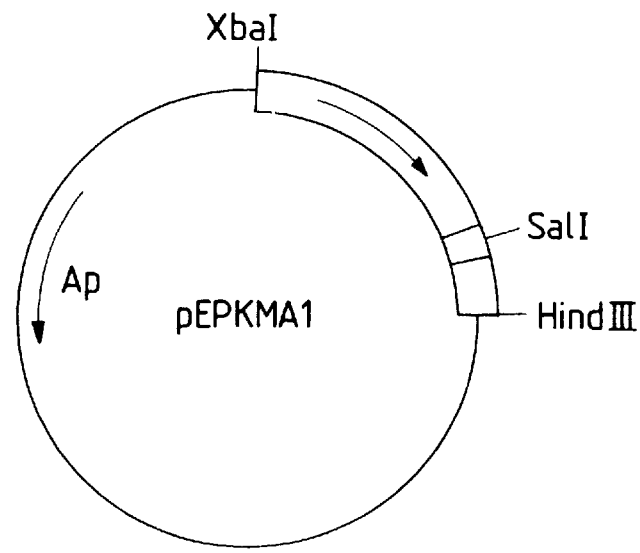
Figure 32:
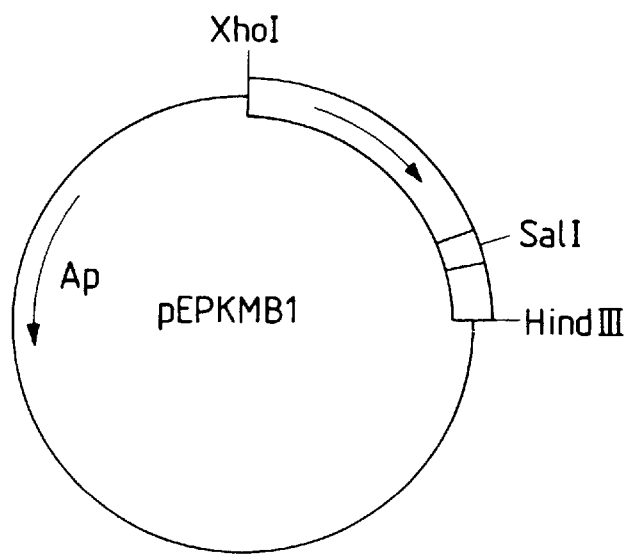

FIG. 32 shows a construction scheme for a plasmid, pEPKMB1.

Figure 33:
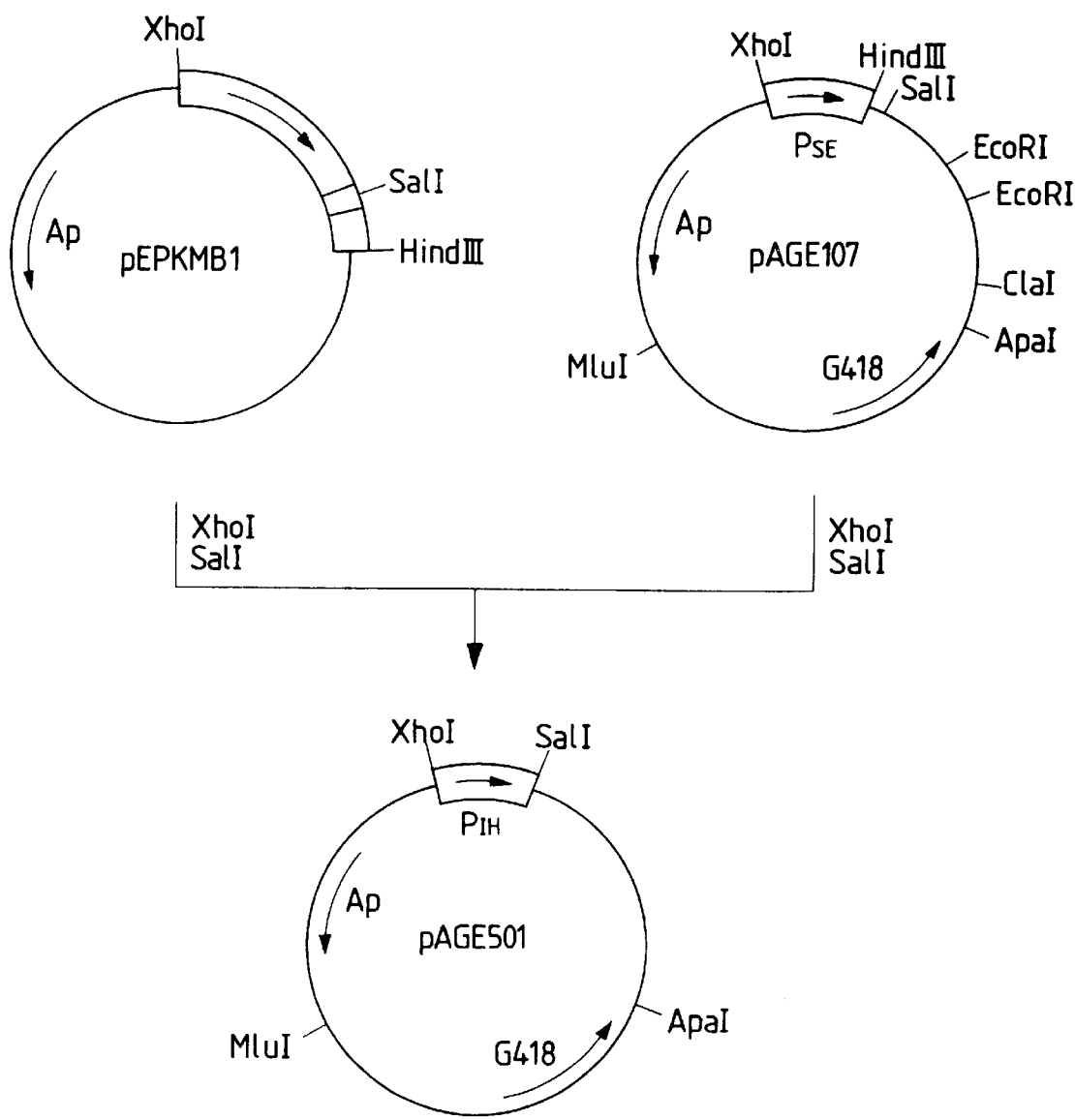

FIG. 33 shows a construction scheme for a plasmid, pAGE501.

Figure 34:
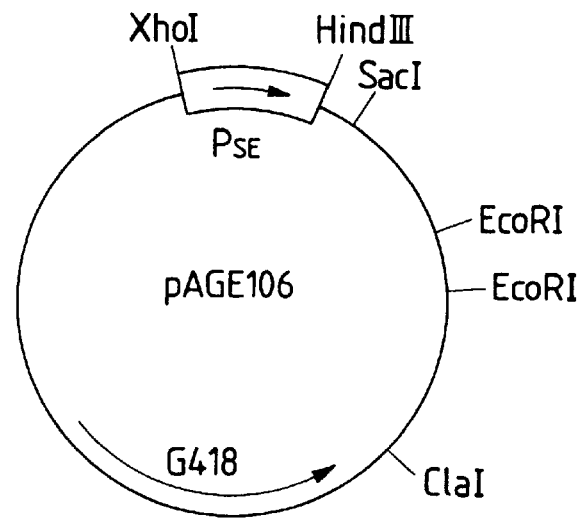
Figure 34:
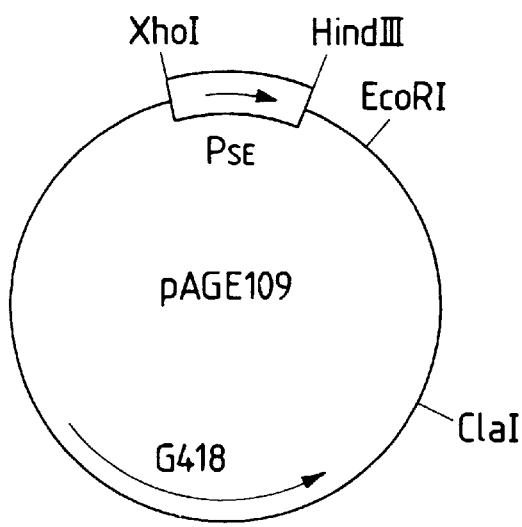

FIG. 34 shows a construction scheme for a plasmid, pAGE109.

Figure 35:
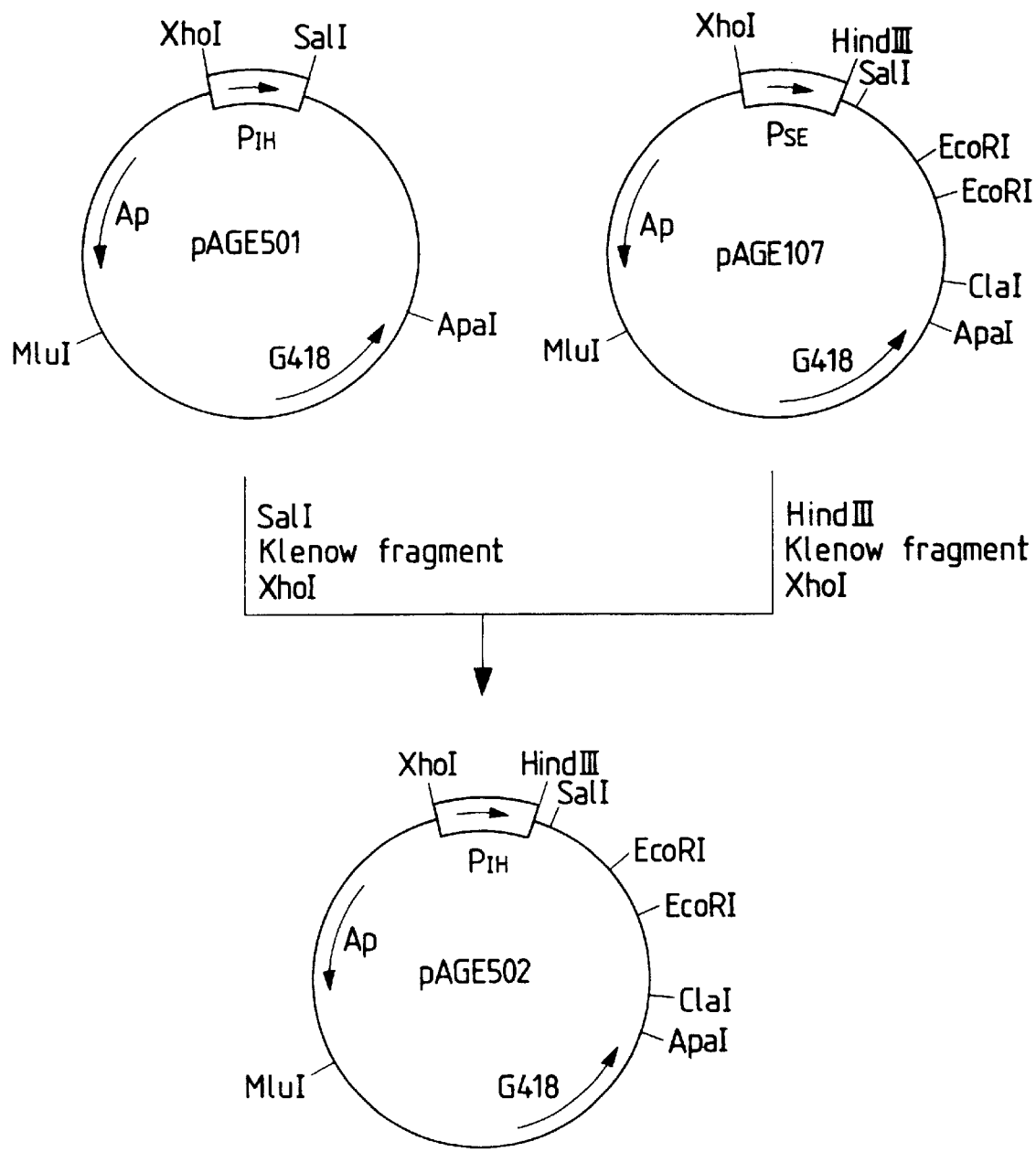

FIG. 35 shows a construction scheme for a plasmid, pAGE502.

Figure 36:
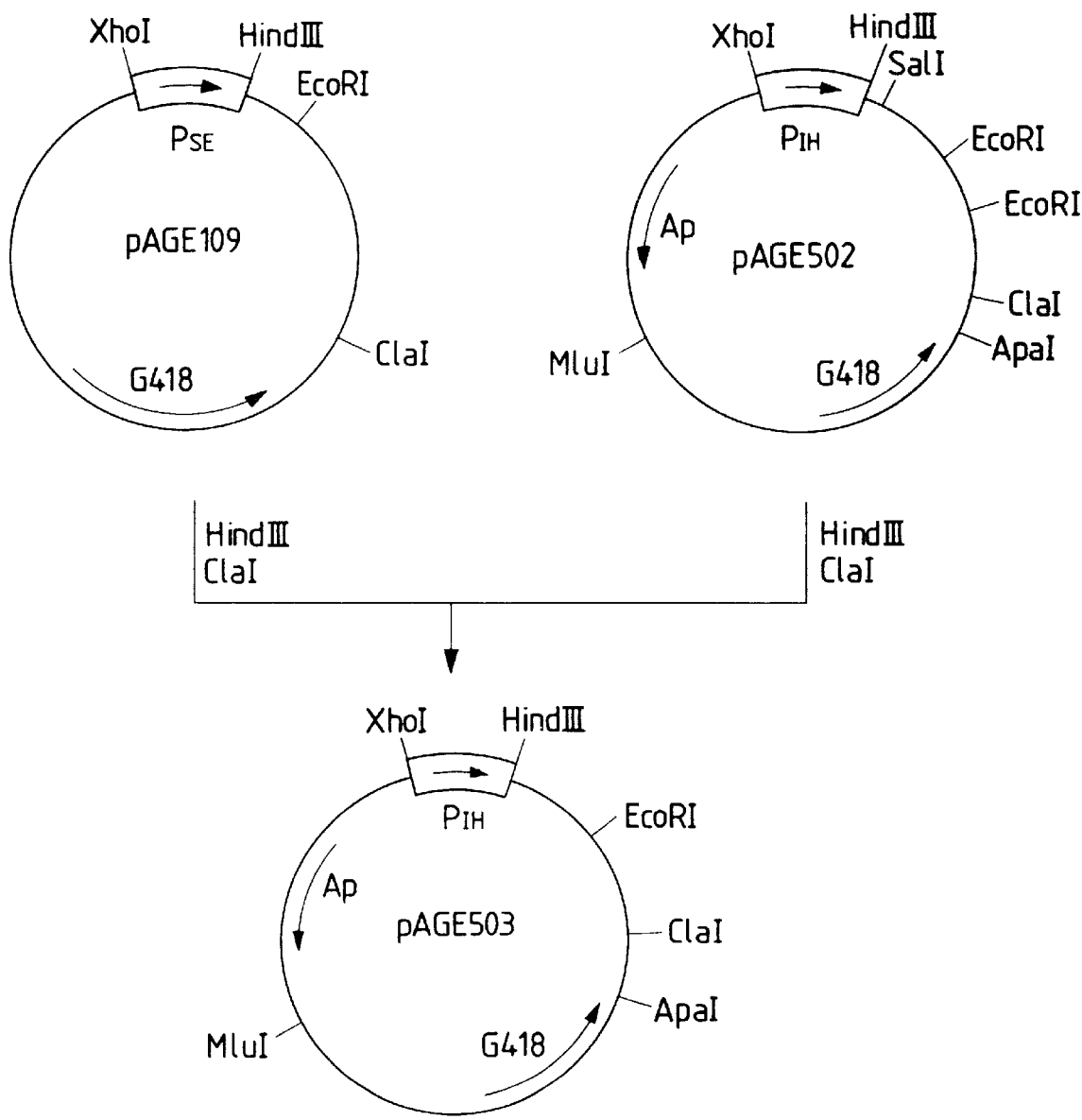

FIG. 36 shows a construction scheme for a plasmid, pAGE503.

Figure 37:
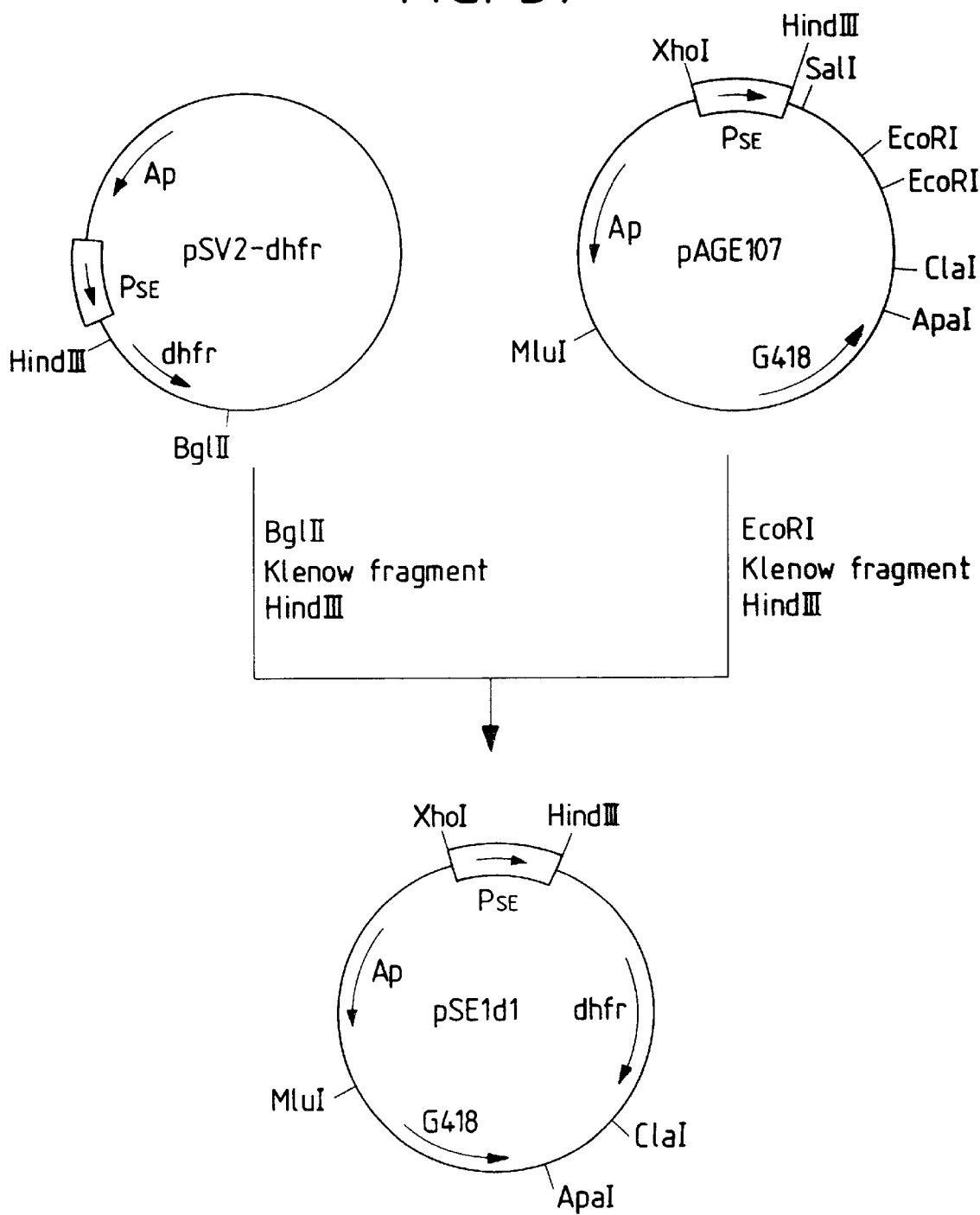

FIG. 37 shows a construction scheme for a plasmid, pSEd1.

Figure 38:
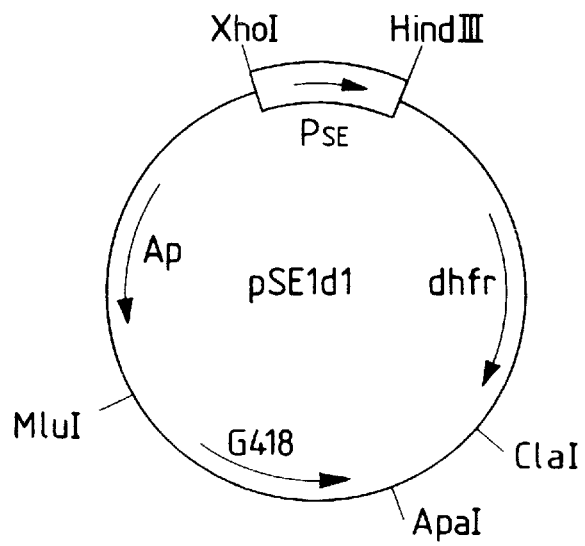
Figure 38:
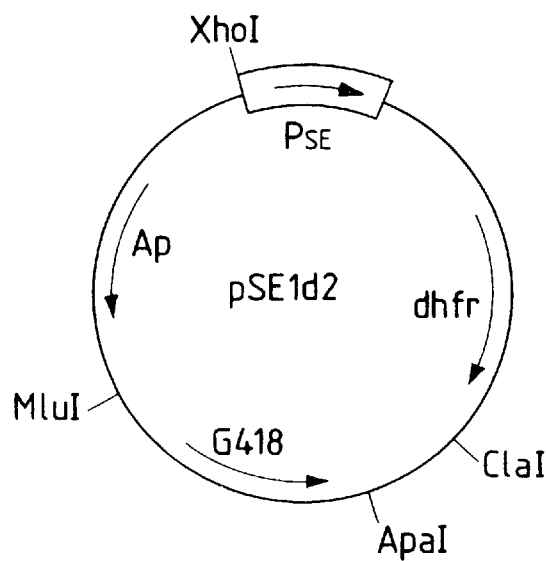

FIG. 38 shows a construction scheme for a plasmid, pSE1D2.

Figure 39:
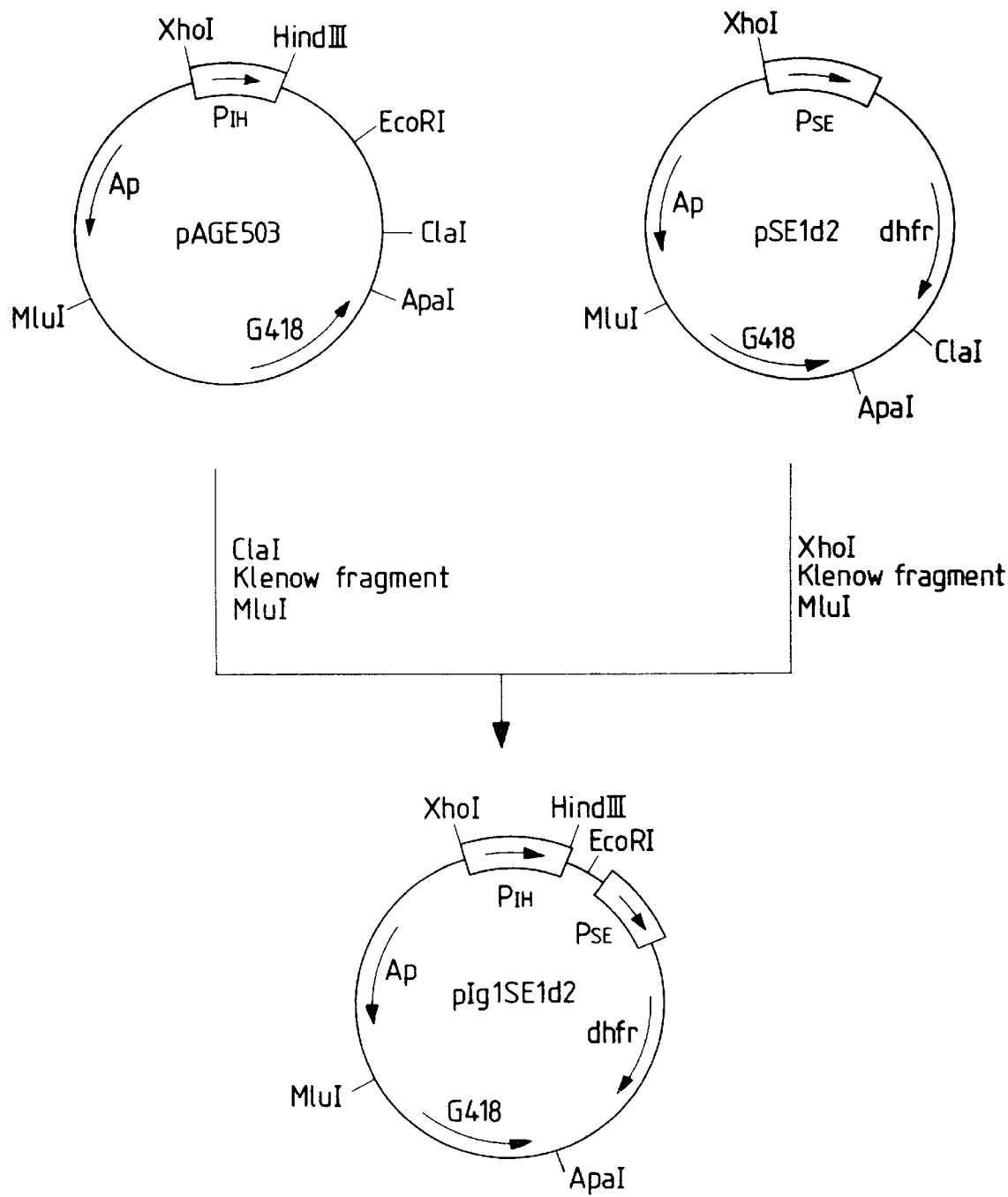

FIG. 39 shows a construction scheme for a plasmid, pIG1SE1d2.

Figure 40:
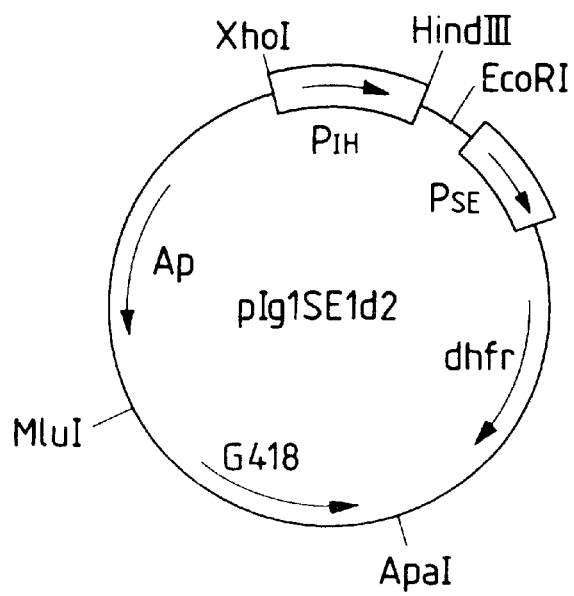
Figure 40:
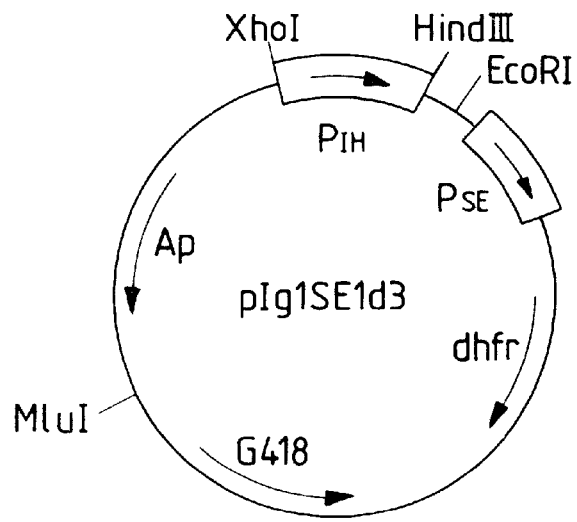

FIG. 40 shows a construction scheme for a plasmid, pIG1SE1d3.

Figure 41:
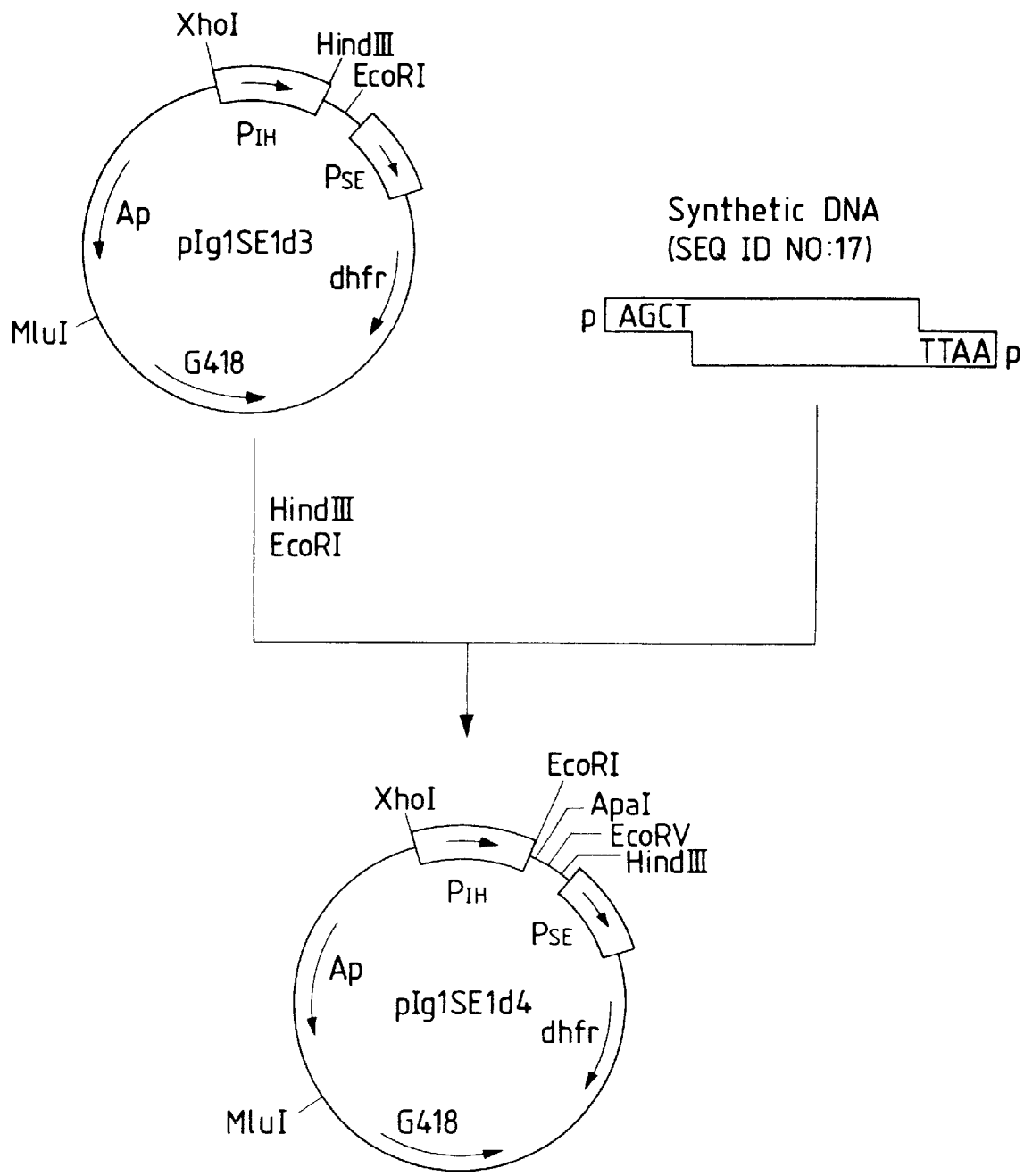

FIG. 41 shows a construction scheme for a plasmid, pIG1SE1d4.

Figure 42:
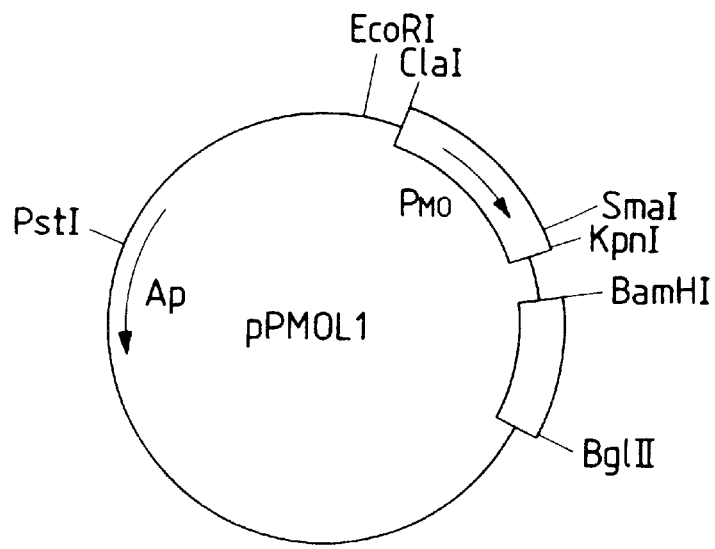
Figure 42:
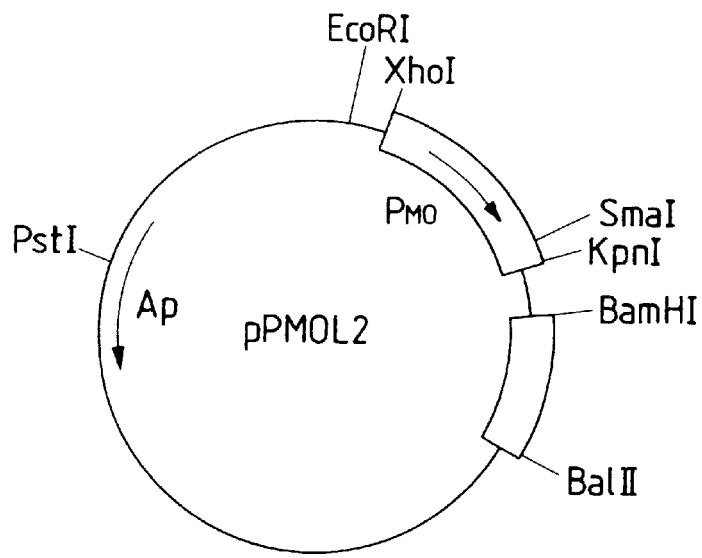

FIG. 42 shows a construction scheme for a plasmid, pPMOL2.

Figure 43:
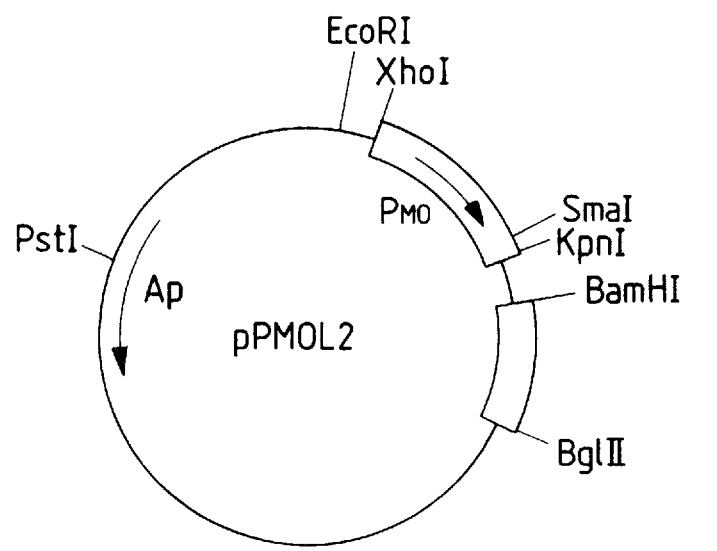
Figure 43:
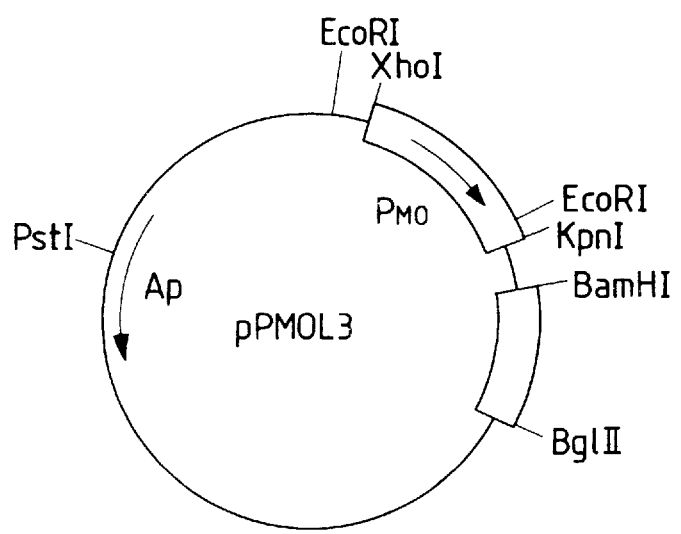

FIG. 43 shows a construction scheme for a plasmid, pPMOL3.

Figure 44:
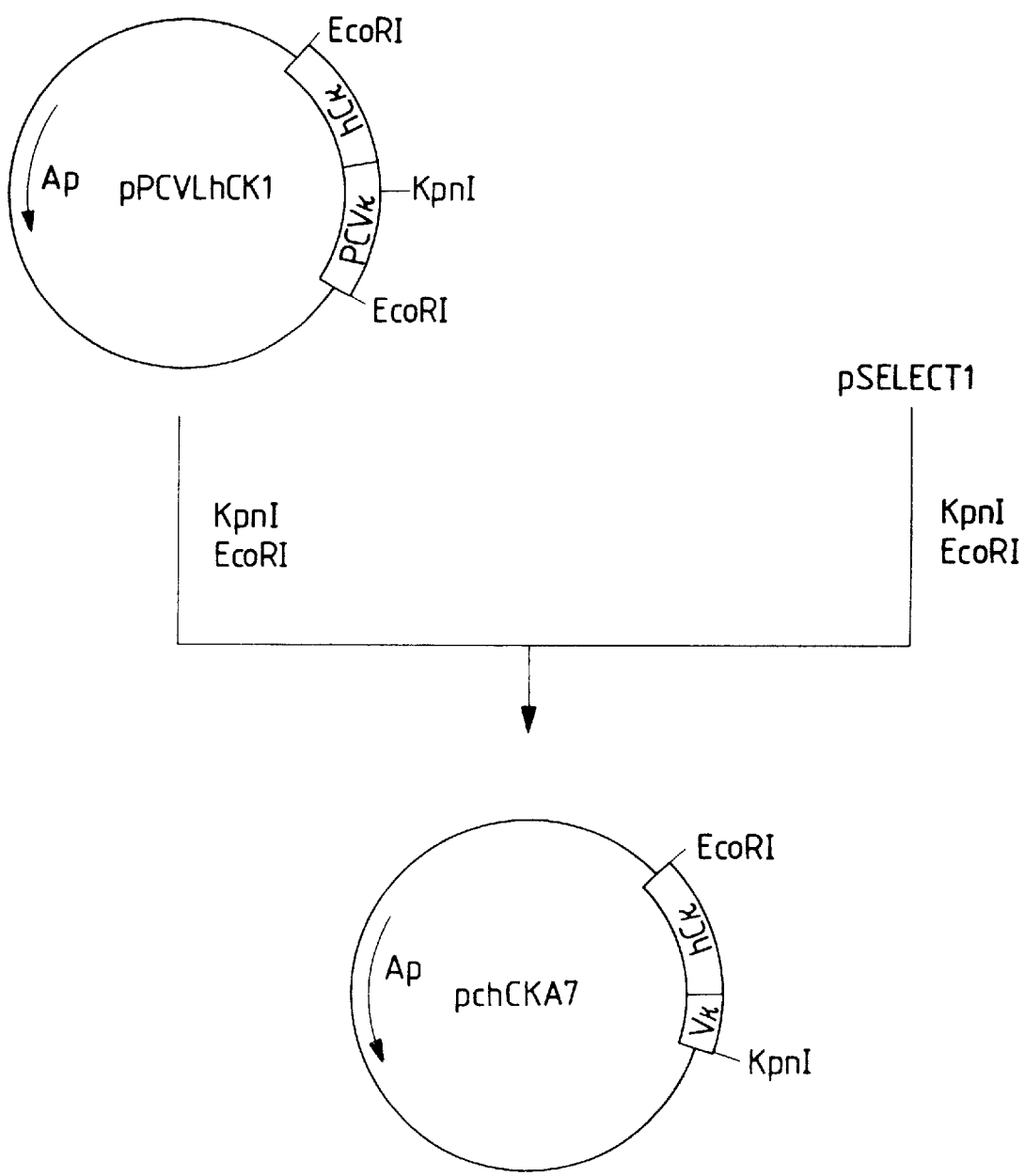

FIG. 44 shows a construction scheme for a plasmid, pchCKA7.

Figure 45:
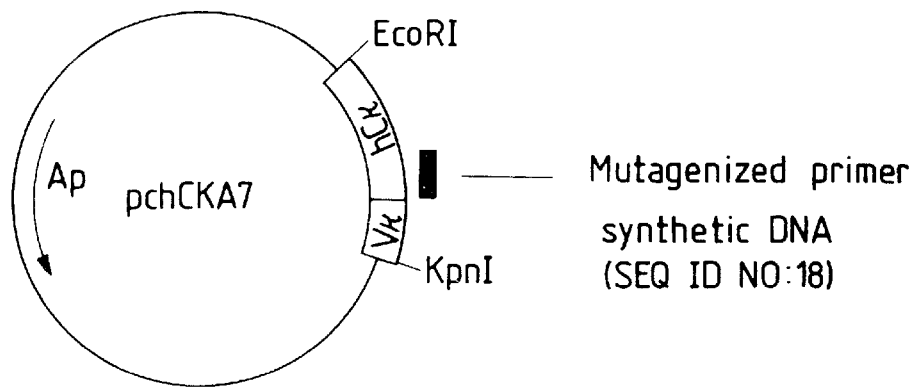
Figure 45:
Figure 45:
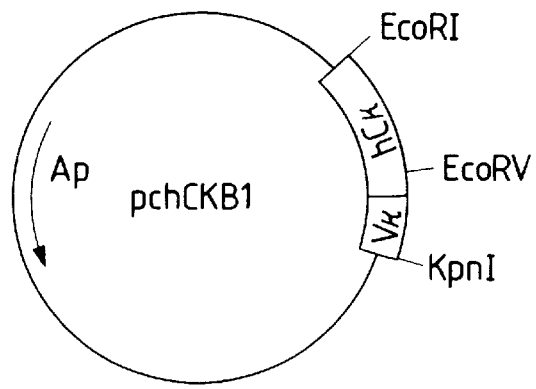
Figure 45:
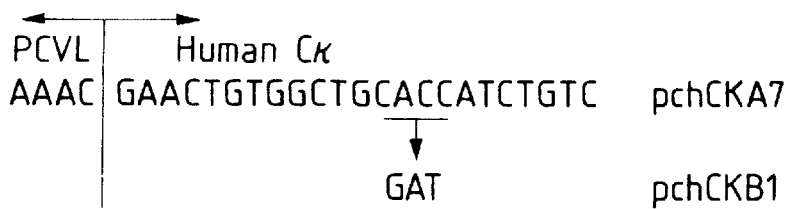

FIG. 45 shows a construction scheme for a plasmid, pchCKB1 (SEQ ID NO:102 and SEQ ID NO:103).

Figure 46:
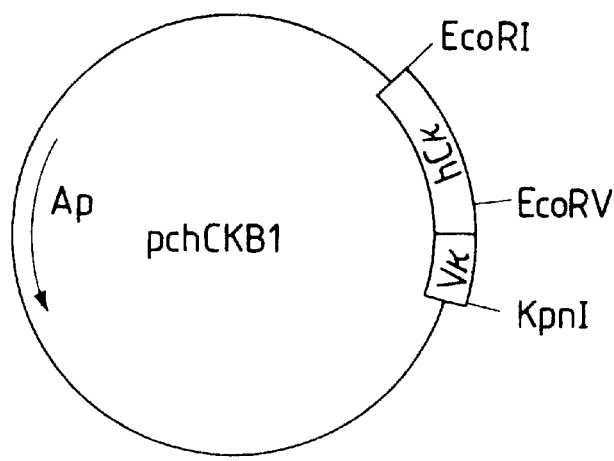
Figure 46:
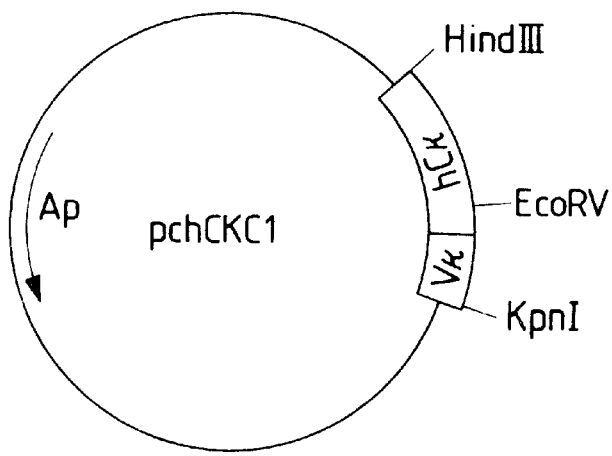

FIG. 46 shows a construction scheme for a plasmid, pckCKC1.

Figure 47:
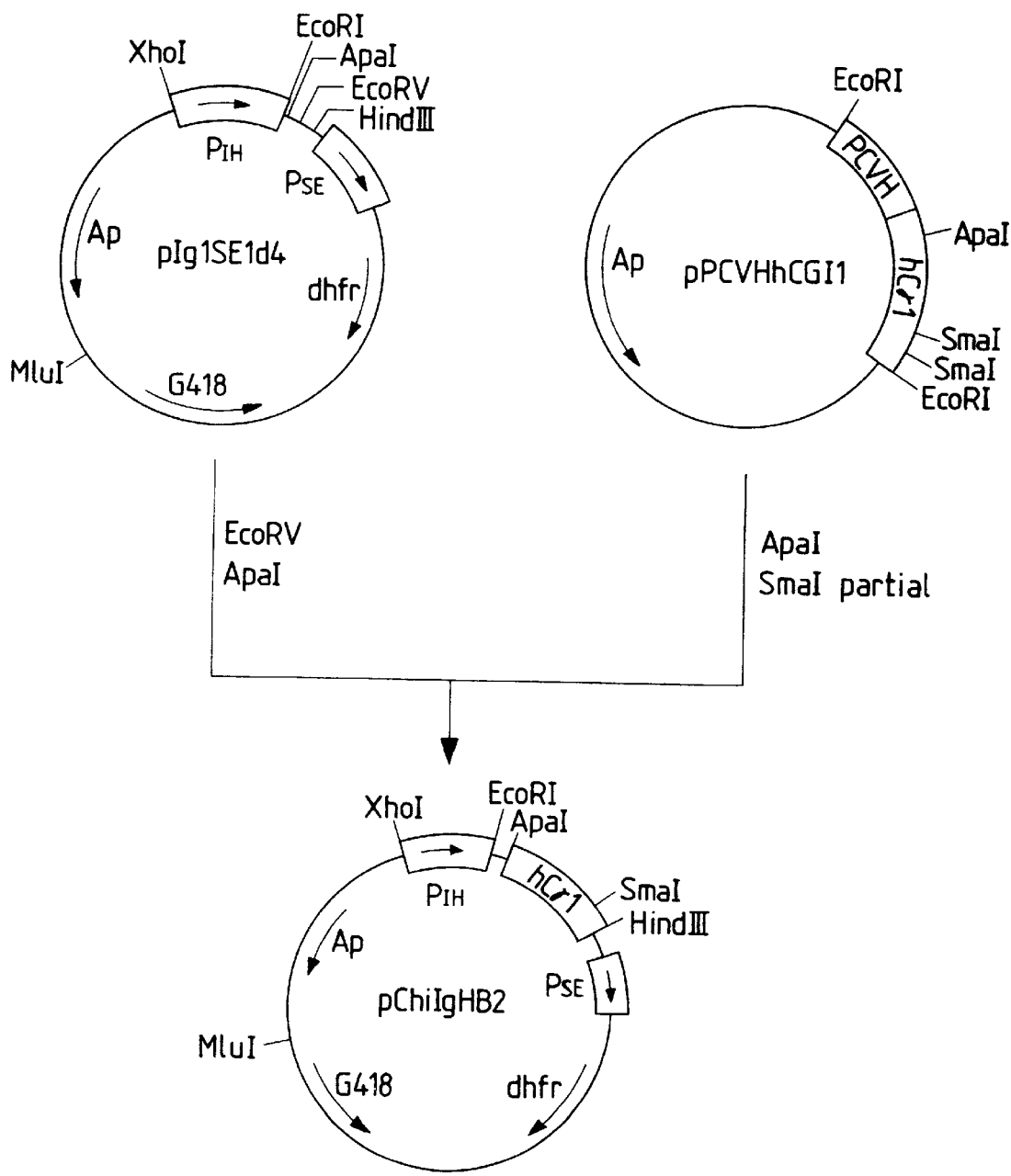

FIG. 47 shows a construction scheme for a plasmid, pChiIgHB2.

Figure 48:
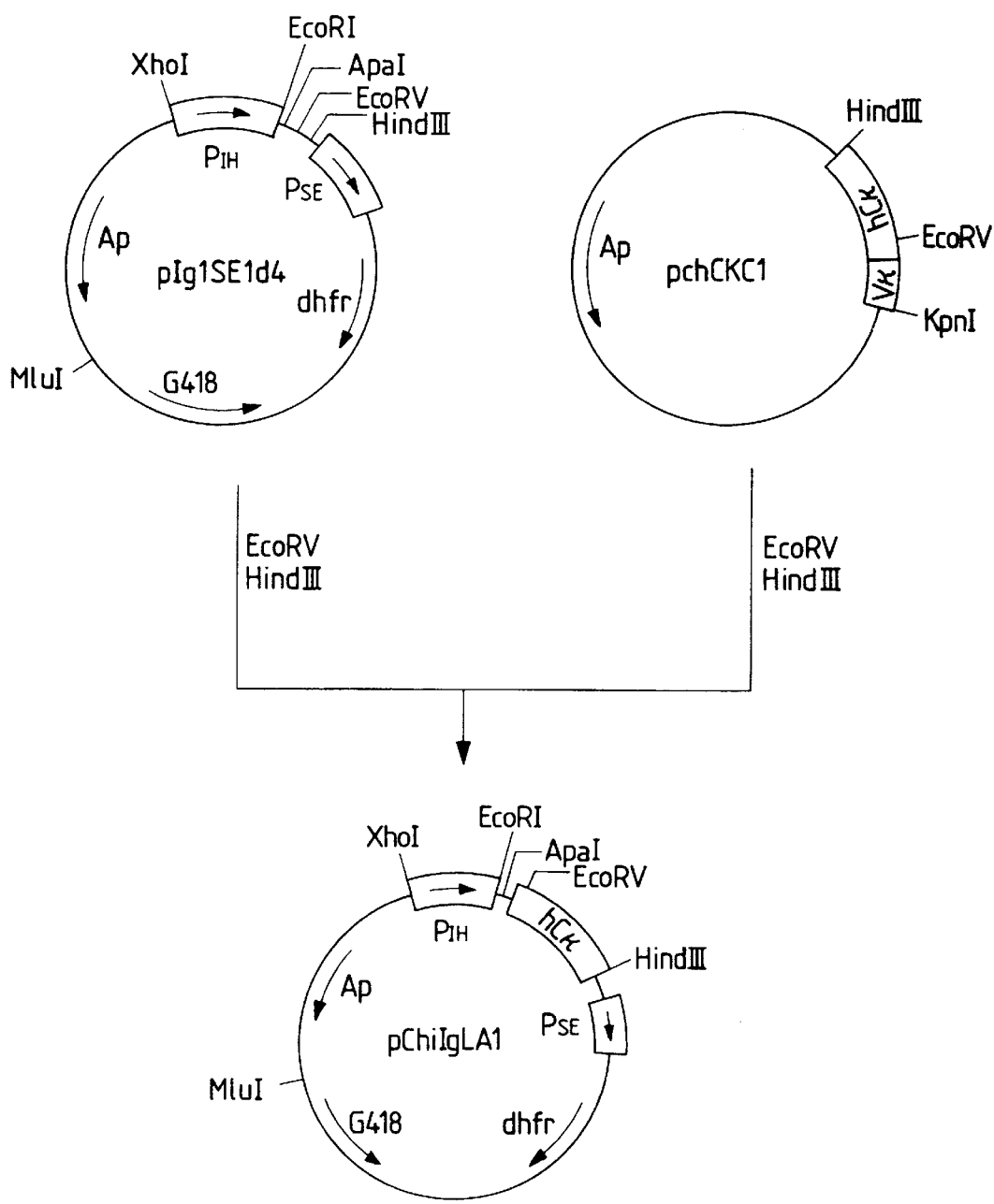

FIG. 48 shows a construction scheme for a plasmid, pChiIgLA1.

Figure 49:
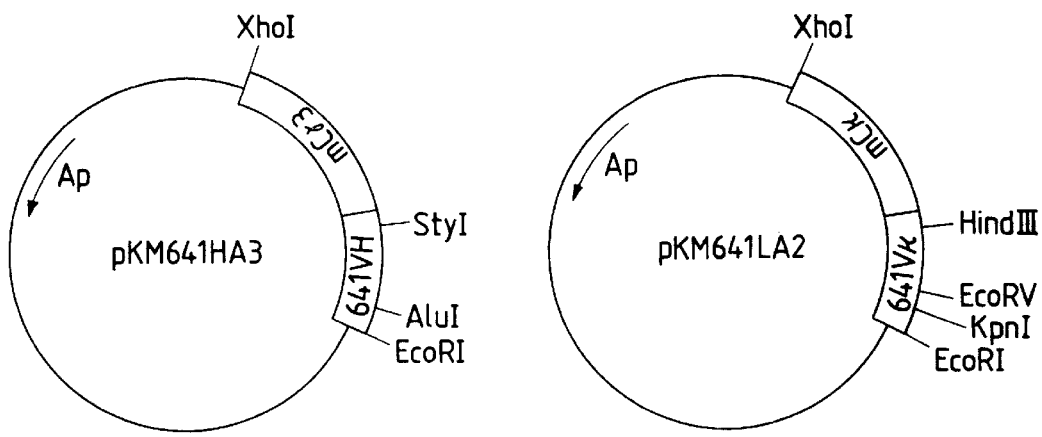

FIG. 49 shows a construction scheme for plasmids, pKM641HA3 and pKM641LA2.

Figure 50:
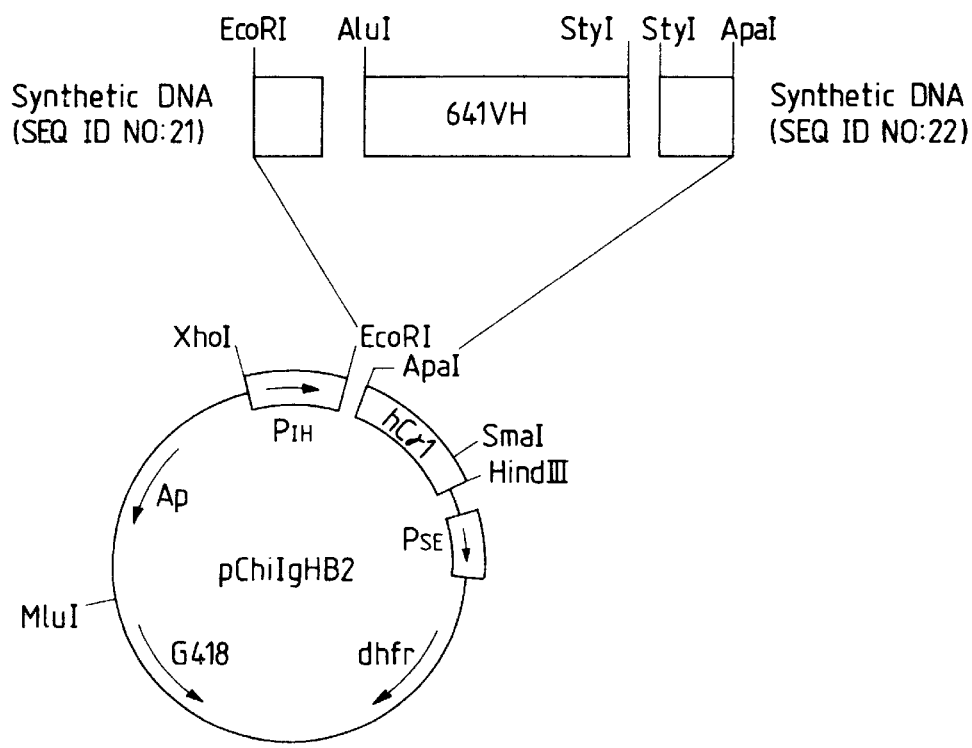

FIG. 50 shows a construction scheme for a plasmid, pChi641HA1.

Figure 51:
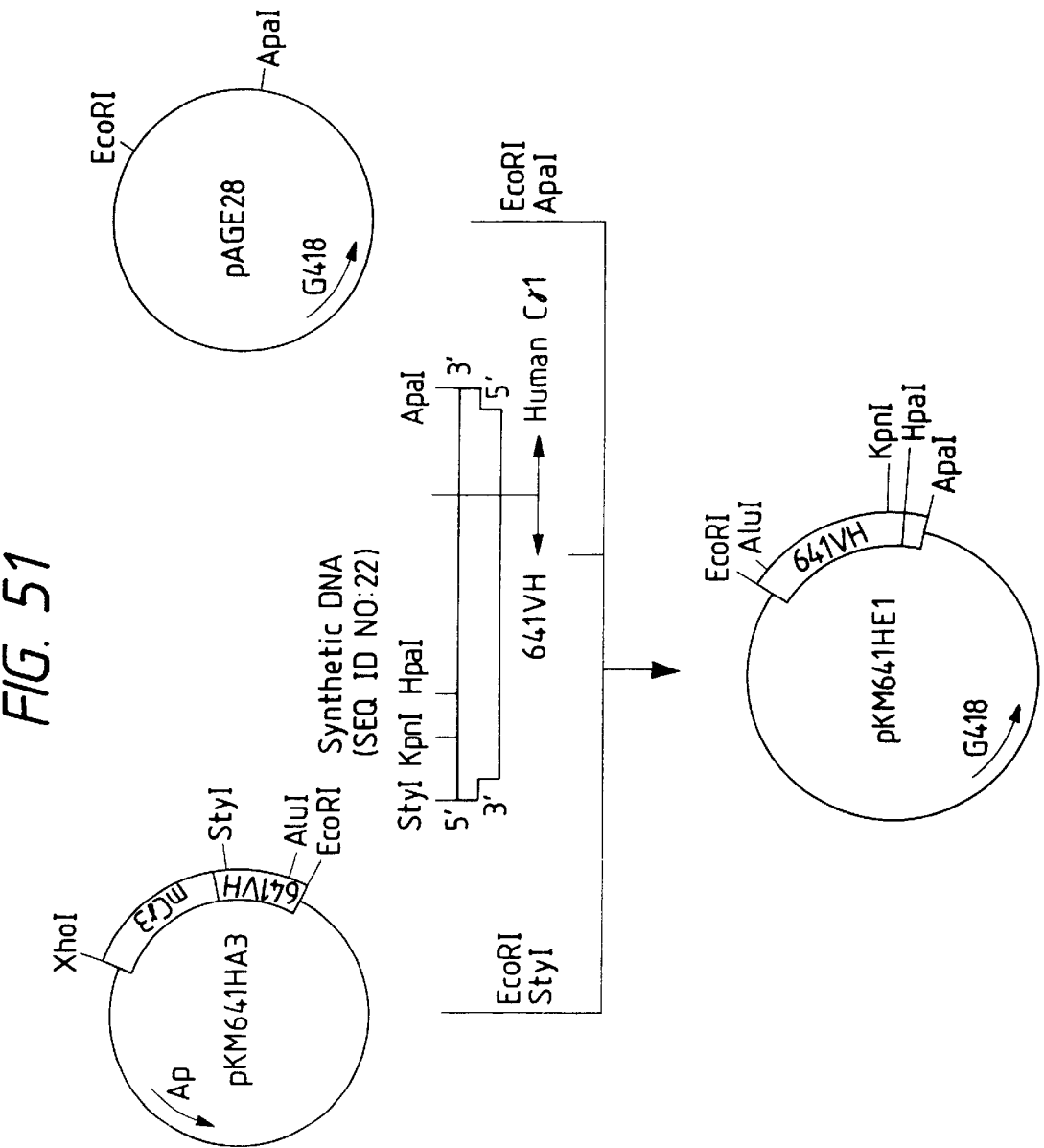

FIG. 51 shows a construction scheme for a plasmid, pKM641HE1.

Figure 52:
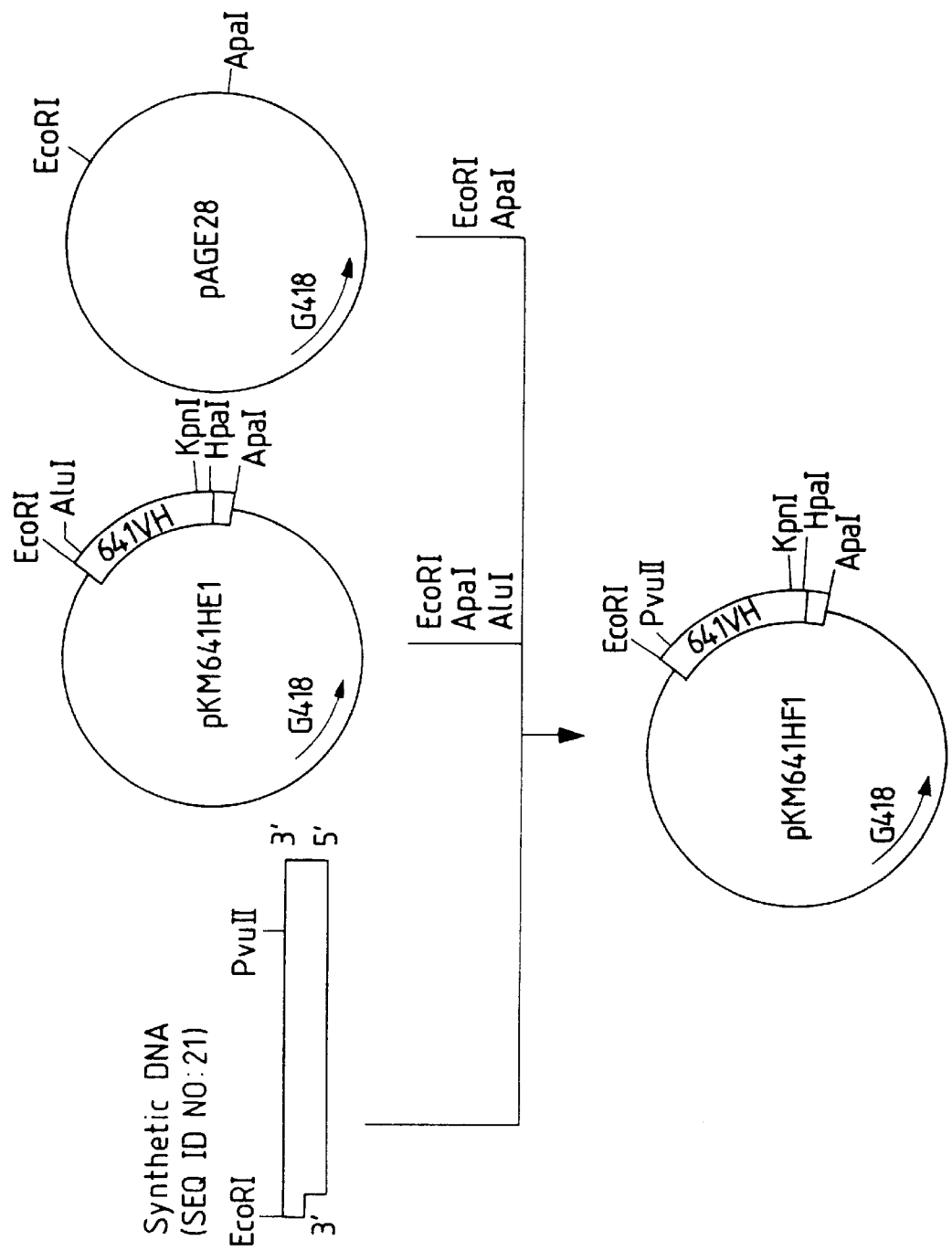

FIG. 52 shows a construction scheme for a plasmid, pKM641HF1.

Figure 53:
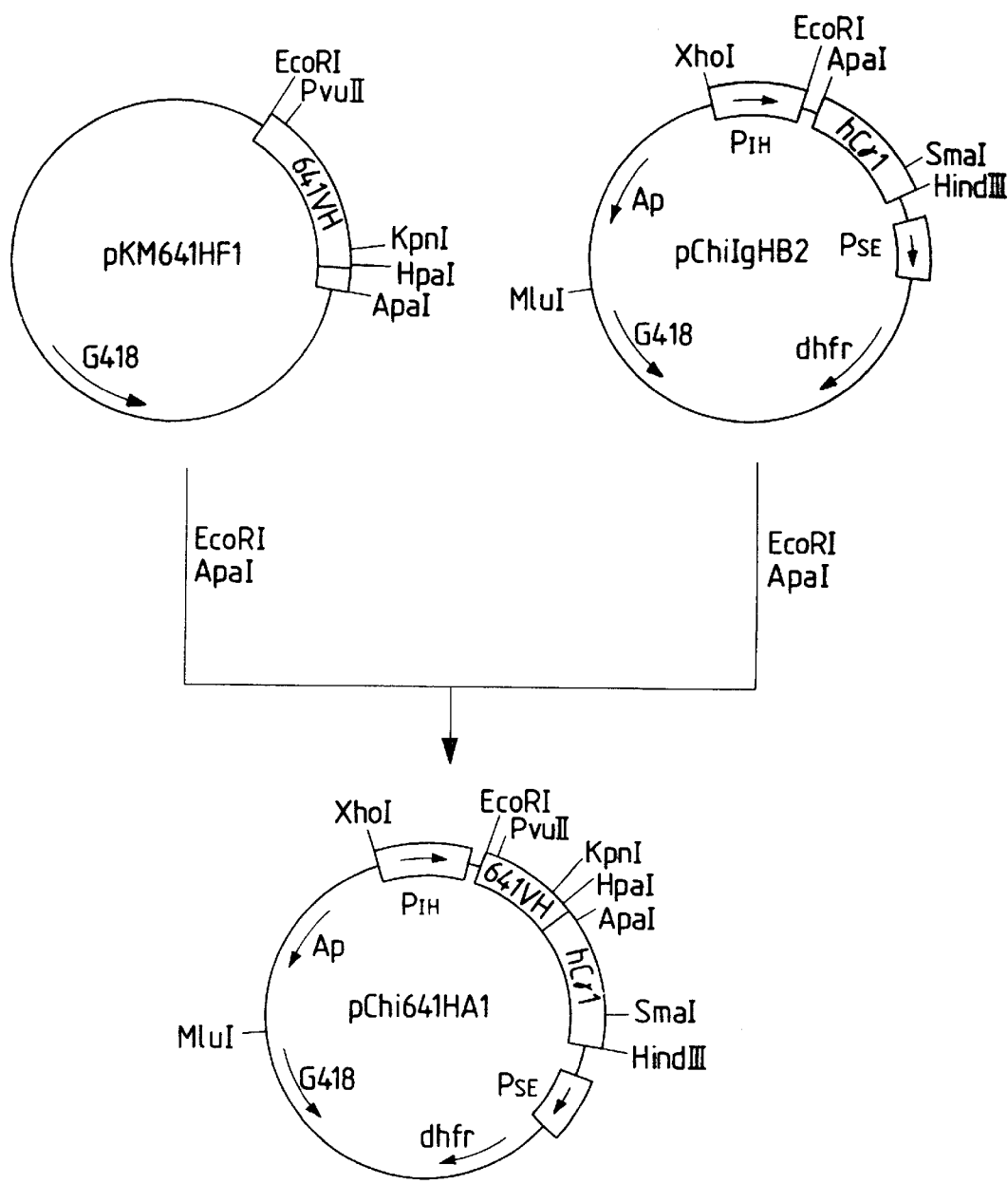

FIG. 53 shows a construction scheme for a plasmid, pChi641HA1.

Figure 54:
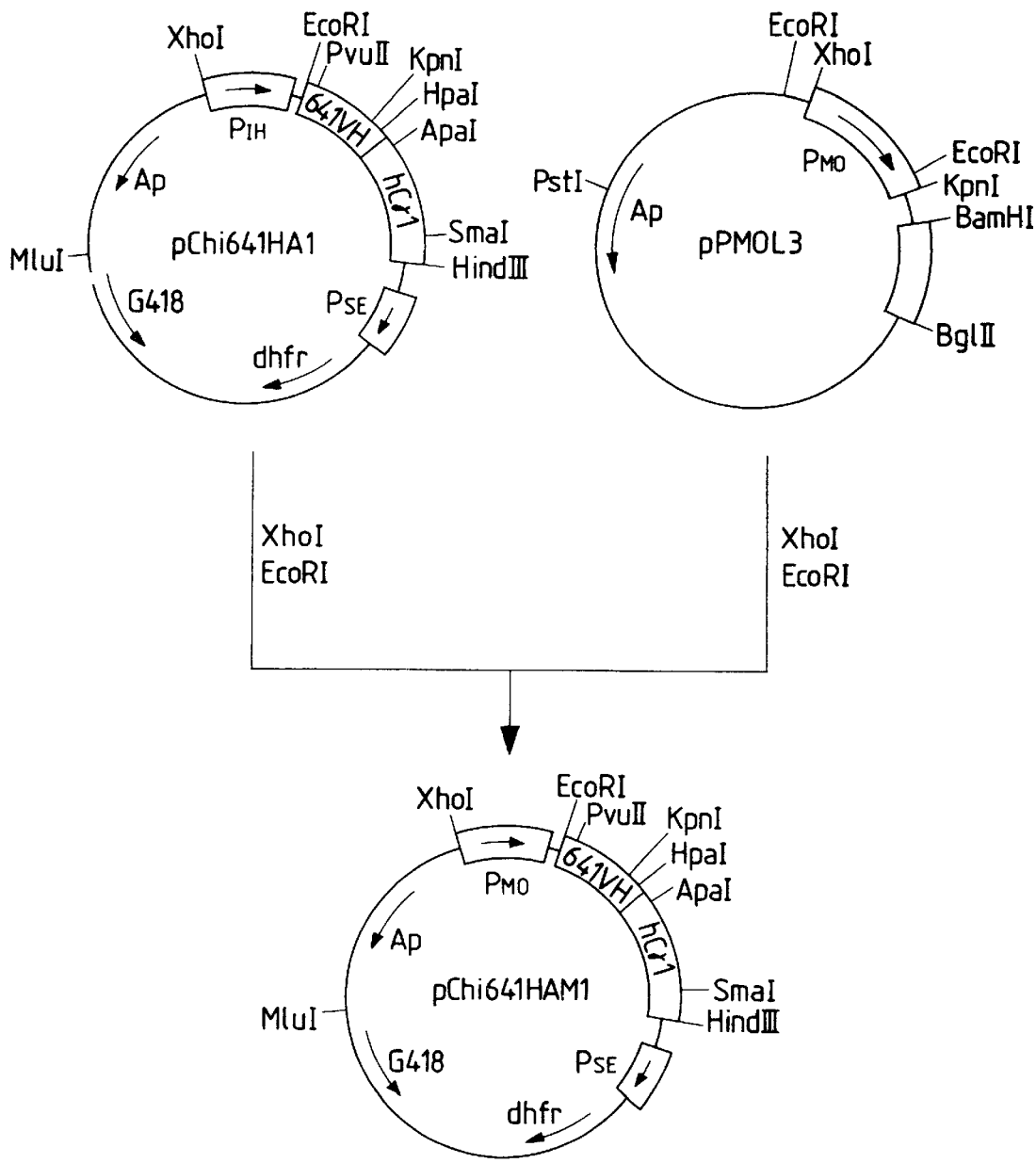

FIG. 54 shows a construction scheme for a plasmid, pChi641HAM1.

Figure 55:
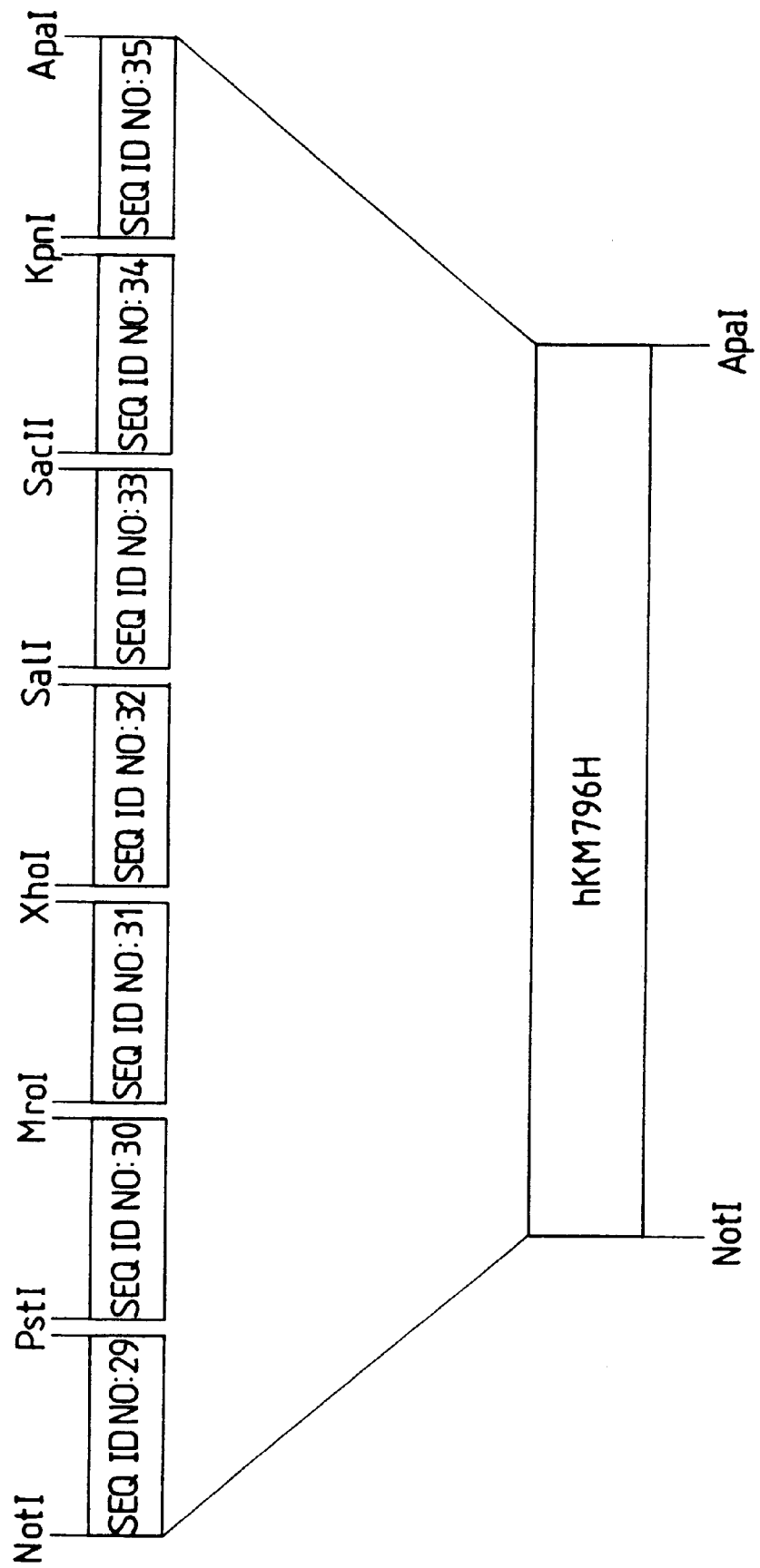

FIG. 55 shows a construction scheme for a DNA, hKM796H.

Figure 56:
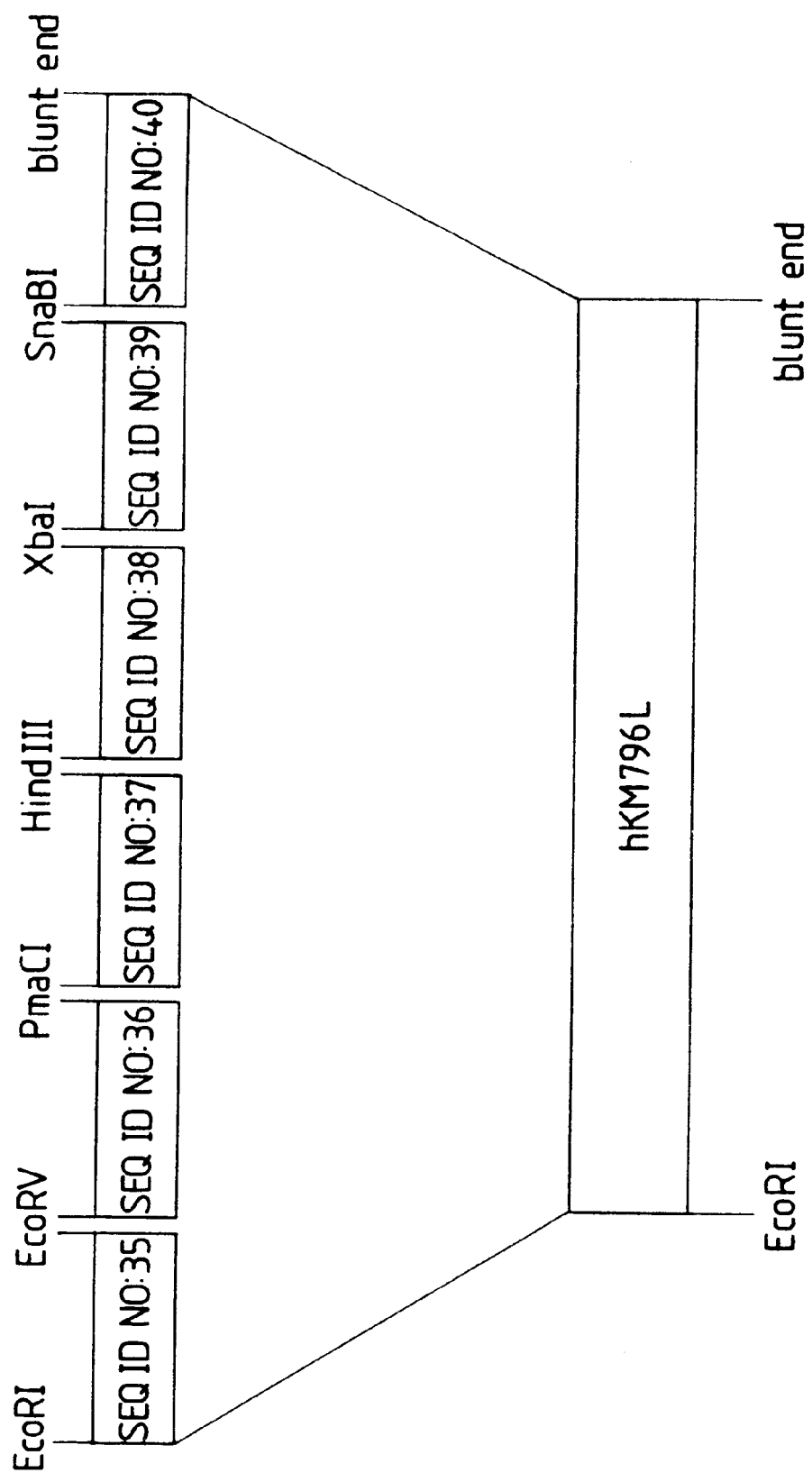

FIG. 56 shows a construction scheme for a DNA, hKM796L.

Figure 57:
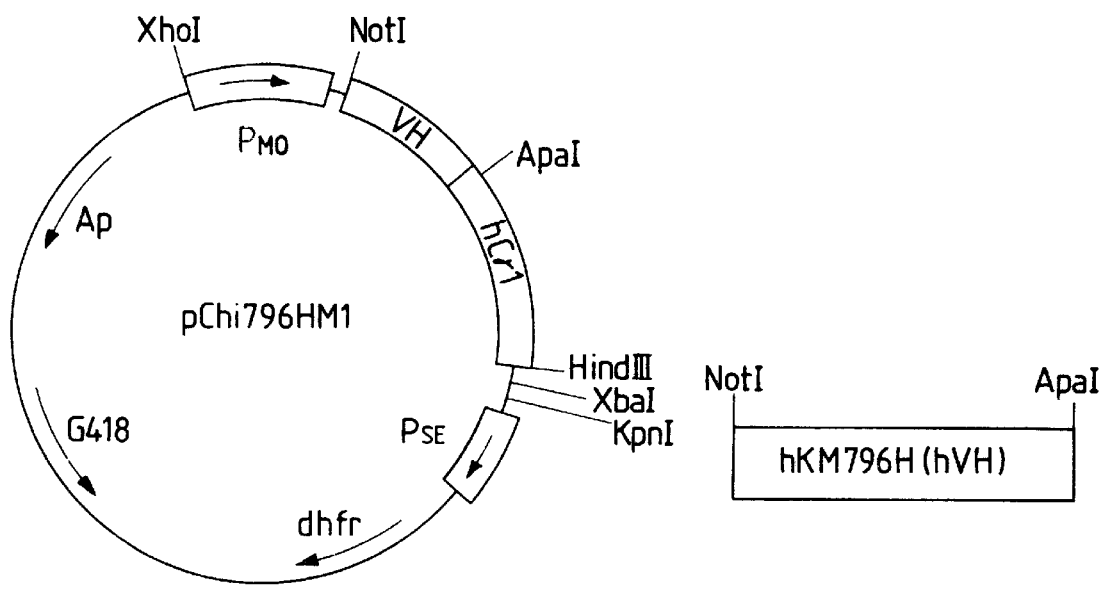
Figure 57:
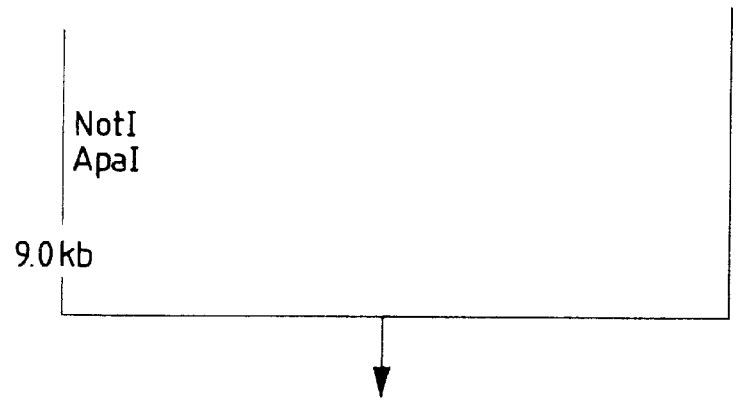
Figure 57:
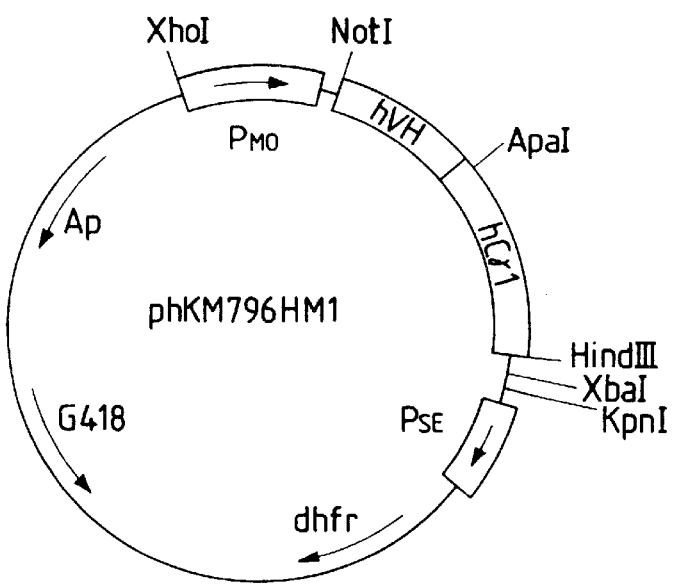

FIG. 57 shows a construction scheme for a plasmid, phKM796HM1.

Figure 58:
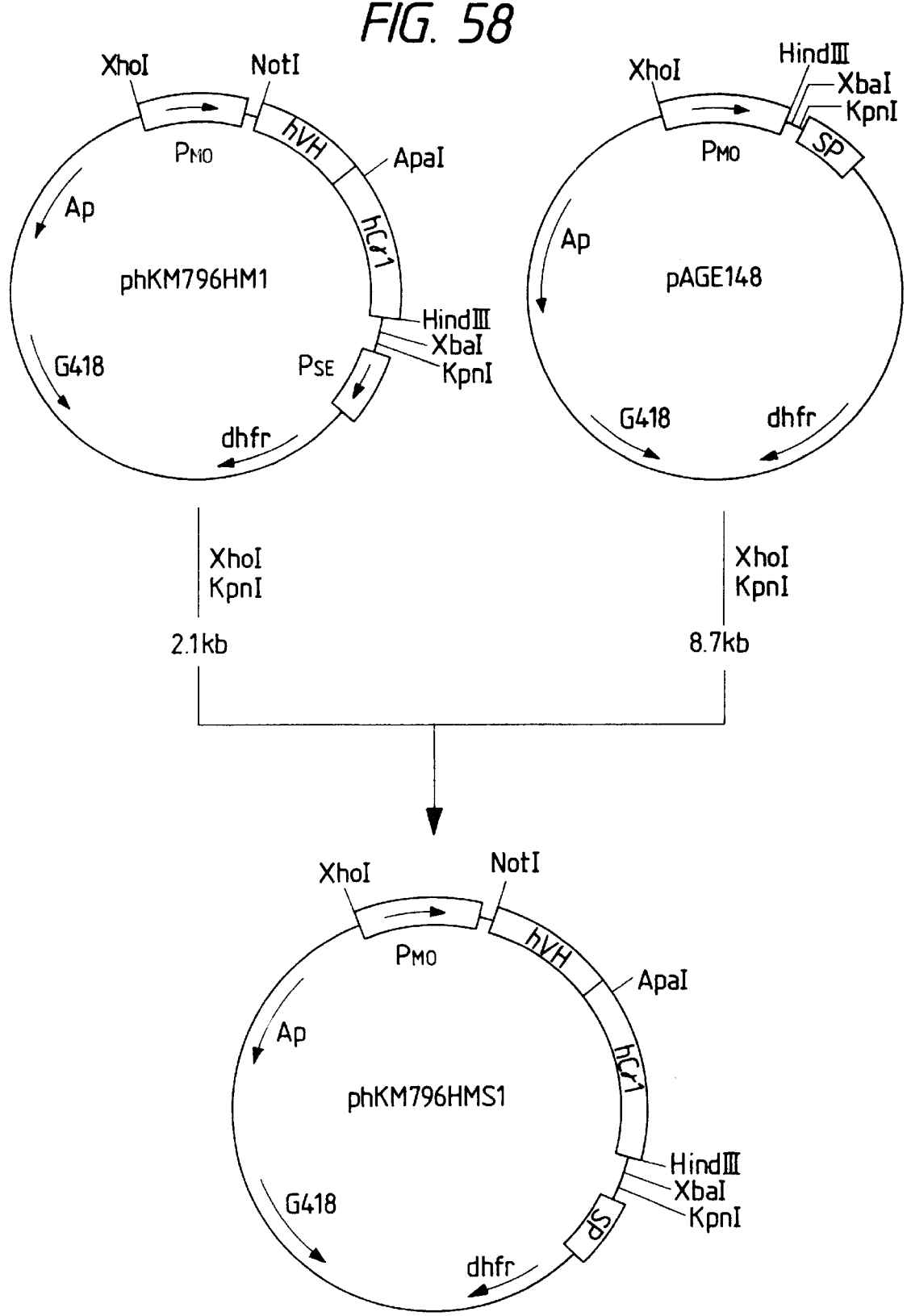

FIG. 58 shows a construction scheme for a plasmid, phKM796HMS1.

Figure 59:
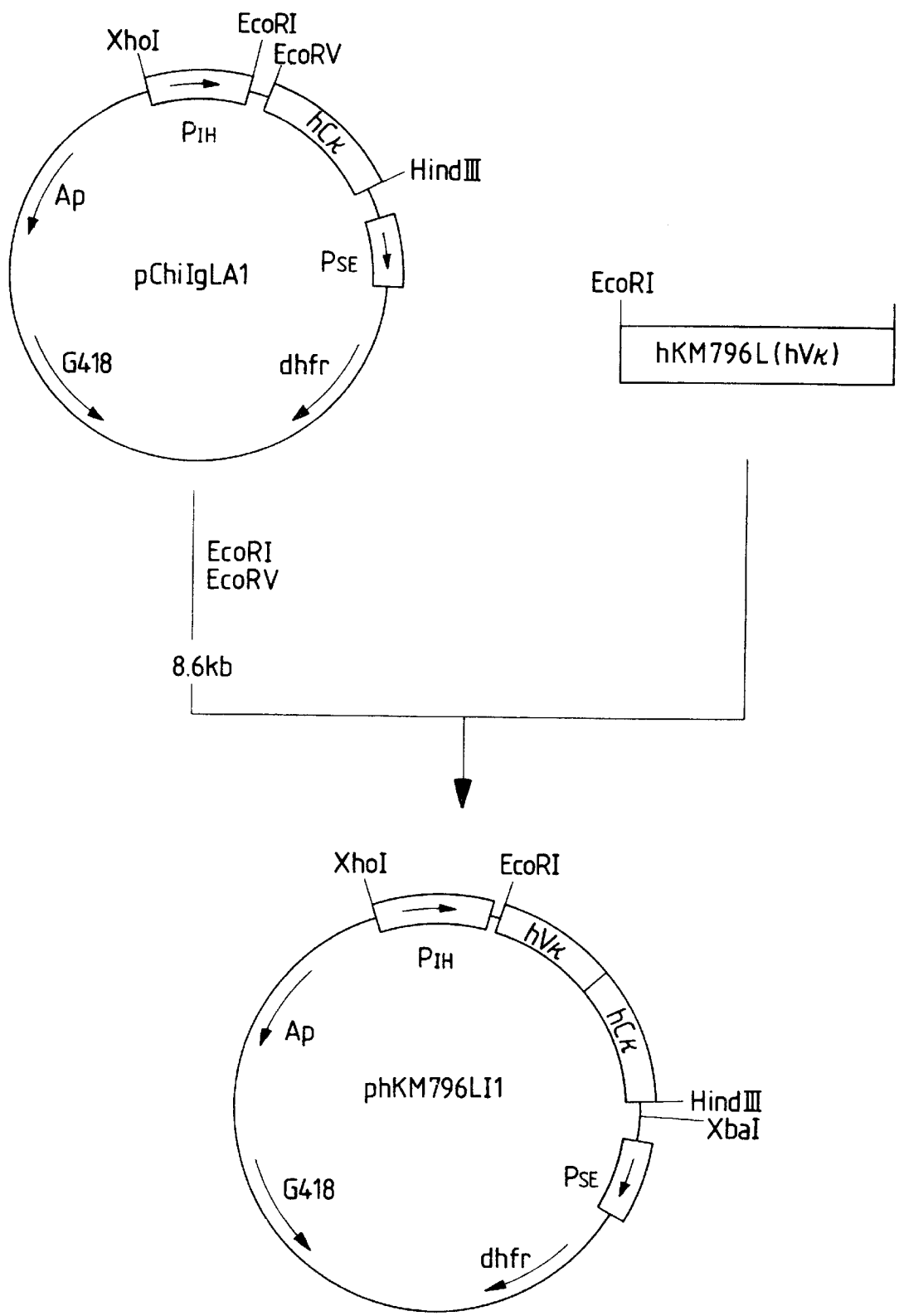

FIG. 59 shows a construction scheme for a plasmid, phKM796LI1.

Figure 60:
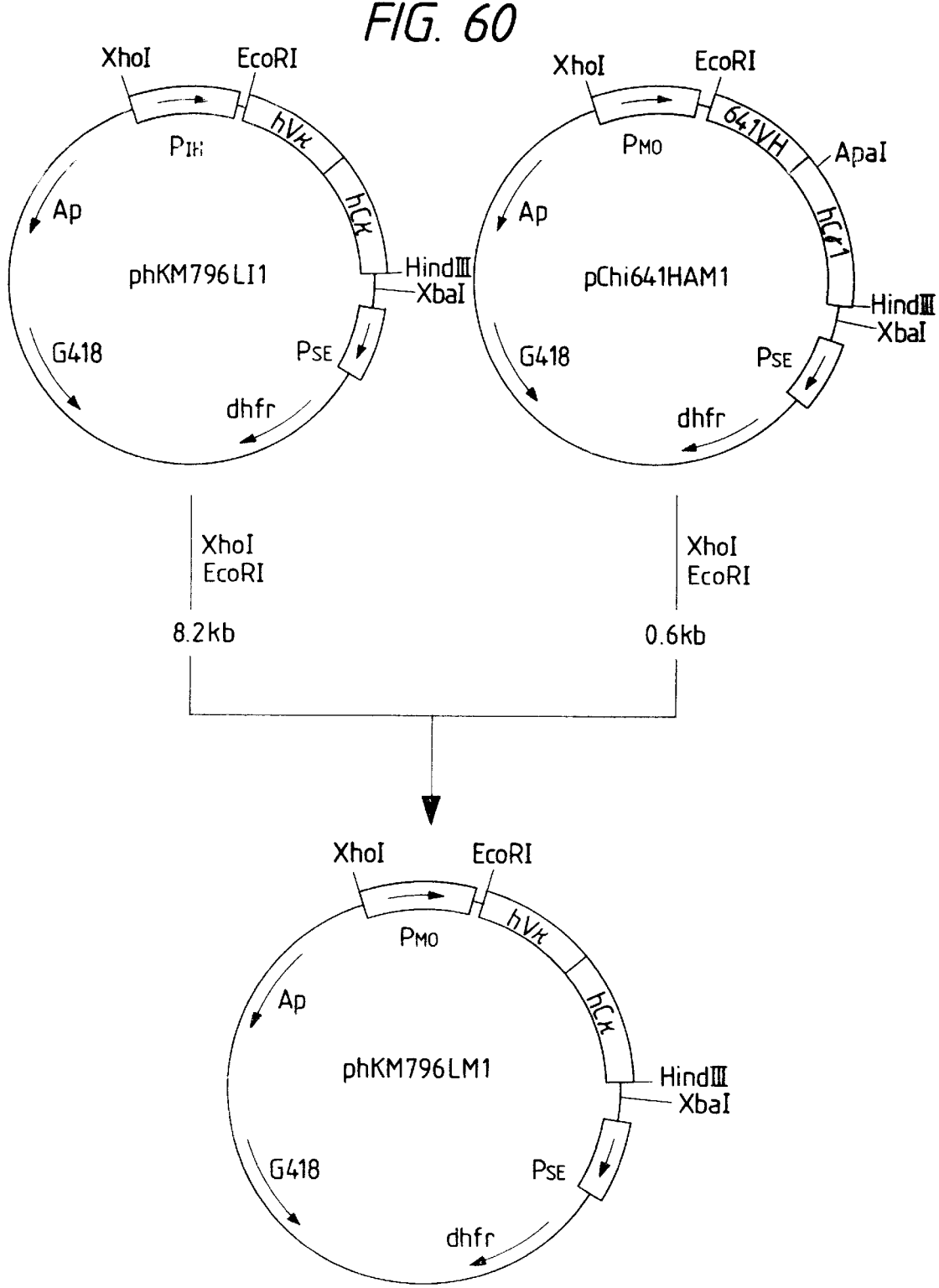

FIG. 60 shows a construction scheme for a plasmid, phKM796LM1.

Figure 61:
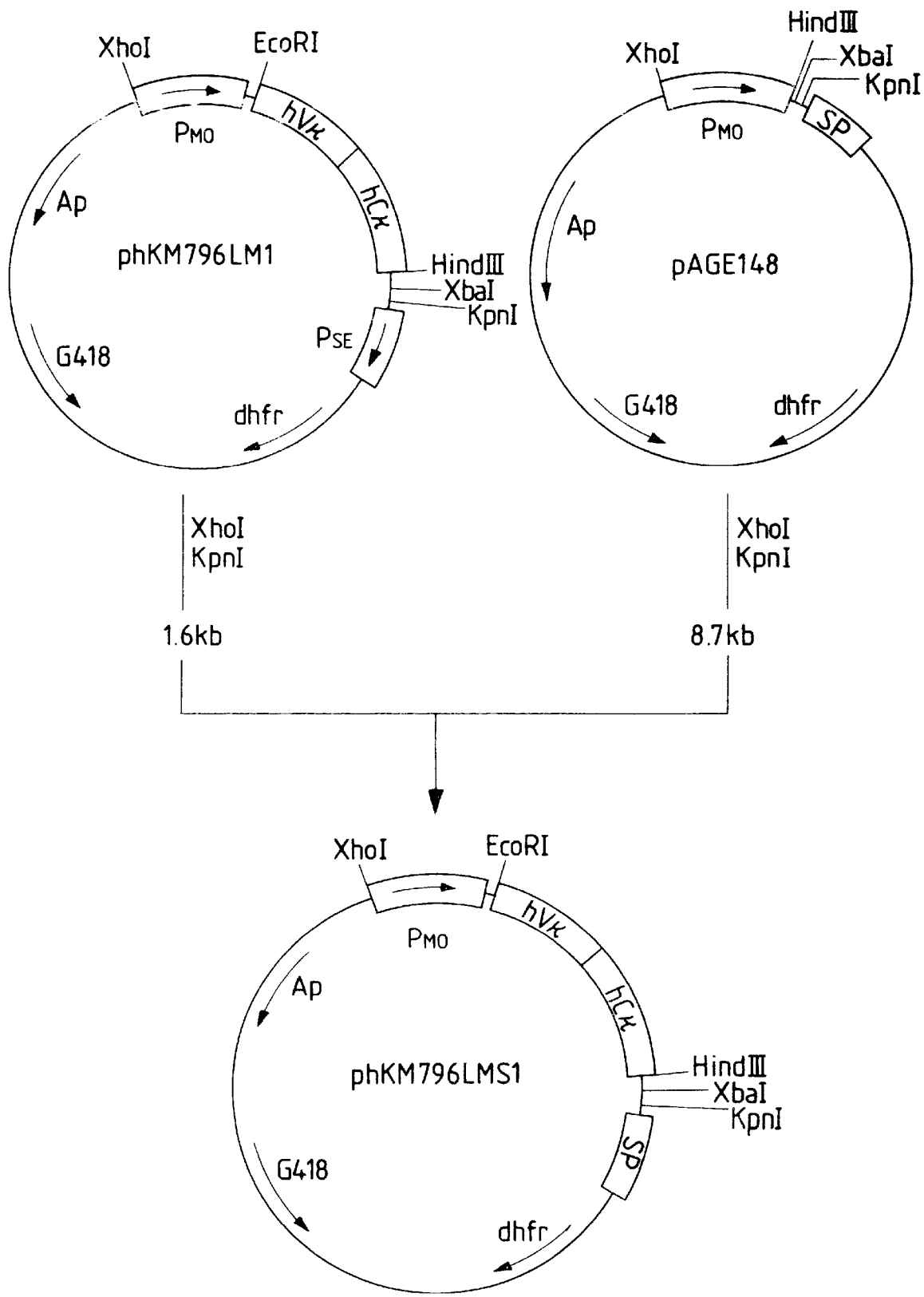

FIG. 61 shows a construction scheme for a plasmid, phKM796LMS1.

Figure 62:
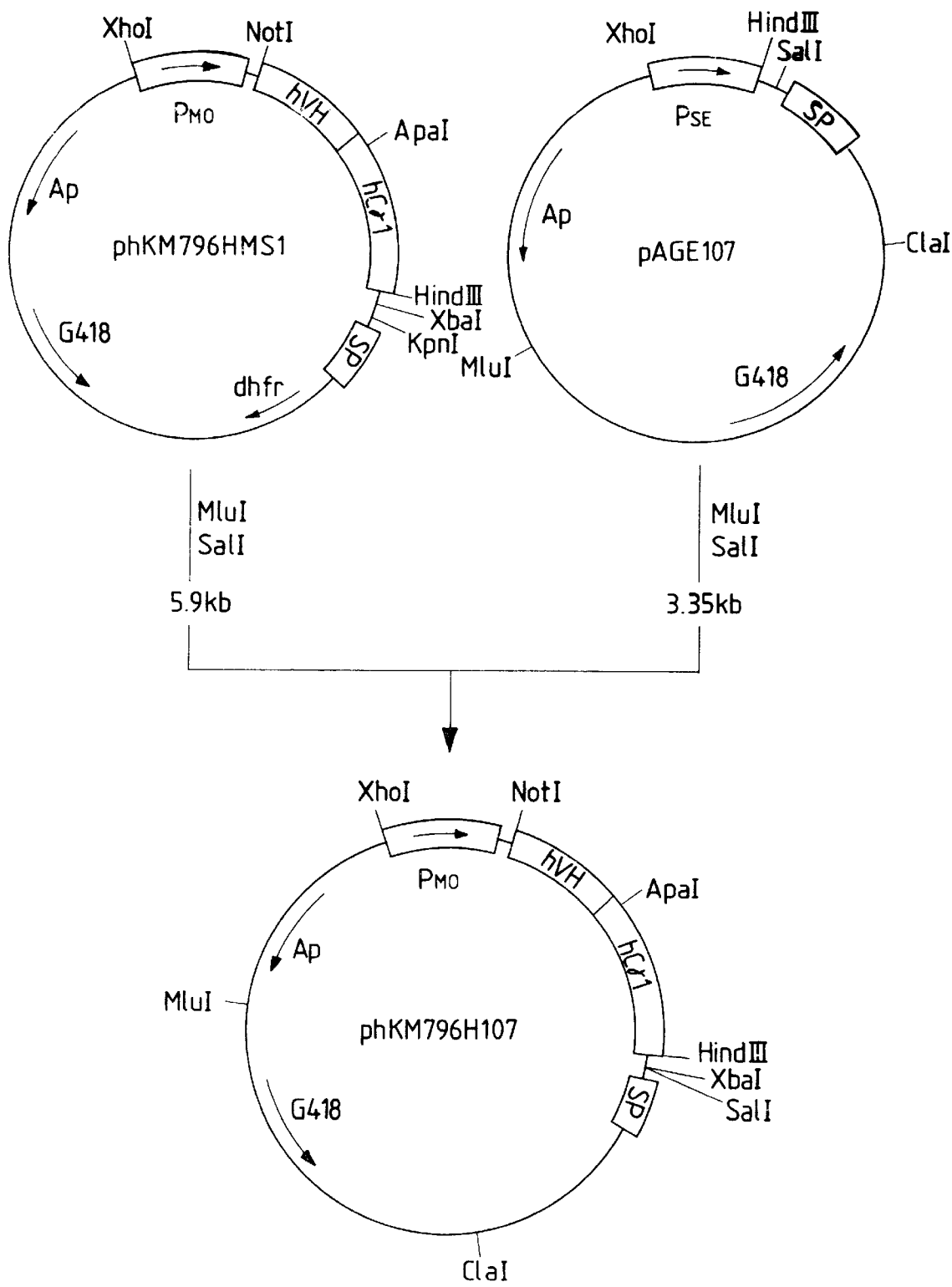

FIG. 62 shows a constfuction scheme for a plasmid, phKM796H107.

Figure 63:
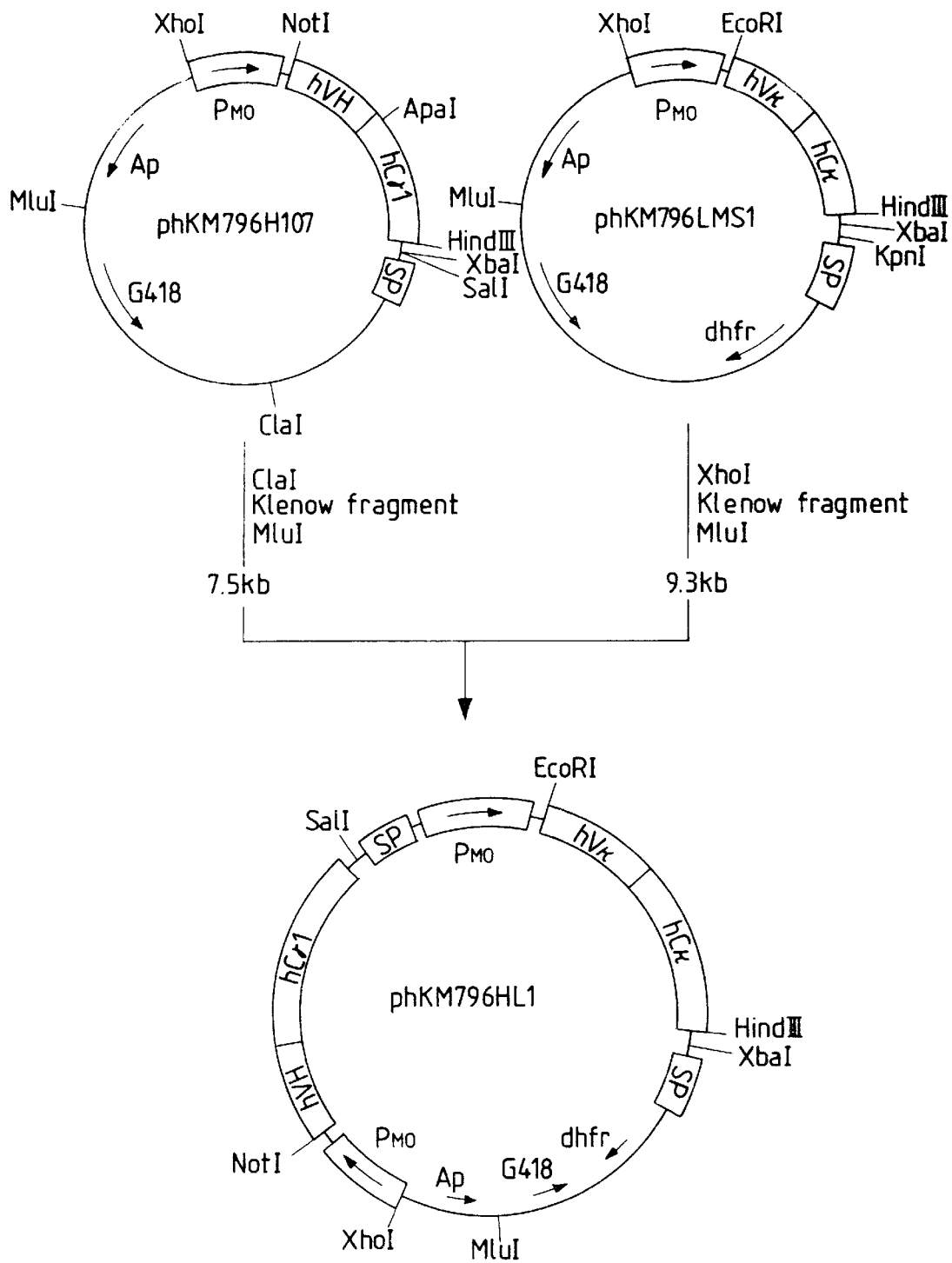

FIG. 63 shows a construction scheme for a plasmid, phKM796HL1.

FIG. 64 shows a construction scheme for a plasmid named pBSA.

FIG. 65 shows a construction scheme for a plasmid named pBSAE.

Figure 66:
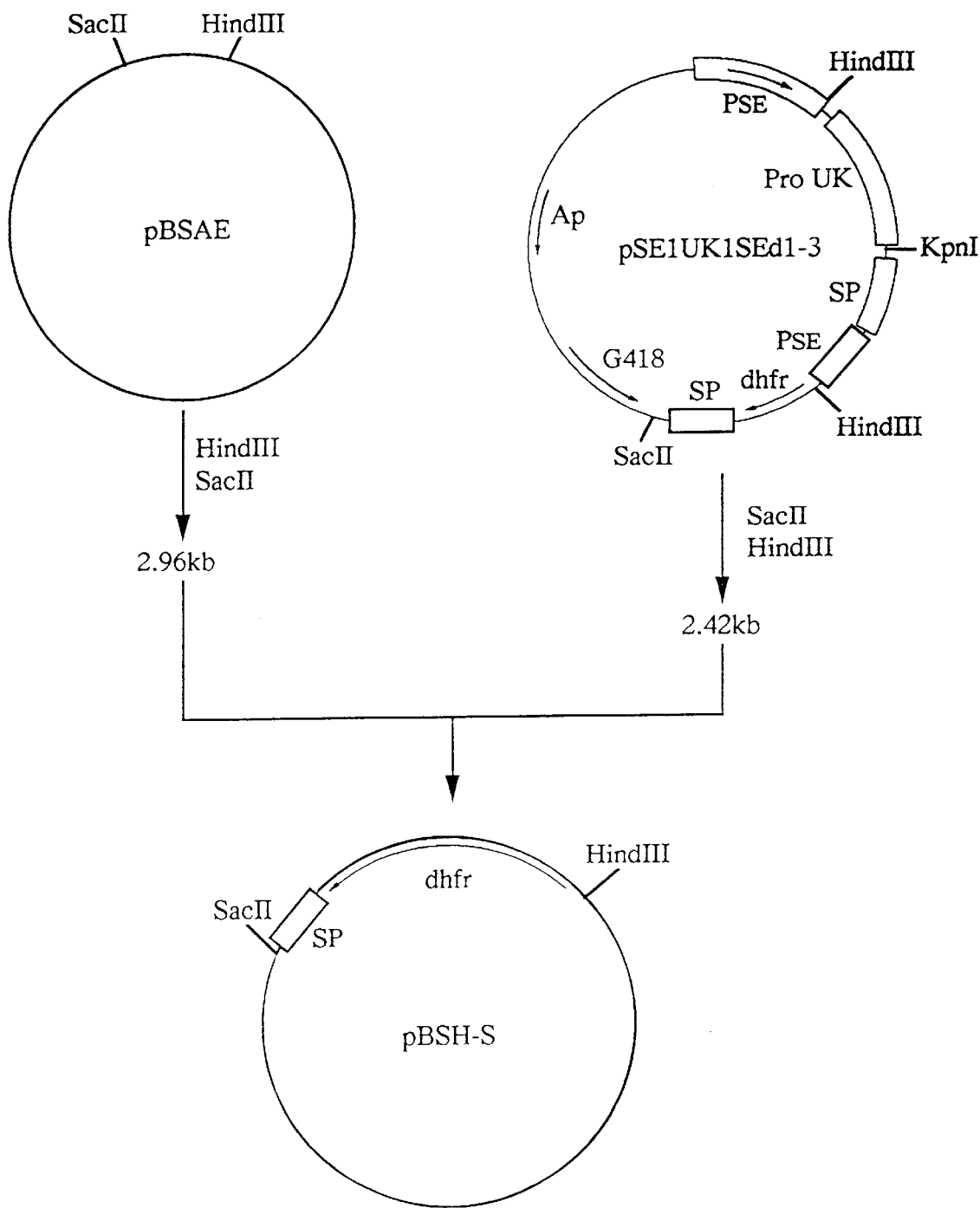

FIG. 66 shows a construction scheme for a plasmid named pBSH-S.

Figure 67:
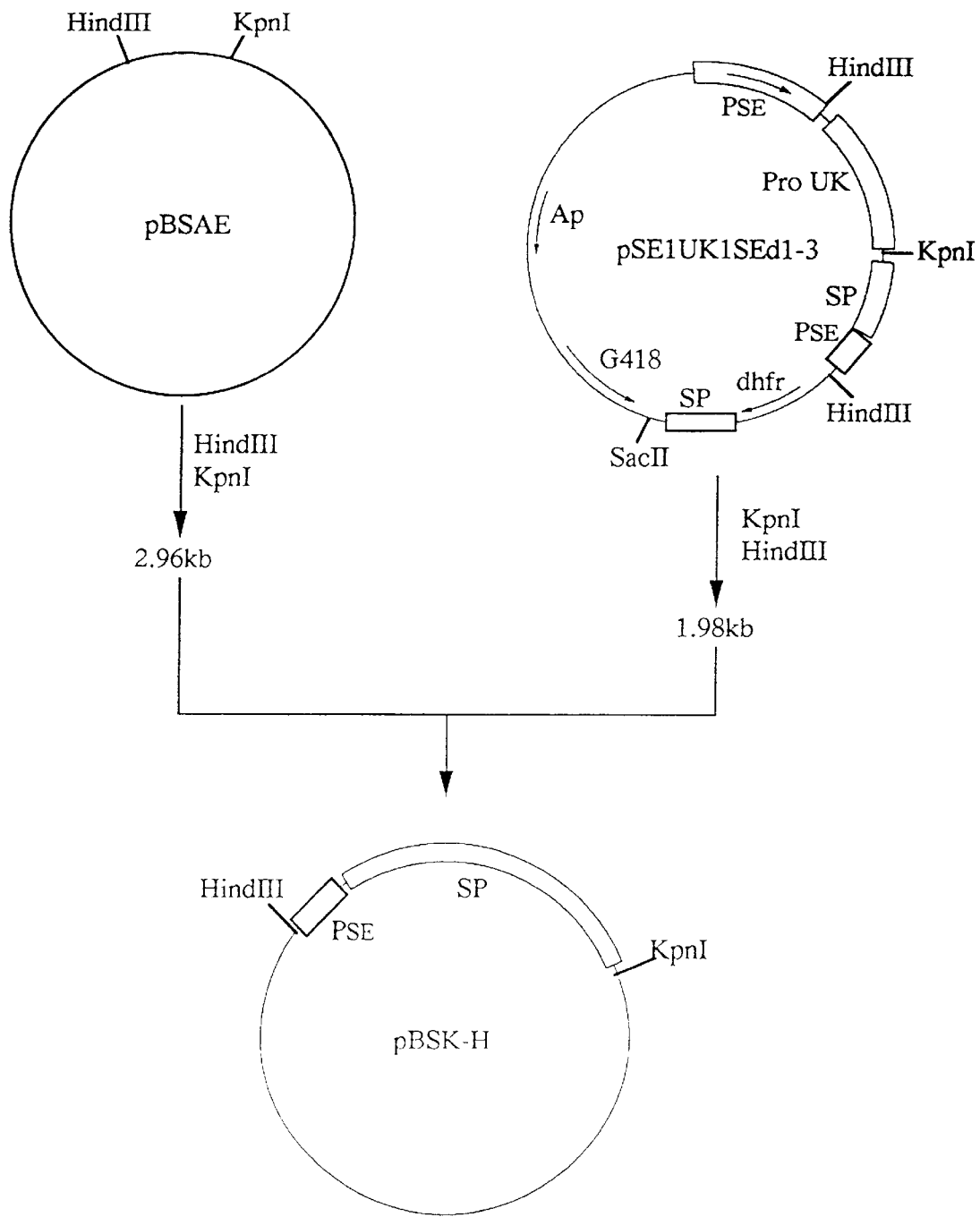

FIG. 67 shows a construction scheme for a plasmid named pBSK-H.

Figure 68:
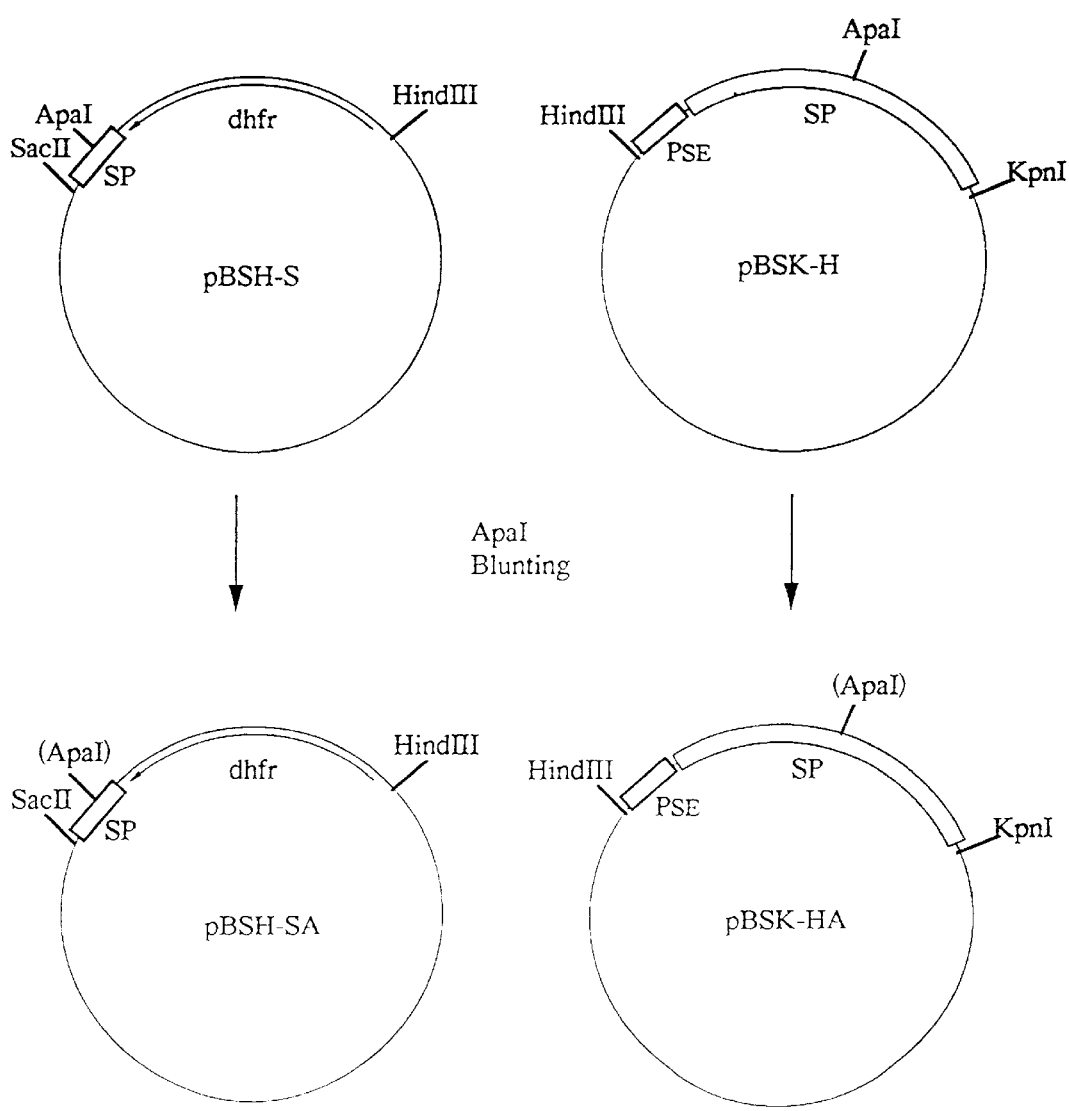

FIG. 68 shows a construction scheme for plasmids named pBSH-SA and pBSK-HA.

Figure 69:
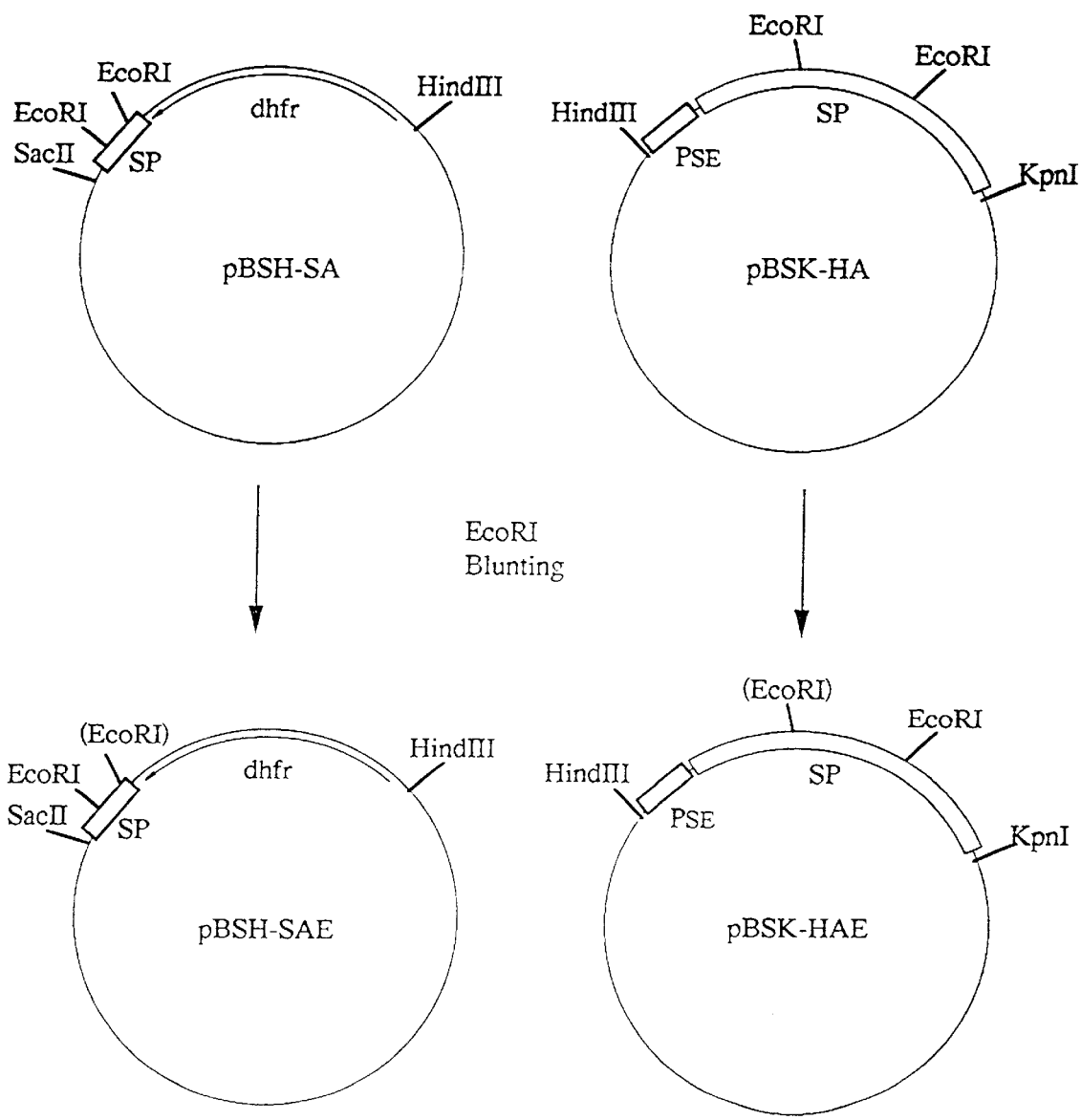

FIG. 69 shows a construction scheme for plasmids named pBSH-SAE and pBSK-HAE.

Figure 70:
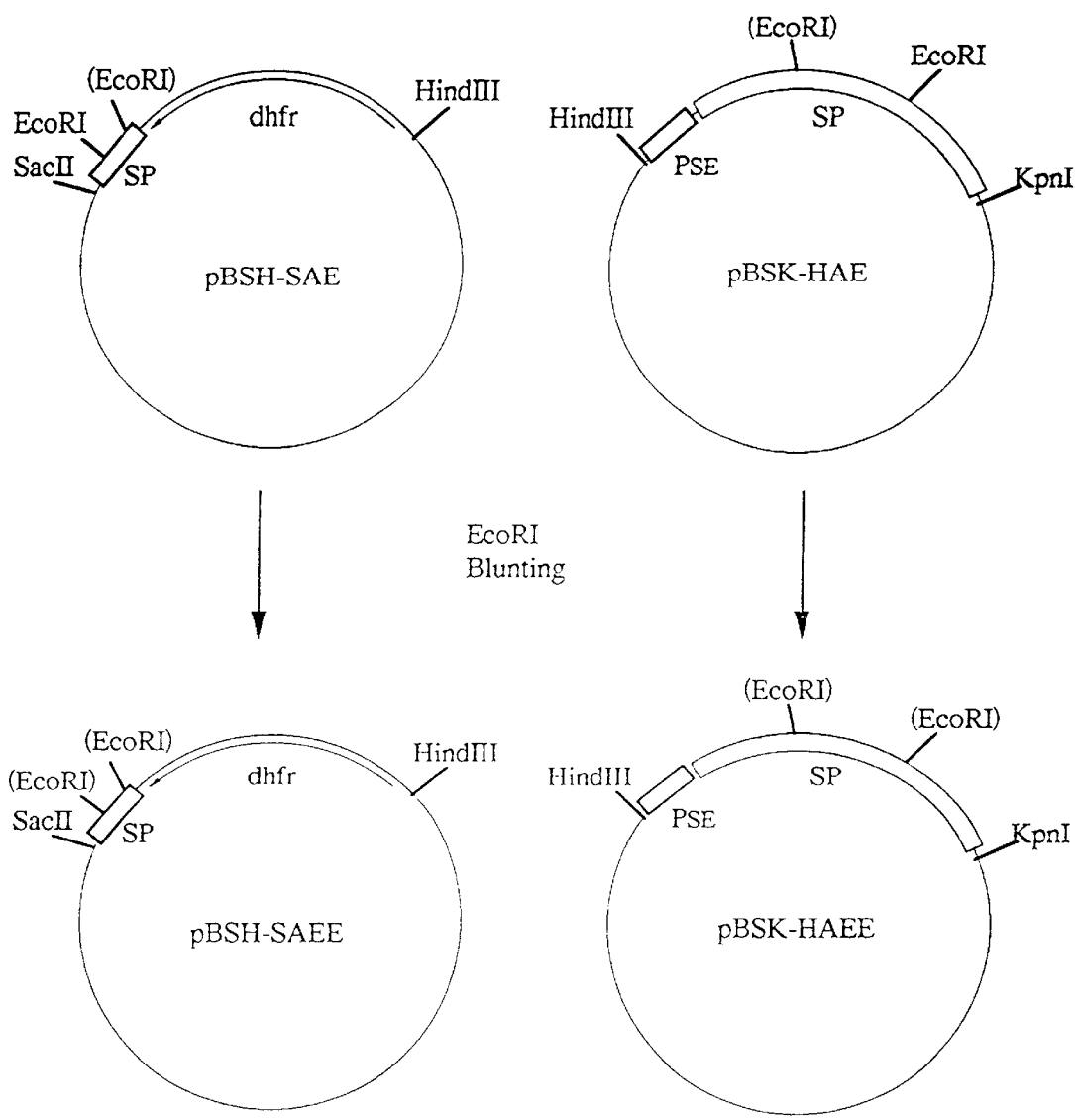

FIG. 70 shows a construction scheme for plasmids named pBSH-SAEE and pBSK-HAEE.

Figure 71:
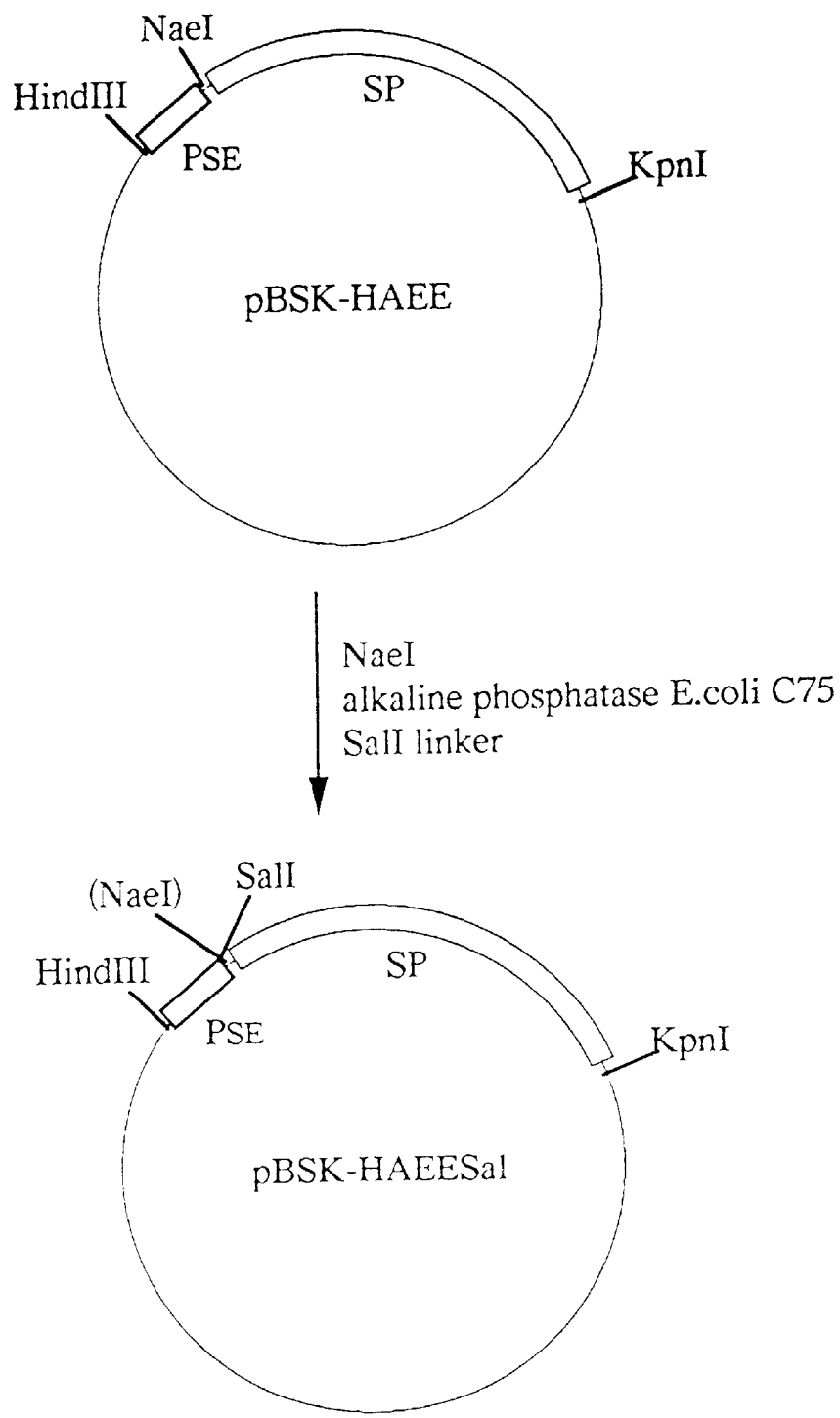

FIG. 71 shows a construction scheme for a plasmid named pBSK-HAEESal.

Figure 72:
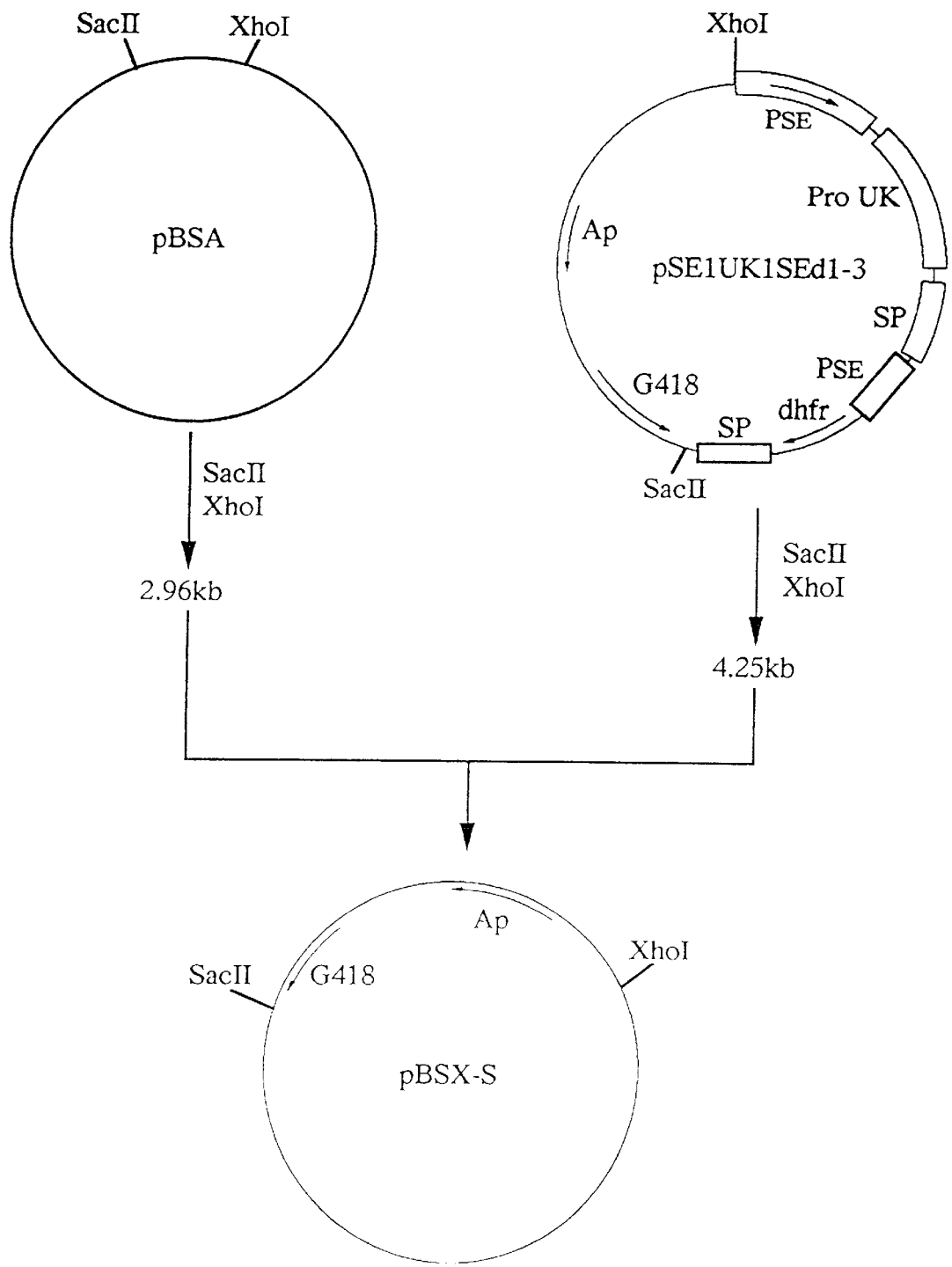

FIG. 72 shows a construction scheme for a plasmid named pBSX-S.

Figure 73:
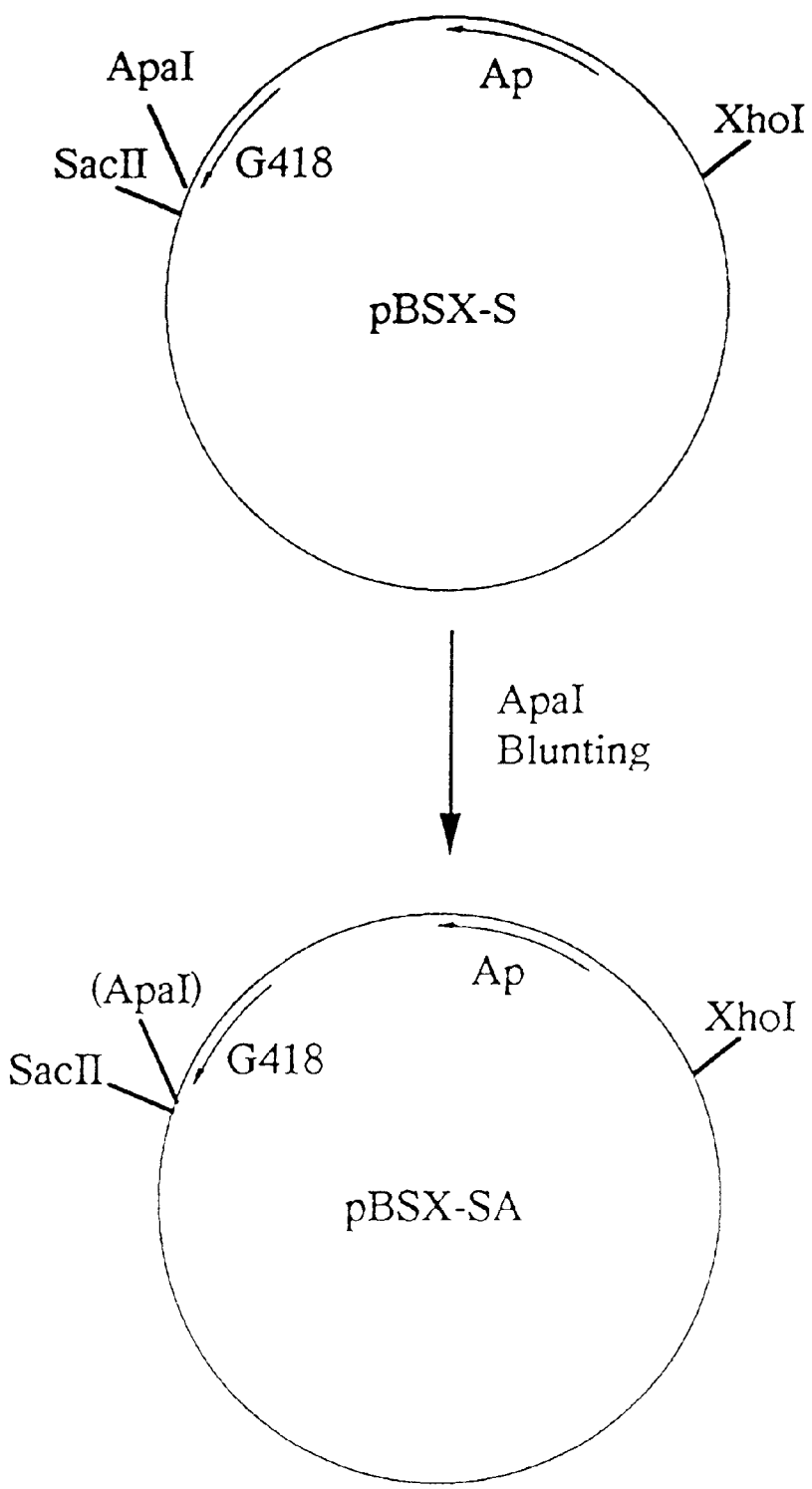

FIG. 73 shows a construction scheme for a plasmid named pBSX-SA.

Figure 74:
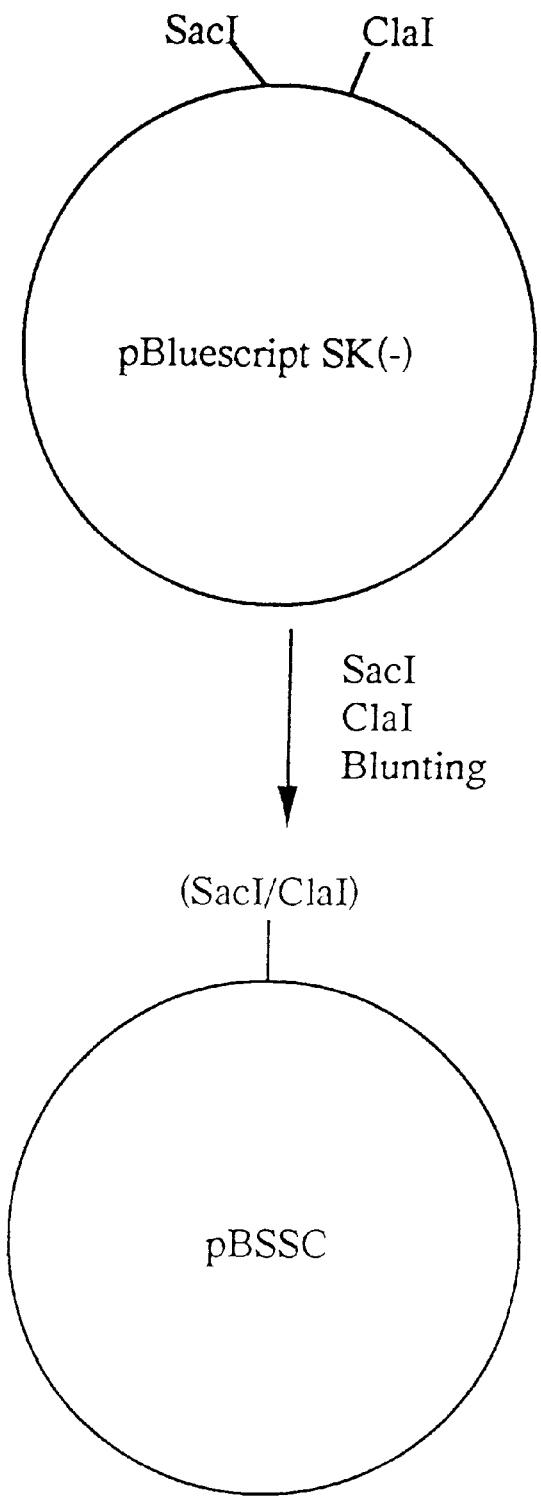

FIG. 74 shows a construction scheme for a plasmid named pBSSC.

Figure 75:
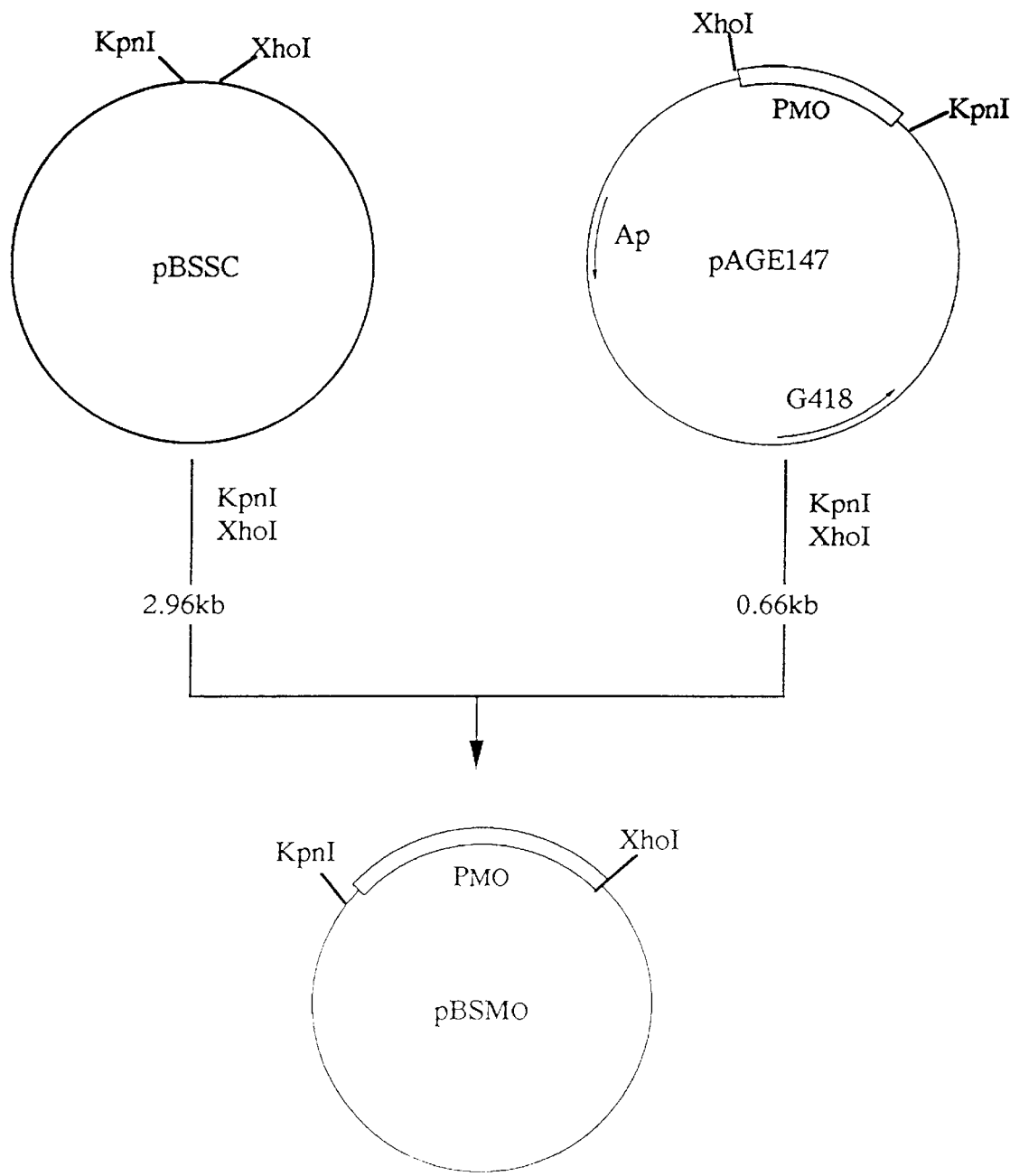

FIG. 75 shows a construction scheme for a plasmid named pBSMo.

Figure 76:
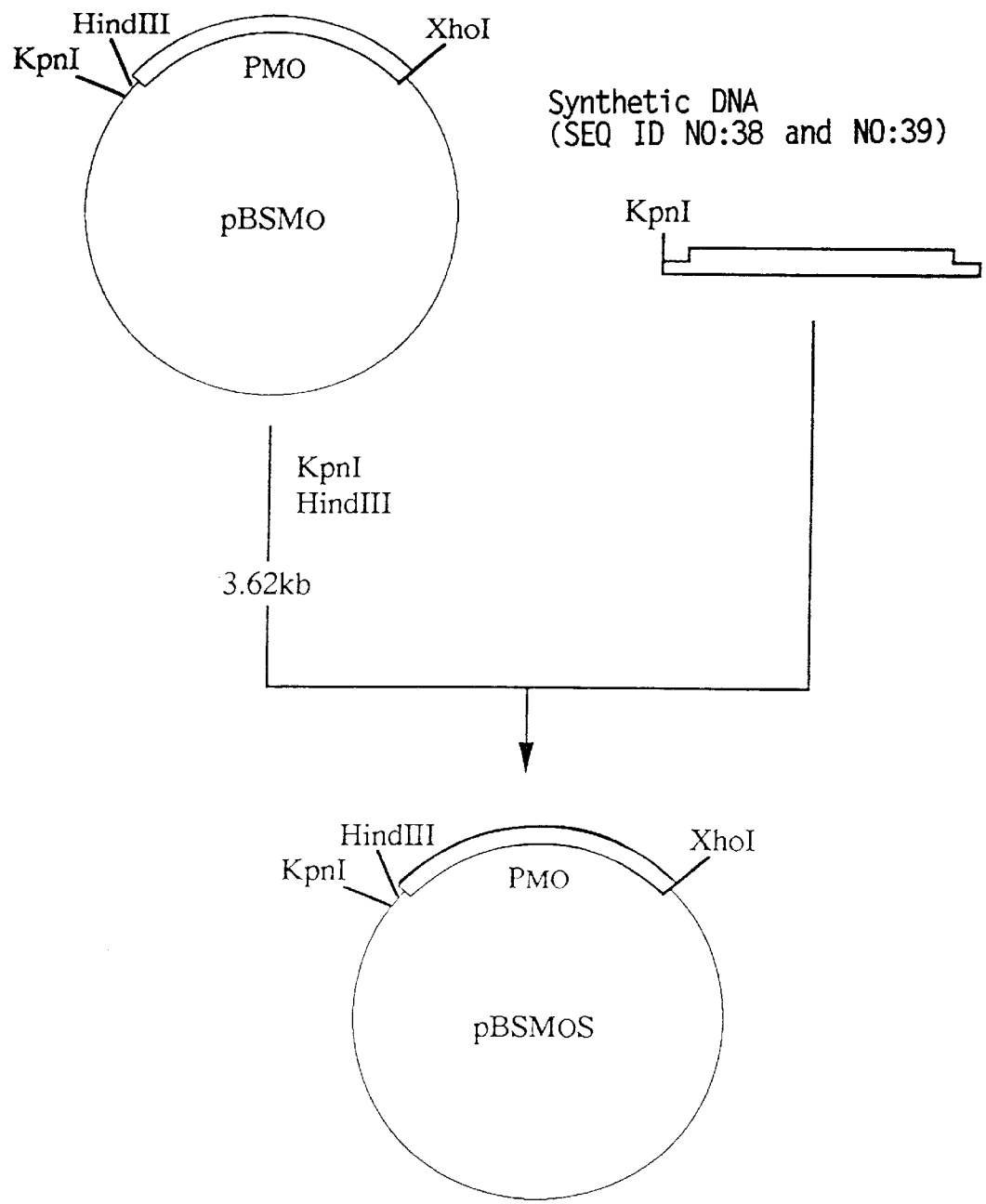

FIG. 76 shows a construction scheme for a plasmid named pBSMoS.

Figure 77:
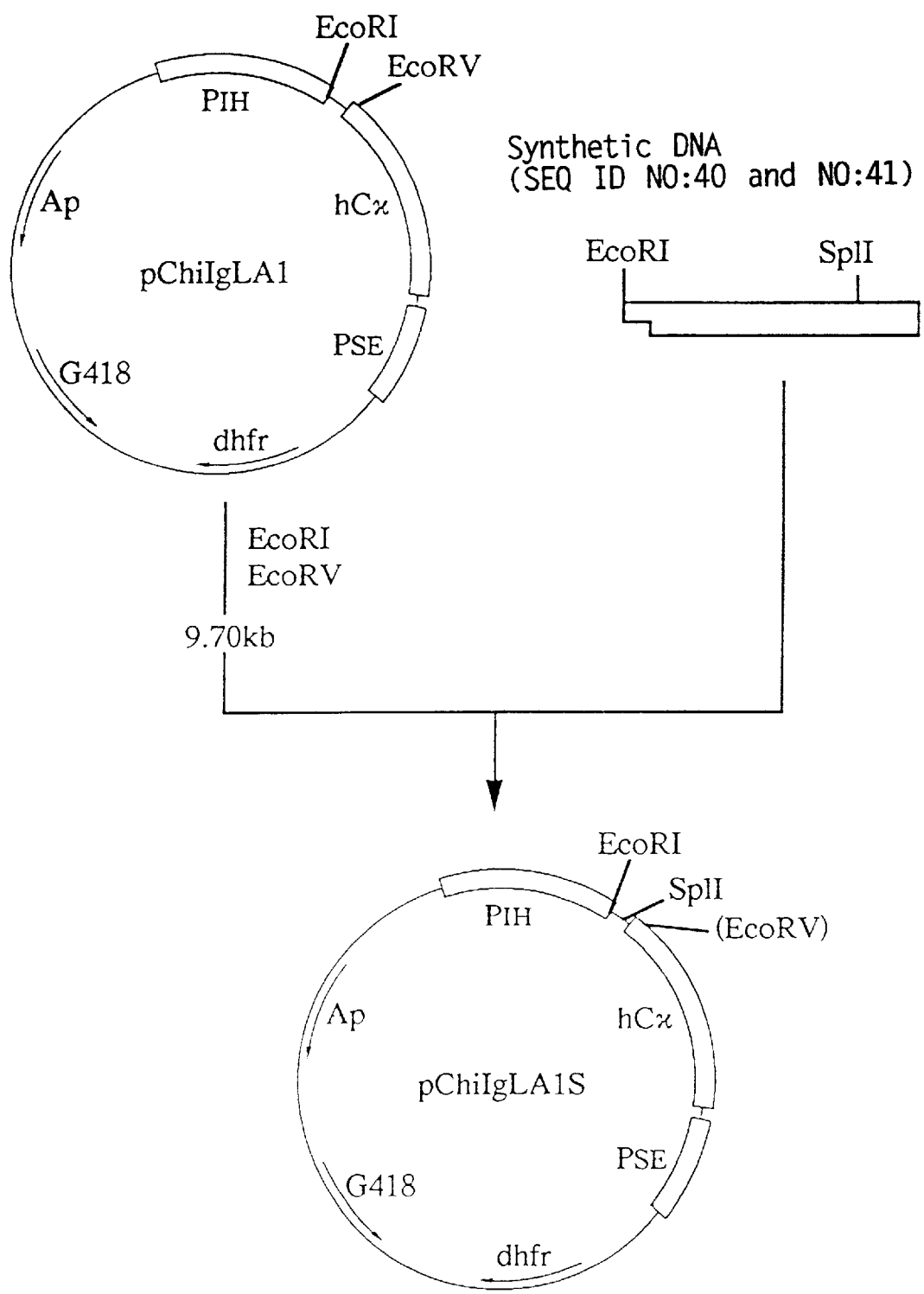

FIG. 77 shows a construction scheme for a plasmid named pChiIgLA1S.

Figure 78:
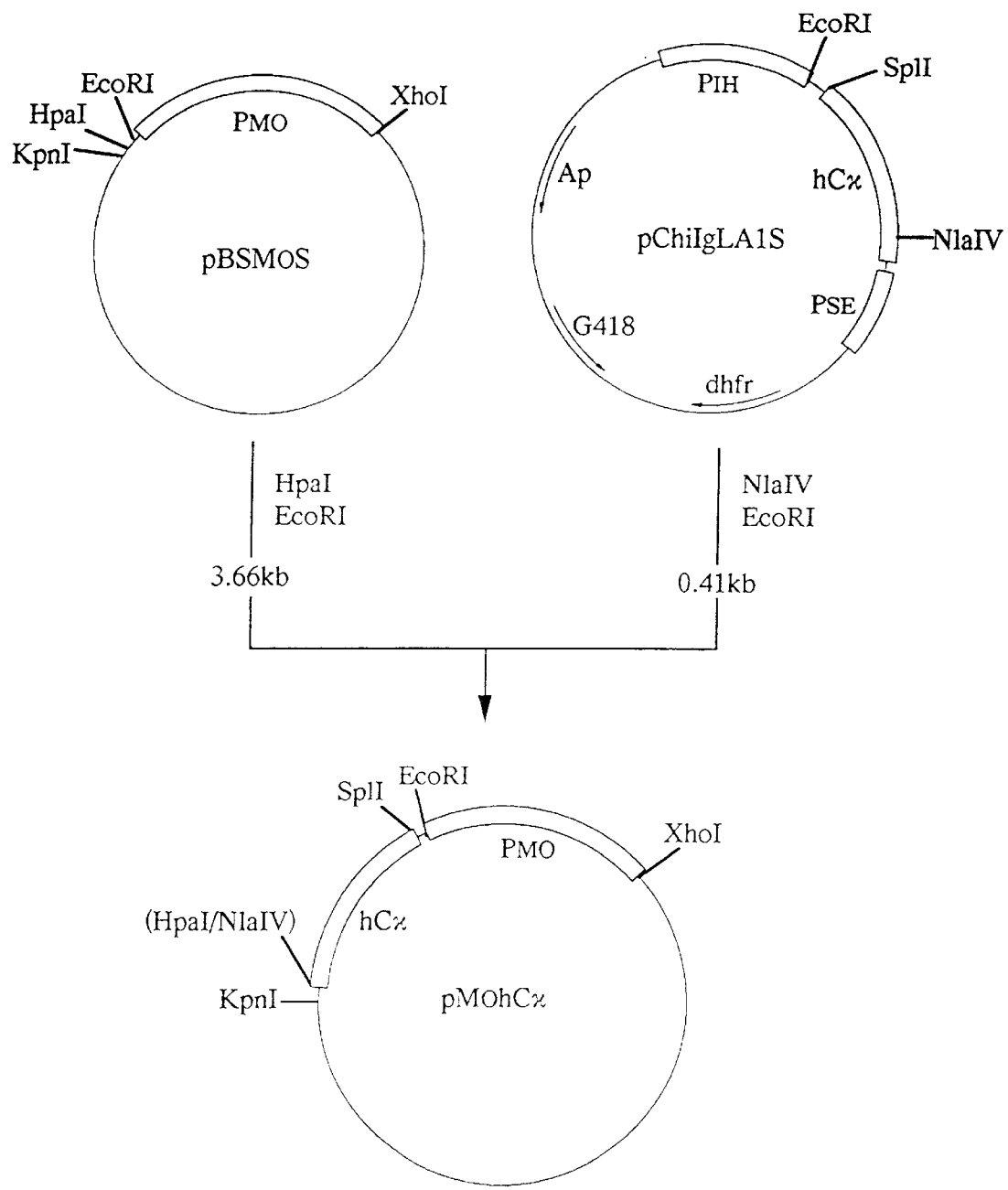

FIG. 78 shows a construction scheme for a plasmid named pMohCκ.

Figure 79:
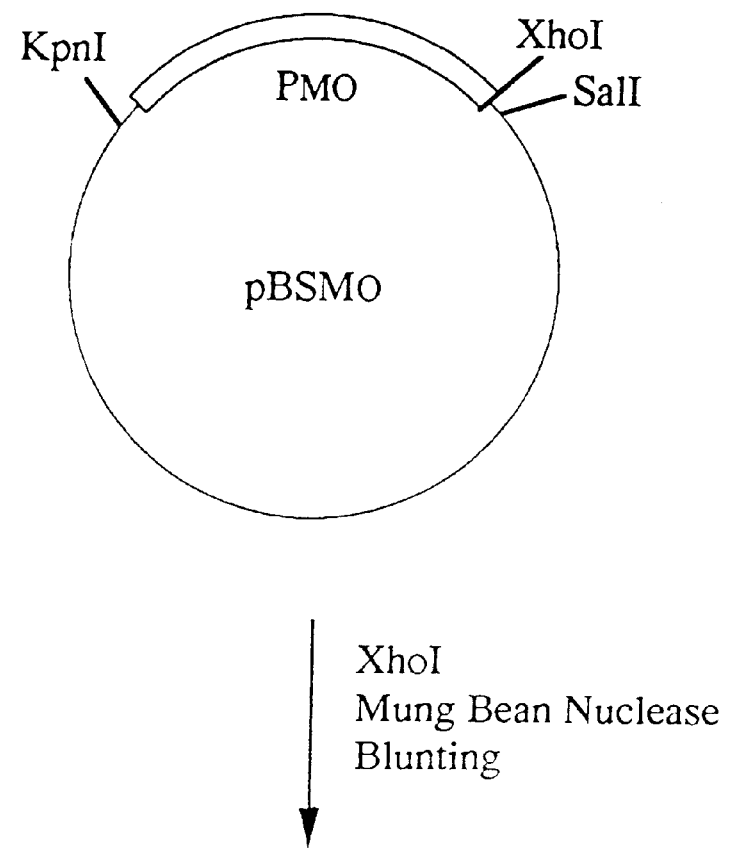
Figure 79:
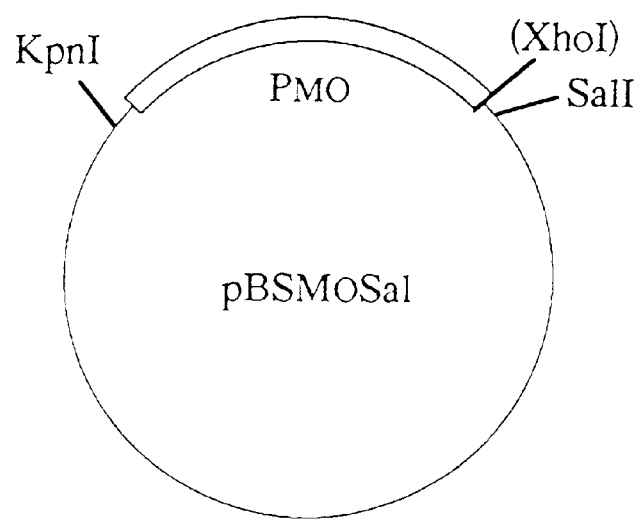

FIG. 79 shows a construction scheme for a plasmid named pBSMoSal.

Figure 80:
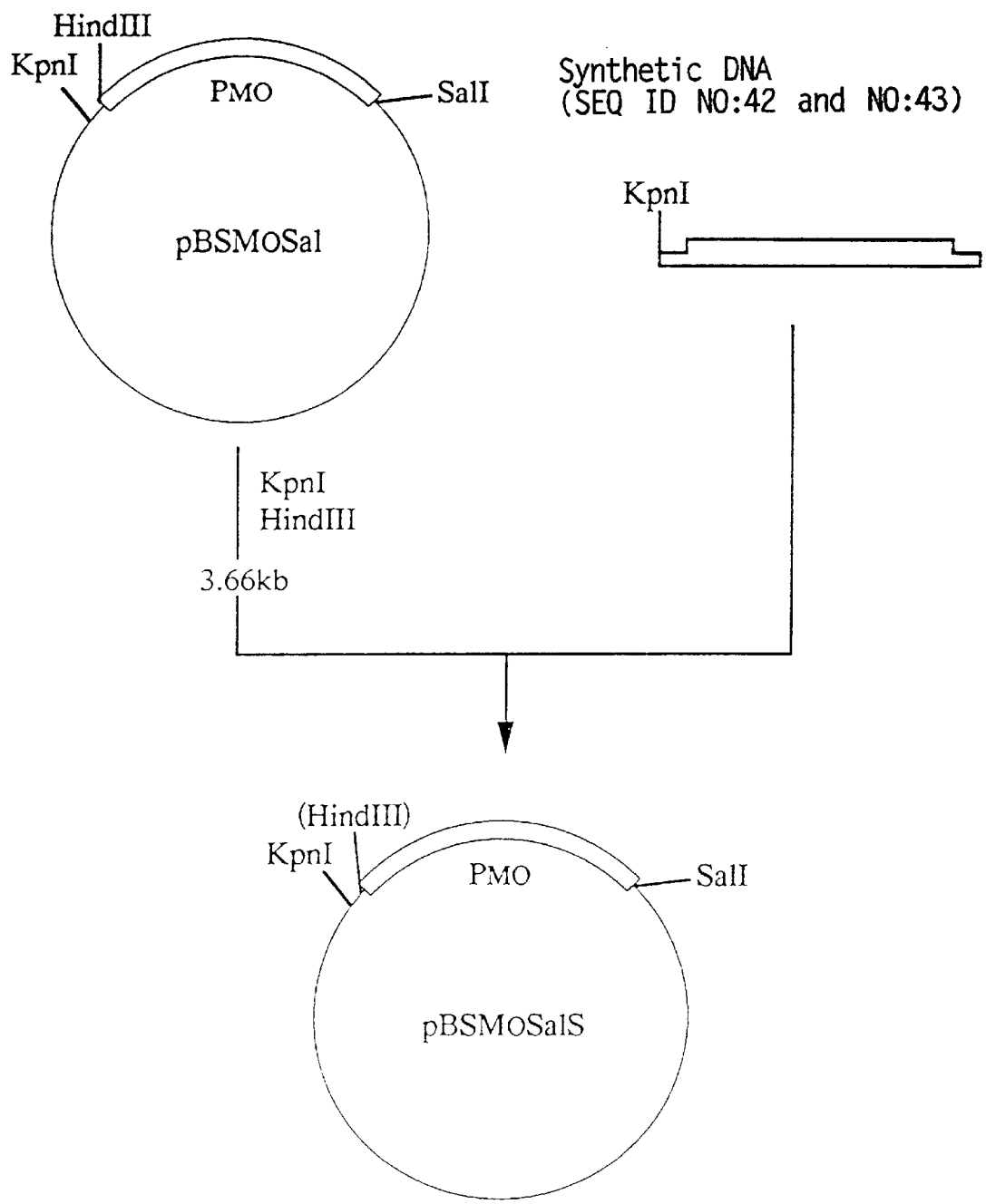

FIG. 80 shows a construction scheme for a plasmid named pBSMoSalS.

Figure 81:
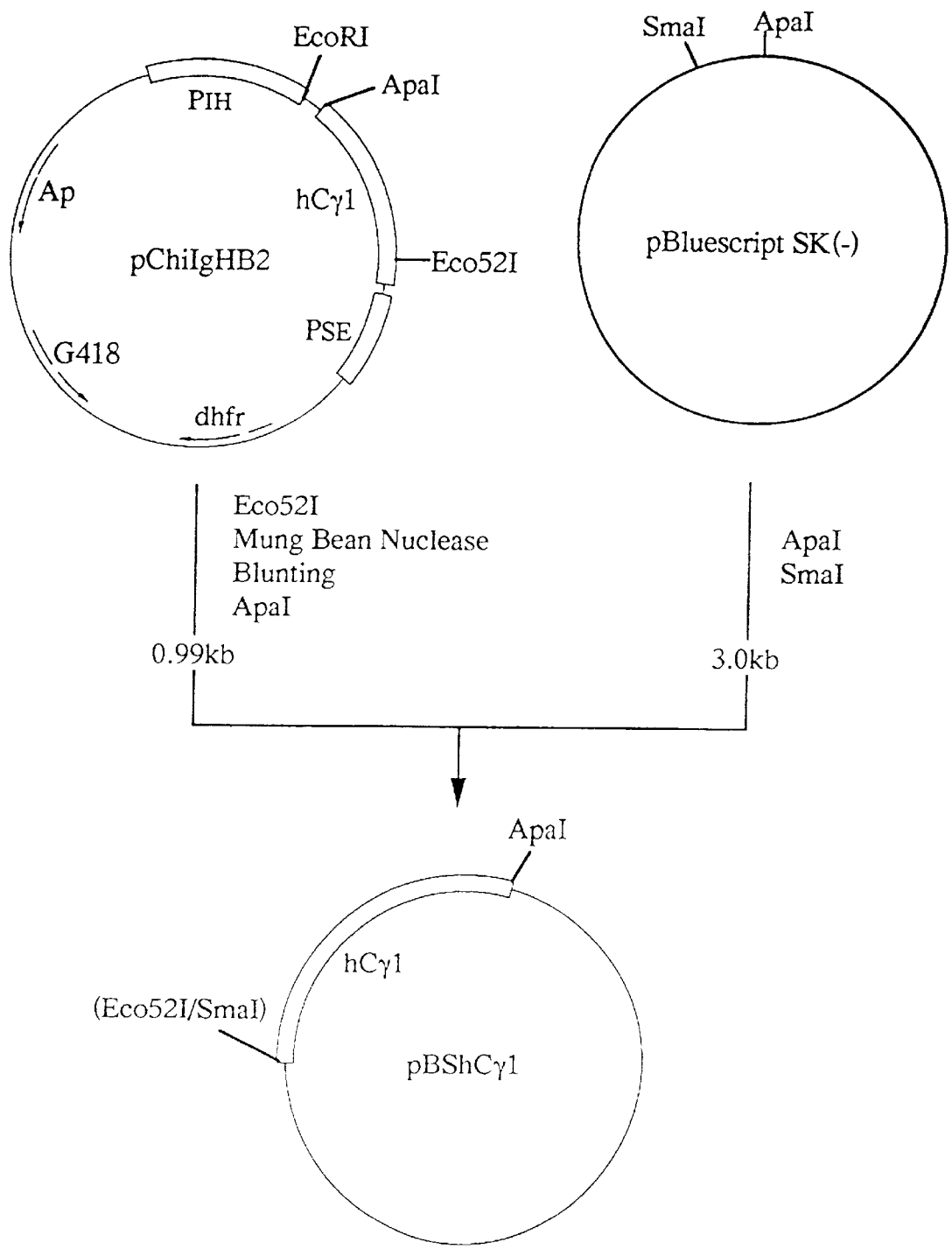

FIG. 81 shows a construction scheme for a plasmid named pBShCγ1.

Figure 82:
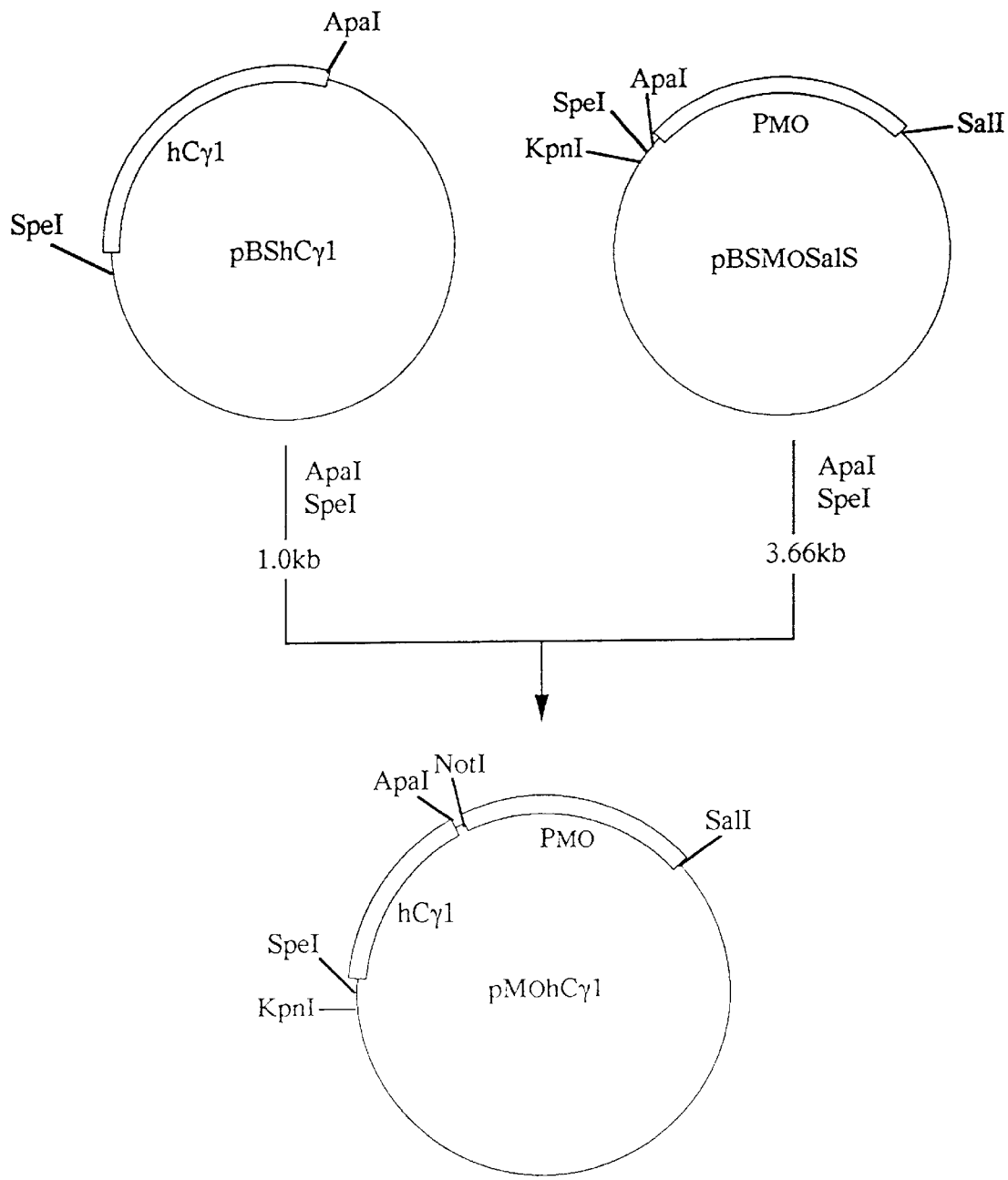

FIG. 82 shows a construction scheme for a plasmid named pMohCγ1.

Figure 83:
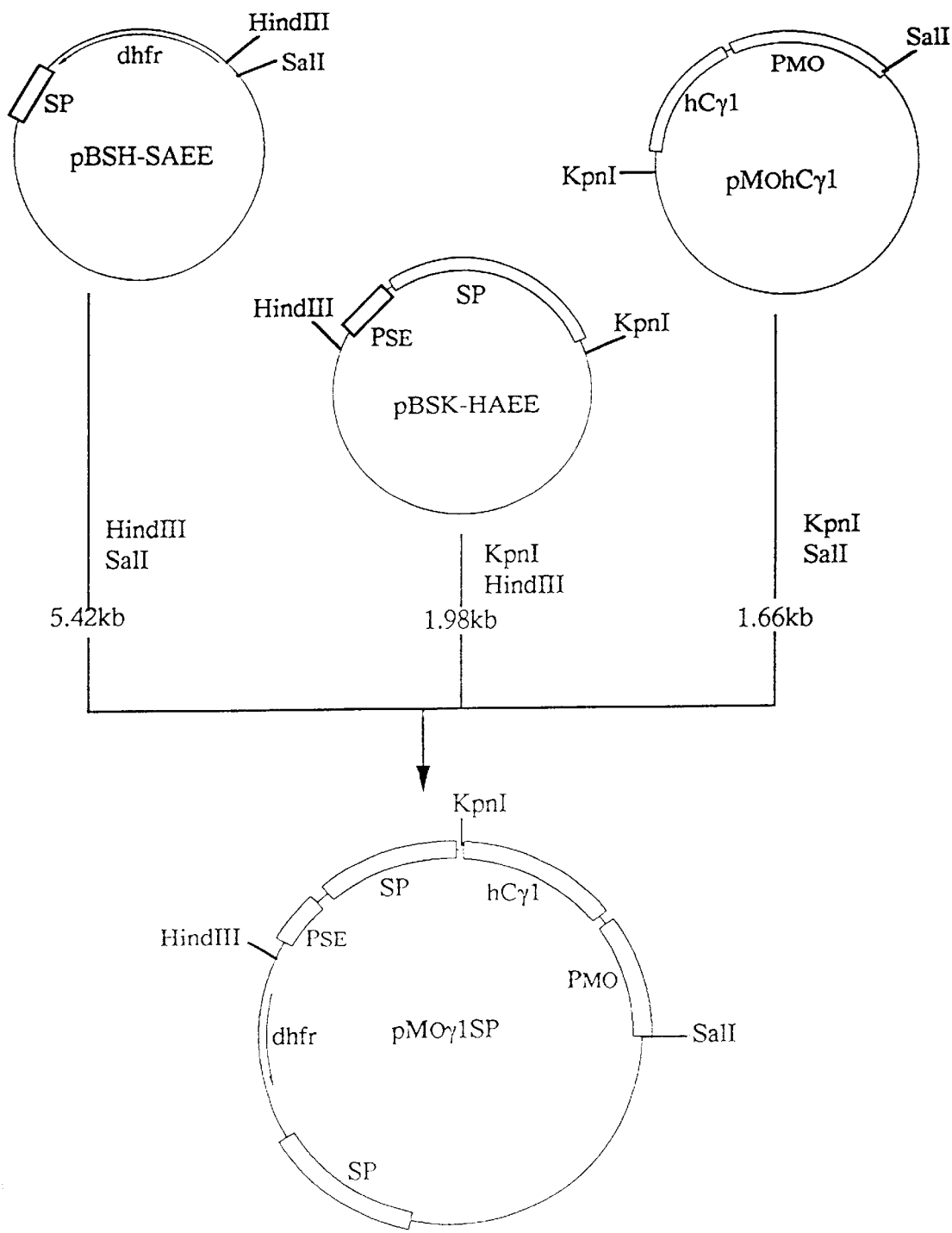

FIG. 83 shows a construction scheme for a plasmid named pMoγ1SP.

Figure 84:
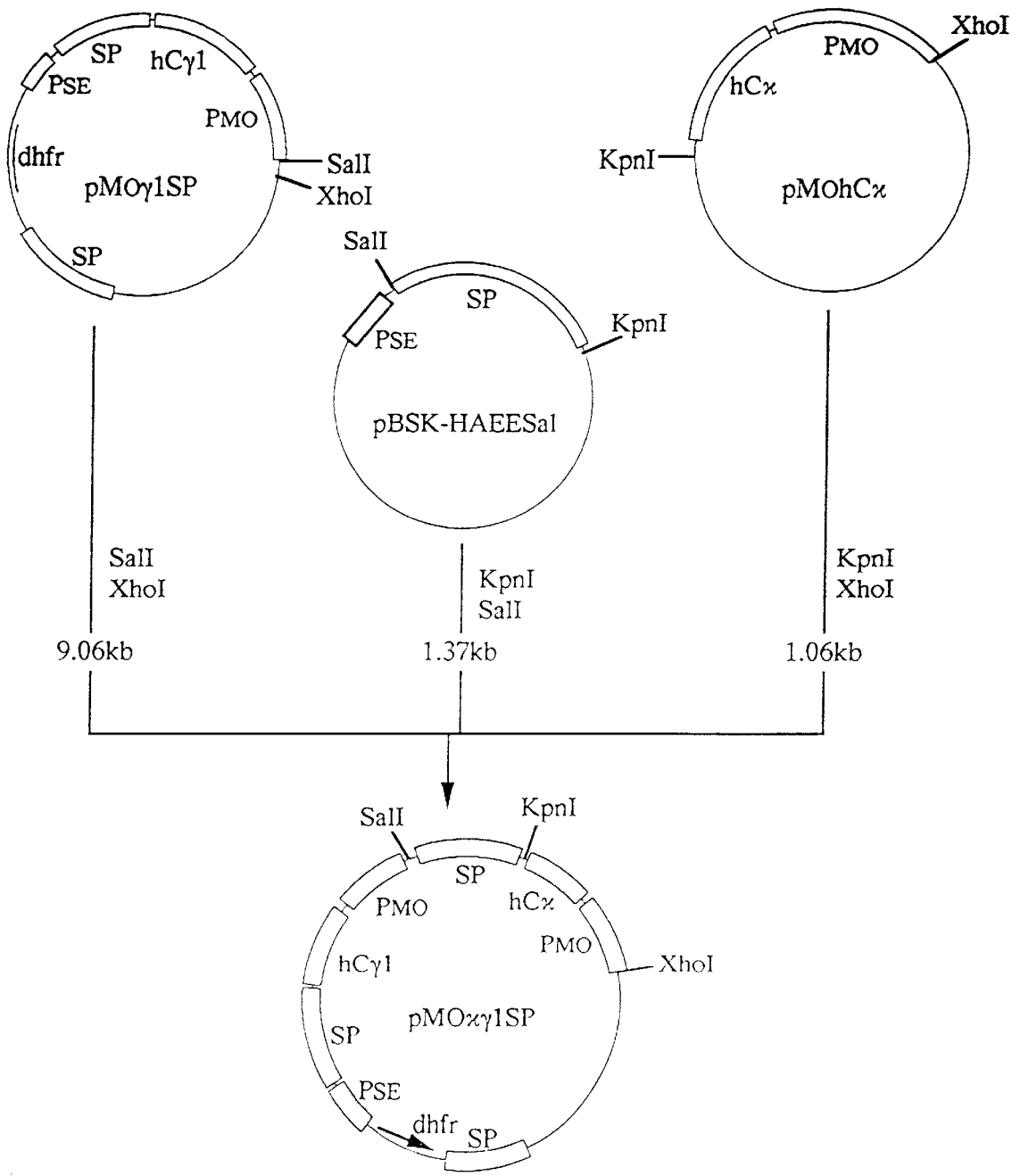

FIG. 84 shows a construction scheme for a plasmid named pMoκγ1SP.

Figure 85:
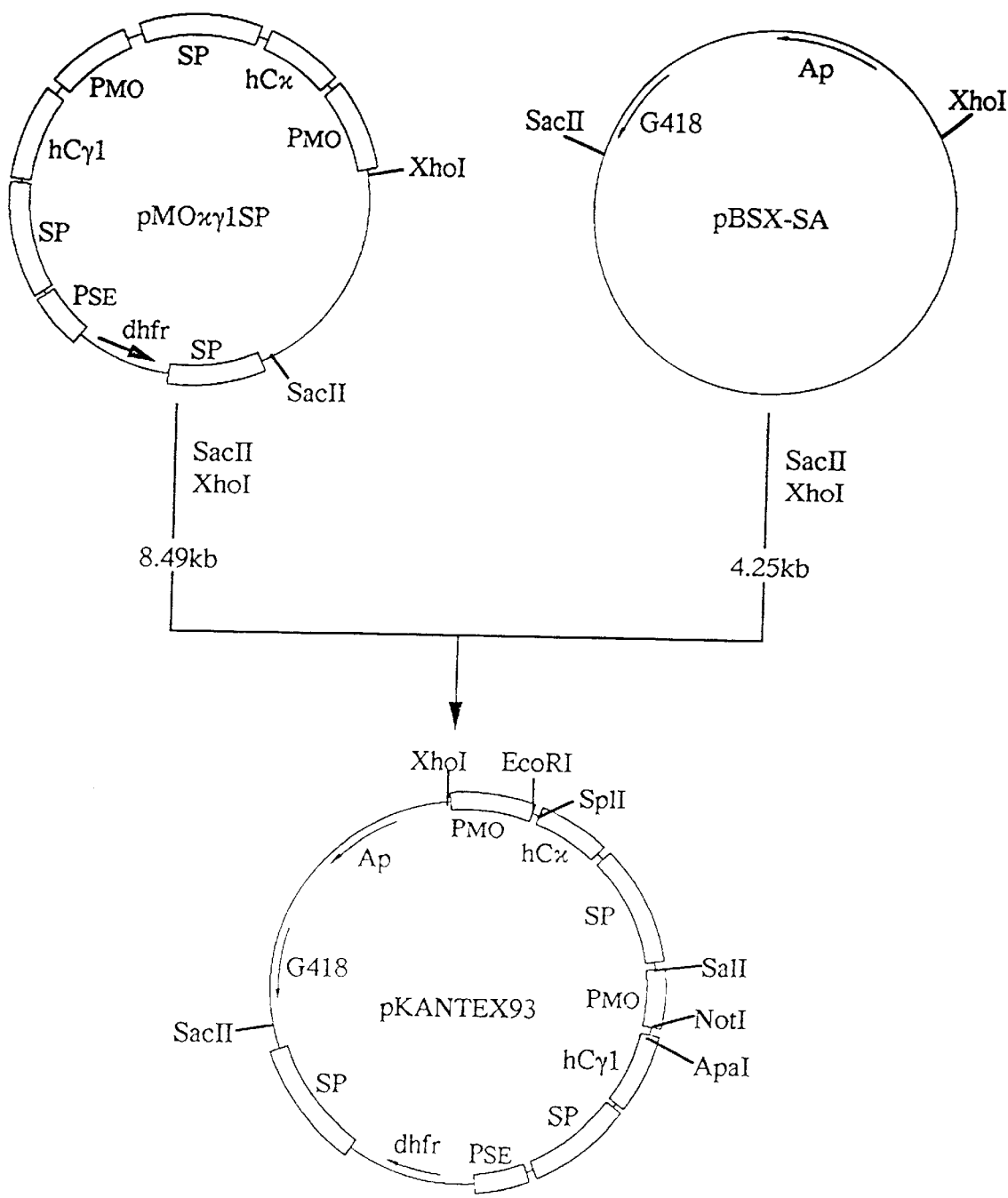

FIG. 85 shows a construction scheme for a plasmid named pKANTEX93.

Figure 86:
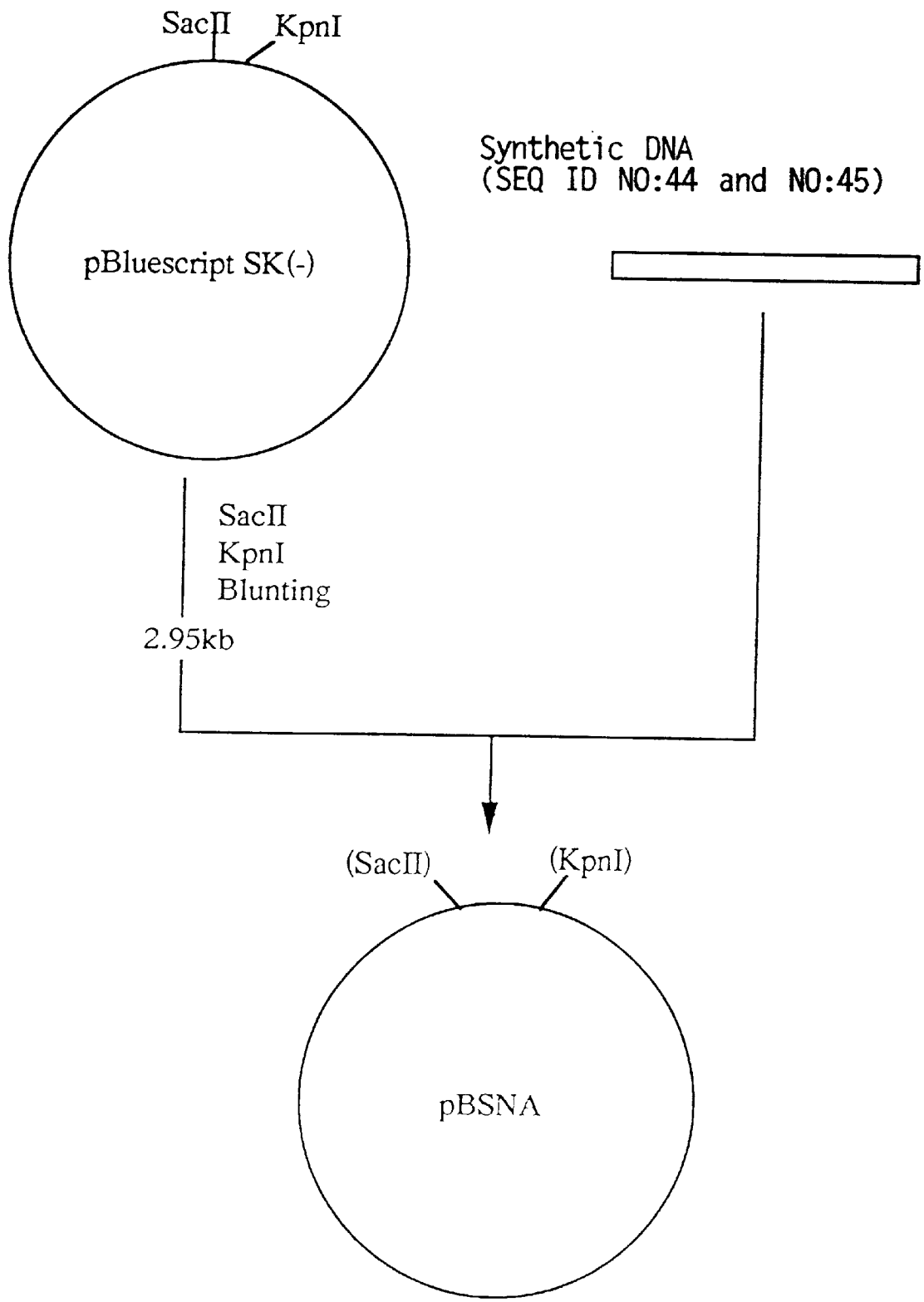

FIG. 86 shows a construction scheme for a plasmid named pBSNA.

Figure 87:
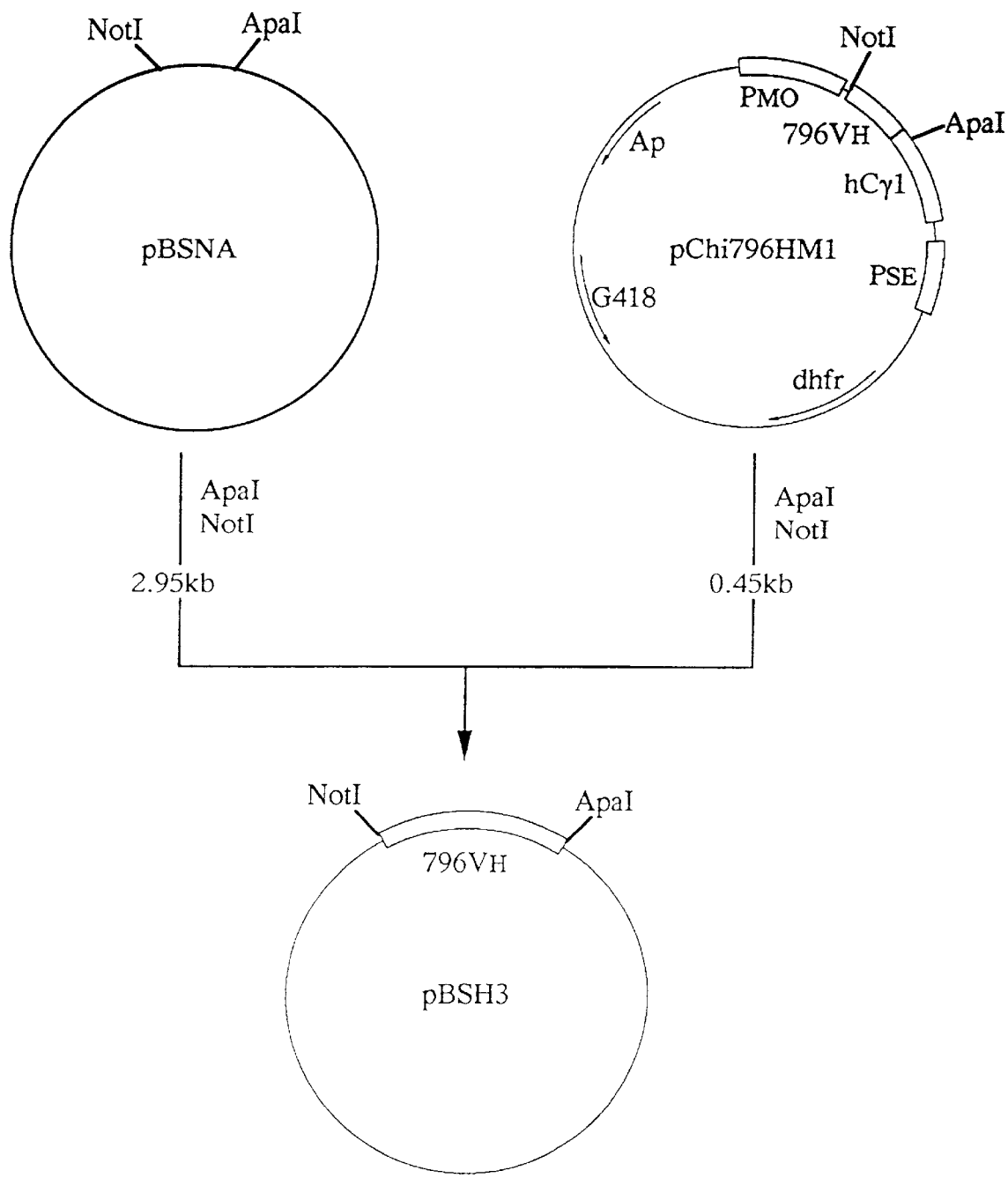

FIG. 87 shows a construction scheme for a plasmid named pBSH3.

Figure 88:
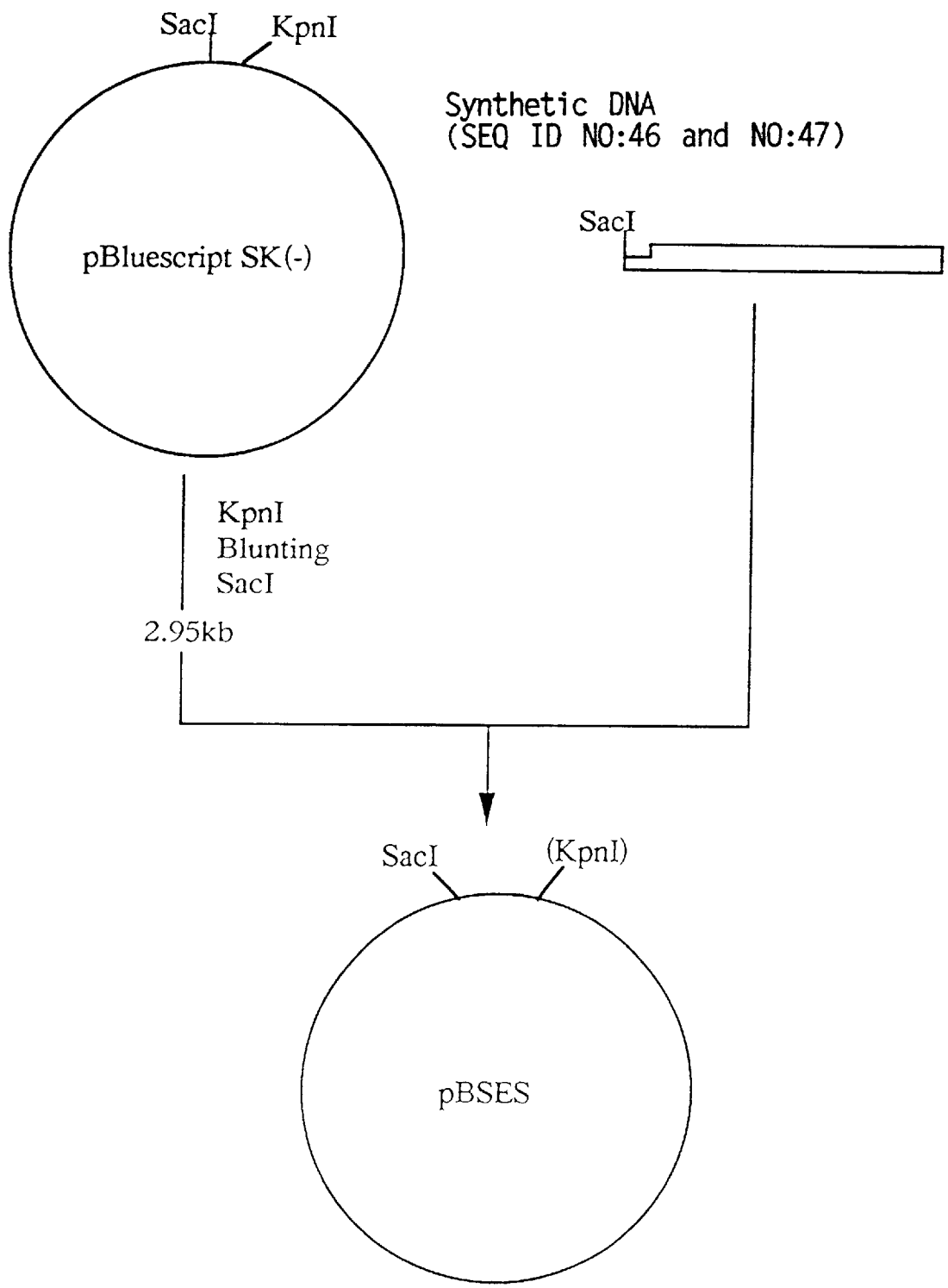

FIG. 88 shows a construction scheme for a plasmid named pBSES.

Figure 89:
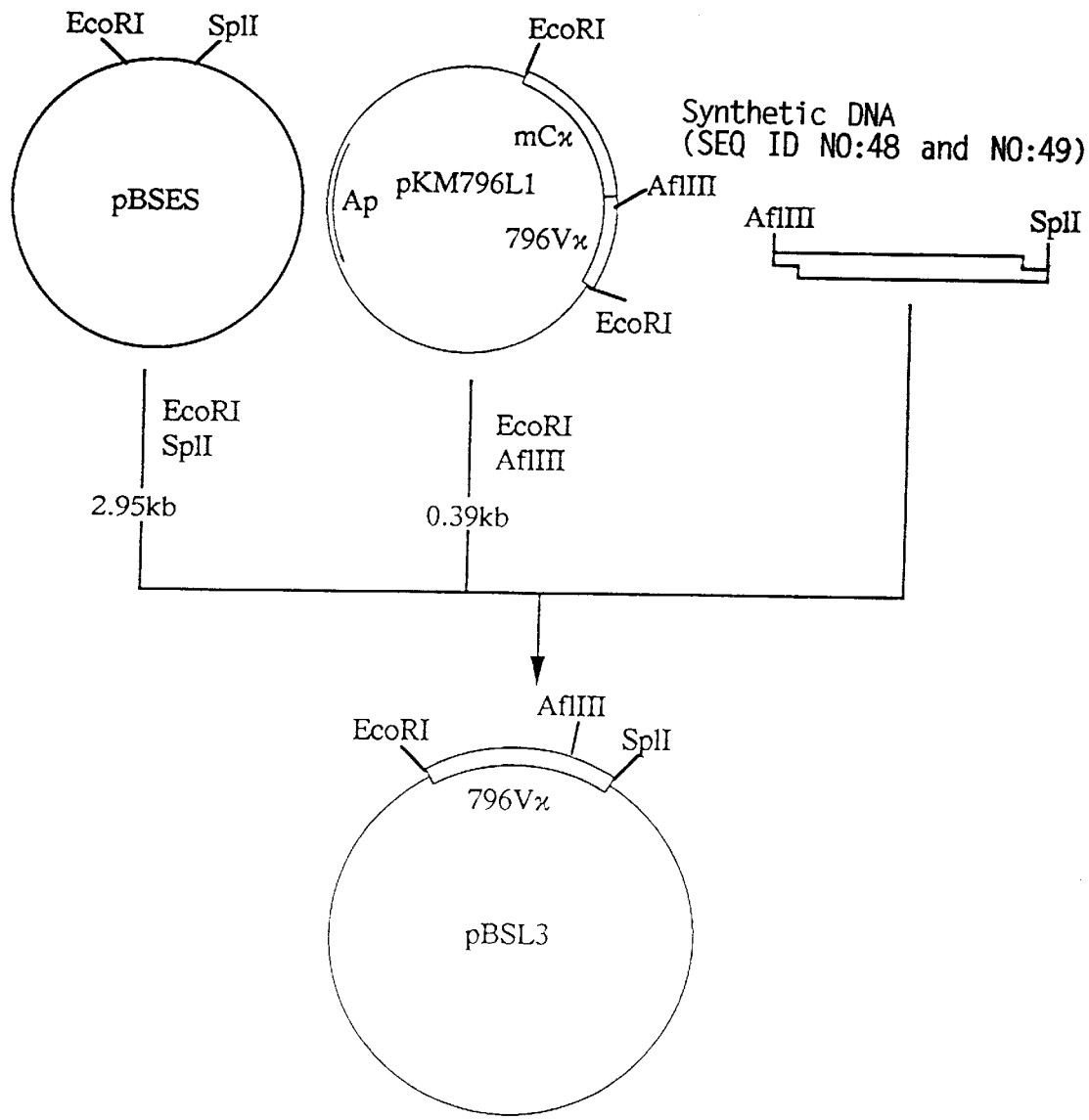

FIG. 89 shows a construction scheme for a plasmid named pESL3.

Figure 90:
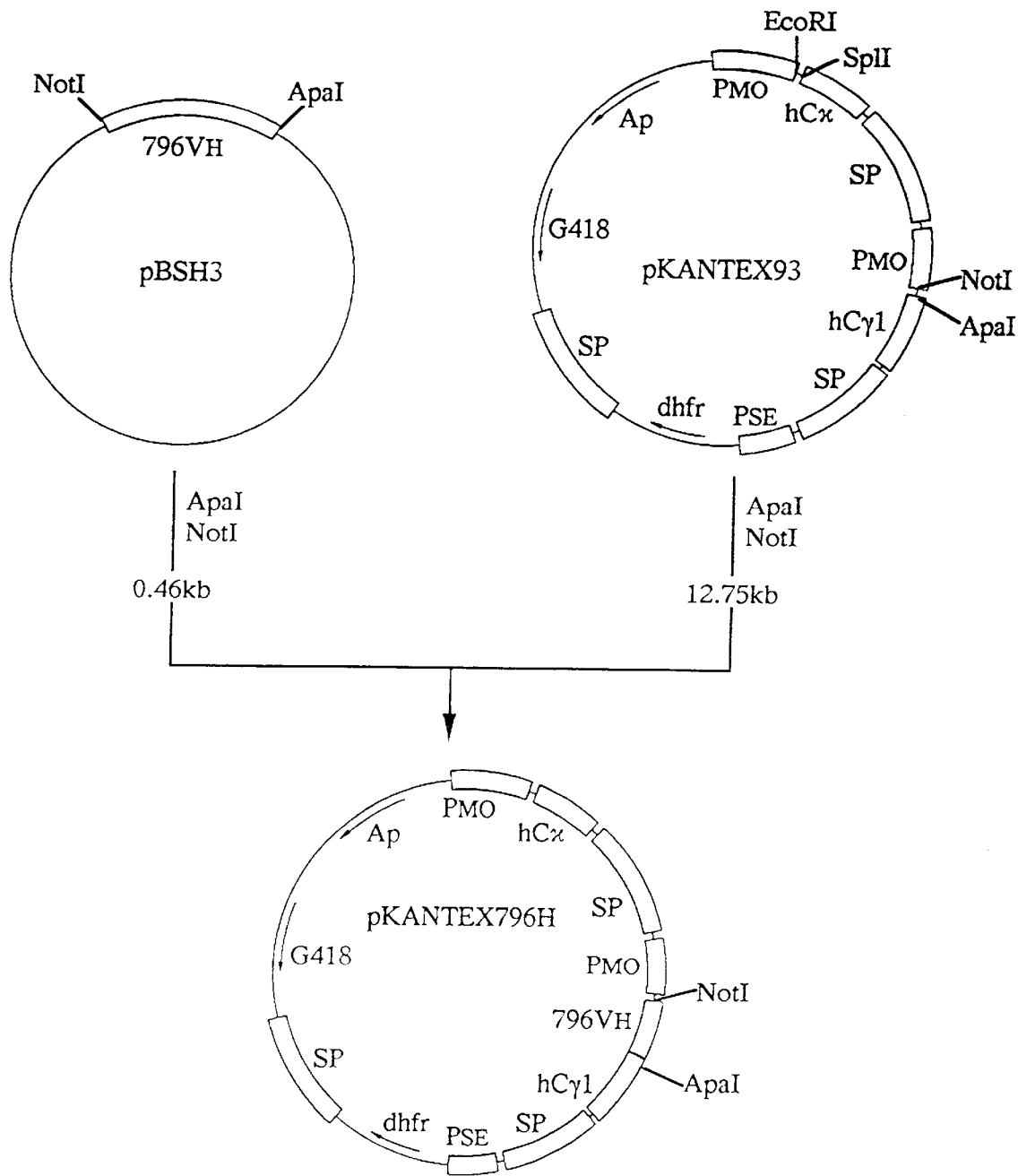

FIG. 90 shows a construction scheme for a plasmid named pKANTEX796H.

Figure 91:
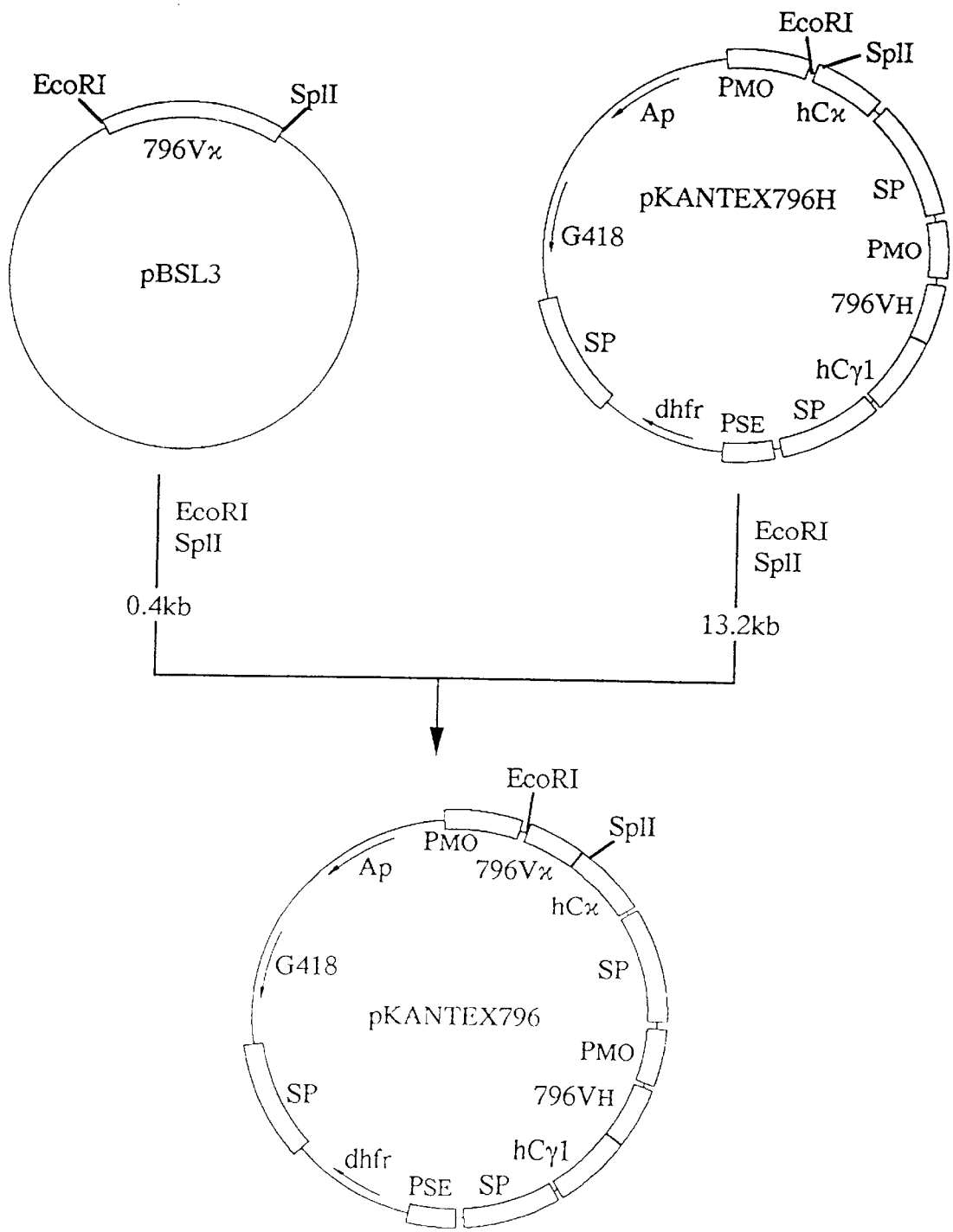

FIG. 91 shows a construction scheme for a plasmid named pKANTEX796.

Figure 92:
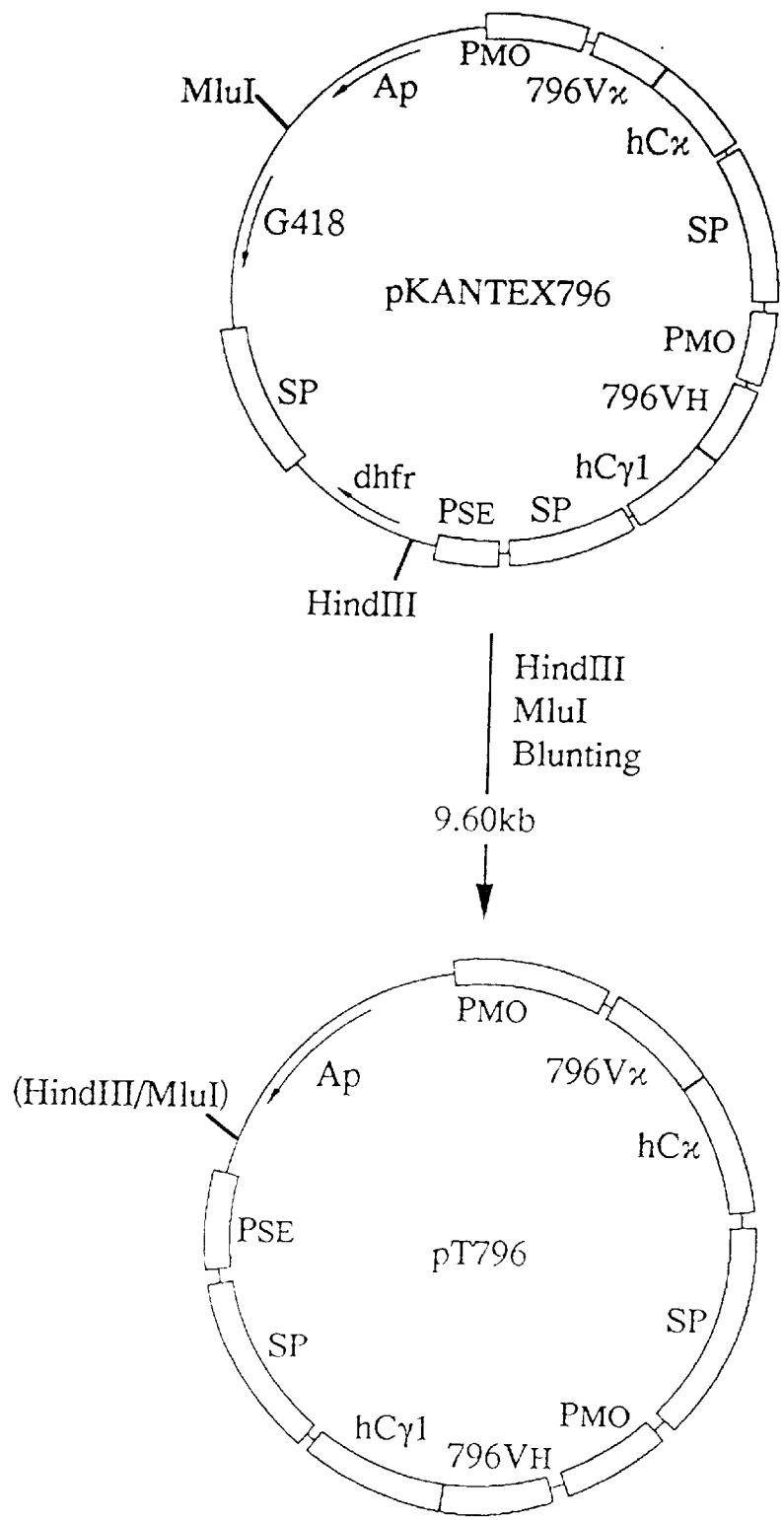

FIG. 92 shows a construction scheme for a plasmid named pT796.

Figure 93:
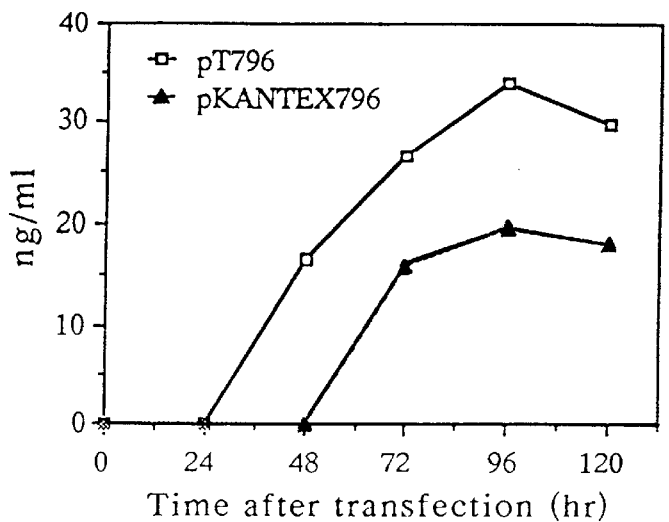

FIG. 93 is a graphic representation of transient human anti-GM$_2$ chimera antibody expression by the plasmids pKANTEX796 and pT796. The ordinate donotes the antibody concentration that showed GM$_2$-binding activity, and the abscissa denotes the time after introduction of the plasmid.

Figure 94:
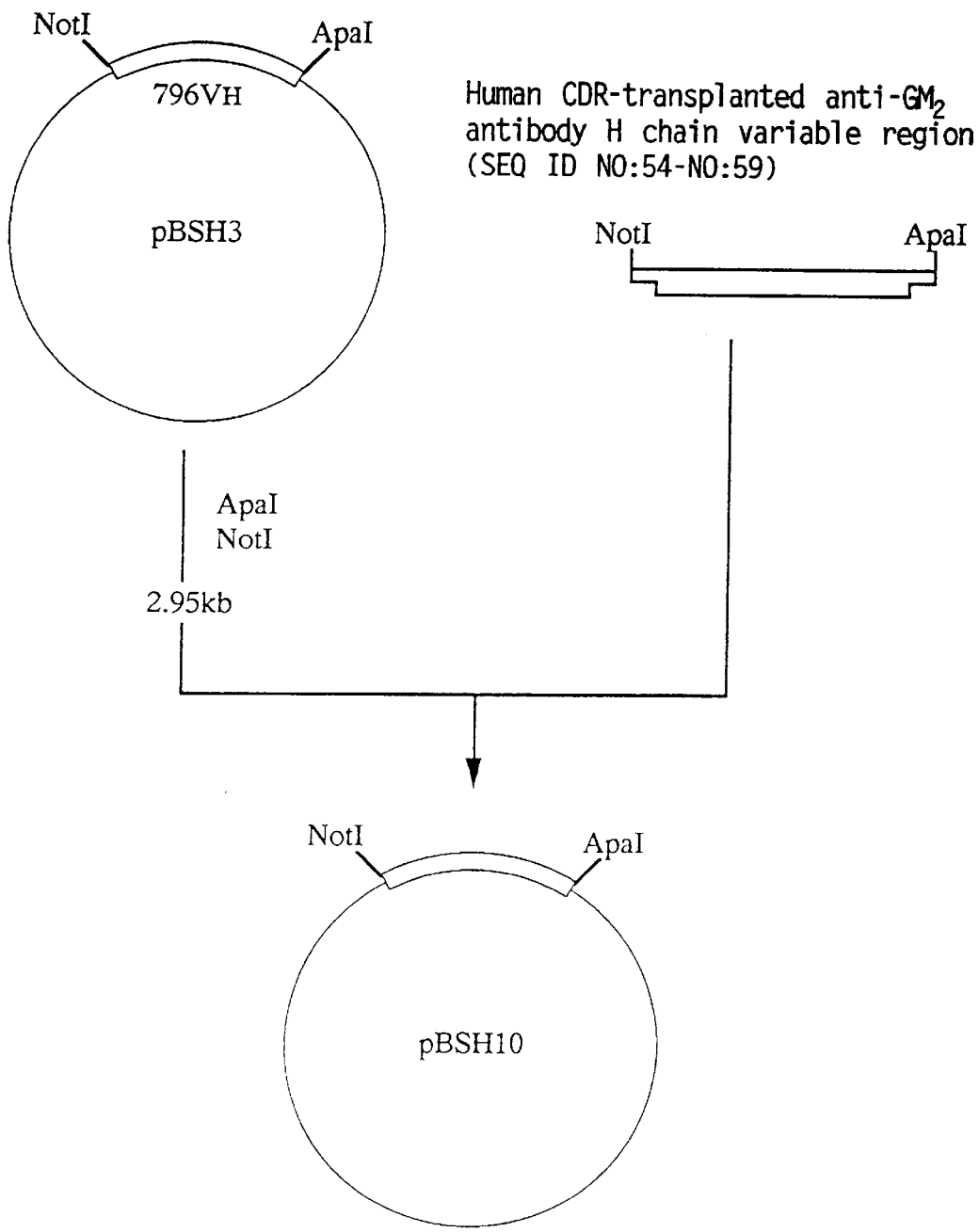

FIG. 94 shows a construction scheme for a plasmid named pBSH10.

Figure 95:
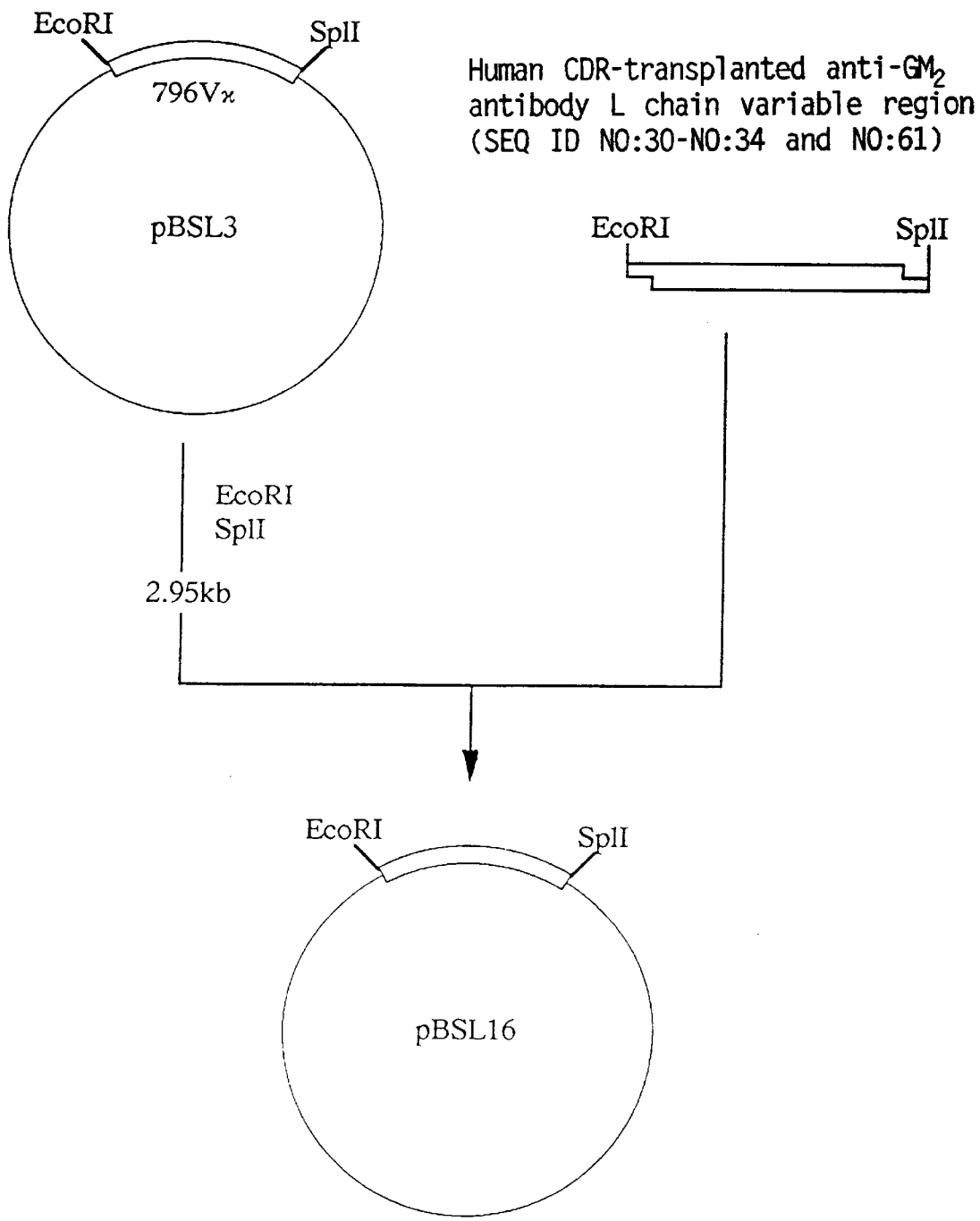

FIG. 95 shows a construction scheme for a plasmid named pBSL16.

Figure 96:
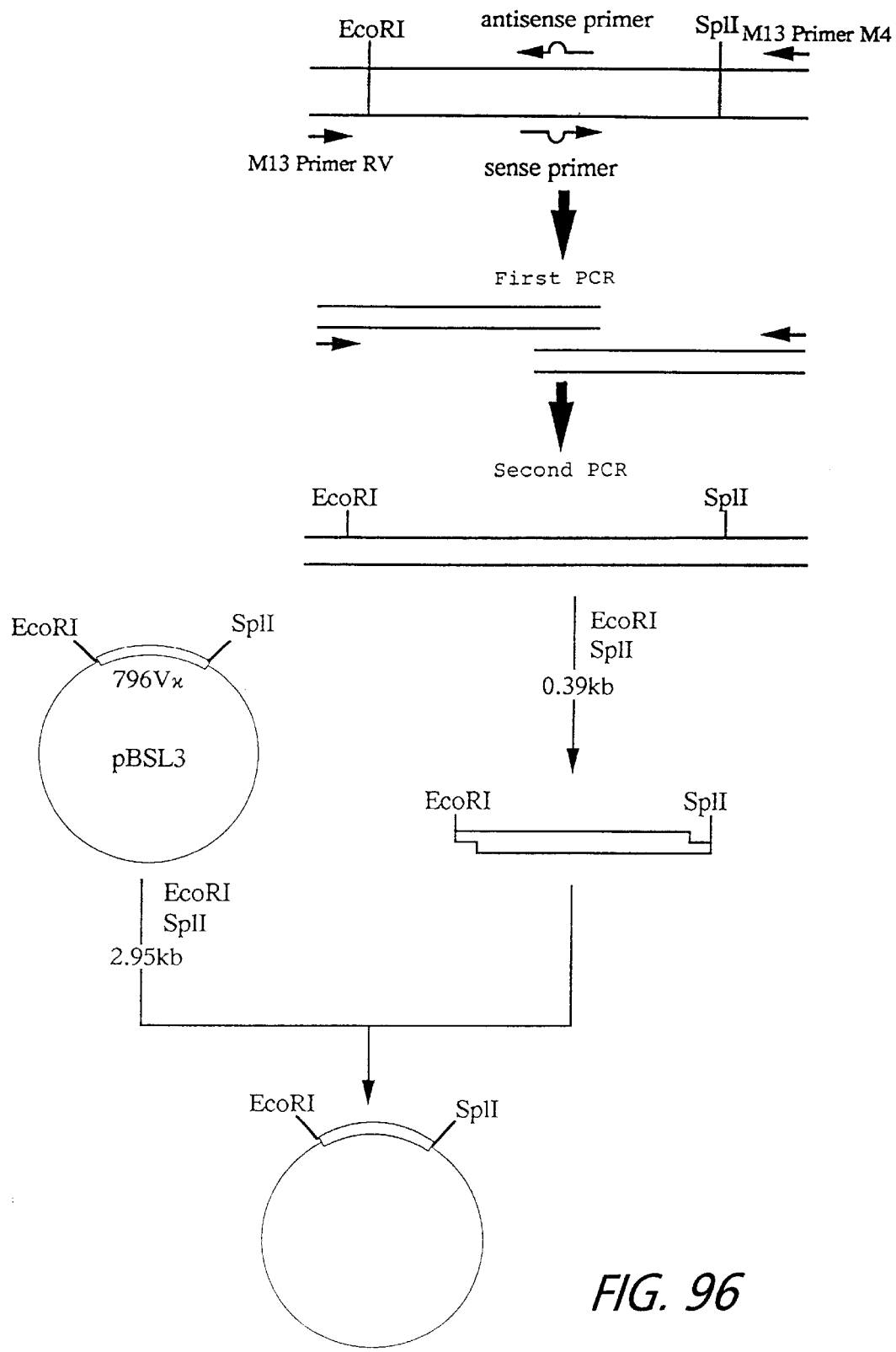

FIG. 96 illustrates a process for mutagenesis by PCR and a process for cloning DNA fragments mutated.

Figure 97:
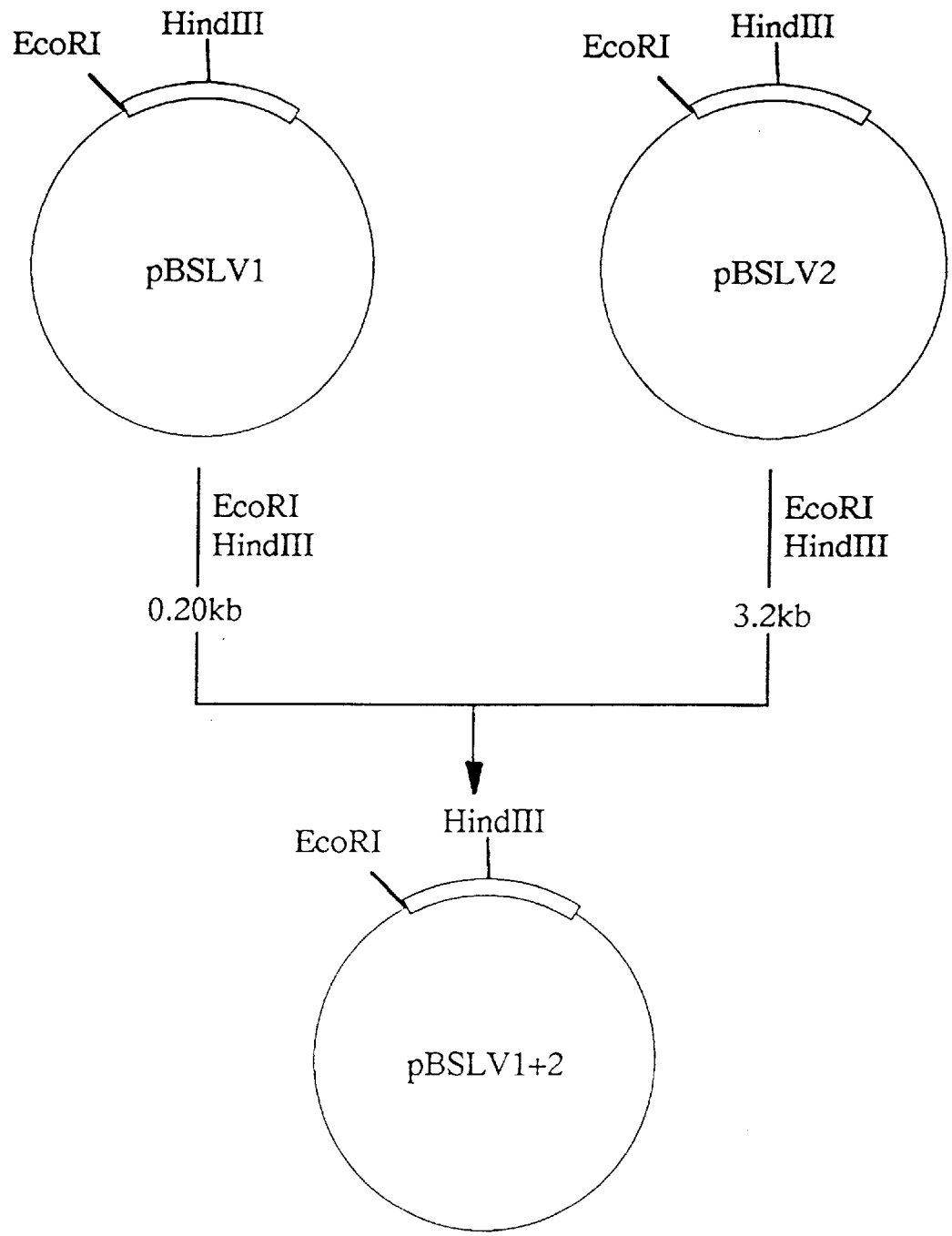

FIG. 97 shows a construction scheme for a plasmid named pBSLV1+2.

Figure 98:
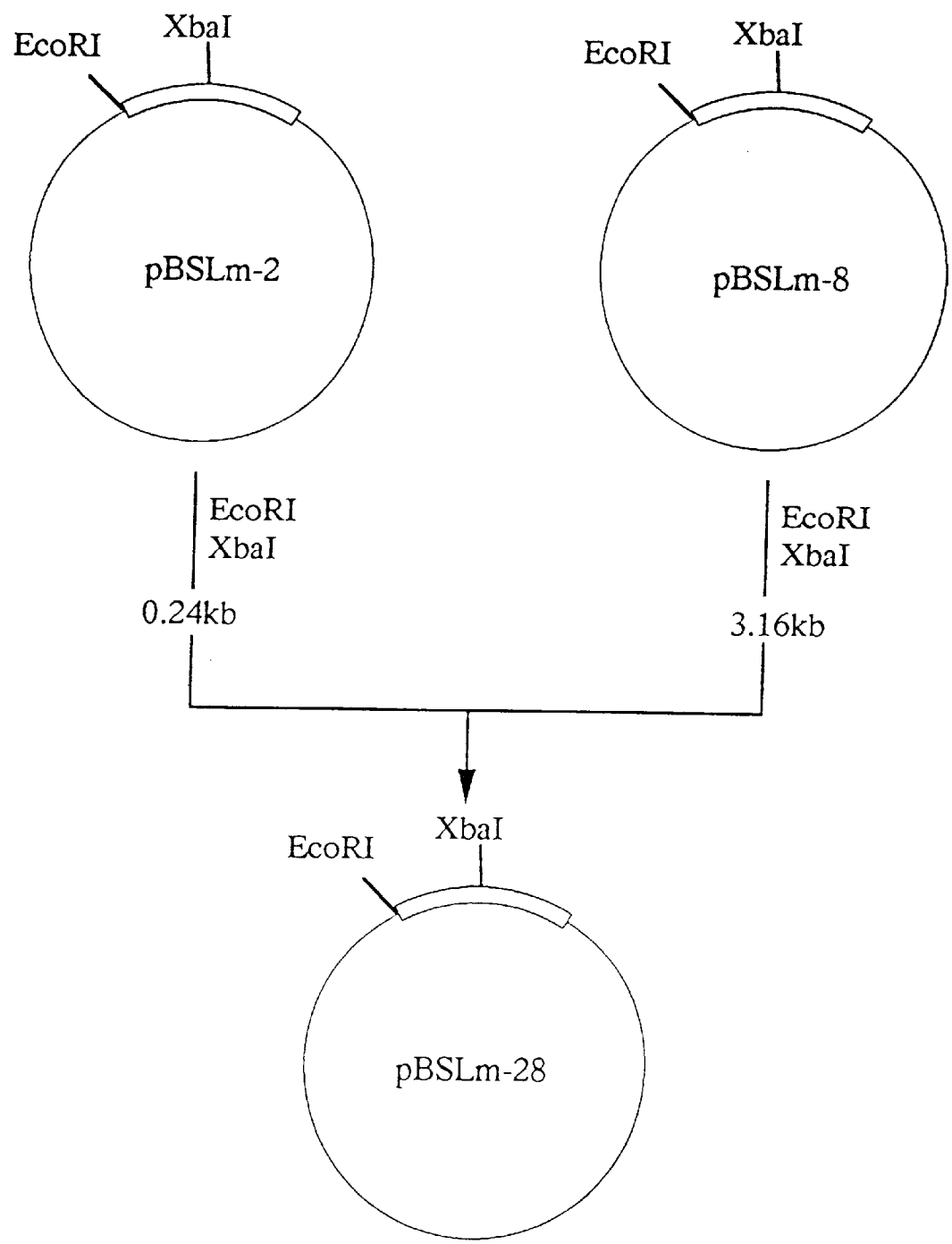

FIG. 98 shows a construction scheme for a plasmid named pBSLm-28.

Figure 99:
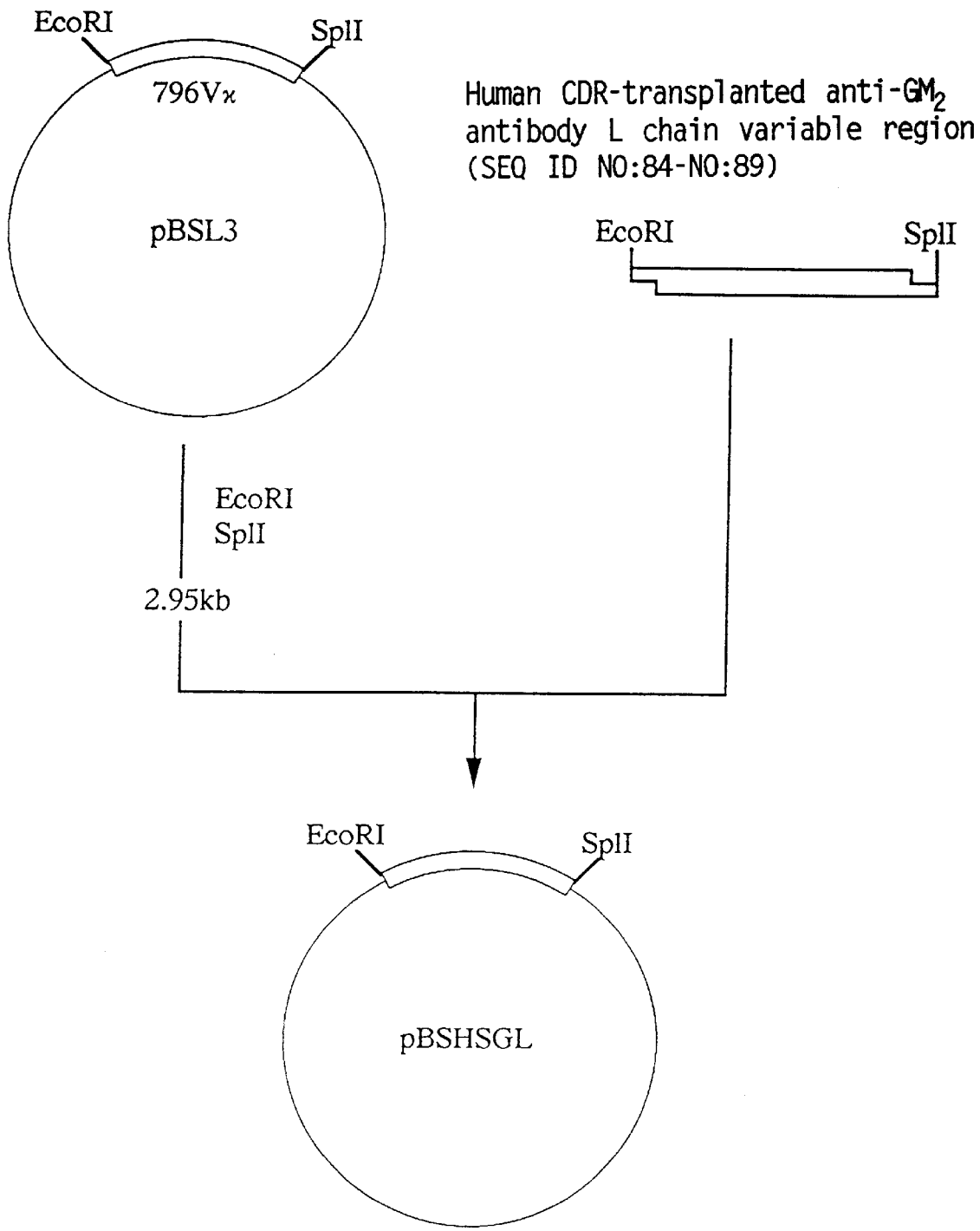

FIG. 99 shows a construction scheme for a plasmid named pBSHSGL.

Figure 100:
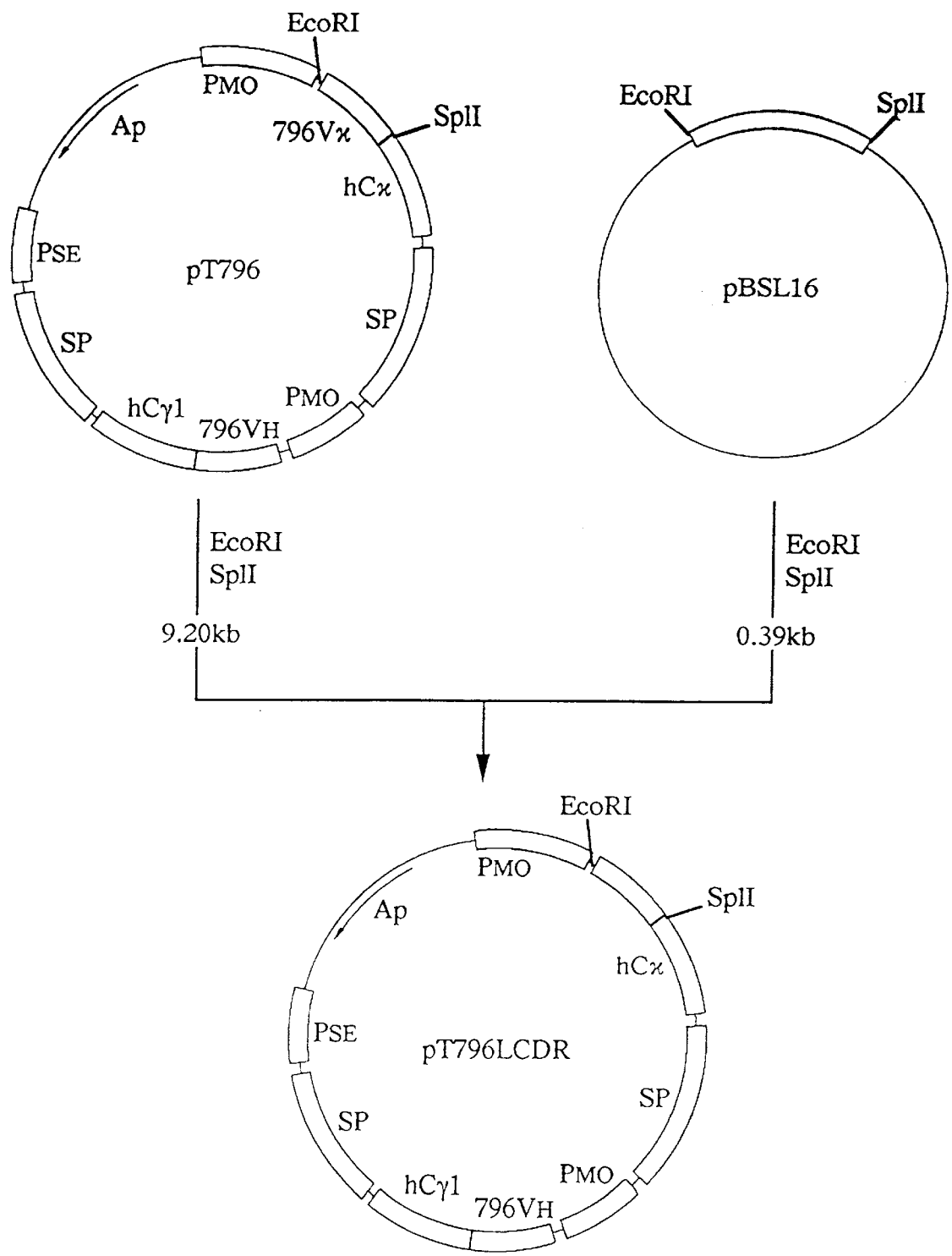

FIG. 100 shows a construction scheme for a plasmid named pT796LCDR.

Figure 101:
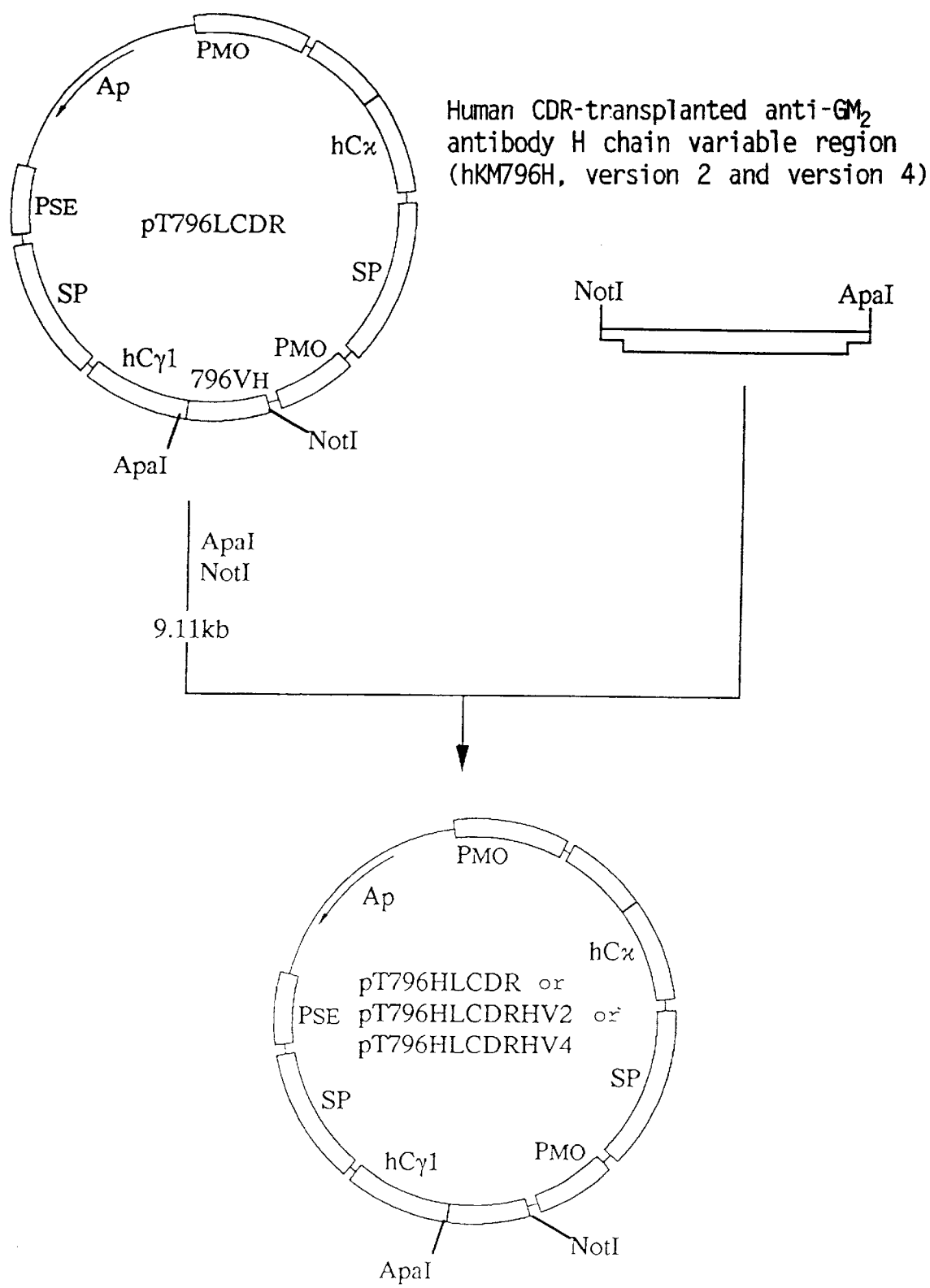

FIG. 101 shows a construction scheme for plasmids named pT796HLCDR, pT796HLCDRHV2 and pT796HLCDRHV4.

Figure 102:
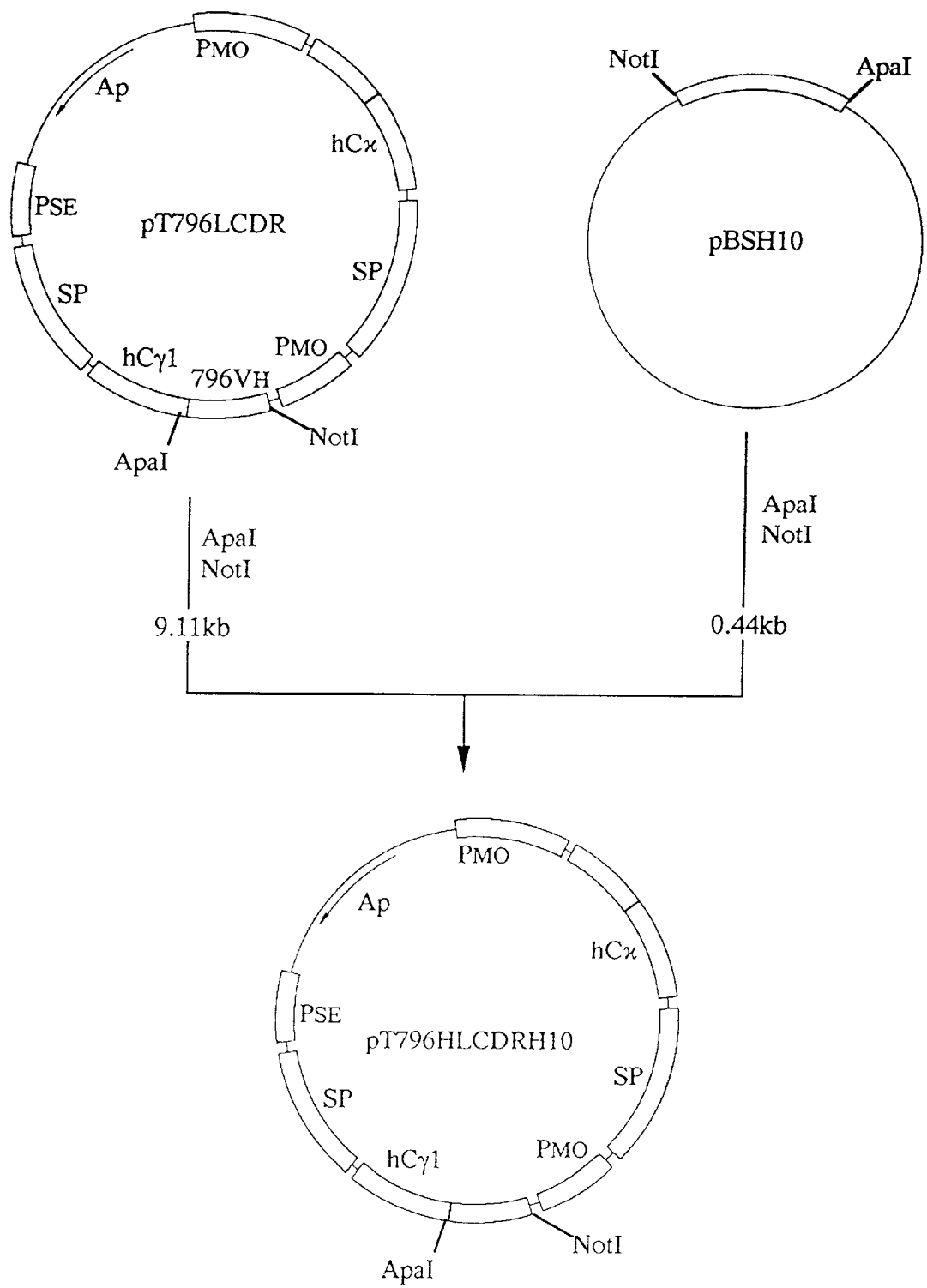

FIG. 102 shows a construction scheme for a plasmid named pT796HLCDRH10.

Figure 103:
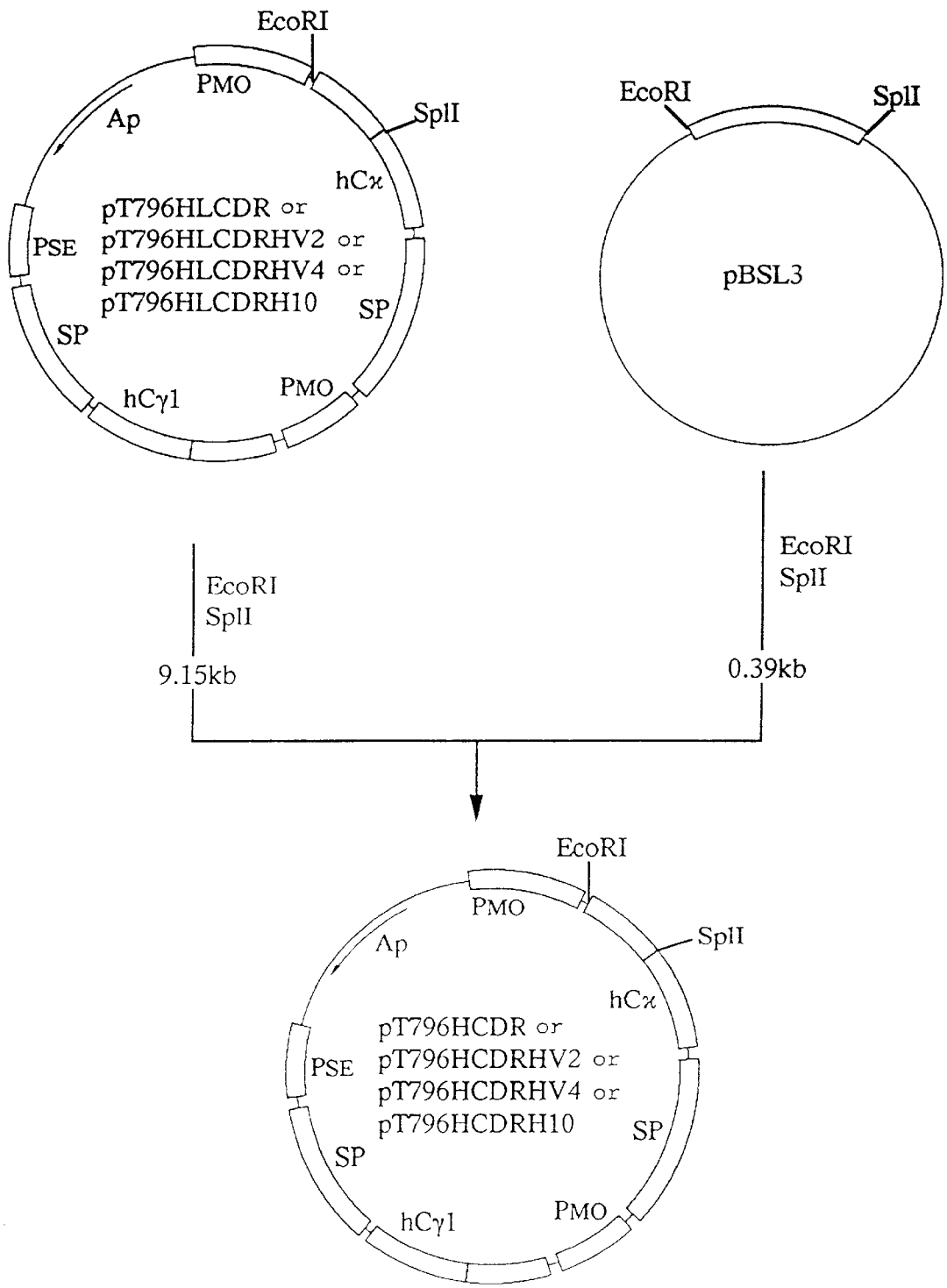

FIG. 103 shows construction scheme for plasmids named pT796HCDR, pT796HCDRHV2, pT796HCDRHV4 and pT796HCDRH10.

Figure 104:
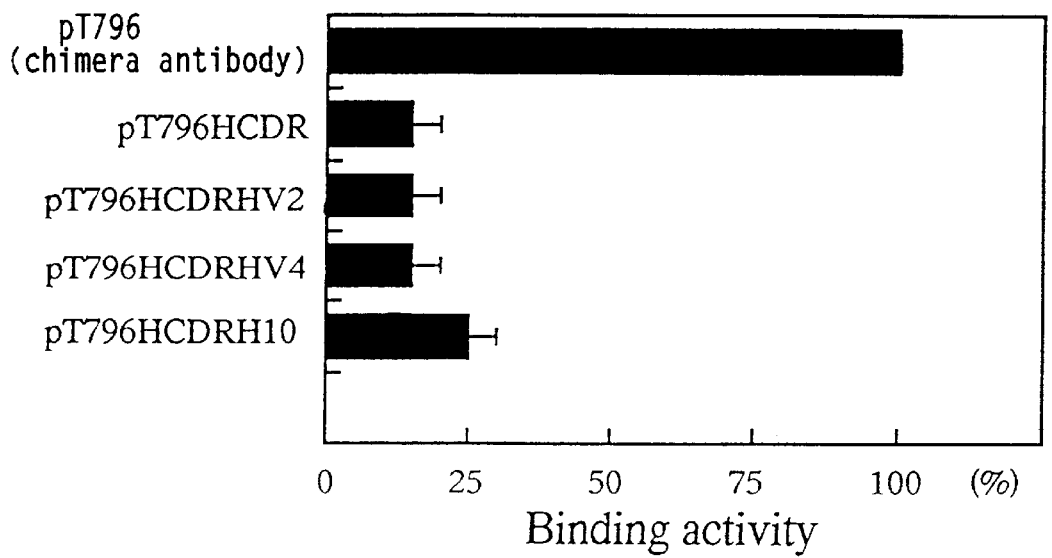

FIG. 104 is a graphic representation of the results of human CDR-transplanted anti-GM$_2$ antibody activity evaluation in terms of transient expression as obtained using the plasmids pT796, pT796HCDR, pT796HCDRHV2, pT796HCDRHV4 and pT796HCDRH10. The ordinate denotes the plasmid used, and the abscissa denotes the relative activity value with the activity obtained with the chimera antibody being taken as 100%.

Figure 105:
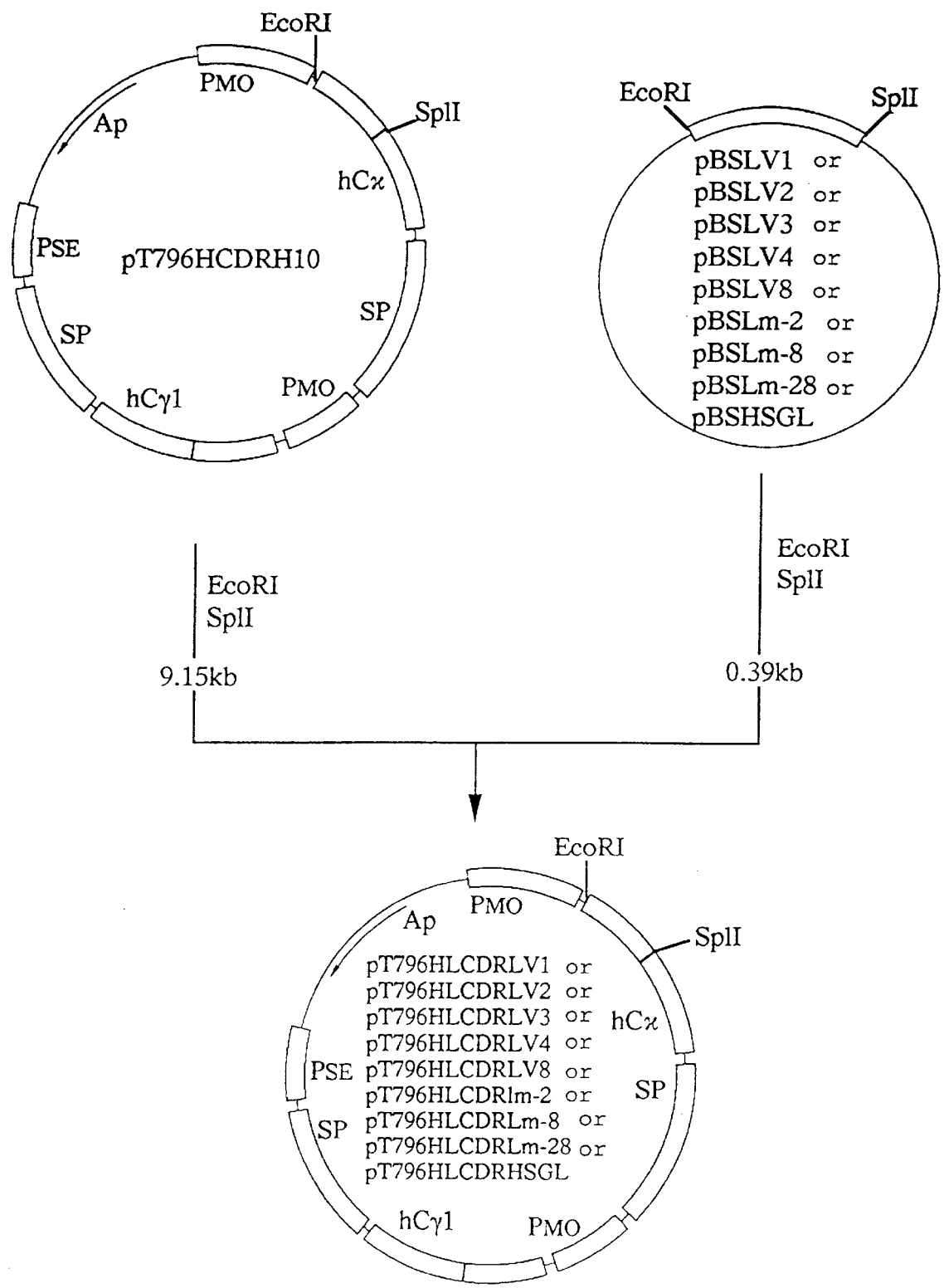

FIG. 105 shows a construction scheme for plasmids named pT796HLCDRLV1, pT796HLCDRLV2, pT796HLCDRLV3, pT796HLCDRLV4, pT796HLCDRLV8, pT796HLCDRLm-2, pT796HLCDRLm-8, pT796HLCDRLm-28 and pT796HLCDRHSGL.

Figure 106:
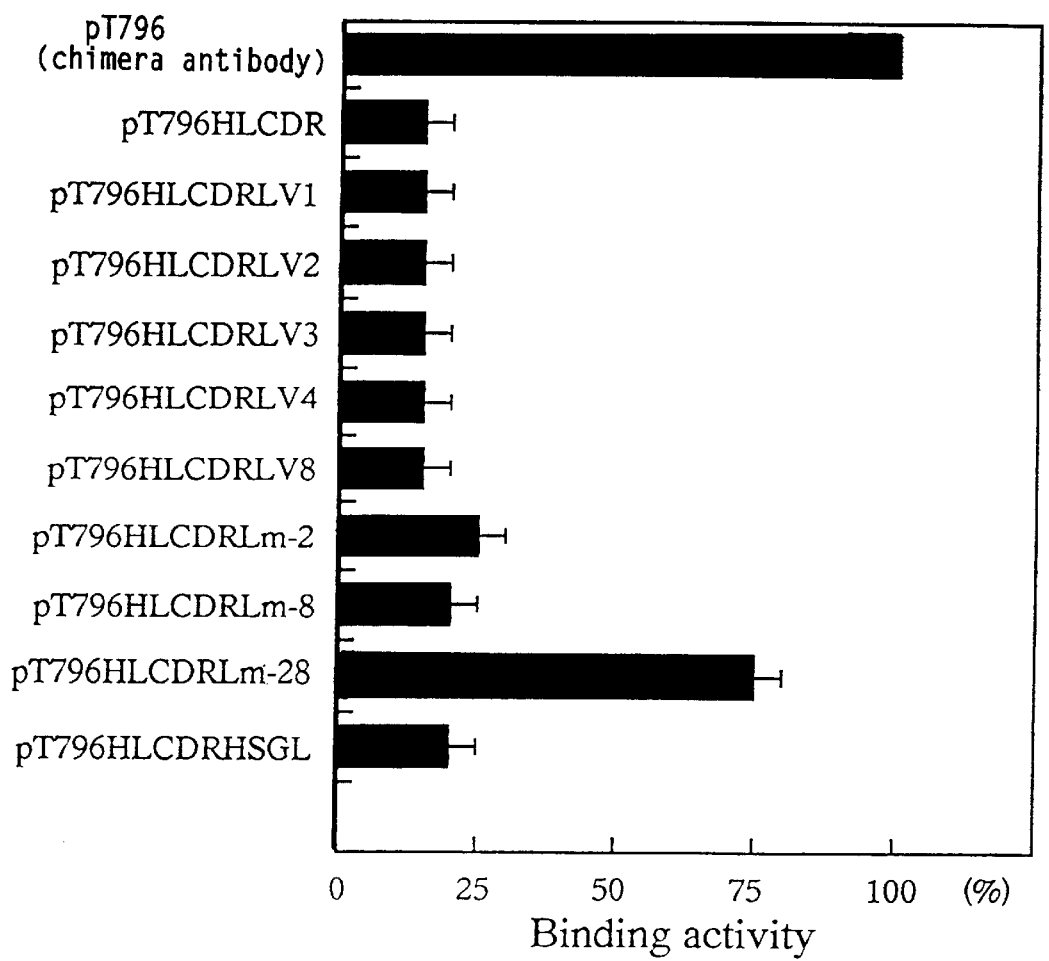

FIG. 106 is a graphic representation of the results of human CDR-transplanted anti-GM$_2$ antibody activity evaluation in terms of transient expression as obtained using the plasmids pT796, pT796HLCDR, pT796HLCDRLV1, pT796HLCDRLV2, pT796HLCDRLV3, pT796HLCDRLV4, pT796HLCDRLV8, pT796HLCDRLm-2, pT796HLCDRLm-8, pT796HLCDRLm-28 and pT796HLCDRHSGL. The ordinate denotes the plasmid used, and the abscissa denotes the relative activity value with the activity obtained with the chimera antibody being taken as 100%.

Figure 107:
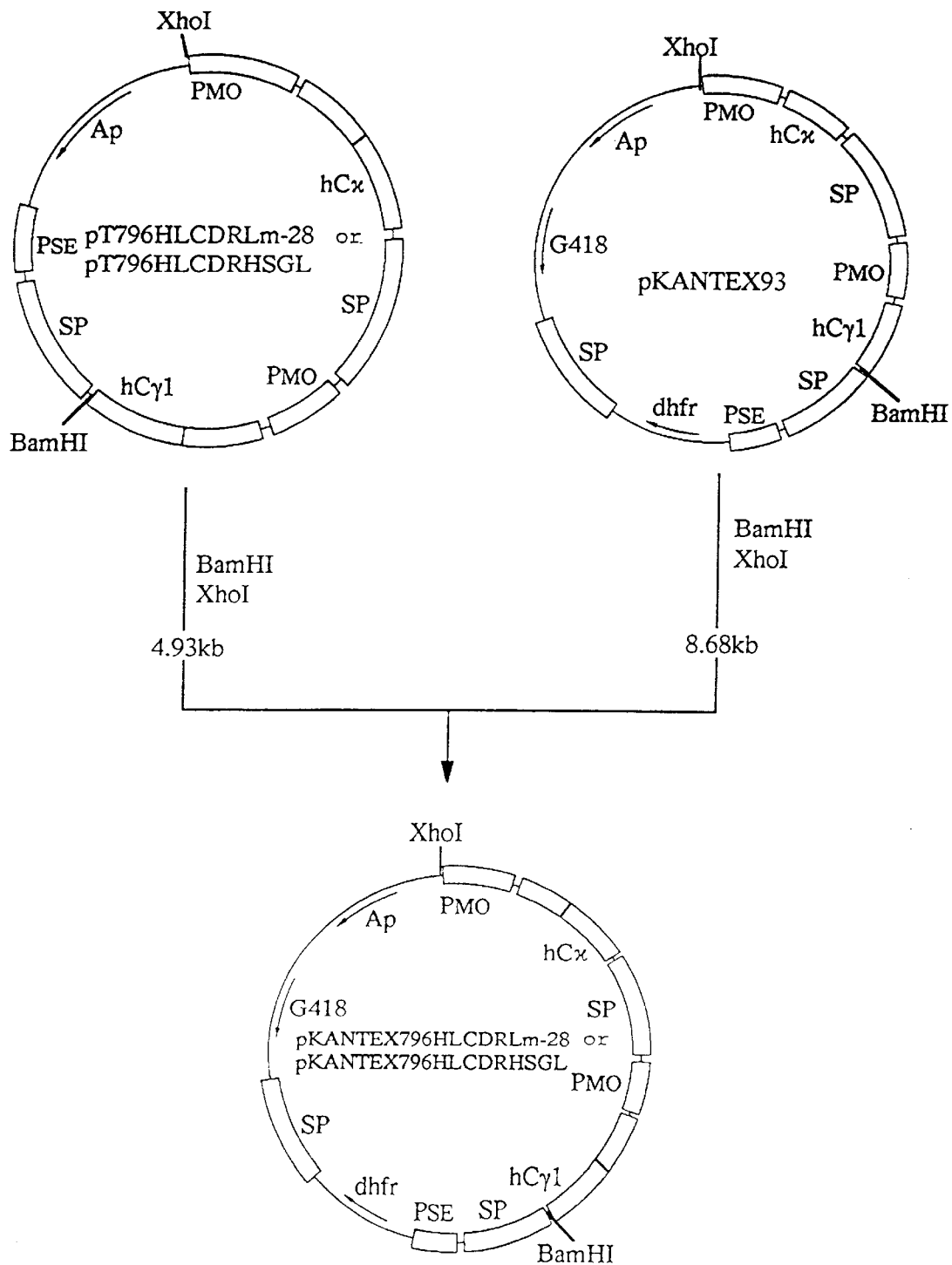

FIG. 107 shows a construction scheme for plasmids named pKANTEX796HLCDRLm-28 and pKANTEX 796HLCDRHSGL.

Figure 108:
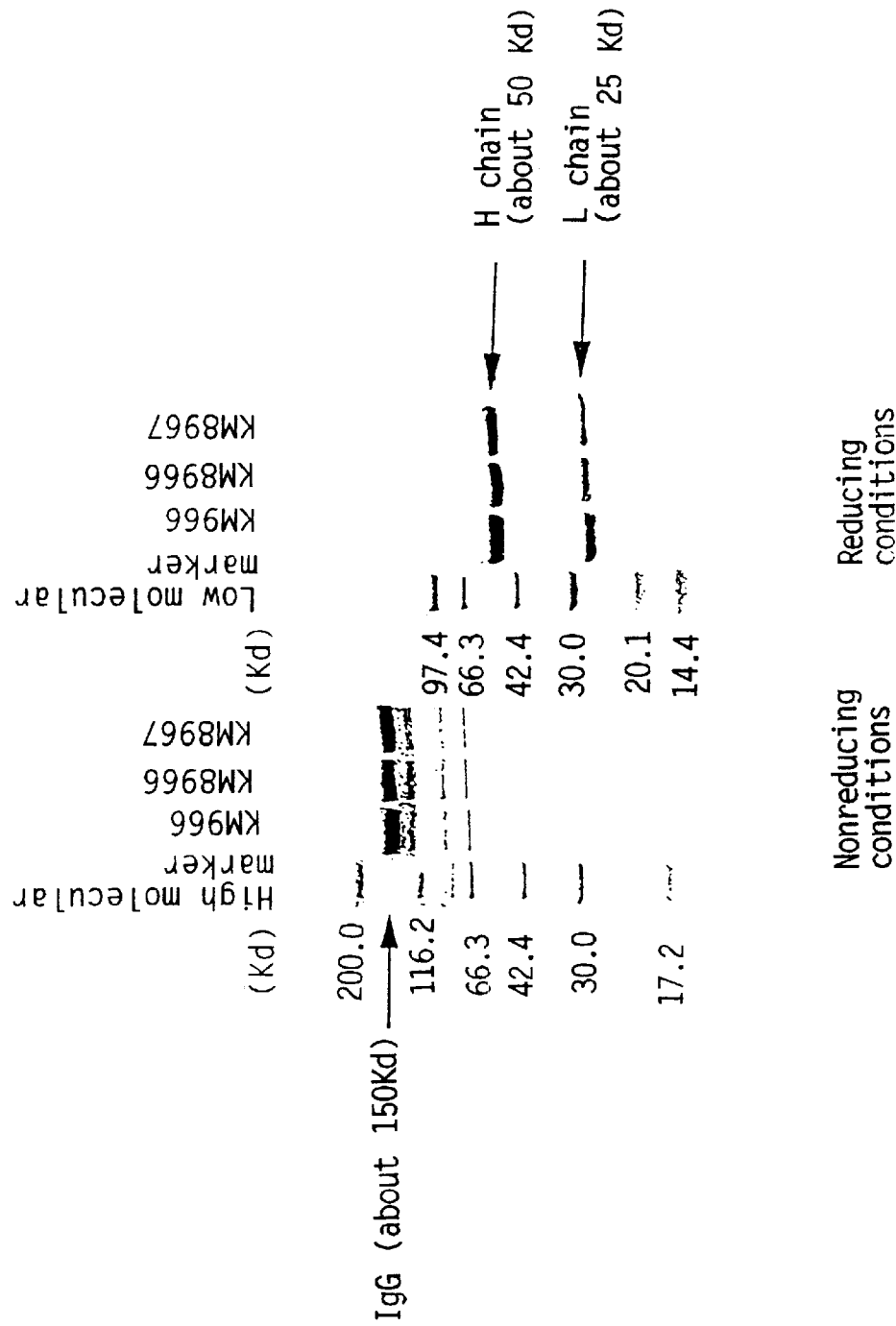

FIG. 108 shows electrophoretic patterns obtained for human anti-GM$_2$ chimera antibody KM966 and purified human CDR-transplanted anti-GM$_2$ antibodies KM8966 and KM8967 by SDS-PAGE (4 to 15% gradient gels used). The patterns shown on the left side are those obtained under reducing conditions, and those on the right under nonreducing conditions. From the left of each lane, the electrophoretic patterns for high-molecular-weight marker, KM966, KM8966, KM8967, low-molecular-weight marker, KM966, KM8966 and KM8967 are shown in that order.

Figure 109:
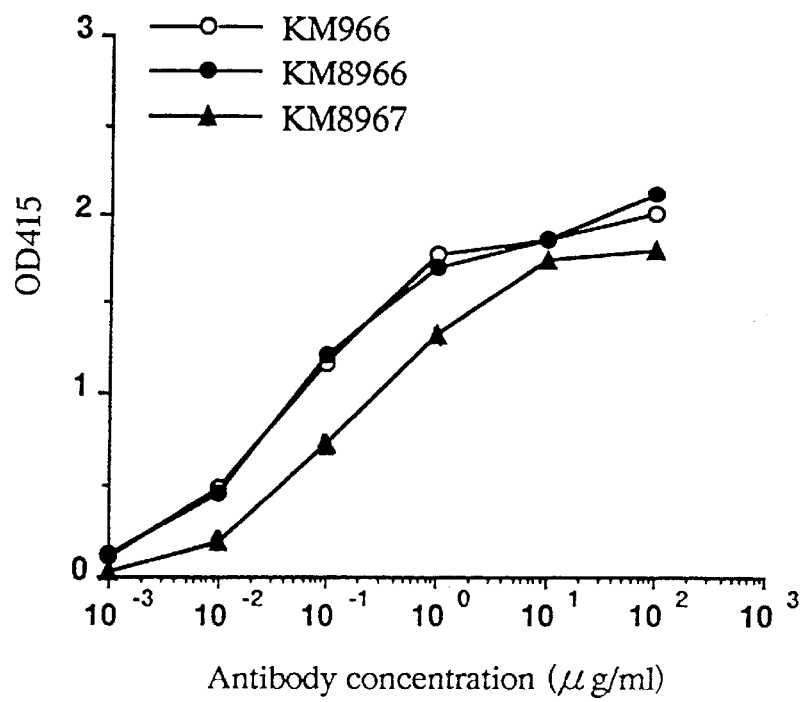

FIG. 109 is a graphic representation of the GM$_2$-binding activities of human anti-GM$_2$ chimera antibody KM966 and purified human CDR-transplanted anti-GM$_2$ antibodies KM8966 and KM8967. The ordinate denotes the GM$_2$-binding activity, and the abscissa the antibody concentration. The plots ○, ● and Δ stand for the GM$_2$-binding activities of KM966, KM8966 and KM8967, respectively.

Figure 110:
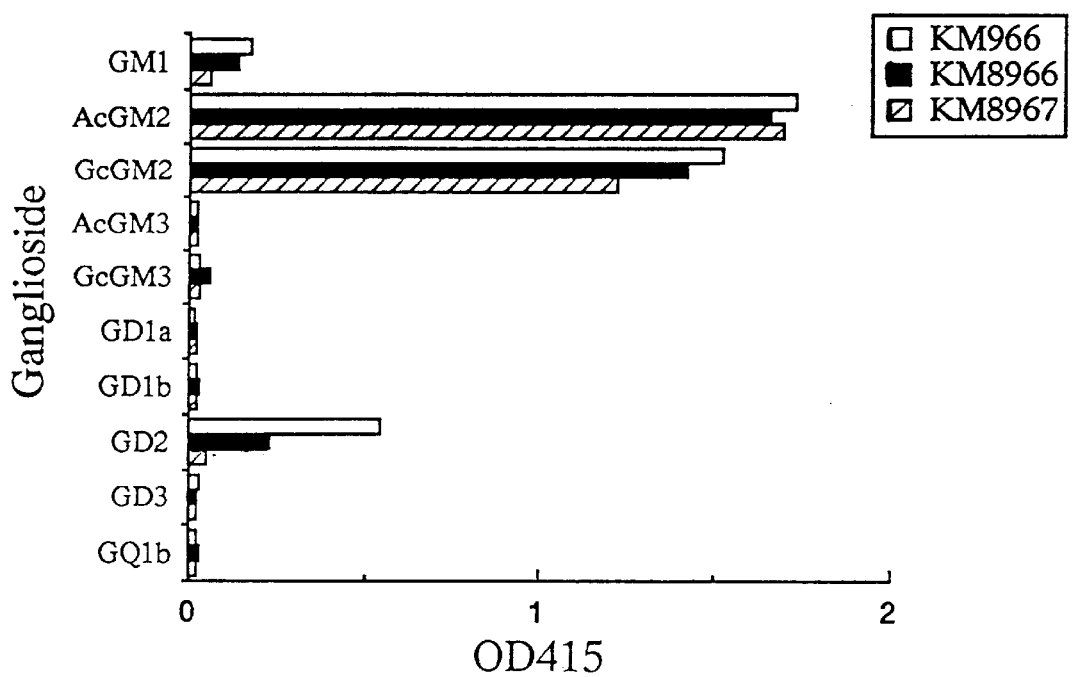

FIG. 110 is a graphic representation of the reactivities of human anti-GM$_2$ chimera antibody KM966 and purified human CDR-transplanted anti-GM$_2$ antibodies KM8966 and KM8967 against various gangliosides. The ordinate denotes the ganglioside species, and the abscissa the binding activity. AcGM2 stands for N-acetyl-GM$_2$, GcGM2 for N-glycolyl-GM$_2$, AcGM3 for N-acetyl-GM$_3$ and GcGM3 for N-glycolyl-GM$_3$. The plots □, ■ and □ stand for the reactivities of KM966, KM8966 and KM8967, respectively.

Figure 111:
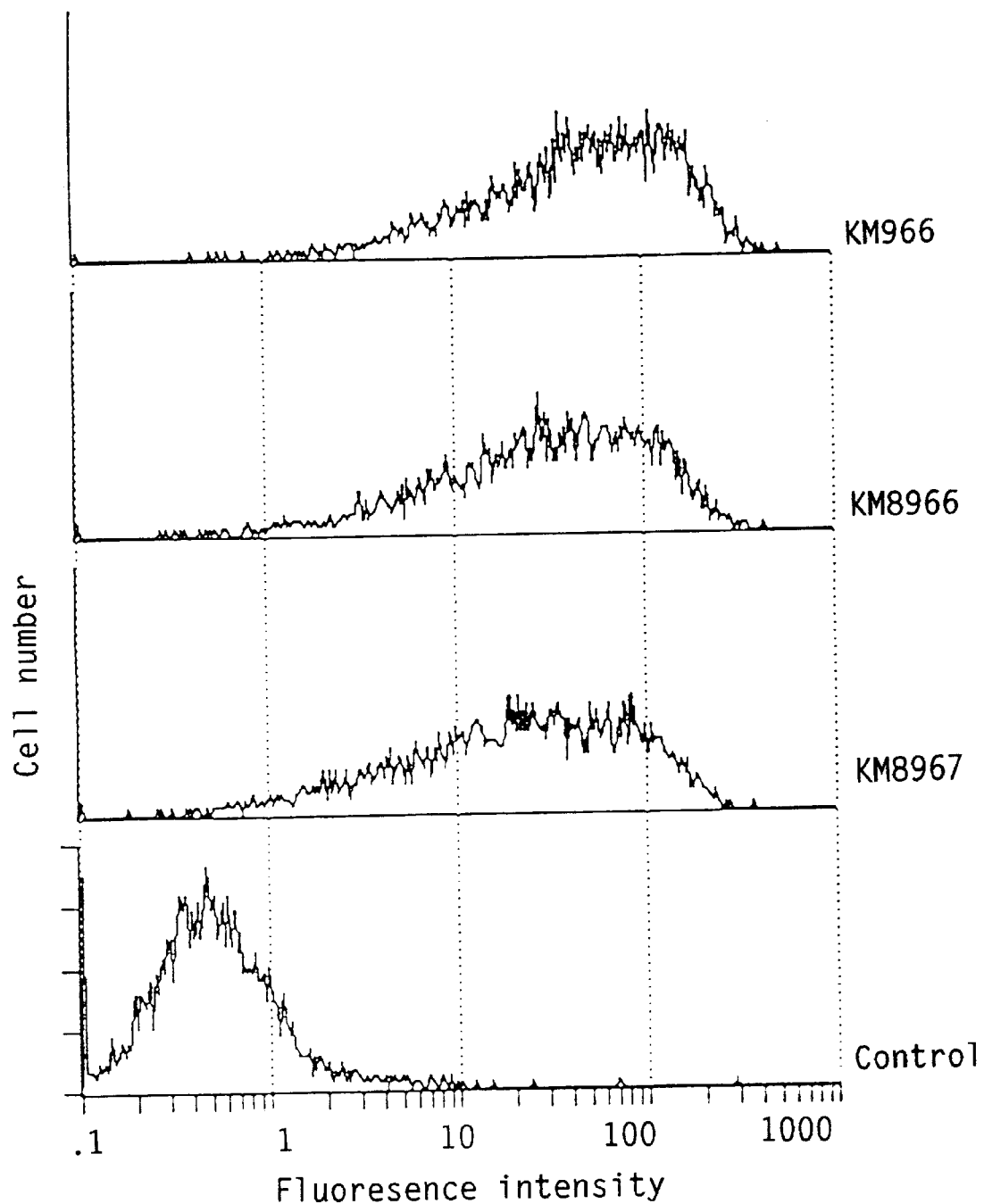

FIG. 111 is a graphic representation of the reactivities of human anti-GM$_2$ chimera antibody KM966 and purified human CDR-transplanted anti-GM$_2$ antibodies KM8966 and KM8967 against the human lung small cell carcinoma cell line SBC-3. The ordinate denotes the number of cells, and the abscissa the fluorescence intensity. From the lowermost graph, the reactivities of control, KM8967, KM8966 and KM966 are shown in that order.

DETAILED DESCRIPTION OF THE INVENTION

The present invention relates to humanized antibodies specific for the ganglioside GM$_2$. The antibodies can be of any of the immunoglobulin (Ig) classes, it is preferable, however, that the antibodies be of the IgG type. The term "humanized antibody", as used herein, includes within its meaning, chimeric human antibody and CDR-grafted antibody. Chimeric human antibodies of the invention include the $V_H$ and $V_L$ of an antibody of an animal other than a human and the $C_H$ and $C_L$ of a human antibody. The CDR-transplanted antibodies of the invention result from the replacement of CDRs of the $V_H$ and $V_L$ of a human antibody with those of the $V_H$ and $V_L$, respectively, of an antibody of an animal other than a human.

An example of a chimeric human antibody of the invention is an antibody the $V_H$ of which contains an amino acid sequence segment as defined by SEQ ID NO:91, including the 1st to 120th amino acids of that sequence, and the $V_L$ of which contains an amino acid sequence segment as defined by SEQ ID NO:92, including the 1st to 107th amino acids of that sequence.

An example of a CDR-transplanted antibody of the invention is an antibody the $V_H$ CDRs of which have the amino acid sequences defined by SEQ ID NO:94, SEQ ID NO:95 and SEQ ID NO:96 and the $V_L$ CDRs of which have the amino acid sequences defined by SEQ ID NO:97, SEQ ID NO:98 and SEQ ID NO:99.

The chimeric human antibodies of the invention can be produced in the following manner:

(1) Preparation of cDNAs coding for the $V_H$ and $V_L$ of an antibody of nonhuman animal cDNAs coding for the $V_H$ and $V_L$ of an antibody of a nonhuman animal, for example a mouse anti-$GM_2$ monoclonal antibody, can be prepared as follows.

mRNAs can be extracted from hybridomas producing the mouse anti-$GM_2$ monoclonal antibody, for example hybridomas producing the mouse anti-$GM_2$ monoclonal antibody KM796, and cDNAs reverse transcribed therefrom. Using the cDNAs, a library can be constructed using phage or plasmid vectors. The recombinant phage or recombinant plasmid containing the cDNA coding for the $V_H$, and the recombinant phage or recombinant plasmid containing the cDNA coding for the $V_L$ can be isolated from the library using a constant region portion or a variable region portion of an antibody of a nonhuman animal, for example a mouse antibody, as a probe. The base sequences of the $V_H$-encoding cDNA and $V_L$-encoding cDNA in the recombinant phage or recombinant plasmid can then be determined. Examples of the nonhuman animals include mice, rats, hamsters and monkeys.

(2) Construction of a vector for chimeric human antibody expression

Expression of chimeric human antibody H chain and L chains can be effected using expression vectors suitable for use in animal cells, inserted into which are the cDNAs coding for the human $C_H$ and $C_L$. Any expression vector suitable for use in animal cells can be used, provided that it allows integration and expression of the human antibody constant region-encoding cDNAs. Examples include pAGE107 [Cytotechnology, 3, 133 (1990)], pAGE103 [J. Biochem., 101, 1307 (1987)], pHSG274 [Gene, 27, 223 (1984)], pKCR [Proc. Natl. Acad. Sci. U.S.A., 78, 1527 (1981)] and pSG1βd2-4 [Cytotechnology, 4, 173 (1990)], among others. Examples of promoters and enhancers suitable for use in such expression vectors include the SV40 early promoter and enhancer [J. Biochem., 101, 1307 (1987)], the Moloney mouse leukemia virus LTR (long terminal repeat) promoter and enhancer [Biochem. Biophys. Res. Commun., 149, 960 (1987)] and the immunoglobulin H chain promoter [Cell, 41, 479 (1985)] and enhancer [Cell, 33, 717 (1983)]. The promoters and enhancers are located in the expression vector in operable linkage with the coding sequences.

(3) Construction of a chimeric human antibody expression vector

The vector for chimeric human antibody H chain and L chain expression, as obtained in (2), is provided with a cloning site upstream of the human constant region, for insertion of a cDNA coding for the variable region of an antibody of a nonhuman animal. Insertion, at this cloning site, of the cDNA coding for the variable region of a nonhuman animal antibody, using a synthetic DNA comprising a 5' terminal base sequence of the human antibody constant region and a 3' terminal base sequence of the variable region of the nonhuman animal antibody and having restriction enzyme sites on both ends, gives a chimeric human antibody expression vector with the cDNA coding for the human antibody constant region and the cDNA coding for the variable region of the nonhuman animal antibody joinedly inserted therein via the synthetic DNA for producing appropriate restriction enzyme sites. The synthetic DNA can be synthesized using a DNA synthesizer based on the 5' terminal base sequence of the human antibody constant region and the base sequence of said 3' terminal base sequence of the nonhuman animal antibody variable region.

(4) Construction of a chimeric human antibody H chain expression vector

A vector for chimeric human antibody H chain expression is constructed, for example, by excising that portion of the human antibody $C_H$-encoding cDNA which covers from the ApaI site near the 5' terminus to the 3' terminus and inserting that portion into an expression vector suitable for use in animal cells. This vector for chimeric human antibody H chain expression is provided with a cloning site for insertion of a cDNA coding for a nonhuman animal $V_H$. cDNA coding for the nonhuman animal $V_H$, excised using an appropriate restriction enzyme, is inserted into the vector at the cloning site using a synthetic DNA comprising that portion of the human antibody $C_H$ gene which covers from the 5' terminus to the ApaI site and the base sequence of a 3' terminal portion of the nonhuman animal antibody $V_H$ gene and having restriction enzyme sites on both ends, to give a chimeric human antibody H chain expression vector which allows no change in the amino acid sequence of $V_H$ upon expression thereof and has appropriate restriction enzyme sites.

(5) Construction of a chimeric human antibody L chain expression vector

A vector for chimeric human antibody L chain expression is constructed, for example by introducing an EcoRV site into the human antibody $C_L$-encoding cDNA in the vicinity of the 5' terminus by mutagenesis, excising that portion which covers from the EcoRV site to the 3' terminus and inserting that portion into a plasmid, such as the plasmid pIg1SE1d4. This vector for chimeric human antibody L chain expression is provided with a cloning site for insertion of the cDNA coding for nonhuman animal $V_L$. The nonhuman animal antibody $V_L$-encoding cDNA, excised with an appropriate restriction enzyme, is inserted into the vector at the cloning site using a synthetic DNA comprising that portion of the human antibody $C_L$ gene which covers from the 5' terminus to the EcoRV site and the base sequence of a 3' terminal portion of the nonhuman animal antibody $V_L$ gene and having restriction enzyme sites on both ends, to give a chimeric human antibody L chain expression vector which allows no change in the amino acid sequence of $V_L$ upon expression thereof.

(6) Introduction of the chimeric human antibody expression vectors into host cells Introduction of the chimeric human antibody H chain expression vector and chimeric human antibody L chain expression vector into host cells gives a transformant producing the chimeric human antibody. In introducing the vectors into host cells, a splicing signal may be introduced into the chimeric human antibody H chain and L chain expression vectors for mRNA stabilization [Cell, 17, 737 (1979)].

The chimeric human antibody H chain and L chain vectors can be introduced into host cells, for example, simultaneously by electroporation [JP-A-2-257891 (the term "JP-A" used herein means an unexamined published Japanese patent application.); Cytotechnology, 3, 133 (1990)]. In addition, an expression vector containing genes coding for both the chimeric human antibody H chain and L chain [tandem expression vector] can be introduced into host cells [BIO/TECHNOLOGY, 9, 64 (1991)]. The use of a tandem expression vector is preferred since a higher level of chimeric human antibody expression can be attained thereby, with approximately equal H chain and L chain expression levels.

An example of a method of producing the CDR-transplanted antibodies of the invention is described as follows.

First, a CDR-transplanted antibody expression vector can be constructed by the method of Winter et al. [Nature, 332, 323 (1988)] as follows.

Three synthetic DNAs are constructed designed so as to comprise the cDNAs coding for three CDR peptides of the $V_H$ of a nonhuman animal antibody, for example, peptides having the amino acid sequences defined by SEQ ID NO:94, SEQ ID NO:95 and SEQ ID NO:96, with DNAs coding for amino acid sequences comprising of several amino acids from both ends of the corresponding CDRs of the $V_H$ of a human antibody being located at the respective both ends of the cDNAs, DNA synthesis is carried out with a plasmid containing the human antibody $V_H$ gene as a template. An example of the human antibody $V_H$ gene-containing plasmid is the M13 plasmid containing a human antibody NEW gene-derived sequence [J. Biol. Chem., 253, 585 (1978); Nature, 332, 323 (1988)].

The DNA obtained is inserted into the vector for chimeric human antibody H chain expression in the same manner as in the construction of the chimeric human antibody expression vector mentioned above to give a CDR-transplanted antibody H chain expression vector.

Similarly, using, as primers, three synthetic DNAs designed to comprise the cDNAs coding for three CDR peptides of the $V_L$ of a nonhuman animal antibody, for example, the peptides having the amino acid sequences defined by SEQ ID NO:97, SEQ ID NO:98 and SEQ ID NO:99, with DNAs coding for amino acid sequences comprising several amino acids from both ends of the corresponding CDRs of the human antibody $V_L$ being located at the respective both ends of said cDNAs, DNA synthesis is carried out with a human antibody $V_L$ gene-containing plasmid as a template. An example of the human antibody $V_L$ gene-containing plasmid is the M13 plasmid containing a human myeloma protein (Bence-Jones protein) REI gene-derived sequence [Eur. J. Biochem., 45, 513 (1974); Nature, 332, 323 (1988)].

By inserting the DNA obtained into a vector for chimeric human L chain expression in the same manner as described in respect of the construction of the chimeric human antibody expression vector, a CDR-transplanted antibody L chain expression vector can be constructed.

It is also possible to construct the CDR-transplanted antibody H chain and L chain expression vectors by synthesizing DNAs coding for the peptides having amino acid sequences resulting from replacement of the three CDRs each of the H chain and L chain of a human antibody with the corresponding CDRs of the H chain and L chain of a nonhuman animal antibody and then inserting the DNAs into a vector for chimeric human antibody H chain or L chain expression in the same manner as described in respect of the construction of the chimeric human antibody expression vector mentioned above.

The CDR-transplanted antibody expression vector can be introduced into host cells in the same manner as the chimeric human antibody expression vector to give a transformant producing the CDR-transplanted antibody.

The host cells suited for the introduction thereinto of the chimeric human antibody or CDR-transplanted antibody expression vector may be any host cells provided that the chimeric human antibody or CDR-transplanted antibody can be expressed therein. Examples include mouse SP2/0-Ag14 cells (ATCC CRL1581; hereinafter, "SP2/0 cells"), mouse P3X63-Ag8.653 cells (ATCC CRL1580), CHO cells deficient in the dihydrofolate reductase gene (hereinafter, "dhfr") [Urlaub et al.: Proc. Natl. Acad. Sci. U.S.A., 77, 4216 (1980)] and rat YB2/3HL.P2.G11.16Ag.20 cells (ATCC CRL1662; hereinafter, "YB2/0 cells"), with YB2/0 cells being preferred.

The transformants producing the chimeric human antibody or CDR-transplanted antibody are selected by the method disclosed in JP-A-2-257891 using PRMI1640 medium containing G418 and fetal calf serum. A particular example of the chimeric human antibody-producing transformant is the transformant KM966 producing a chimeric human antibody that reacts with the ganglioside $GM_2$. Examples of human CDR-transplanted antibody-producing transformants include the transformants KM8966 and KM8967 each producing a human CDR-transplanted antibody that reacts with the ganglioside $GM_2$. KM966 has been deposited with the Fermentation Research Institute, Agency of Industrial Science and Technology, of 1-3, Higashi 1-chome, Tsukuba-shi, Ibaraki 305 JAPAN, as of Jul. 15, 1992 under the deposit number FERM BP-3931. KM8966 and KM8967 have also deposited with the above-described institute as of May 23, 1995 under the deposit numbers FERM BP-5105 and FERM BP-5106, respectively.

When the transformant obtained is cultivated in a medium, the chimeric human antibody or CDR-transplanted antibody can be produced and accumulated in the culture fluid. The activity of the chimeric human antibody or CDR-transplanted antibody in the medium can be determined by an enzyme-linked immunosorbent assay (ELISA; E. Harlow et al. (ed.): Antibodies—A Laboratory Manual, Cold Spring Harbor Laboratory, 1988). The antibody productivity of the transformant can be increased by utilizing a dhfr amplification system as disclosed in JP-A-2-257891.

The chimeric human antibody and CDR-transplanted antibody can be purified from the culture supernatants obtained as mentioned above using a protein A column (E. Harlow et al. (ed.): Antibodies—A Laboratory Manual, Cold Spring Harbor Laboratory, 1988). As noted above, the chimeric human antibody KM966, which reacts with the ganglioside $GM_2$, is a specific example of the thus-obtained chimeric human antibodies and CDR-transplanted antibodies.

The reactivity of the chimeric human antibody or CDR-transplanted antibody of the invention can be checked by ELISA. The molecuar weight of the purified antibody H chain or L chain or whole antibody molecule can be determined by polyacrylamide gel electrophoresis (SDS-PAGE) or Western blotting (E. Harlow et al. (ed.): Antibodies—A Laboratory Manual, Cold Spring Harbor Laboratory, 1988).

The binding activity of the chimeric human antibody or CDR-transplanted antibody that reacts with the ganglioside $GM_2$ of cultured cancer cells can be measured, for example, by the fluorescent antibody technique or by ELISA. The complement dependent cytotoxic activity (CDC activity) and antibody dependent cell mediated cytotoxic activity (ADCC activity) of the chimeric human antibody or CDR-transplanted antibody are measured by the methods of Ohta et al. [Cancer Immunol. Immunother., 36, 260 (1993)].

The humanized antibodies of the invention specifically bind to human cancer cells and exhibit CDC activity and ADCC activity against human cancer cells and therefore are useful in the treatment of human cancers, among others.

The humanized antibodies according to the present invention can be used alone as an anticancer agent. They may be formulated into an anticancer composition together with at least one pharmaceutically acceptable carrier. For instance, the humanized antibodies are dissolved in physiological saline, an aqueous solution of glucose, lactose or mannitol and the like. The powder of the humanized antibodies for injection can be prepared by lyophilizing the humanized antibodies in accordance with the conventional method and mixing the lyophilized products with sodium chloride. The anticancer composition may further contain additives conventionally used well known in the art of medical preparation, for example, pharmaceutically acceptable salts.

The humanized antibodies according to the present invention can be administered in the form of the above-described anticancer composition to mammals including human in a dose of 0.2 to 20 mg/kg/day. The dose may vary depending on the age, condition, etc. of patients. The administration of the anticancer composition can be effected by intravenous injection once a day (single administration or consecutive administration) or intermittently one to three times a week or once every two to three weeks.

The anticancer composition is expected to be useful for treating cancer such as melanoma, neuroblastoma and glioma.

The following Examples and Reference Examples are further illustrative of the present invention, but are not to be construed to limit the scope of the present invention.

EXAMPLE 1

Production of Chimeric Human Anti-$GM_2$ Antibodies

1. Isolation of mRNAs From Hybridoma Cells Producing the Mouse Anti-$GM_2$ Monoclonal Antibody KM-796 or KM-750 and From Hybridoma Cells Producing the Rat Anti-$GM_2$ Monoclonal Antibody KM-603

Using mRNA extraction kit Fast Track (product number K1593-02) manufactured by Invitorogen and following the description of the manual attached to the kit, mRNAs were isolated from $1\times10^8$ cells each of the mouse anti-$GM_2$ monoclonal antibody KM-796-producing hybridoma cell line (FERM BP-3340), the mouse anti-$GM_2$ monoclonal antibody KM-750-producing hybridoma cell line (FERM BP-3339) and the rat anti-$GM_2$ monoclonal antibody KM-603-producing hybridoma cell line (FERM BP-2636).

2. Construction of Monoclonal Antibody KM-796 and KM-750 H Chain and L Chain cDNA Libraries Using cDNA Synthesis Kit (product number 27-9260-01) manufactured by Pharmacia and following the manual attached to the kit, cDNA having the EcoRI adapter on both ends was synthesized from 5 $\mu$g each of the KM-796- and KM-750-derived mRNAs obtained as described in Paragraph 1 above. About 6 $\mu$g of each cDNA product obtained was dissolved in 10 $\mu$l of sterilized water and fractionated by agarose gel electrophoresis, and a cDNA fragment (about 1.8 kb) corresponding to the IgG antibody H chain and a cDNA fragment (about 1.0 kb) corresponding to the L chain were recovered (about 0.1 $\mu$g each). Then, 0.1 $\mu$g of each cDNA fragment of about 1.8 kb and 0.1 $\mu$g of each cDNA fragment of about 1.0 kb were respectively dissolved in 11.5 $\mu$l of T4 ligase buffer, together with 1 $\mu$g of the Lambda ZAPII vector (cleaved with EcoRI and then treated with calf intestine alkaline phosphatase; product of Stratagene). After addition of 175 units of T4 DNA ligase, each solution was incubated at 12° C. for 24 hours and then at room temperature for 2 hours. A 4-$\mu$l portion of each reaction mixture was subjected to packaging into the lambda phage in the conventional manner [Maniatis et al. (ed.): Molecular Cloning, 2.95 Cold pring Harbor Laboratory, 1989] using Giga Pak Gold (Stratagene), followed by transfection, in the conventional manner [Maniatis et al. (ed.): Molecular Cloning, 2.95–107, Cold Spring Harbor Laboratory, 1989] of the *Escherichia coli* strain XL1-Blue [Biotechniques, 5, 376 (1987)] attached to Giga Pak Gold, to give about $4\times10^3$ phage clones each as a KM-796 or KM-750 H chain or L chain cDNA library. Then the phage clones of each library were fixed on a nitrocellulose filter in the conventional manner [Maniatis et al. (ed.): Molecular Cloning, 2.112, Cold Spring Harbor Laboratory, 1989].

3. Construction of KM-603 H Chain and L Chain cDNA Libraries

Using 5 ug of the KM-603 MRNA obtained as mentioned above in Paragraph 1 and cDNA Synthesis Kit (product number 27-9260-01) manufactured by Pharmacia, cDNA having the EcoRI adapter on both ends was synthesized. About 6 $\mu$g of the cDNA produced was dissolved in 10 $\mu$l of sterilized water and fractionated by agarose gel electrophoresis. A cDNA fragment (about 2.2 kb) corresponding to the IgG antibody H chain and a cDNA fragment (about 1.0 kb) corresponding to the L chain were recovered (about 0.1 $\mu$g each). Then 0.1 $\mu$g of the cDNA fragment of about 2.2 kb and 0.1 $\mu$g of the cDNA fragment of about 1.0 kb were respectively dissolved in 11.5 $\mu$l of T4 ligase buffer, together with 1 $\mu$g of the Lambda ZAPII vector (cleaved with EcoRI and then treated with calf intestine alkaline phosphatase; product of Stratagene) and, after addition of 175 units of T4 DNA ligase, the resultant solution was incubated at 12° C. for 24 hours and then at room temperature for 2 hours. A 4-$\mu$l portion of each reaction mixture was subjected to packaging into the lambda phage in the conventional manner [Maniatis et al. (ed.): Molecular Cloning, 2.95, Cold Spring Harbor Laboratory, 1989] using Giag Pak Gold (Stratagene), followed by transfection, in the conventional manner [Maniatis et al. (ed.): Molecular Cloning, 2.95–107, Cold Spring Harbor Laboratory, 1989], of the *Escherichia coli* strain XL-Blue attached to Giga Pak Gold, whereby about $1\times10^4$ phage clones were obtained each as a KM-603 H chain or L chain cDNA library. Then, the phage clones of each library were fixed on a nitrocellulose filter in the conventional manner [Maniatis et al. (ed.): Molecular Cloning, 2.112, Cold Spring Harbor Laboratory, 1989].

4. Cloning of the KM-796 and KM-750 H Chain and L Chain cDNAs

Figure 1:
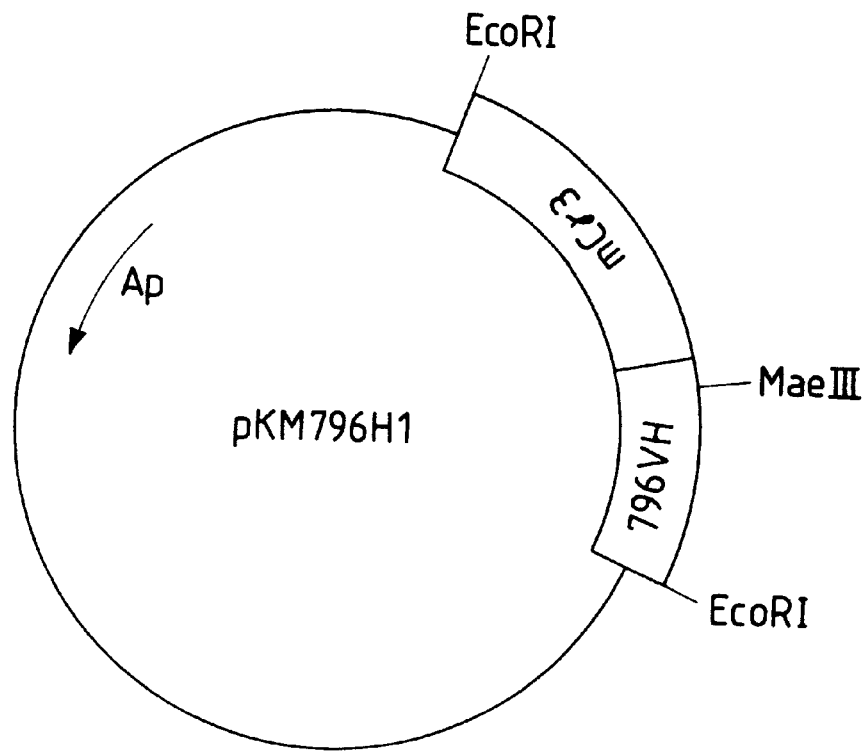
FIG. 1 illustrates plasmids, pKM796H1 and pKM796L1.
Figure 1:
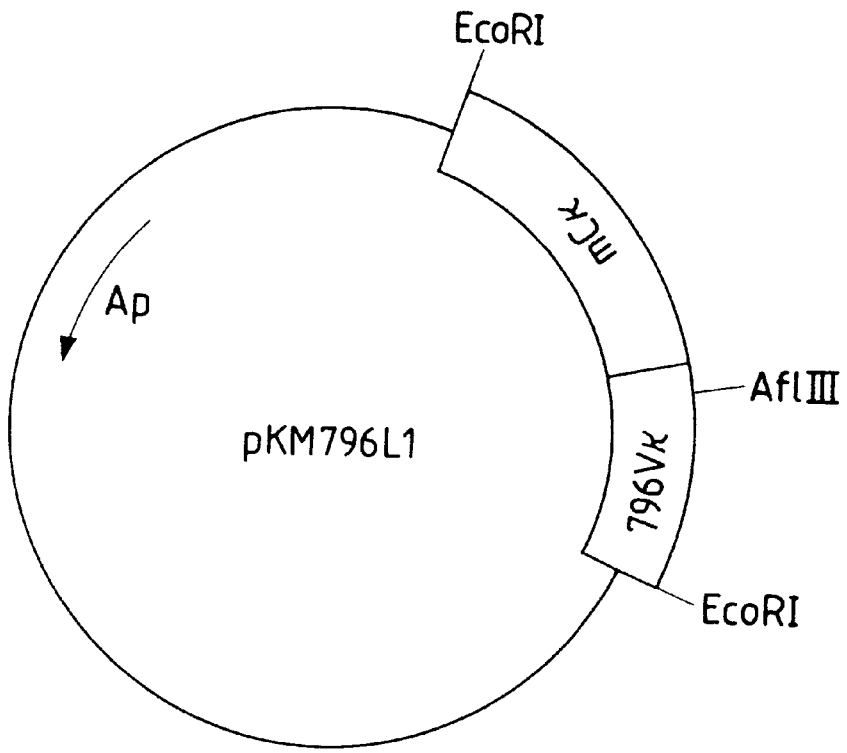
Figure 2:
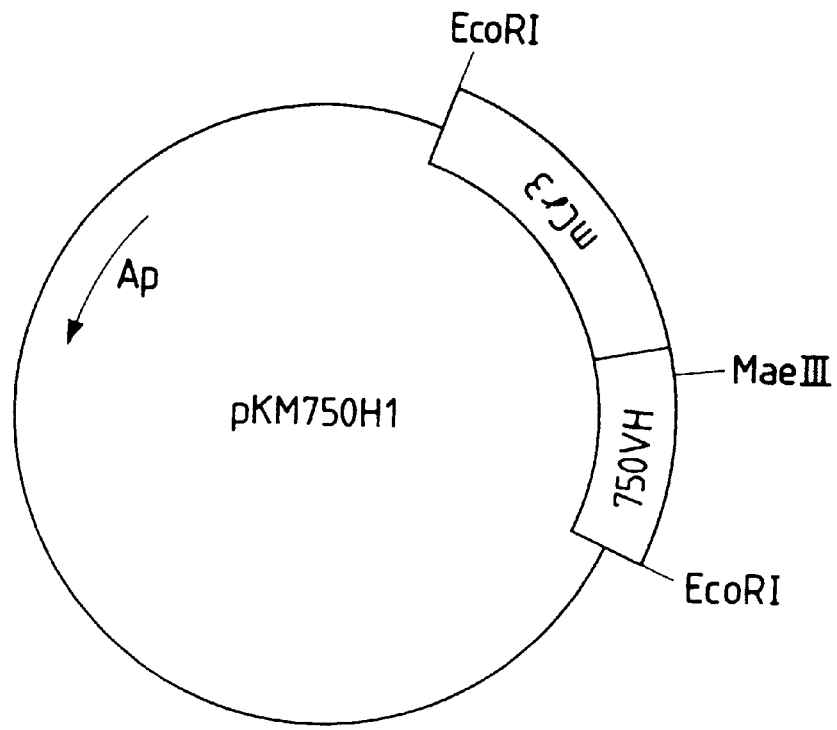
FIG. 2 illustrates plasmids, pKM750H1 and pKM750L1.
Figure 2:
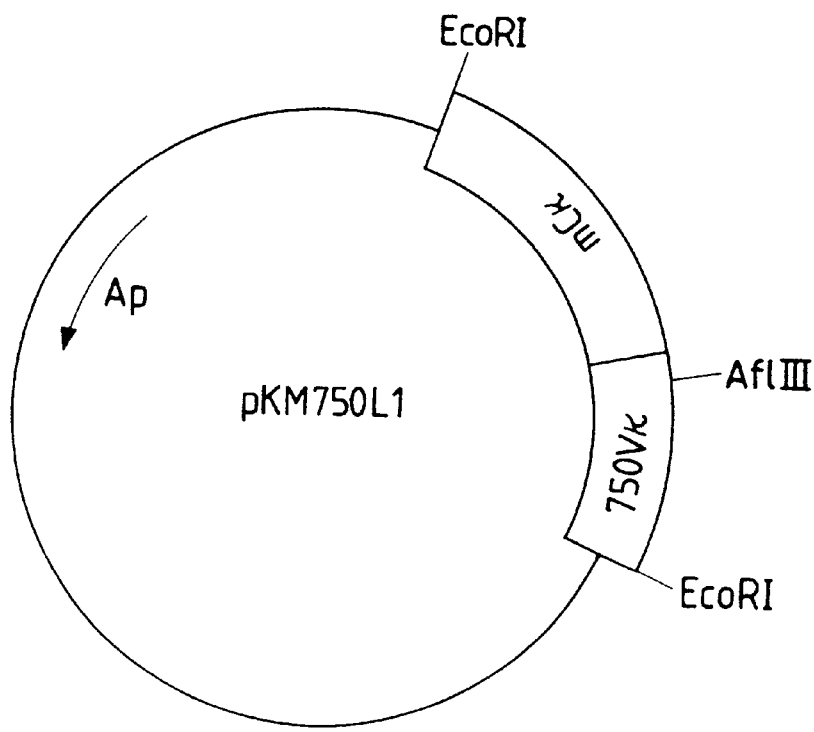

From among the KM-796 and KM-750 H chain cDNA libraries and L chain cDNA libraries constructed as described above in Paragraph 2, phage clones firmly bound at 65° C. to a probe prepared by labeling a mouse immunoglobulin constant region cDNA [for the H chain, the BamHI-XhoI fragment of the mouse Cγ3 cDNA (Wels et al: EMBO J., 3, 2041–2046, 1984); for the L chain, the HpaI-XhoI fragment of the mouse Cκ cDNA (Hieter et at.: Cell, 22, 197–207, 1980)] with $^{32}$P were recovered in the conventional manner [Maniatis et al.: Molecular Cloning, 2.108, Cold Spring Harbor Laboratory, 1989]. Then, using a ZAP-cDNA Synthesis Kit (cDNA synthesis kit; product number sc200400) manufactured by Stratagene, phage clones were converted into pBluescript plasmids, and a KM-796 H chain cDNA-containing recombinant plasmid (pKM796H1) and a KM-796 L chain cDNA-containing recombinant plasmid (pKM796L1) (FIG. 1) as well as a KM-750 H chain cDNA-containing recombinant plasmid (pKM750H1) and a KM-750 L chain cDNA-containing recombinant plasmid (pKM750L1) (FIG. 2) were obtained. Cleavage of pKM796H1, pKM750H1, pKM796L1 and pKM750L1 with EcoRI revealed that a cDNA fragment of about 1.8 kb had been inserted into pKM796H1 and pKM750H1 and a cDNA fragment of about 0.9 kb into pKM796L1 and pKM750L1.

5. Cloning of KM-603 H Chain and L Chain cDNAs

Figure 3:
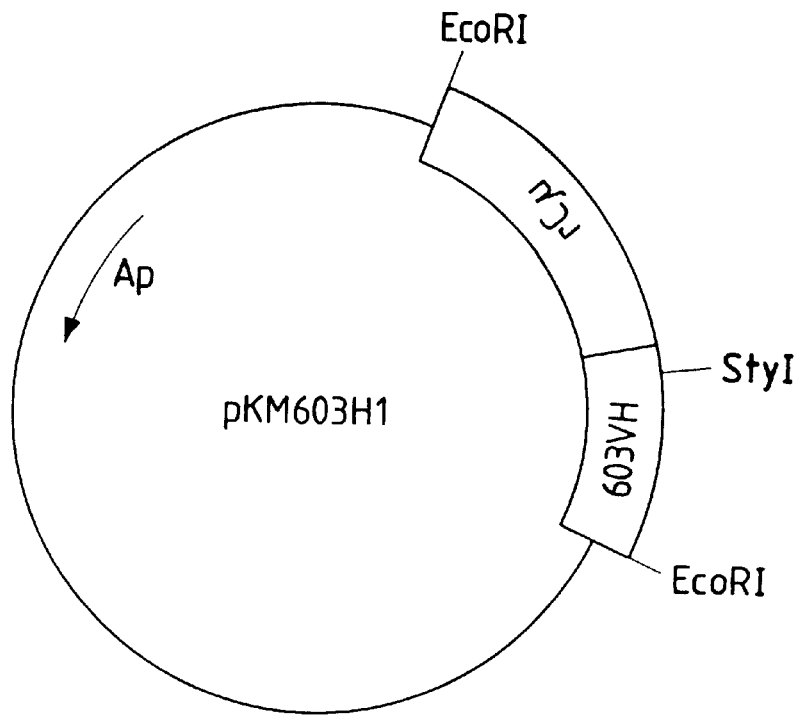
FIG. 3 illustrates plasmids, pKM603H1 and pKM603L1.
Figure 3:
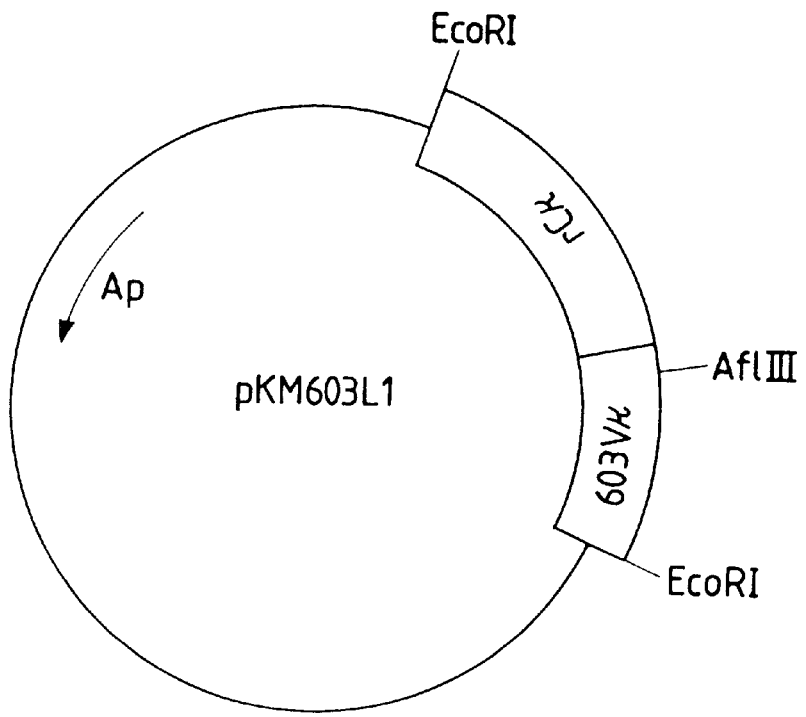

Phage clones firmly bound at 65° C. to a probe prepared by labeling a mouse immunoglobulin constant region chromosomal gene [mouse Cμ gene-containing SmaI-KpnI fragment of about 11.5 kb (Kataoka et al.: Proc. Natl. Acad. Sci. U.S.A., 77, 919–923, 1980) and mouse Cκ gene-containing HindIII-BamHI fragment of about 3 kb (Sakano et al.: Nature, 280, 288, 1979)] with $^{32}$P were isolated from the KM-603 H chain cDNA library and L chain cDNA library constructed as mentioned above in Paragraph 3 in the conventional manner [Maniatis et al. (ed.): Molecular Cloning, 2.108, Cold Spring Harbor Laboratory, 1989]. Then, using ZAP-cDNA Synthesis kit (product number sc200400) manufactured by Stratagene, the phage clones were converted to pBluescript plasmids and a KM-603 H chain cDNA-containing recombinant plasmid, pKM603H1, and a KM-603 L chain cDNA-containing recombinant plasmid, pKM603L1, were obtained (FIG. 3). Cleavage of pKM603H1 and pKM603L1 revealed that pKM603H1 contained a cDNA fragment of about 2.0 kb as inserted therein and pKM603L1 a cDNA fragment of about 0.9 kb as inserted therein.

6. Base Sequences of the Variable Regions in the H Chain cDNA and L Chain cDNA

The base sequences of the variable regions in the H chain cDNA and L chain cDNA obtained as mentioned above in Paragraphs 4 and 5 were determined by the dideoxy method [Maniatis et al. (ed.): Molecular Cloning, 13.42, Cold Spring Harbor Laboratory, 1989] using Sequenase Version 2.0 DNA Sequencing Kit manufactured by United States Biochemical Corporation. All the cDNA had a methionine codon, presumably the initiation codon ATG, at the 5' terminus and were leader sequence-containing full-length cDNAs. Based on the base sequences of the respective cDNAs, the amino acid sequences of the H chain and L chain of KM-796, KM-750 and KM-603 were deduced. The amino acid sequence of the KM-796 H chain is shown in SEQ ID NO:91, that of the L chain of KM-796 and KM-750 in SEQ ID NO:92, that of the KM-750 H chain in SEQ ID NO:93, that of the KM-603 H chain in SEQ ID NO:4 and that of the KM-603 L chain in SEQ ID NO:5.

7. Construction of KM-796- and KM-750-Derived Chimeric Human Antibody H Chain and L Chain Expression Vectors (1) Construction of a vector, pAGE147, carrying the Moloney mouse leukemia virus terminal repeat promoter/enhancer The plasmid pPMOL1 (2 μg), described in JP-A-1-63394, was dissolved in 30 μl of 10 mM Tris-hydrochloride buffer (pH 7.5) containing 6 mM magnesium chloride and 6 mM 2-mercaptoethanol, 20 units of SmaI was added, and digestion was carried out at 30° C. for 3 hours. Then, sodium chloride was added to a concentration of 50 mM, 20 units of ClaI was added, and digestion was conducted at 37° C. for 2 hours. The reaction mixture was subjected to agarose gel electrophoresis, and a DNA fragment (about 0.6 kb) containing the Moloney mouse leukemia virus terminal repeat promoter/enhancer was recovered.

Then, the following two synthetic DNAs were synthesized using an automatic DNA synthesizer (model 380A manufactured by Applied Biosystems Co., Ltd.).

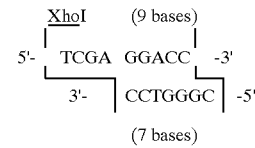

The thus-obtained synthetic DNAs (25 picomoles each) were dissolved in 10 μl of 50 mM Tris-hydrochloride buffer (pH 7.6) containing 10 mM magnesium chloride, 5 mM DTT (dithiothreitol), 0.1 mM EDTA and 0.5 mM adenosine triphosphate (hereinafter, "ATP"), 5 units of T4 DNA kinase was added, and 5'-phosphorylation was carried out at 37° C. for 30 minutes.

The plasmid pPMOL1-derived ClaI-SmaI fragment (0.6 kb, 0.05 μg) and two 5'-phosphorylated synthetic DNAs (1 picomole each), obtained as described above, and a HindIII linker (5'-pCAAGCTTG-3'; Takara Shuzo) (1 picomole) were dissolved in 30 μl of 66 mM Tris-hydrochloride buffer (pH 7.5) containing 6.6 mM magnesium chloride, 10 mM DTT and 0.1 mM ATP, 200 units of T4 DNA ligase (Takara Shuzo; hereinafter the same shall apply) were added, and ligation was carried out at 12° C. for 16 hours. The resultant DNA fragment was recovered by ethanol precipitation and dissolved in 20 μl of 10 mM Tris-hydrochloride buffer (pH 7.5) containing 6 mM magnesium chloride, 100 mM sodium chloride and 6 mM 2-mercaptoethanol, 10 units of HindIII and 10 units of XhoI were added, and digestion was carried out at 37° C. for 2 hours. The reaction was terminated by phenol-chloroform extraction, and the DNA fragment was recovered by ethanol precipitation.

Separately, 1 μg of the plasmid pAGE107 [Cytotechnology, 3, 133 (1990)] was dissolved in 30 μl of 10 mM Tris-hydrochloride buffer (pH 7.5) containing 6 mM magnesium chloride, 100 mM sodium chloride and 6 mM 2-mercaptoethanol, 10 units of HindIII and 10 units of XhoI were added, and digestion was carried out at 37° C. for 2 hours. The reaction mixture was subjected to agarose gel electrophoresis, and a DNA fragment (about 6.0 kb) containing the G418 resistance gene and ampicillin (hereinafter, "Ap") resistance gene was recovered.

Figure 4:
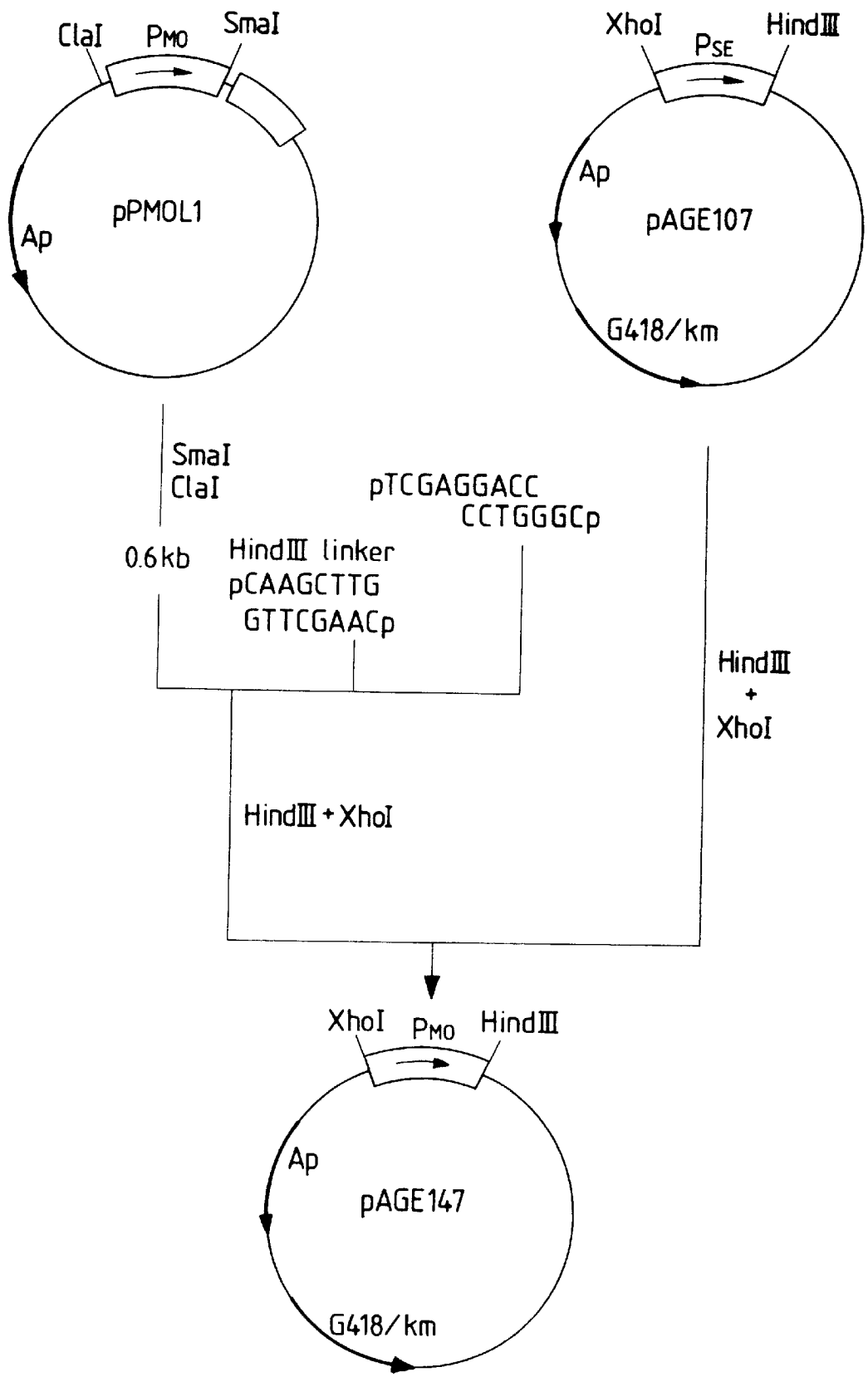
FIG. 4 shows a construction scheme for a plasmid, pAGE147.

The plasmid pAGE107-derived HindIII-XhoI fragment (6.0 kb, 0.3 μg) and plasmid pPMOL1-derived HindIII-XhoI fragment (0.63 kb, 0.01 μg) obtained as mentioned above were dissolved in 20 μl of 66 mM Tris-hydrochloride buffer (pH 7.5) containing 6.6 mM magnesium chloride, 10 mM DTT and 0.1 mM ATP, 200 units of T4 DNA ligase were added, and ligation was carried out at 12° C. for 16 hours. The thus-obtained recombinant plasmid DNA was used to transform *Escherichia coli* HB101, and the plasmid pAGE147 shown in FIG. 4 was obtained.

(2) Construction of a vector, pAGE148, carrying the β-globin 3' splicing signal (SP)

For introducing the β-globin 3' splicing signal into the chimeric human antibody expression vector at a site downstream from the antibody constant region gene, a vector (pAGE148), was constructed as follows, which contained the β-globin 3' splicing signal and the same genes as those in the chimeric human antibody expression vector (except for the human antibody constant region gene).

Two μg of pSE1UK1SEd1-3, described in JP-A-2-257851, were added to 30 μl of 10 mM Tris-hydrochloride buffer (pH 7.5) containing 10 mM magnesium chloride, 50 mM sodium chloride and 1 mM DTT. After addition of 10 units of HindIII, digestion was carried out at 37° C. for 4 hours. The reaction mixture was subjected to phenol-chloroform extraction and then to ethanol precipitation. The precipitate was dissolved in 20 μl of DNA polymerase I buffer, 5 units of Escheichia coli-derived DNA polymerase I Klenow fragment were added, and the 5' cohesive ends produced by HindIII digestion were rendered blunt by incubation at 22° C. for 30 minutes. The reaction mixture was subjected to phenol-chloroform extraction and then to ethanol precipitation, 30 μl of 10 mM Tris-hydrochloride buffer (pH 7.5) containing 10 mM magnesium chloride and 1 mM DTT and 10 units of KpnI were added, and digestion was effected at 37° C. for 4 hours. The reaction mixture was subjected to phenol-chloroform extraction and then to ethanol precipitation, 30 μl of 50 mM Tris-hydrochloride buffer (pH 7.5) containing 10 mM magnesium chloride, 100 mM sodium chloride and 1 mM DTT and 10 units of XhoI were added, and digestion was carried out at 37° C. for 4 hours. The reaction mixture was fractionated by agarose gel electrophoresis and two DNA fragments, about 6.67 kb and about 1.98 kb in size, were recovered (about 0.2 μg each).

Then, 2 μg of pAGE147 obtained in (1) was added to 30 μl of 10 mM Tris-hydrochloride buffer (pH 7.5) containing 10 mM magnesium chloride and 1 mM DTT, 10 units of KpnI was added, and digestion was effected at 37° C. for 4 hours. The reaction mixture was subjected to phenol-chloroform extraction and then to ethanol precipitation, 30 μl of 50 mM Tris-hydrochloride buffer (pH 7.5) containing 10 mM magnesium chloride, 100 mM sodium chloride and 1 mM DTT and 10 units of XhoI were added, and digestion was carried out at 37° C. for 4 hours. The reaction mixture was fractionated by agarose gel electrophoresis and about 0.2 μg of a DNA fragment of about 0.66 kb was recovered.

Figure 5:
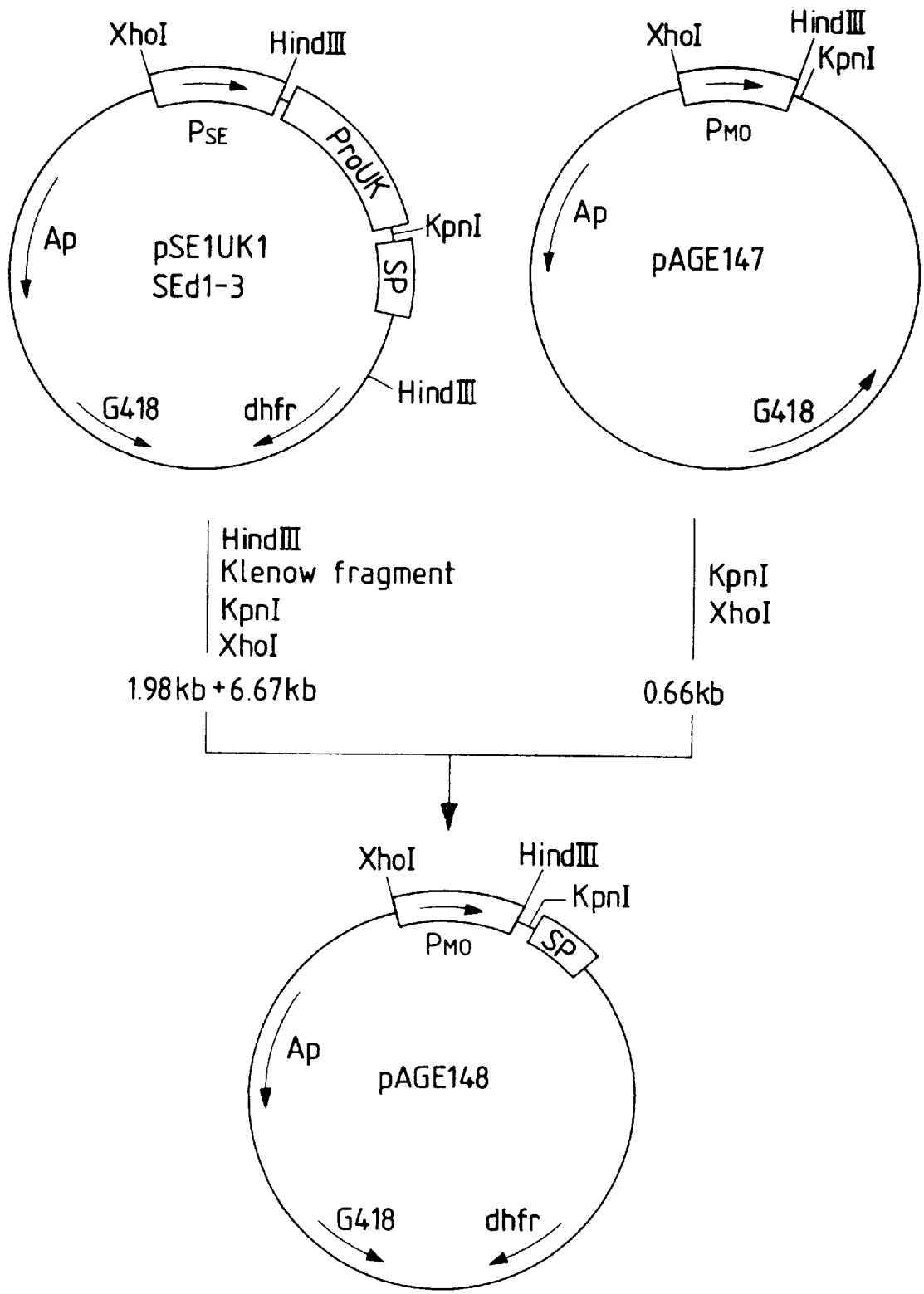
FIG. 5 shows a construction scheme for a plasmid, pAGE148.

Then, 0.1 μg of the XhoI-HindIII fragment (about 6.67 kb) of pSE1UK1SEd1-3, as obtained above, 0.1 μg of the KpnI-HindIII fragment (about 1.98 kb), obtained above, and 0.1 μg of the XhoI-KpnI fragment (about 0.66 kb) of pAGE147, as obtained above, were dissolved in a total of 20 μl of T4 ligase buffer. Three hundred fifty units of T4 ligase were added to the solution, and ligation was carried out at 4° C. for 24 hours. The thus-obtained recombinant plasmid DNA was used to transform *Escherichia coli* HB101, and the plasmid pAGE148 shown in FIG. 5 was obtained.

Figure 6:
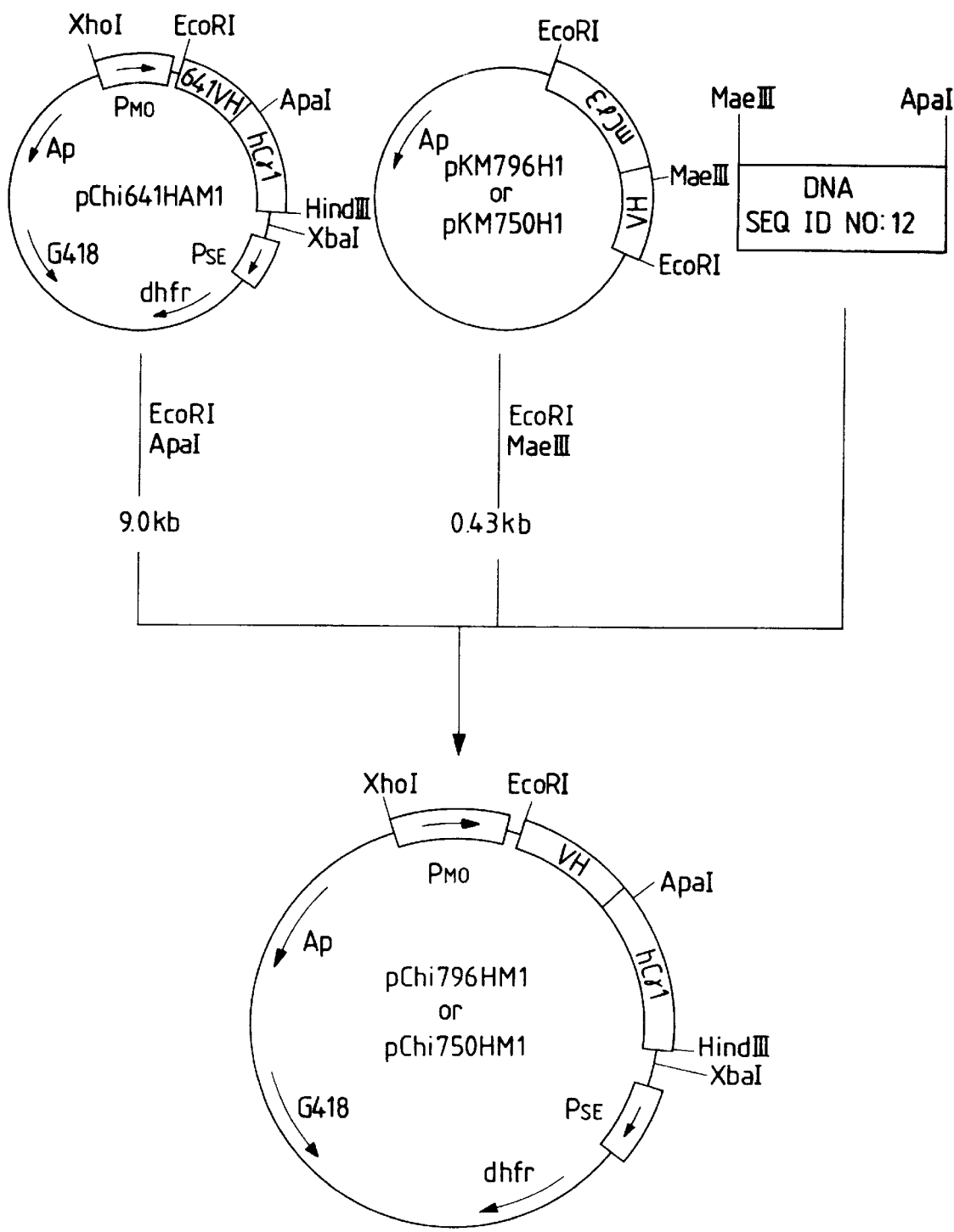
FIG. 6 shows a construction scheme for plasmids, pChi796HM1 and pChi750HM1.

(3) Construction of KM-796- and KM-750-derived chimeric human antibody H chain expression vectors First, the cDNA coding for the antibody variable region in the plasmid pKM796H1 or pKM750H1 was excised by cleavage at the 5'-terminal EcoRI site and the MaeIII site near the 3' end of said cDNA and joined, together with a synthetic DNA having the base sequence shown in SEQ ID NO:12, to the chimeric human antibody H chain expression vector pChi641HAM1, as follows (FIG. 6).

Three μg of pKM796H1 or pKM750H1, obtained in Paragraph 4, were added to 30 μl of 50 mM Tris-hydrochloride buffer (pH 7.5) containing 10 mM magnesium chloride, 100 mM sodium chloride and 1 mM DTT. Further, 10 units of EcoRI and 10 units of MaeIII were added, and digestion was effected at 37°0 C. for 4 hours. The reaction mixture was fractionated by agarose gel electrophoresis and about 0.3 μg of a DNA fragment of about 0.43 kb was recovered. Then, 3 μg of pChi641HAM1, obtained in Reference Example 2, was added to 30 μl of 10 mM Tris-hydrochloride buffer (pH 7.5) containing 10 mM magnesium chloride and 1 mM DTT, 10 units of EcoRI and 10 units of ApaI were also added, and digestion was carried out at 37° C. for 4 hours. The reaction mixture was fractionated by agarose gel electrophoresis and about 1.0 μg of a DNA fragment of about 9.0 kb was recovered. Then, 0.1 μg of the EcoRI-MaeIII fragment (about 0.43 kb) of pKM796H1 or pKM750H1, as obtained above, 0.1 μg of the EcoRI-ApaI fragment (about 9.0 kb) of pChi641HAM1, as obtained above, and 0.3 μg of a synthetic DNA having the base sequence shown in SEQ ID NO:12 were dissolved in a total of 20 μl of T4 ligase buffer, 350 units of T4 ligase was further added to the solution, and ligation was carried out at 4° C. for 24 hours. The thus-obtained recombinant plasmid DNA was used to transform *Escherichia coli* HB101. In this way, the plasmids pChi796HM1 and pChi750HM1, shown in FIG. 6, were obtained.

Figure 7:
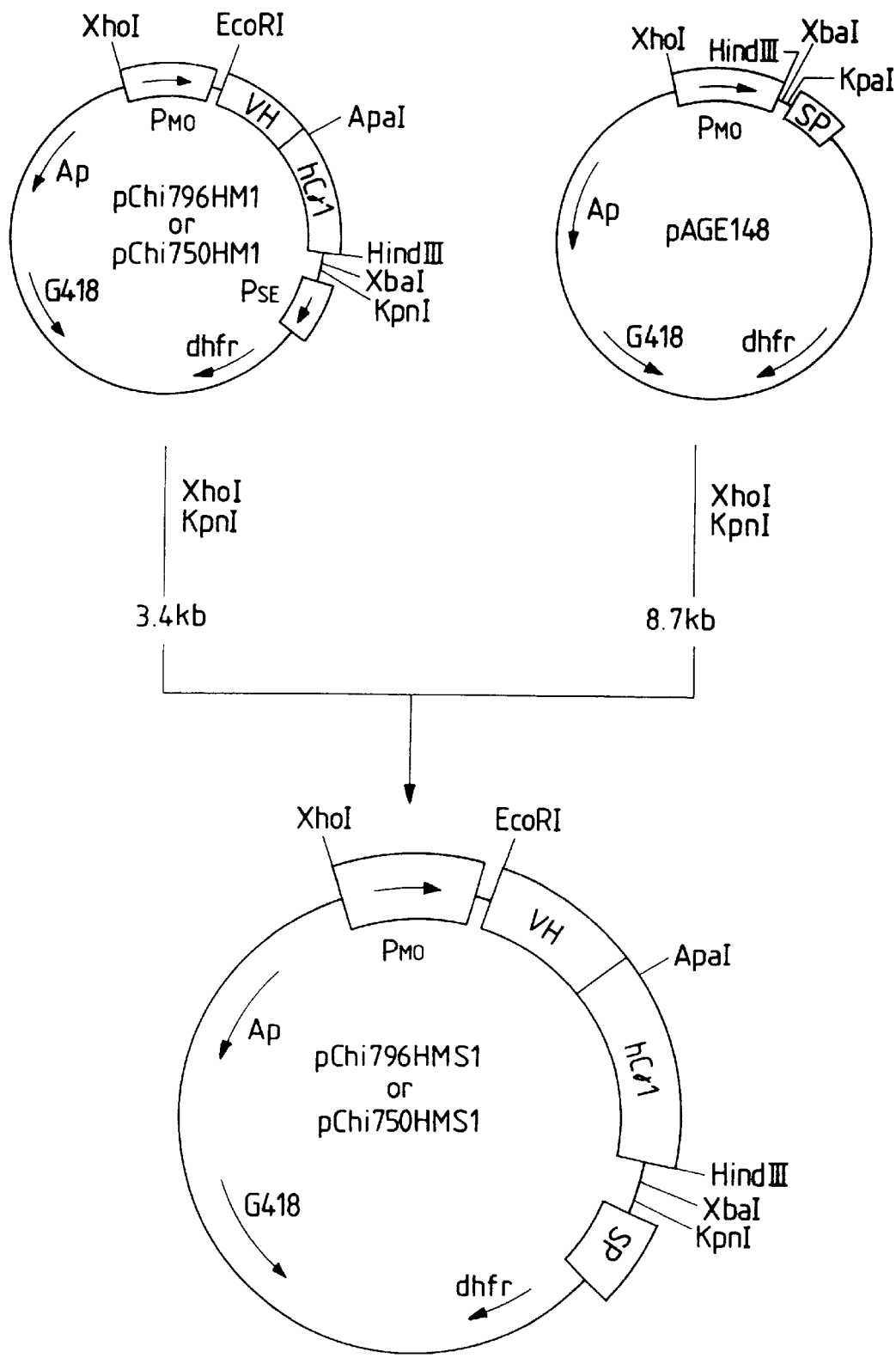
FIG. 7 shows a construction scheme for plasmids, pChi796HMS1 and pChi750HMS1.

Then, the β-globin 3' splicing signal was introduced into the plasmids pChi796HM1 and pChi750HM1 by the method described below to construct KM796- and KM-750-derived chimeric human antibody H chain expression vectors (FIG. 7).

Three μg of pChi796HM1 or pChi750HM1 were added to 30 μl of 33 mM Tris-acetate buffer (pH 7.9) containing 10 mM magnesium acetate, 66 mM potassium acetate, 0.5 mM DTT and 0.01% bovine serum albumin (hereinafter, "BSA"). Ten units of XhoI and 10 units of KpnI were also added, and digestion was carried out at 37° C. for 4 hours. The reaction mixture was fractionated by agarose gel electrophoresis and about 0.3 μg of a DNA fragment of about 3.4 kb was recovered. Then, 3 μg of pAGE148 obtained in (2) was added to 30 μl of 33 mM Tris-acetate buffer (pH 7.9) containing 10 mM magnesium acetate, 66 mM potassium acetate, 0.5 mM DTT and 0.01% BSA; 10 units of XhoI and 10 units of KpnI were further added, and digestion was effected at 37° C. for 4 hours. The reaction mixture was fractionated by agarose gel electrophoresis and about 0.3 μg of a DNA fragment of about 8.7 kb was recovered. Then, 0.1 μg of the XhoI-KpnI fragment of pChi796HM1 or pKM750HM1 and 0.1 μg of the XhoI-KpnI fragment of pAGE148 were dissolved in a total of 20 μl of T4 ligase buffer, 350 units of T4 ligase was further added to the solution, and ligation was carried out at 4° C. for 24 hours. The thus-obtained recombinant plasmid DNA was used to transform *Escherichia coli* HB101. The plasmids pChi796HMS1 and pChi750HMS1 shown in FIG. 7 were thus obtained.

Figure 8:
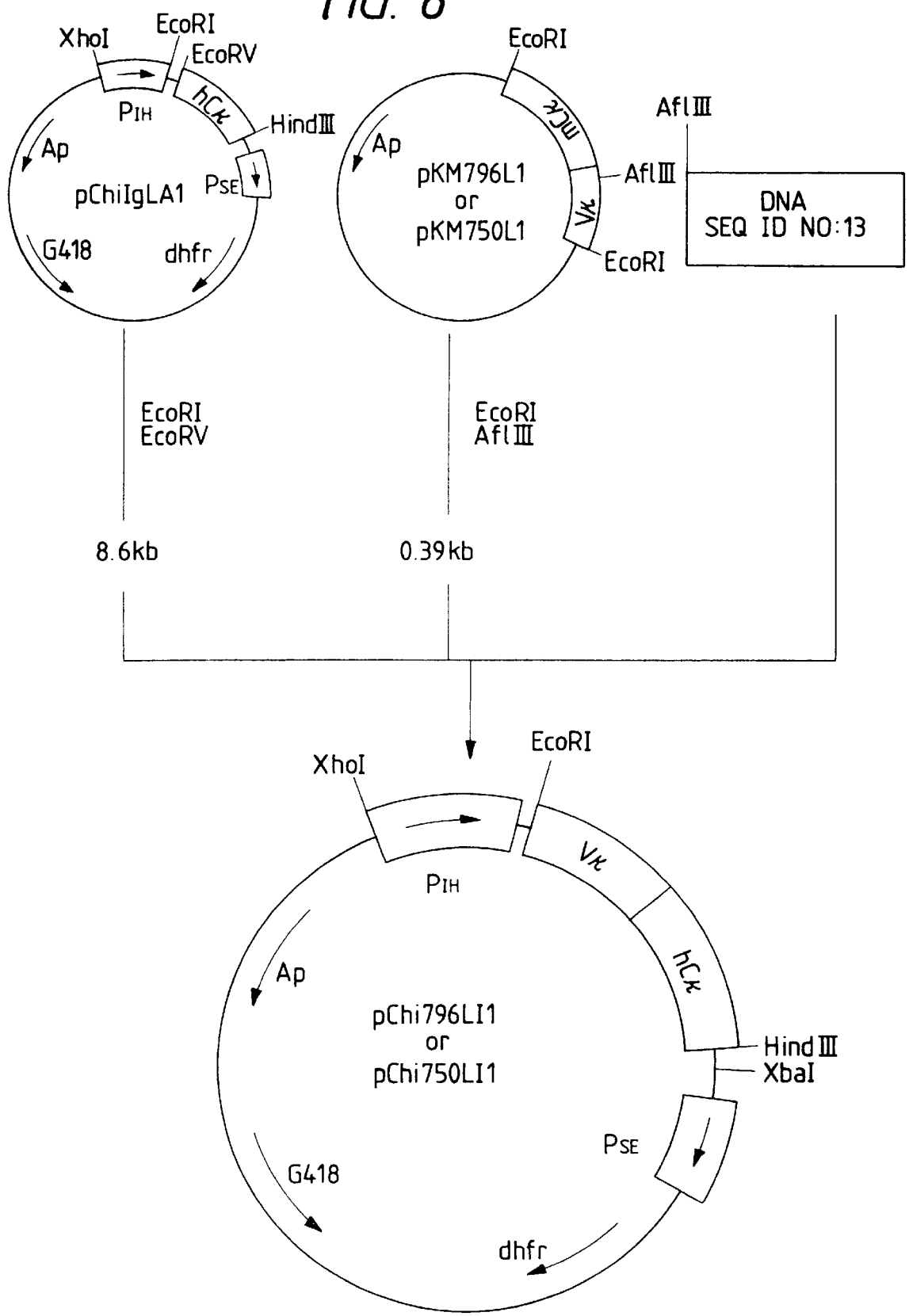
FIG. 8 shows a construction scheme for plasmids, pChi796LI1 and pChi750LI1.

(4) Construction of KM-796- and KM-750-derived chimeric human antibody L chain expression vectors First, the cDNA coding for the antibody variable region in the plasmid pKM796L1 or PKM750L1 was excised by cleavage at the 5'-terminal EcoRI site and the Af1III site near the 3' end of said cDNA and joined, together with a synthetic DNA having the base sequence shown in SEQ ID NO:13, to the chimeric human antibody L chain expression vector pChiIgLA1, as follows (FIG. 8).

Three μg of pKM796L1 or pKM750L1 were added to 30 μl of 50 mM Tris-hydrochloride buffer (pH 7.5) containing 10 mM magnesium chloride, 100 mM sodium chloride and 1 mM DTT. Further, 10 units of EcoRI and 10 units of Af1III were added, and digestion was effected at 37° C. for 4 hours. The reaction mixture was fractionated by agarose gel electrophoresis and about 0.3 μg of a DNA fragment of about 0.39 kb was recovered. Then, 3 μg of pChiIgLA1 obtained in Reference Example 1 was added to 30 μl of 50 mM Tris-hydrochloride buffer (pH 7.5) containing 10 mM magnesium chloride, 100 mM sodium chloride and 1 mM DTT, 10 units of EcoRI and 10 units of EcoRV were further added, and digestion was carried out at 37° C. for 4 hours. The reaction mixture was fractionated by agarose gel electrophoresis and about 1 μg of a DNA fragment of about 8.6 kb was recovered.

Then, 0.1 μg of the EcoRI-AflIII fragment of pKM796L1 or pKM750L1, as obtained above, 0.1 μg of the EcoRI-EcoRV fragment of pChiIgLA1, as obtained above, and 0.3 μg of a synthetic DNA, having the base sequence shown in SEQ ID NO:13, were dissolved in a total of 20 μl of T4 ligase buffer; 350 units of T4 ligase was further added to the solution, and ligation was carried out at 4° C. for 24 hours. The thus-obtained recombinant plasmid DNA was used to transform *Escherichia coli* HB101. In this way, the plasmids pChi796LI1 and pChi750LI1 shown in FIG. 8 were obtained.

Figure 9:
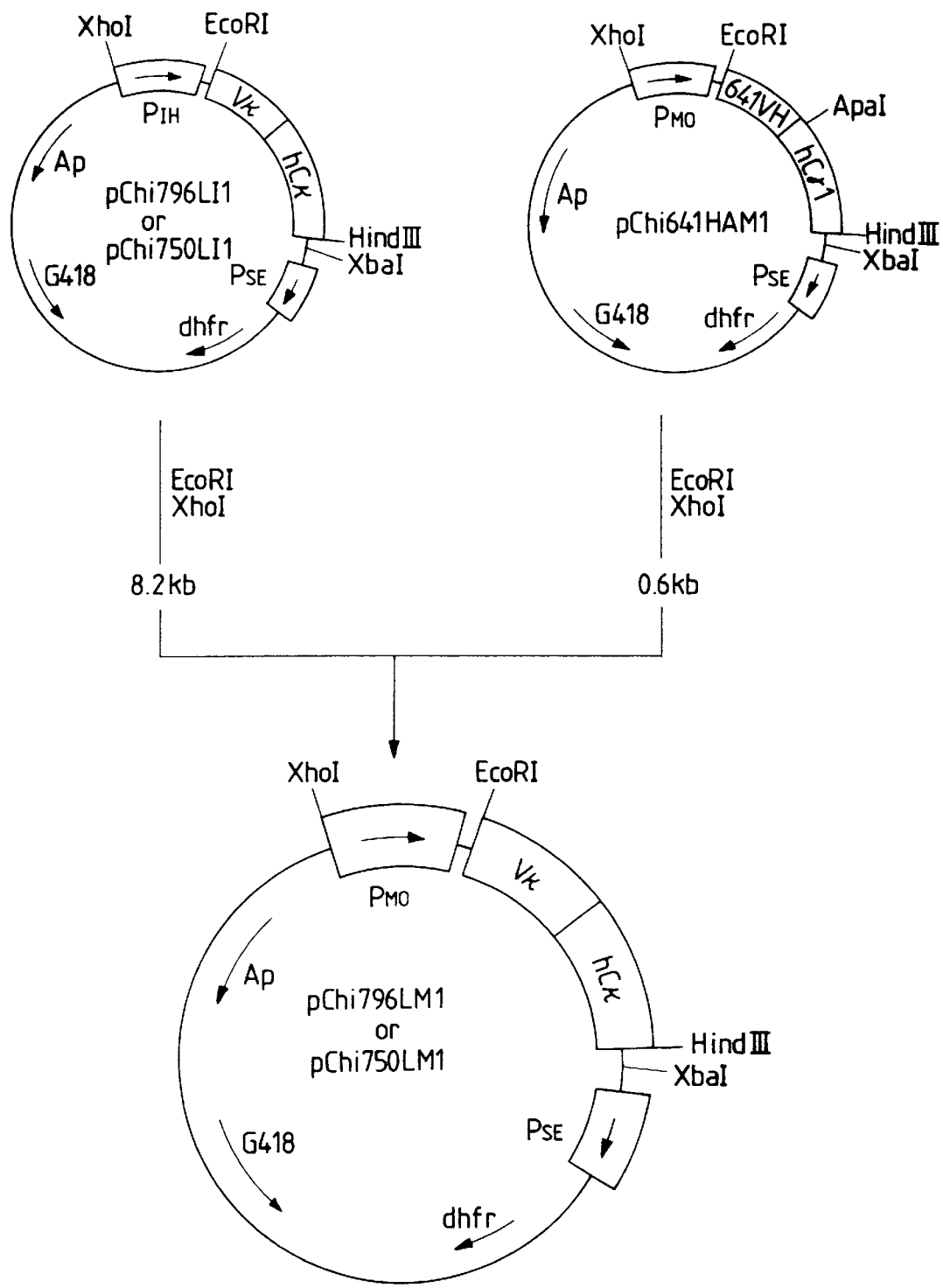
FIG. 9 shows a construction scheme for plasmids, pChi796LM1 and pChi750LM1.

Then, the Moloney mouse leukemia virus terminal repeat promoter/enhancer was introduced into the plasmids pChi796LI1 and pChi750LI1 in the following manner (FIG. 9).

Three μg of pChi796LI1 and pChi750LI1 were added to 30 μl of 50 mM Tris-hydrochloride buffer (pH 7.5) containing 10 mM magnesium chloride, 100 mM sodium chloride and 1 mM DTT. Further, 10 units of EcoRI and 10 units of XhoI were added, and digestion was effected at 37° C. for 4 hours. The reaction mixture was fractionated by agarose gel electrophoresis and about 0.3 μg of a DNA fragment of about 8.2 kb was recovered Then, 3 μg of the chimric human antibody H chain expression vector pChi641HAM1 obtained in Reference Example 2 was added to 30 μl of 50 mM Tris-hydrochloride buffer (pH 7.5) containing 10 mM magnesium chloride, 100 mM sodium chloride and 1 mM DTT, 10 units of EcoRI and 10 units of XhoI were further added, and digestion was carried out at 37°0 C. for 4 hours. The reaction mixture was fractionated by agarose gel electrophoresis and about 0.3 μg of a DNA fragment of about 0.6 kb was recovered.

Then, 0.1 μg of the EcoRI-XhoI fragment of pChi796LI1 or pKM750LI1 as obtained above and 0.1 μg of the EcoRI-XhoI fragment of pChi641HAM1 as obtained above were dissolved in a total of 20 μl of T4 ligase buffer, 350 units of T4 ligase was further added to the solution, and ligation was carried out at 4° C. for 24 hours. The thus-obtained recombinant plasmid DNA was used to transform *Escherichia coli* HB101. In this way, the plasmids pChi796LM1 and pChi750LM1 shown in FIG. 9 were obtained.

Figure 10:
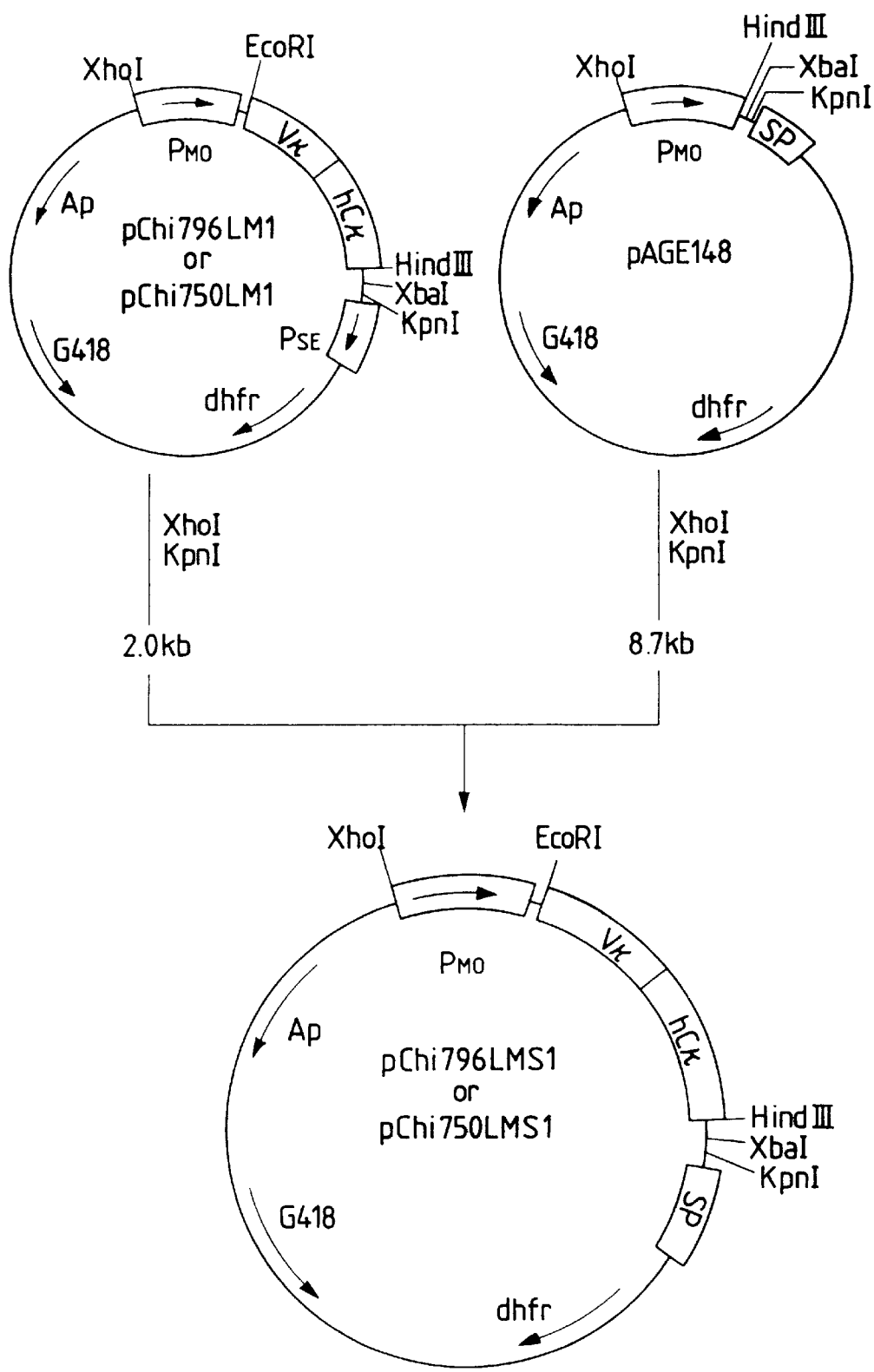
FIG. 10 shows a construction scheme for plasmids, pChi796LMS1 and pChi750LMS1.

Then, the β-globin 3' splicing signal was introduced into the plasmids pChi796LM1 and pChi750LM1 in the manner mentioned below to construct KM-796- and KM-750-derived chimeric human antibody L chain expression vectors (FIG. 10).

Three μg of pChi796LM1 or pChi750LM1 were added to 30 μl of 33 mM Tris-acetate buffer (pH 7.9) containing 10 mM magnesium acetate, 66 mM potassium acetate, 0.5 mM DTT and 0.01% BSA. Further, 10 units of XhoI and 10 units of KpnI were added, and digestion was carried out at 37° C. for 4 hours. The reaction mixture was fractionated by agarose gel electrophoresis and about 0.3 μg of a DNA fragment of about 2.0 kb was recovered. Then, 3 μg of pAGE148 obtained in (2) was added to 30 μl of 33 mM Tris-acetate buffer (pH 7.9) containing 10 mM magnesium acetate, 66 mM potassium acetate, 0.5 mM DTT and 0.0% BSA; 10 units of XhoI and 10 units of KpnI were further added, and digestion was carried out at 37° C. for 4 hours. The reaction mixture was fractionated by agarose gel electrophoresis and about 0.3 μg of a DNA fragment of about 8.7 kb was recovered. Then 0.1 μg of the XhoI-KpnI fragment of pChi796LM1 or pKM750LM1 as obtained above and 0.1 μg of the XhoI-KpnI fragment of pAGE148 were dissolved in a total of 20 μl of T4 ligase buffer, 350 units of T4 ligase was further added, and ligation was carried out at 4° C. for 24 hours. The thus-obtained recombinant plasmid DNA was used to transform *Escherichia coli* HB101. In this way, the plasmids pChi796LMS1 and pChi750LMS1 shown in FIG. 10 were obtained.

Figure 11:
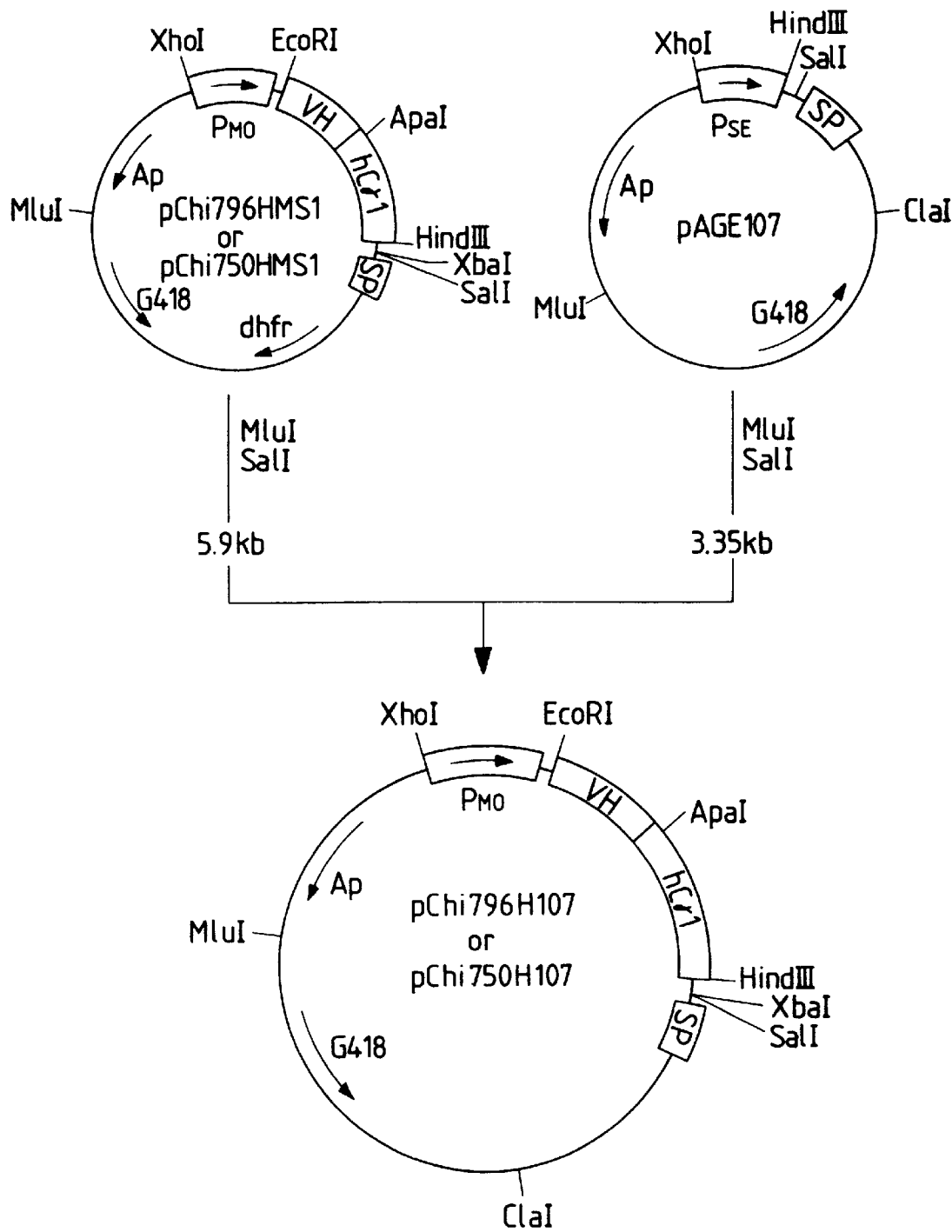
FIG. 11 shows a construction scheme for plasmids, pChi796H107 and pChi750H107.
Figure 12:
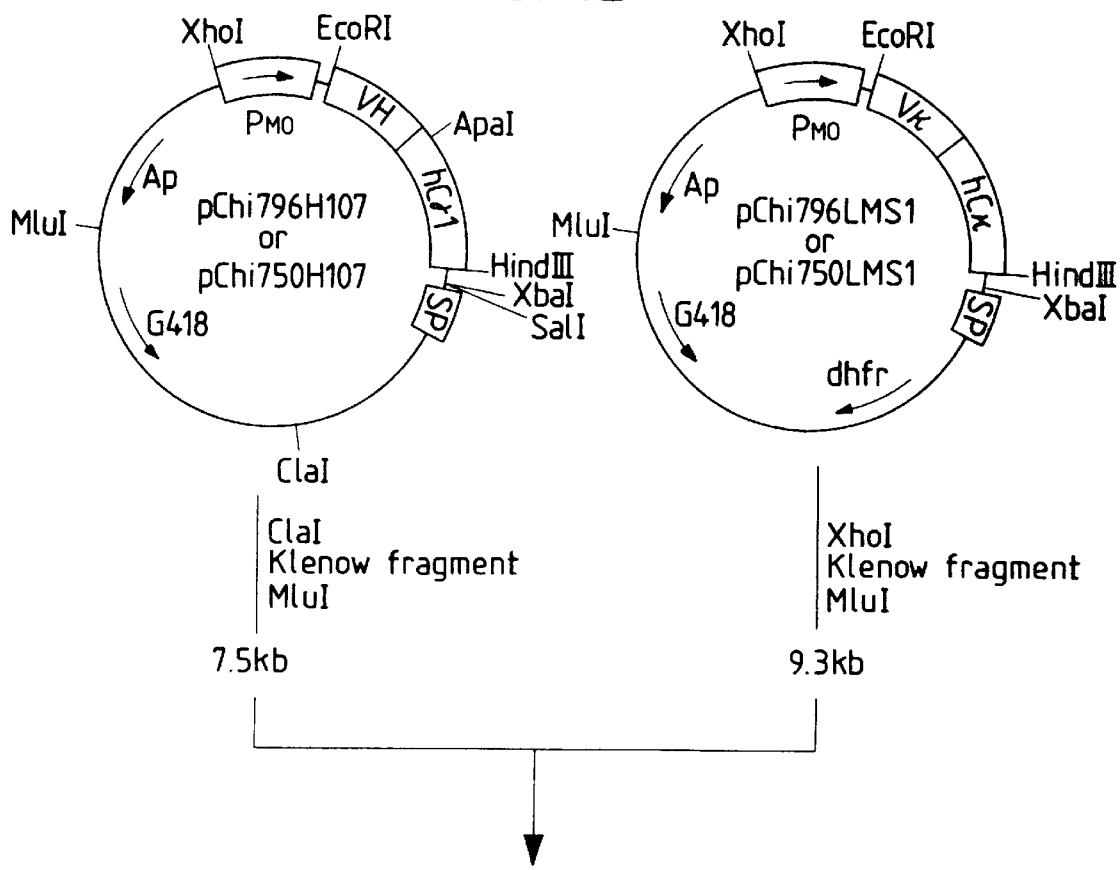
FIG. 12 shows a construction scheme for plasmids, pChi796HL1 and pChi750HL1.
Figure 12:
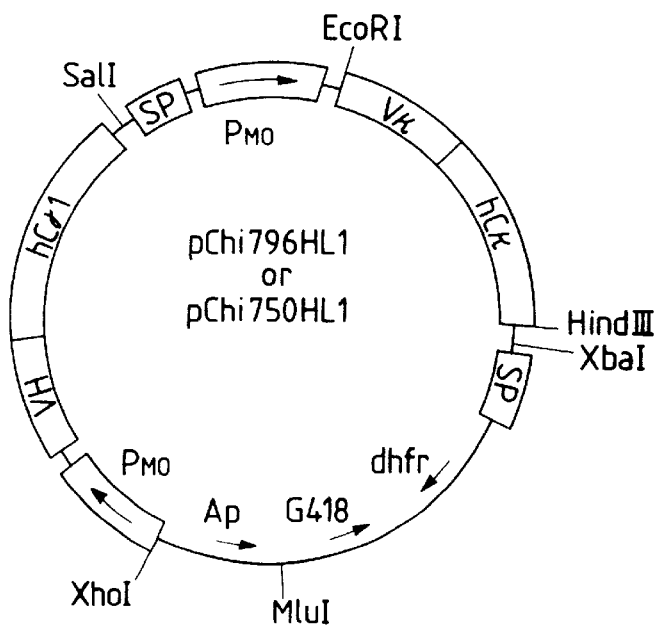

8. Construction of KM-796- and KM-750-Derived Chimeric Human Antibody H Chain and L Chain Tandem Expression Vectors Tandem expression vectors containing the chimeric human antibody H chain-encoding cDNA and L chain-encoding cDNA on one and the same vector were constructed (FIG. 11 and FIG. 12).

Three μg of pChi796HMS1 or pChi750HMS1, obtained in Paragraph 7, were added to 30 μl of 10 mM Tris-hydrochloride buffer (pH 7.5) containing 10 mM magnesium chloride, 50 mM sodium chloride and 1 mM DTT. Further, 10 units of MluI and 10 units of SalI were added, and digestion was carried out at 37° C. for 4 hours. The reaction mixture was fractionated by agarose gel electrophoresis. In each case, about 0.3 μg of a DNA fragment of about 5.9 kb was recovered. Then, 2 μg of pAGE107 described in EP-A-0 405 285 was dissolved in 30 μl of 10 mM Tris-hydrochloride buffer (pH 7.5) containing 10 mM magnesium chloride, 50 mM sodium chloride and 1 mM DTT; 10 units of MluI and 10 units of SalI were further added, and digestion was carried out at 37° C. for 4 hours. The reaction mixture was fractionated by agarose gel electrophoresis and about 0.2 μg of a DNA fragment of about 3.55 kb was recovered. Then, 0.1 μg of the MluI-SalI fragment of pChi796HMS1 or pChi750HMS1 and 0.1 μg of the MluI-SalI fragment of pAGE107 were dissolved in a total of 20 μl of T4 ligase buffer, 350 units of T4 ligase was added, and ligation was carried out at 4° C. for 24 hours. The thus-obtained recombinant plasmid DNA was used to transform *Escherichia coli* HB101 to give the plasmid pChi796H107 or pChi750H107 shown in FIG. 11.

Then, 3 μg of pChi796H107 or pChi750H107 was added to 30 μl of 10 mM Tris-hydrochloride buffer (pH 7.5) containing 10 mM magnesium chloride, 50 mM sodium chloride and 1 mM DTT, 10 units of ClaI was further added, and digestion was carried out at 37° C. for 4 hours. The reaction mixture was subjected to phenol-chloroform extraction and then to ethanol precipitation. The precipitate was dissolved in 20 μl of DNA polymerase I buffer, 5 units of *Escherichia coli*-derived DNA polymerase I Klenow fragment was added, and the mixture was incubated at 22° C. for 30 minutes for rendering the cohesive ends formed upon ClaI digestion blunt-ended. The reaction mixture was further subjected to phenol-chloroform extraction and then to ethanol precipitation. To the precipitate were added 30 μl of 10 mM Tris-hydrochloride buffer (pH 7.5) containing 10 mM magnesium chloride, 50 mM sodium chloride and 1 mM DTT, and 10 units of MluI. Digestion was carried out at 37° C. for 4 hours and the reaction mixture was fractionated by agarose gel electrophoresis. In each case, about 0.3 μg of a DNA fragment of about 7.5 kb was recovered. Then, 3 μg of pChi796LMS1 or pChi750LMS1 was added to 30 μl of 20 mM Tris-hydrochloride buffer (pH 8.5) containing 10 mM magnesium chloride, 100 mM potassium chloride and 1 mM DTT, 10 units of XhoI was further added, and digestion was carried out at 37° C. for 4 hours. The reaction mixture was subjected to phenol-chloroform extraction and then to ethanol precipitation. The precipitate was dissolved in 20 μl of DNA polymerase I buffer, 5 units of *Escherichia coli*-derived DNA polymerase I Klenow fragment was added, and the mixture was incubated at 22° C. for 30 minutes for rendering the cohesive ends formed upon XhoI digestion blunt-ended. The reaction mixture was further subjected to phenol-chloroform extraction and then to ethanol precipitation. To the precipitate was added 30 μl of 10 mM Tris-hydrochloride buffer (pH 7.5) containing 10 mM magnesium chloride, 50 mM sodium chloride and 1 mM DTT as well as 10 units of MluI. Digestion was carried out at 37° C. for 4 hours and the reaction mixture was fractionated by agarose gel electrophoresis. In each case, about 0.3 μg of a DNA fragment of about 9.3 kb was recovered. Then, 0.1 μg of the MluI-ClaI fragment of pChi796H107 or pChi750H107, as obtained above, and 0.1 μg of the MluI-XhoI fragment of pChi796LMS1 or pChi750LMS1, as obtained above, were dissolved in a total of 20 μl of T4 ligase buffer; 350 units of T4 ligase was further added, and ligation was carried out at 4° C. for 24 hours. The thus-obtained recombinant plasmid DNA was used to transform *Escherichia coli* HB101, and the plasmid pChi796HL1 or pChi750HL1 shown in FIG. 12 was obtained.

Figure 13:
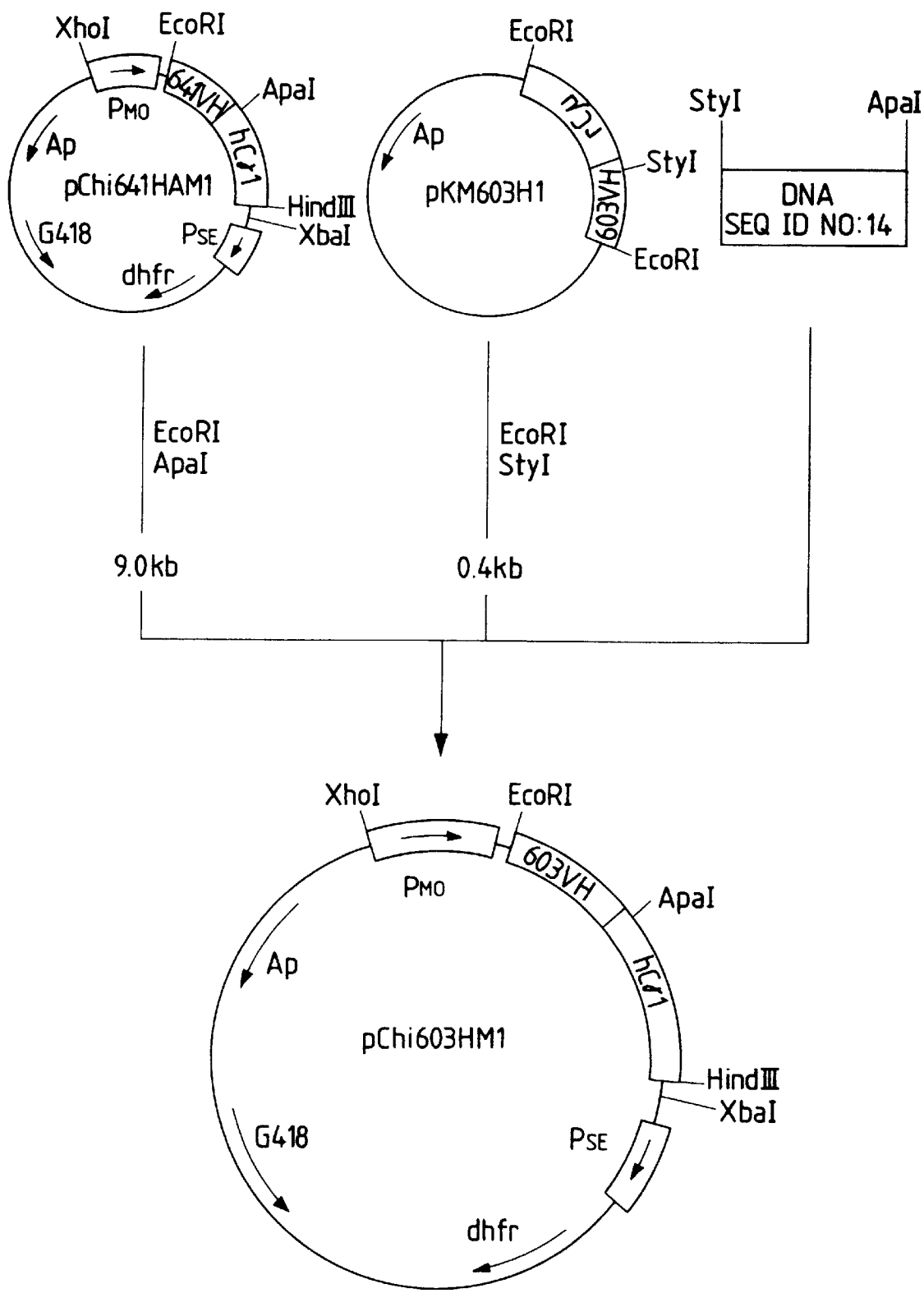
FIG. 13 shows a construction scheme for a plasmid, pChi603HM1.

Construction of a KM-603-Derived Chimeric Human Antibody H Chain Expression Vector First, the antibody variable region-encoding cDNA of the plasmid pKM603H1 was excised by cleavage at the 5'terminal EcoRI site and the StyI site near the 3' end of said cDNA and joined to the chimeric human antibody H chain expression vector pChi641HAM1 together with a synthetic DNA having the base sequence shown in SEQ ID NO:14 in the following manner (FIG. 13).

Three μg of pKM603H1 obtained in Paragraph 5 were added to 30 μl of 50 mM Tris-hydrochloride buffer (pH 7.5) containing 10 mM magnesium chloride, 100 mM sodium chloride and 1 mM DTT, followed by further addition of 10 units of EcoRI and 10 units of StyI. Digestion was carried out at 37° C. for 4 hours. The reaction mixture was fractionated by agarose gel electrophoresis and about 0.3 μg of a 0.4-kb DNA fragment was recovered. Then, 3 μg of pChi641HAM1, obtained in Reference Example 2, was added to 30 μl of 10 mM Tris-hydrochloride (pH 7.5) containing 10 mM magnesium chloride and 1 mM DTT, 10 units of EcoRI and 10 units of ApaI were further added, and digestion was effected at 37° C. for 4 hours. The reaction mixture was fractionated by agarose gel electrophoresis and about 1.0 μg of a DNA fragment of about 9.0 kb was recovered. Then, 0.1 μg of the EcoRI-StyI fragment (about 0.4 kb) of pKM603H1, as obtained above, and 0.1 μg of the EcoRI-ApaI fragment (about 9.0 kb) of pChi641HAM1, as obtained above, were dissolved, together with 0.3 μg of a synthetic DNA having the base sequence shown in SEQ ID NO:14, in a total of 20 μl of T4 ligase buffer; 350 units of T4 ligase was added to the solution, and ligation was effected at 4° C. for 24 hours. The thus-obtained recombinant plasmid DNA was used to transform *Escherichia coli* HB101 and the plasmid pChi603HM1 shown in FIG. 13 was obtained.

Figure 14:
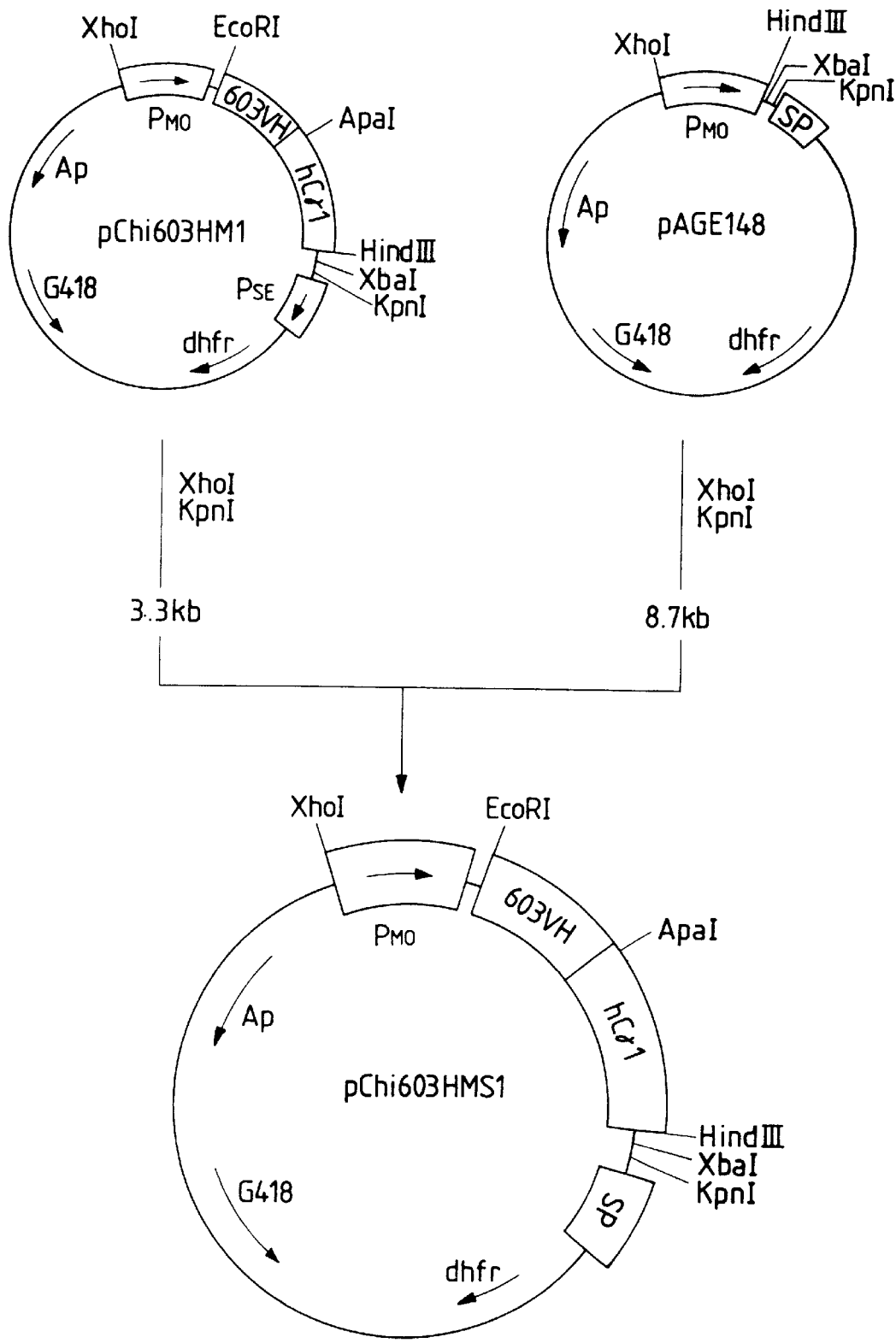
FIG. 14 shows a construction scheme for a plasmid, pChi603HMS1.

Then, a KM-603-derived chimeric human antibody H chain expression vector was constructed by introducing the β-globin 3' splicing signal into the plasmid pChi603HM1 in the following manner (FIG. 14).

Three μg of pChi603HM1 obtained above were added to 30 μl of 33 mM Tris-acetate buffer (pH 7.9) containing 10 mM magnesium acetate, 66 mM potassium acetate, 0.5 mM DTT and 0.01% BSA. Further, 10 units of XhoI and 10 units of KpnI were added, and digestion was carried out at 37° C. for 4 hours. The reaction mixture was fractionated by agarose gel electrophoresis and about 0.3 μg of a DNA fragment of about 3.3 kb was recovered.

Then, 3 μg of pAGE148 obtained in Paragraph 7 (2) was added to 30 μl of 33 mM Tris-acetate buffer (pH 7.9) containing 10 mM magnesium acetate, 66 mM sodium acetate, 0.5 mM DTT and 0.01% BSA; 10 units of XhoI and 10 units of KpnI were further added, and digestion was carried out at 37° C. for 4 hours. The reaction mixture was fractionated by agarose gel electrophoresis and about 0.3 μg of a DNA fragment of about 8.7 kb was recovered. Then, 0.1 μg of the XhoI-KpnI fragment of pChi603HM1, as obtained above, and 0.1 μg of the XhoI-KpnI fragment of pAGE148, as obtained above, were dissolved in a total of 20 μl of T4 ligase buffer; 350 units of T4 ligase was added to the solution, and ligation was carried out at 4° C. for 24 hours. The thus-obtained recombinant plasmid DNA was used to transform *Escherichia coli* HB101 and the plasmid pChi603HMS1 shown in FIG. 14 was obtained.

Figure 15:
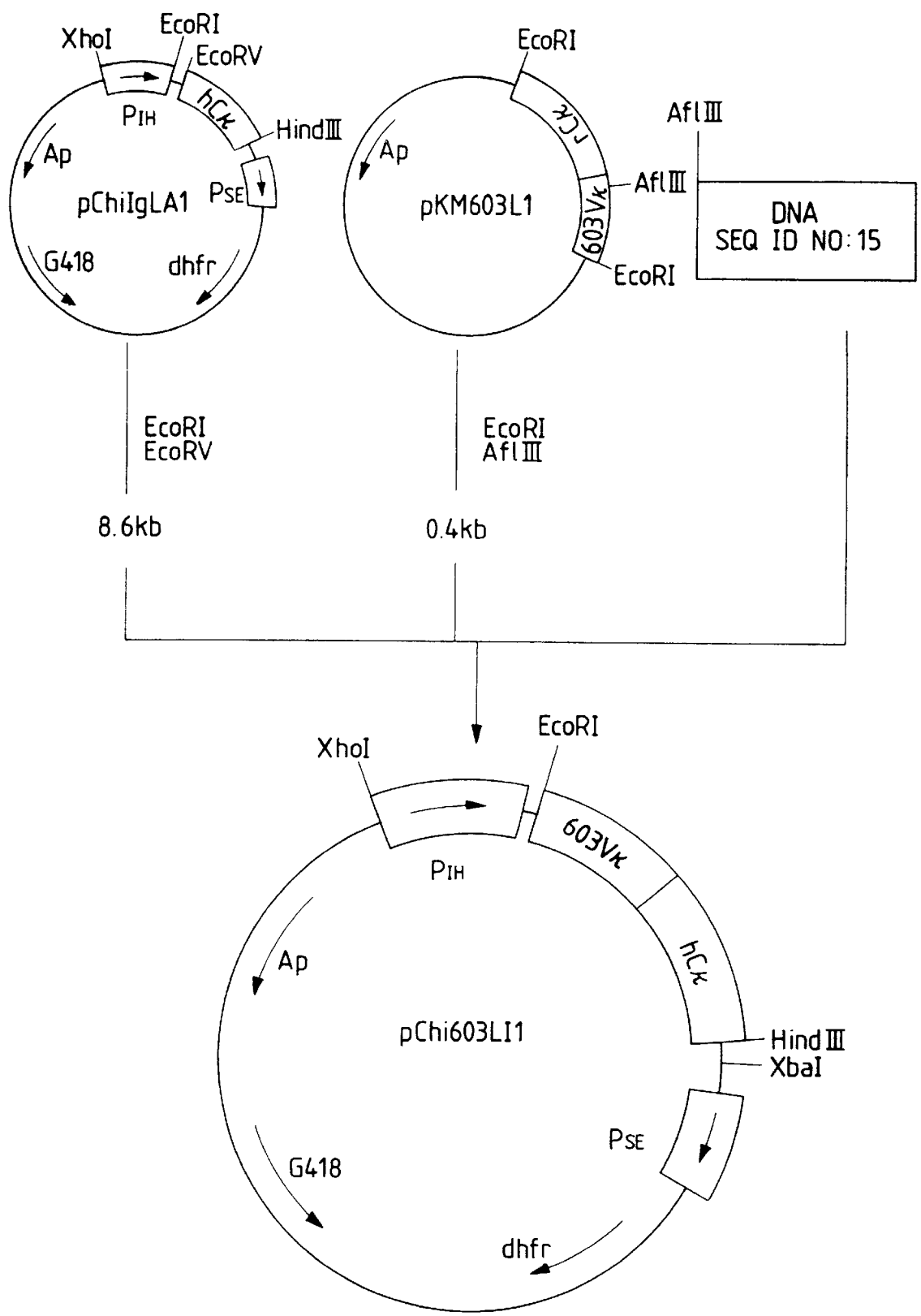
FIG. 15 shows a construction scheme for a plasmid, pChi603LI1.

10. Construction of a KM-603-Derived Chimeric Human Antibody L Chain Expression Vector First, the antibody variable region cDNA in the plasmid pKM603L1 was excised by cleavage at the 5' terminal EcoRI site and the AflIII site near the 3' end and joined to the chimeric human antibody L chain expression vector pChiIgLA1 together with a synthetic DNA having the base sequence defined by SEQ ID NO:15 (FIG. 15).

Thus, 3 μg of pKM603L1 obtained in Paragraph 5 was added to 30 μl of 50 mM Tris-hydrochloride buffer (pH 7.5) containing 10 mM magnesium chloride, 100 mM sodium chloride and 1 mM DTT, 10 units of EcoRI and 10 units of AflIII were further added, and digestion was carried out at 37° C. for 4 hours. The reaction mixture was fractionated by agarose gel electrophoresis and about 0.3 μg of a DNA fragment of about 0.4 kb was recovered. Then, 3 μg of pChiIgLA1 obtained in Reference Example 1 was added to 30 μl of 50 mM Tris-hydrochloride buffer (pH 7.5) containing 10 mM magnesium chloride, 100 mM sodium chloride and 1 mM DTT, 10 units of EcoRI and 10 units of EcoRV were further added, and digestion was carried out at 37° C. for 4 hours. The reaction mixture was fractionated by agarose gel electrophoresis and about 1 μg of a DNA fragment of about 8.6 kb was recovered. Then, 0.1 μg of the EcoRI-AflIII fragment of pKM603L1, as obtained above, 0.1 μg of the EcoRI-EcoRV fragment of pChiIgLA1, as obtained above, and 0.3 μg of a synthetic DNA, having the base sequence defined by SEQ ID NO:15, were dissolved in a total of 20 μl of T4 ligase buffer; 350 units of T4 ligase was added to the solution, and ligation was carried out at 4° C. for 24 hours. The thus-obtained recombinant plasmid DNA was used to transform *Escherichia coli* HB101 and the plasmid pChi603LI1 shown in FIG. 15 was obtained.

Figure 16:
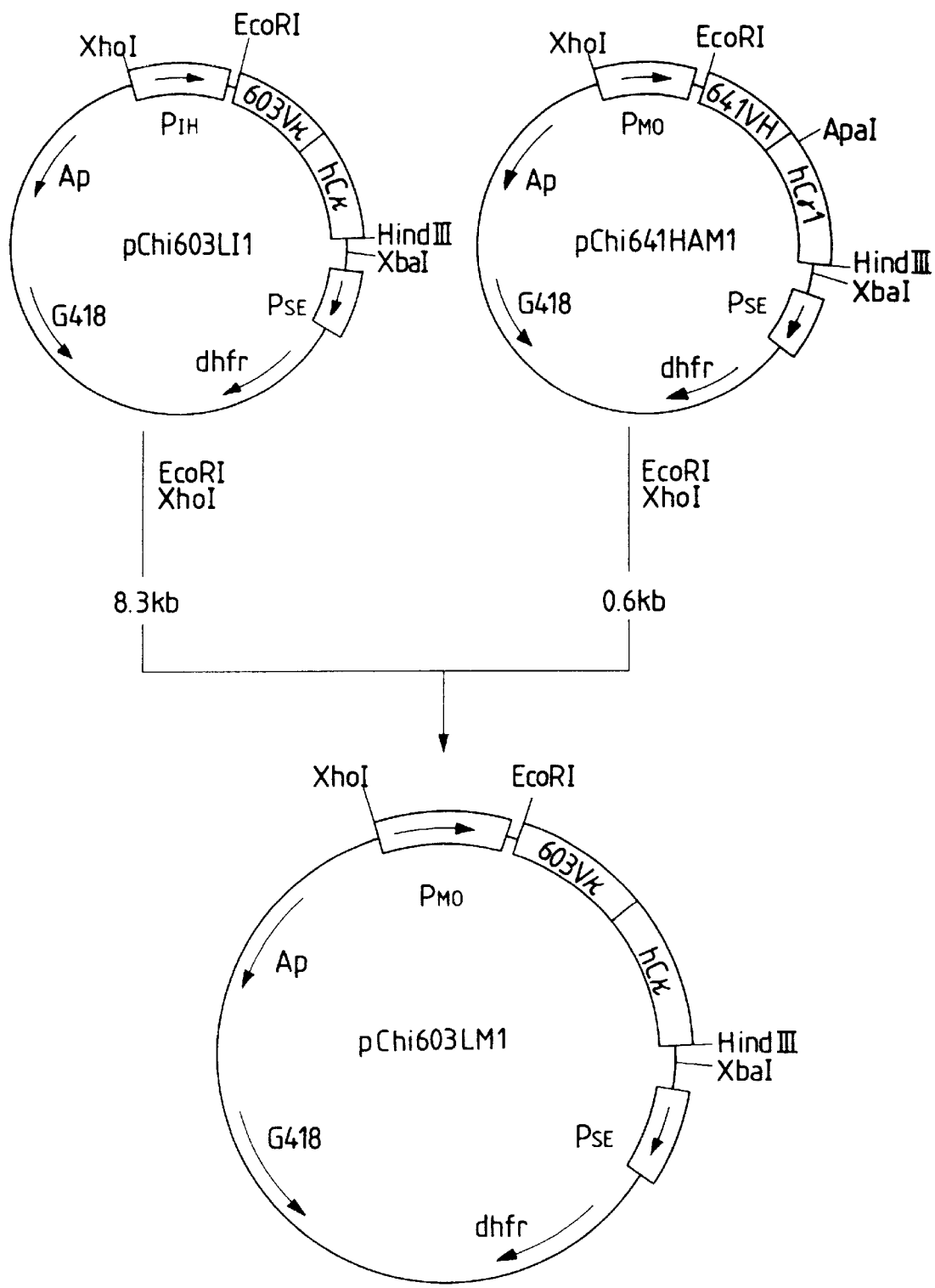
FIG. 16 shows a construction scheme for a plasmid, pChi603LM1.

Then, the Moloney mouse leukemia virus terminal repeat promoter/enhancer was introduced into the plasmid pChi603LI1 in the following manner (FIG. 16).

Thus, 3 μg of pChi603LI1 obtained above was added to 30 μl of 50 mM Tris-hydrochloride buffer (pH 7.5) containing 10 mM magnesium chloride, 100 mM sodium chloride and 1 mM DTT, 10 units of EcoRI and 10 units of XhoI were further added, and digestion was carried out at 37° C. for 4 hours. The reaction mixture was fractionated by agarose gel electrophoresis and about 0.3 μg of a DNA fragment of about 8.3 kb was recovered. Then, 3 μg of pChi641HAM1 obtained in Reference Example 2 was added to 30 μl of 50 mM Tris-hydrochloride buffer (pH 7.5) containing 10 mM magnesium chloride, 100 mM sodium chloride and 1 mM DTT, 10 units of EcoRI and 10 units of XhoI were further added, and digestion was effected at 37° C. for 4 hours. The reaction mixture was fractionated by agarose gel electrophoresis and about 0.3 μg of a DNA fragment of about 0.6 kb was recovered. Then, 0.1 μg of the EcoRI-XhoI fragment of pChi603LI1, as obtained above, and 0.1 μg of the EcoRI-XhoI fragment of pChi641HAM1, as obtained above, were dissolved in a total of 20 μl of T4 ligase buffer; 350 units of T4 ligase was added to the solution, and ligation was effected at 4° C. for 24 hours. The thus-obtained recombinant plasmid DNA was used to transform *Eschrichia coli* HB101 to give the plasmid pChi603LM1 shown in FIG. 16.

Figure 17:
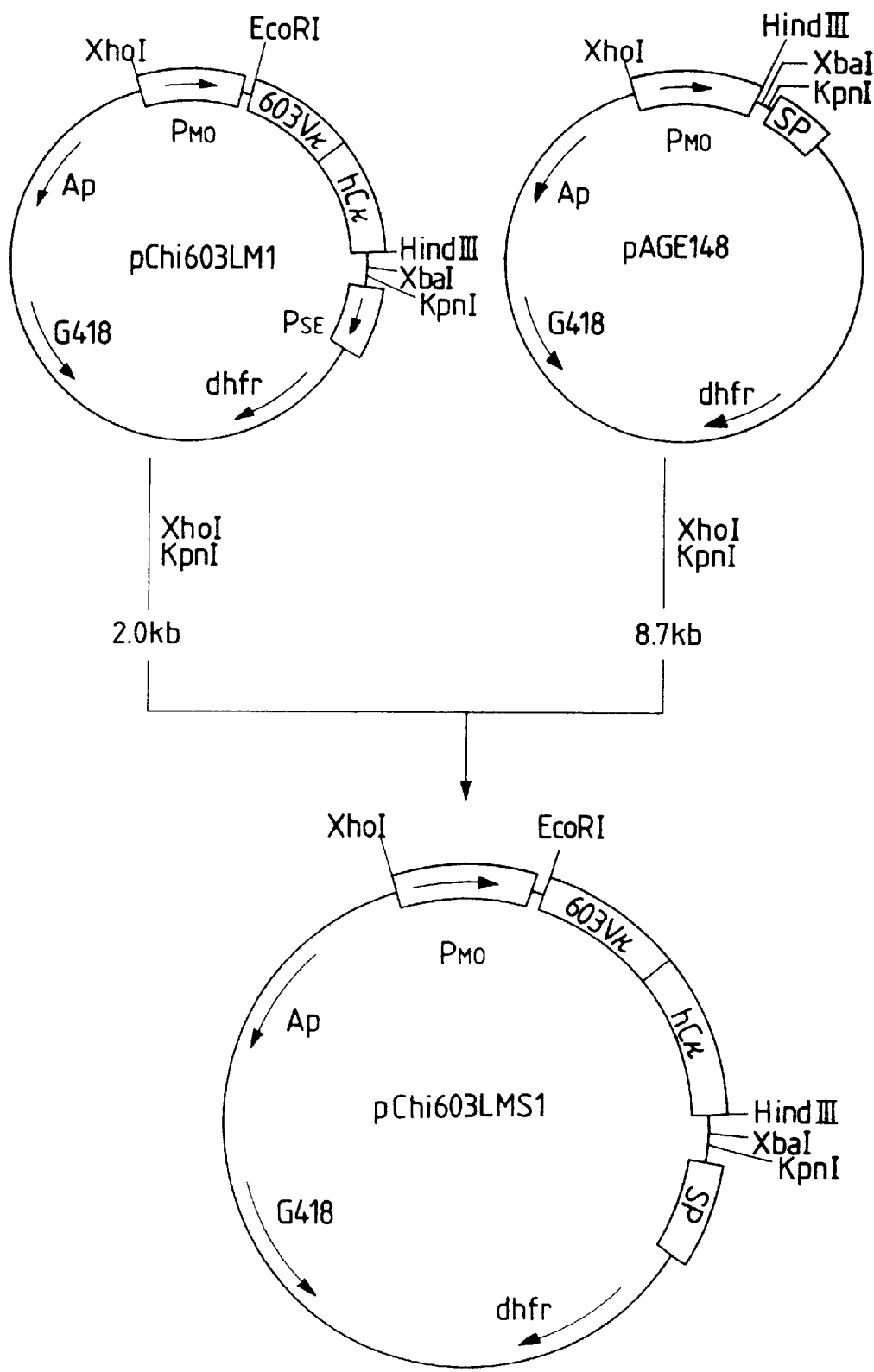
FIG. 17 shows a construction scheme for a plasmid, pChi603LMS1.

A KM-603-derived chimeric human antibody L chain expression vector was then constructed by introducing the β-globin 3' splicing signal into the plasmid pChi603LM1, as follows (FIG. 17).

Thus, 3 μg of pChi603LM1 obtained above was added to 30 μl of 33 mM Tris-acetate buffer (pH 7.9) containing 10 mM magnesium acetate, 66 mM potassium acetate, 0.5 mM DTT and 0.01% BSA, 10 units of XhoI and 10 units of KpnI were further added, and digestion was effected at 37° C. for 4 hours. The reaction mixture was fractionated by agarose gel electrophoresis and about 0.3 μg of a DNA fragment of about 2.0 kb was recovered. Then, 3 μg of pAGE148 obtained in Paragraph 7 (2) was added to 30 μl of 33 mM Tris-acetate buffer (pH 7.9) containing 10 mM magnesium acetate, 66 mM potassium acetate, 0.5 mM DTT and 0.01% BSA, 10 units of XhoI and 10 units of KpnI were further added, and digestion was effected at 37° C. for 4 hours. The reaction mixture was fractionated by agarose gel electrophoresis and about 0.3 μg of a DNA fragment of about 8.7 kb was recovered. Then, 0.1 μg of the XhoI-KDnI fragment of pChi603LM1, as obtained above, and 0.1 μg of the XhoI-KpnI fragment of pAGE148, as obtained above, were dissolved in a total of 20 μl of T4 ligase buffer; 350 units of T4 ligase was added to the solution, and ligation was carried out at 4° C. for 24 hours. The thus-obtained recombinant plasmid DNA was used to transform *Escherichia coli* HB101 to give the plasmid pChi603LMS1 shown in FIG. 17.

11. Expression of the KM-796- and KM-750-Derived Chimeric Human Anti-GM2 Antibody in YB2/0 Cells The plasmids were introduced into YB2/0 cells by the electroporation method of Miyaji et al. [Cytotechnbology, 3, 133–140 (1990)].

After introduction of 4 μg of pChi750HL1 or pChi796HL1 obtained in Paragraph 8 into $4 \times 10^6$ YB2/0 (ATCC CRL1581) cells, the cells were suspended in 40 ml of RPMI-1640-FCS(10) [RPMI1640 medium (Nissui Pharmaceutical) containing 10% of FCS, 1/40 volume of 7.5% NaHCO$_3$, 3% of 200 mM L-glutamine solution (Gibco) and 0.5% of penicillin-streptomycin solution (Gibco; containing 5,000 units/ml penicillin and 5,000 μg/ml streptomycin)], and the suspension was distributed in 200-μl portions into wells of 96-well microtiter plates. After 24 hours of incubation at 37° C. in a CO$_2$ incubator, G418 (Gibco) was added to a concentration of 0.5 mg/ml and then incubation was continued for 1 to 2 weeks. Transformant colonies appeared, the culture fluid was recovered from each well in which the cells had grown to confluence and an enzyme-linked immunosorbent assay (ELISA) was conducted for anti-GM$_2$ chimeric human antibody activity measurement.

Enzyme-Linked Immunosorbent Assay (ELISA)

In a solution of 5 ng of phosphatidylcholine (Sigma) and 2.5 ng of cholesterol (Sigma) in 2 ml of ethanol was dissolved 2 ng of GM$_2$ (N-acetyl-GM$_2$; Boehringer Mannheim) or some other ganglioside. The solution or dilutions thereof were respectively distributed in 20-μl portions into wells of 96-well microtiter plates (Greiner) and, after air drying, blocking was effected with PBS containing 1% BSA. Each culture supernatant for each transformant, each purified mouse monoclonal antibody solution and each purified chimeric human antibody solution were distributed in 50- to 100-μl portions into the wells and the reaction was allowed to proceed at room temperature for 1 to 2 hours. The wells were then washed with PBS, and 50 to 100 μl of peroxidase-labeled antibody were added thereto followed by reaction at room temperature for 1 to 2 hours. The wells were washed with PBS and an ABTS substrate solution [prepared by dissolving 550 mg of 2,2'-azinobis(3-ethylbenzothiazoline-6-sulfonic acid) diammonium salt in 0.1M citrate buffer (pH 4.2) and adding, just prior to use, hydrogen peroxide to a concentration of 1 μl/ml] was added in 50- to 100-μl portions to each well for color development, followed by OD$_{415}$ measurement.

The clone showing the highest activity in ELISA among the clones obtained gave a chimeric human anti-GM$_2$ antibody content of about 1.0 μg/ml of culture fluid.

Cells of the clone showing the above-mentioned chimeric human anti-GM$_2$ antibody activity were suspended in RPMI1640-FCS(10) medium containing 0.5 mg/ml G418 and 50 nM methotrexate (hereinafter, "MTX") to a concentration of 1 to $2 \times 10^5$ cells/ml, and the suspension was distributed in 2-ml portions into wells of 24-well plates. Incubation was performed at 37° C. in a CO$_2$ incubator for 1 to 2 weeks to induce 50 nM MTX-resistant clones. At the time of confluence, the chimeric human anti-GM$_2$ antibody activity in each culture fluid was determined by ELISA. The 50 nM MTX-resistance clone showing the highest activity among the clones obtained showed a chimeric human anti-GM$_2$ antibody content of about 5.0 μg/ml.

Cells of the above 50 nM MTX-resistant clone were suspended in RPMI1640-FCS(10) medium containing 0.5 mg/ml G418 and 200 nM MTX to a concentration of 1 to $2 \times 10^5$ cells/ml, and the suspension was distributed in 2-ml portions into wells of 24-well plates. Incubation was carried out at 37° C. in a CO$_2$ incubator for 1 to 2 weeks to induce 200 nM MTX-resistant clones. At the time of confluence, each culture fluid was assayed for chimeric human anti-GM$_2$ antibody activity by ELISA. The 200 nM MTX-resistant clone showing the highest activity among the clones obtained had a chimeric human anti-GM$_2$ antibody content of about 10 μg/ml. The 200 nM MTX-resistant clones obtained from pChi750HL1 and pChi796HL1 were named transformants "KM966" (KM-796-derived chimeric human antibody KM966-producing strain) and "KM967" (KM-750-derived chimeric human antibody KM967-producing strain), respectively.

The following SDS-polyacrylamide gel electrophoresis (SDS-PAGE) confirmed that the above transformants KM966 and KM967 express the respective chimeric human anti-GM$_2$ antibodies.

Figure 18:
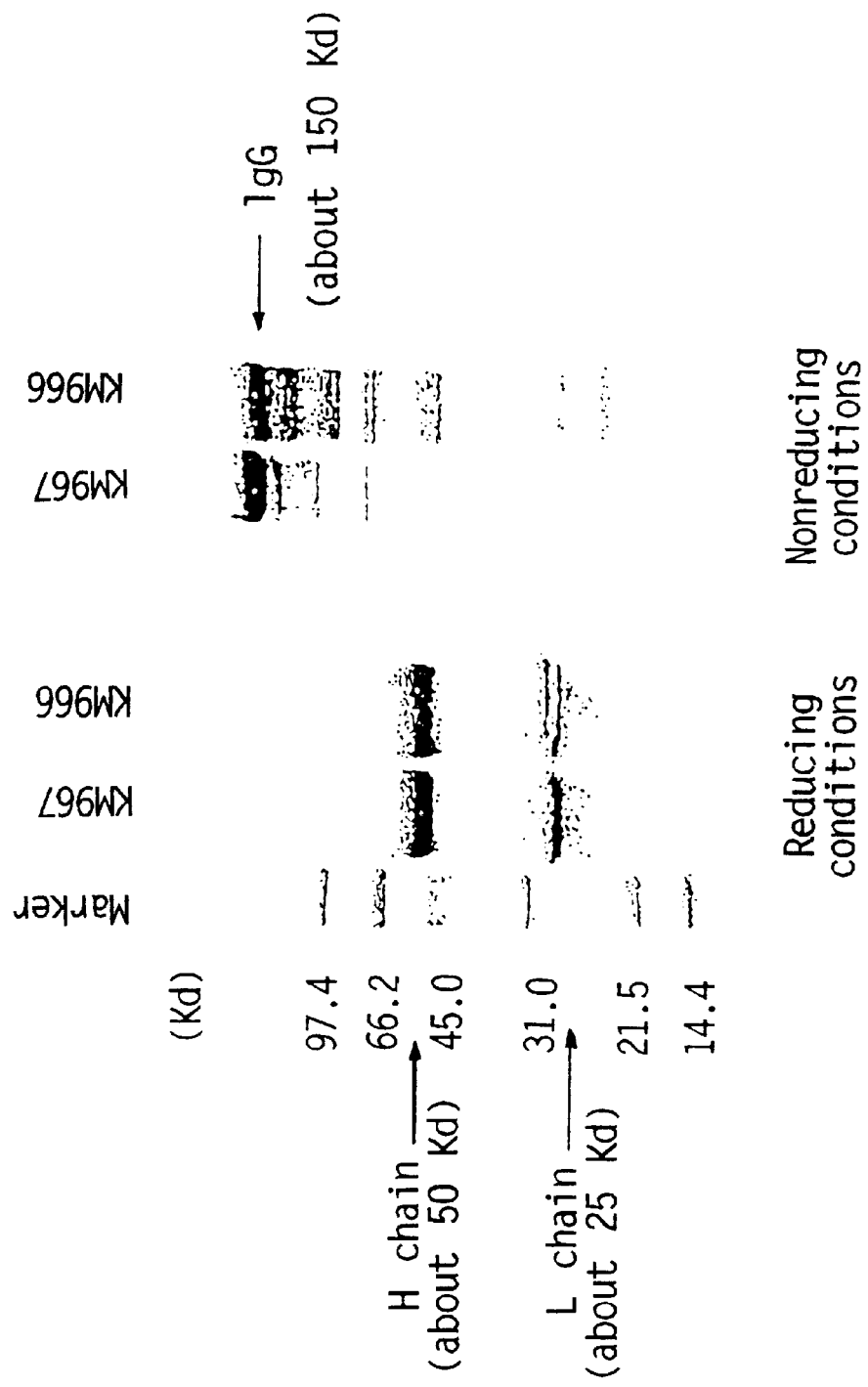
FIG. 18 shows the electrophoretic patterns in SDS-PAGE (using 4–15% gradient gels) of purified chimeric human anti-$GM_2$ antibodies, KM966 and KM967. The patterns obtained under reducing conditions are shown on the left side and those obtained under nonreducing conditions on the right side. From the left, the lanes include low molecular weight markers, KM967 and KM966 (reducing conditions), and KM967 and KM966 (nonreducing conditions).

The transformants KM966 and KM967 were each suspended in GIT medium (Nippon Pharmaceutical) containing 0.5 mg/ml G418 and 200 nM MTX to a concentration of 1 to $2 \times 10^5$ cells/ml. Each suspension was distributed in 100-ml portions into 175 cm$^2$ flasks (Greiner). Cultivation was performed at 37° C. in a CO$_2$ incubator for 5 to 7 days. At the time of confluence, the culture fluid was recovered. Treatment of about 1 liter of the culture fluid with Affi-Gel Protein A MAPS-II kit (Bio-Rad) gave about 5 mg of a purified chimeric human anti-GM$_2$ antibody for each transformant. About 2 μg of the purified chimeric human anti-GM$_2$ antibody KM966 or KM967 was electrophoresed by the conventional method [Laemmli: Nature, 227, 680 (1970)] for molecular weight checking. The results are shown in FIG. 18. As shown in FIG. 18, both KM966 and KM967 gave an antibody H chain molecular weight of about 50 kilodaltons and an antibody L chain molecular weight of about 25 kilodaltons under reducing conditions, indicating the correctness in molecular weight of the H chain and L chain expressed. For each of KM966 and KM967, the molecular weight of the chimeric human antibody under nonreducing conditions was about 150 kilodaltons, indicating that the antibody expressed was composed of two H chains and two L chains and was correct in size.

12. Expression of KM-603-Derived Chimeric Human Anti-$GM_2$ Antibodies in SP2/0 Cells A 2-$\mu$g portion of the plasmid pChi603HMS1 or pChi603LMS1 obtained in Paragraph 9 was introduced into $4\times10^6$ cells of YB2/0 (ATCC CRL1581) by electroporation in the same manner in Paragraph 11. The cells were suspended in 40 ml of RPMI1640-FCS(10) and the suspension was distributed in 200-$\mu$l portions into wells of 96-well microtiter plates. After 24 hours of incubation in a $CO_2$ incubator at 37° C., G418 (Gibco) was added to a concentration of 0.5 mg/ml and incubation was continued for 1 to 2 weeks. Transformant colonies appeared. The culture fluid was recovered from confluent wells and the chimeric human anti-$GM_2$ antibody activity was measured by ELISA as described above. The clone showing the highest chimeric human anti-$GM_2$ antibody activity among the clones obtained gave a chimeric human anti-$GM_2$ antibody content of about 0.1 $\mu$g/ml of culture fluid.

Cells of the clone showing the above-mentioned chimeric human anti-$GM_2$ antibody activity were suspended in RPMI1640-FCS(10) medium containing 0.5 mg/ml G418 and 50 nM MTX to a concentration of 1 to $2\times10^5$ cells/ml and the suspension was distributed in 2-ml portions into wells of 24-well plates. Clones resistant to 50 nM MTX were induced by incubating in a $CO_2$ incubator at 37° C. for 2 to 3 weeks. When confluence was attained, the culture fluids were subjected to ELISA for chimeric human anti-$GM_2$ antibody activity measurement. Among the 50 nM MTX-resistant clones obtained, the clone showing the highest activity gave a chimeric human anti-$GM_2$ antibody content of about 0.3 $\mu$g/ml of culture fluid.

Cells of the above 50 nM MTX-resistant clone were suspended in RPMI1640-FCS(10) medium containing 0.5 mg/ml G418 and 200 nM MTX to a concentration of 1 to $2\times10^5$ cells/ml and the suspensions as distributed in 2-ml portions into well of 24-well plates. Clones resistant to 200 nM MTX were induced by following incubation in a $CO_2$ incubator at 37° C. for 2 to 3 weeks. When confluence was attained, the chimeric human anti-$GM_2$ antibody activity in the culture fluid was measured by ELISA. Among the 200 nM MTX-resistant clones obtained, the clone showing the highest activity gave a chimeric human anti-$GM_2$ antibody content of about 0.5 $\mu$g/ml of culture fluid.

Cells of the above 200 nM MTX-resistant clone were suspended in RPMI1640-FCS(10) medium containing 0.5 mg/ml G418 and 500 nM MTX to a concentration of 1 to $2\times10^5$ cells/ml and the suspension was distributed in 2-ml portions into well of 24-well plates. Clones resistant to 500 nM MTX were induced by following incubation in a $CO_2$ incubator at 37° C. for 1 to 2 weeks. When confluence was attained, the chimeric human anti-$GM_2$ antibody activity in the culture fluid was determined by ELISA. Among the 500 nM MTX-resistant clones obtained, the one showing the highest activity gave a chimeric human anti-$GM_2$ antibody content of about 1.0 $\mu$g/ml of culture fluid. This 500 nM MTX-resistant clone was named "transformant KM968".

The following SDS-PAGE confirmed the expression of a chimeric human anti-$GM_2$ antibody in the above transformant KM968.

Figure 19:
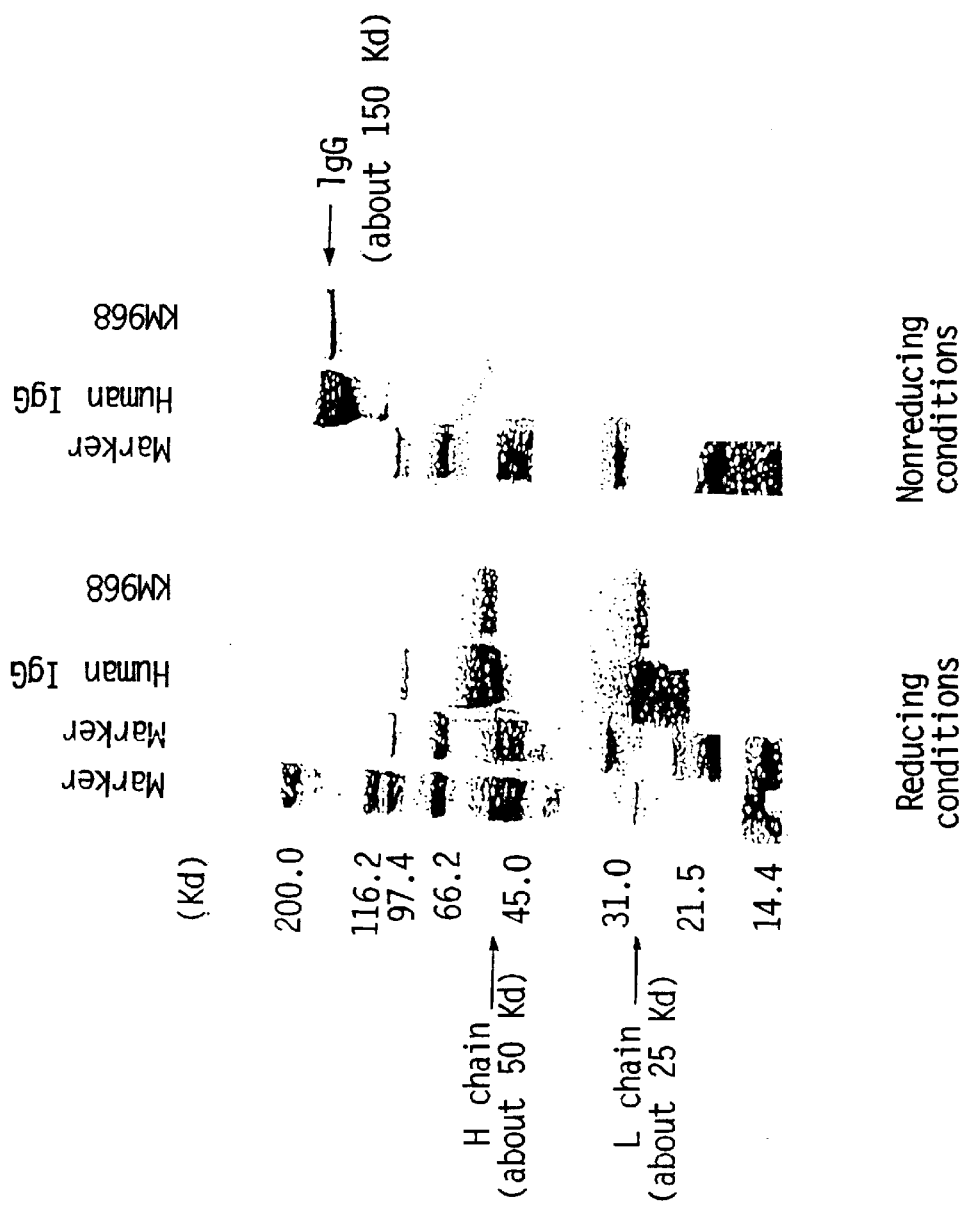
FIG. 19 shows the electrophoretic patterns in SDS-PAGE (using 4–15% gradient gels) of a purified chimeric human anti-$GM_2$ antibody, KM968. The pattern obtained under reducing conditions is shown on the left side and that obtained under nonreducing conditions on the right side. From the left, the lanes include high molecular weight markers, low molecular weight markers, a standard human IgG, KM968 (reducing conditions), the same low molecular weight markers, the standard human IgG, and KM968 (nonreducing conditions).
Figure 20A:
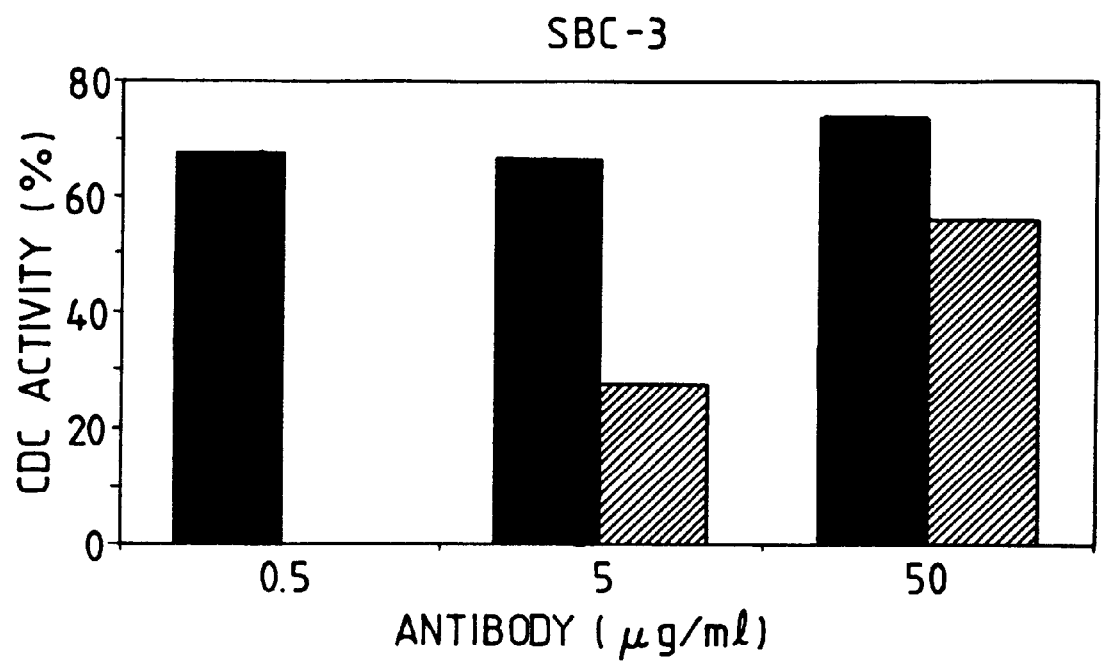
FIG. 20 graphically shows the CDC (complement dependent cytotoxicity) activities of KM966 against the human lung small cell carcinoma cell lines SBC-3 and LU-135. The ordinate indicates the cytotoxic activity and the abscissa the concentration of the antibody added. The solid bars indicate the CDC activities of KM-696 and the shaded bars the CDC activities of KM966.
Figure 20B:
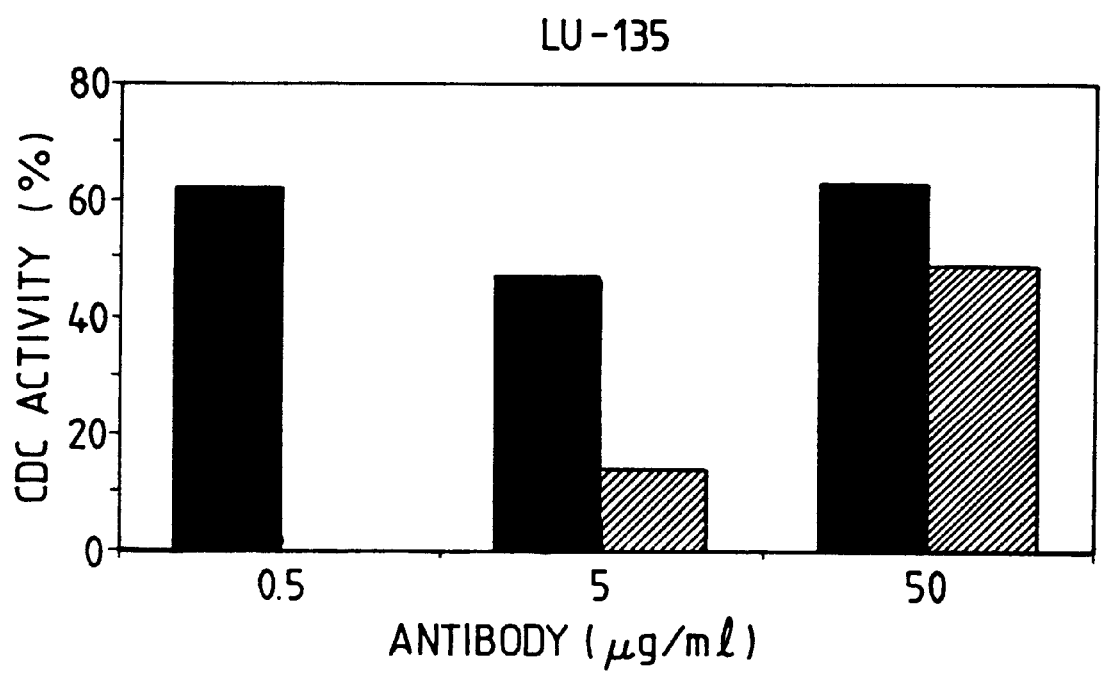
Figure 21A:
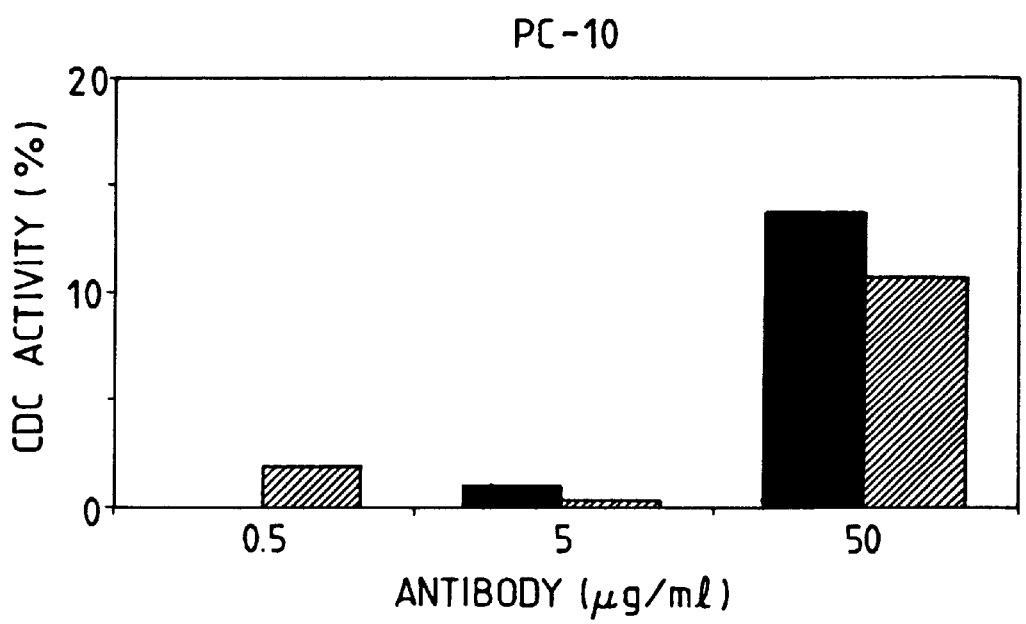
FIG. 21 graphically shows the CDC activities of KM966 against the human lung squamous cell carcinoma cell line PC-10 and human lung adenocarcinoma cell line RERF-LC-MS. The ordinate indicates the cytotoxicity and the abscissa the concentration of the antibody added. The solid bars indicate the CDC activities of KM-696 and the shaded bars the CDC activities of KM966.
Figure 21B:
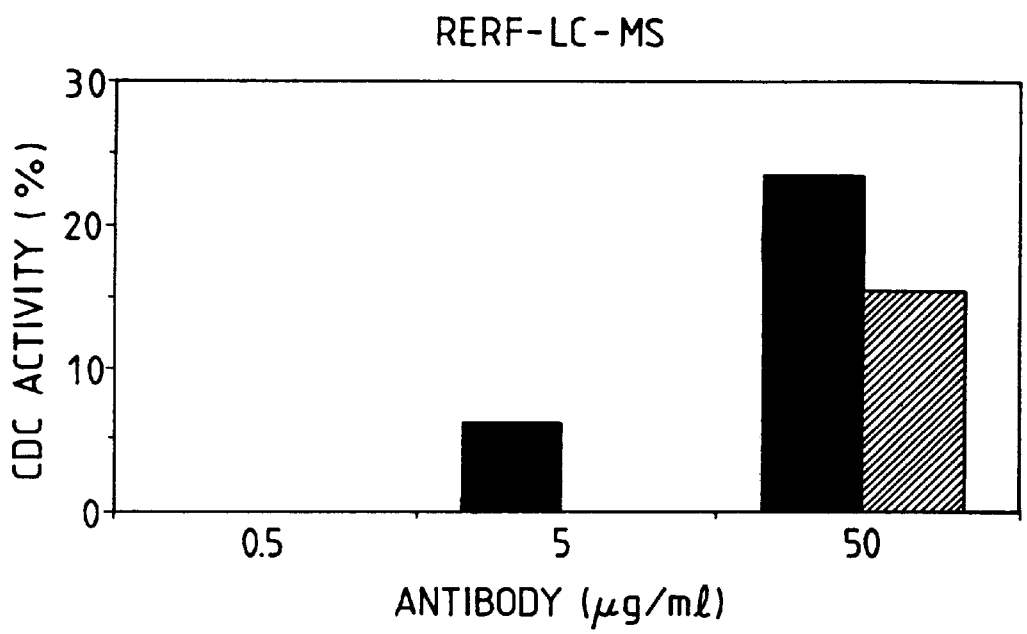
Figure 22A:
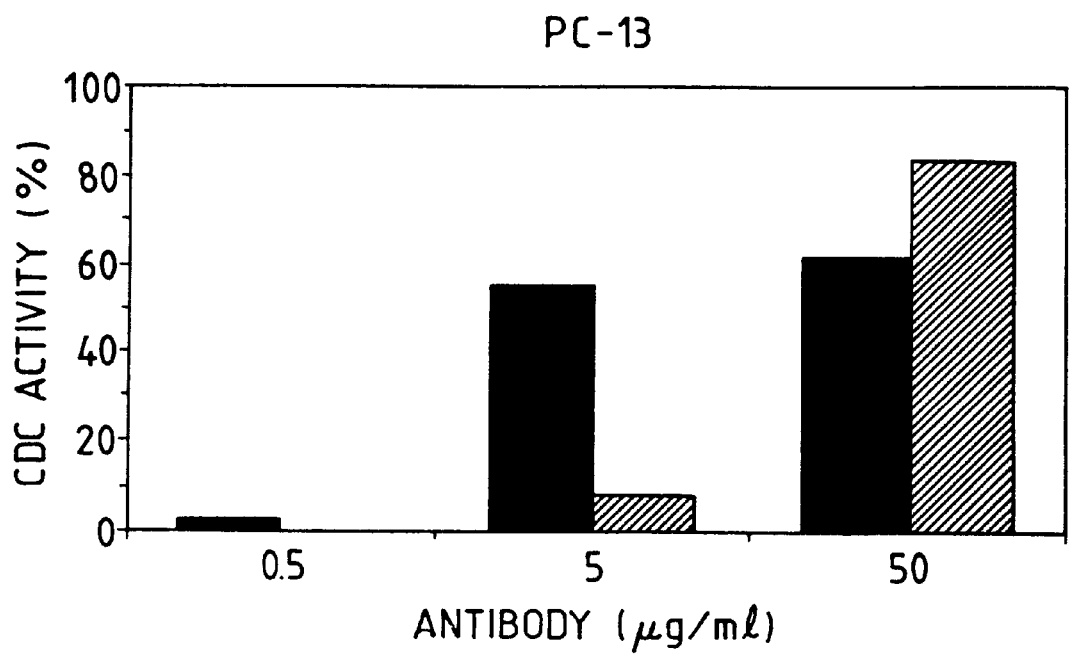
FIG. 22 graphically shows the CDC activities of KM966 against the human lung large cell carcinoma cell line PC-13 and human neuroblastoma cell line NAGAI. The ordinate indicates the cytotoxic activity and the abscissa the concentration of the antibody added. The solid bars indicate the CDC activities of KM-696 and the shaded bars the CDC activities of KM966.
Figure 22B:
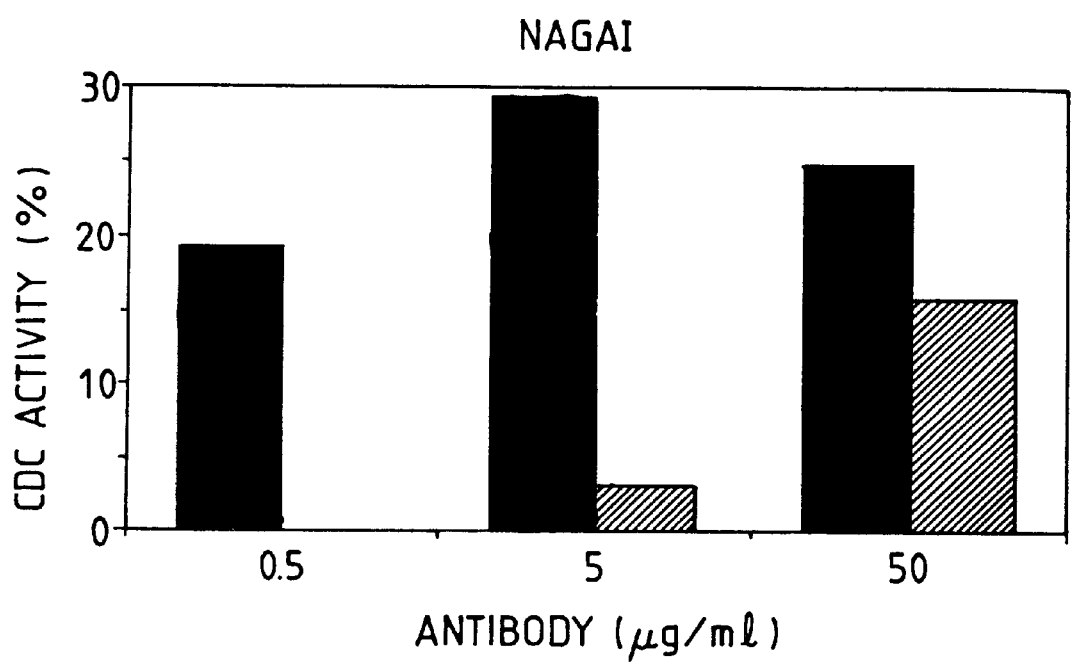
Figure 23A:
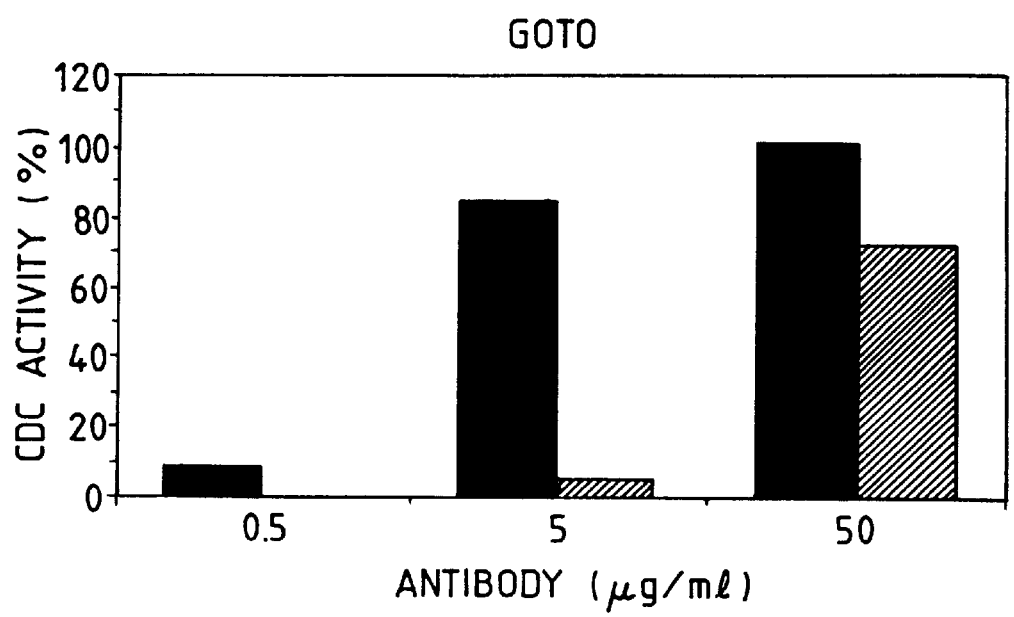
FIG. 23 graphically shows the CDC activities of KM966 against the human neuroblastoma cell line GOTO and human brain tumor cell line A172. The ordinate indicates the cytotoxic activity and the abscissa the concentration of the antibody added. The solid bars indicate the CDC activities of KM696 and the shaded bars the CDC activities of KM966.
Figure 23B:
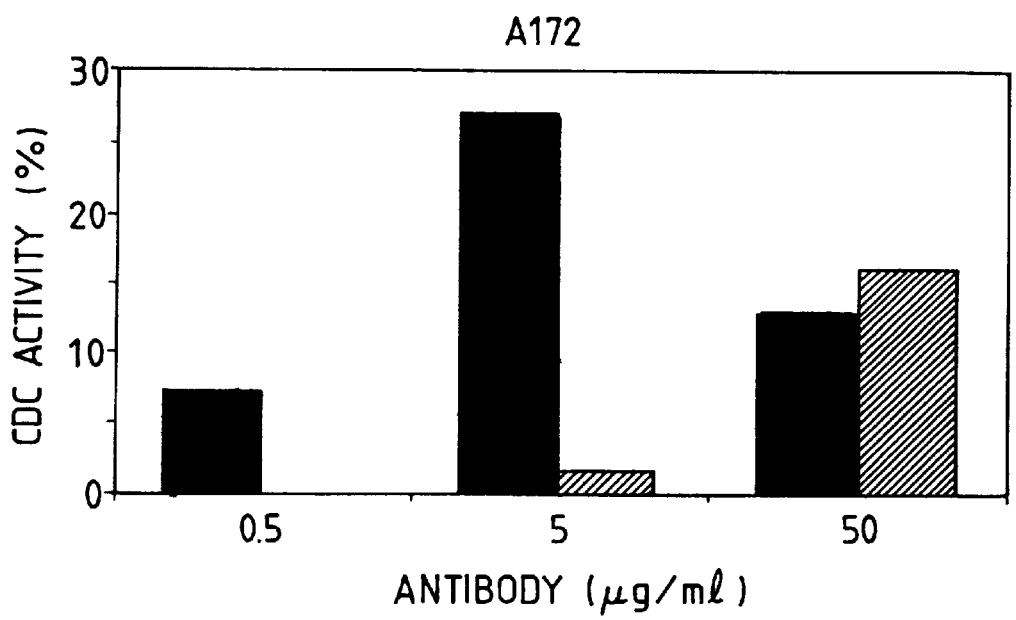
Figure 24A:
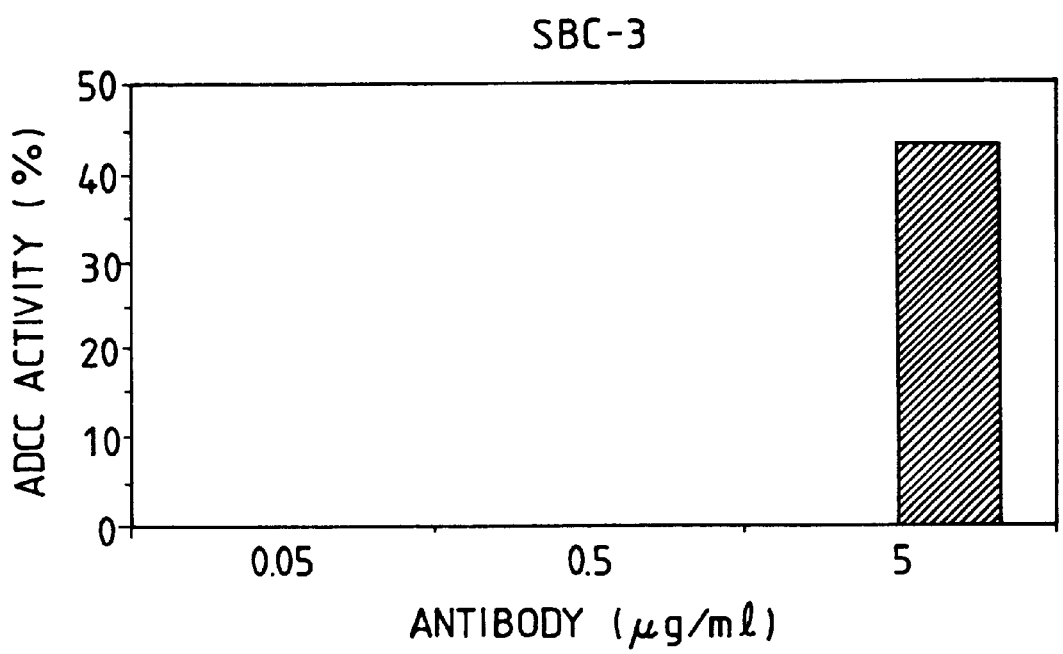
FIG. 24 graphically shows the ADCC (antibody dependent cell mediated cytotoxicity) activities of KM966 against the human lung small cell carcinoma cell lines SBC-3 and LU-135. The ordinate indicates the cytotoxic activity and the abscissa the concentration of the antibody added. The solid bars indicate the ADCC activities of KM-696 and the shaded bars the ADCC activities of KM966.
Figure 24B:
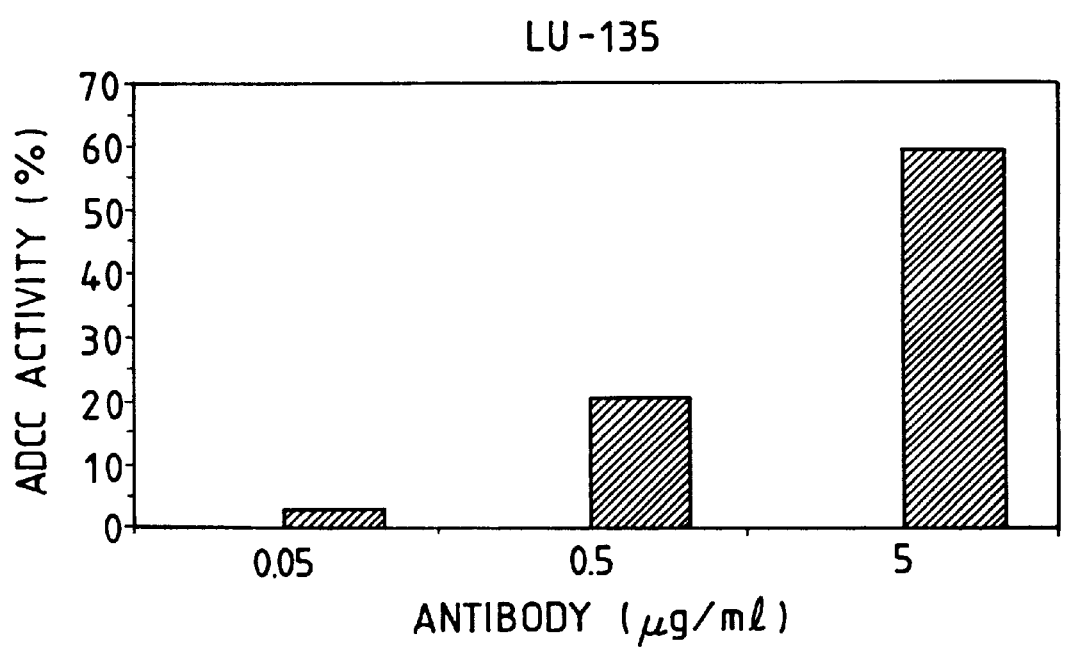
Figure 25A:
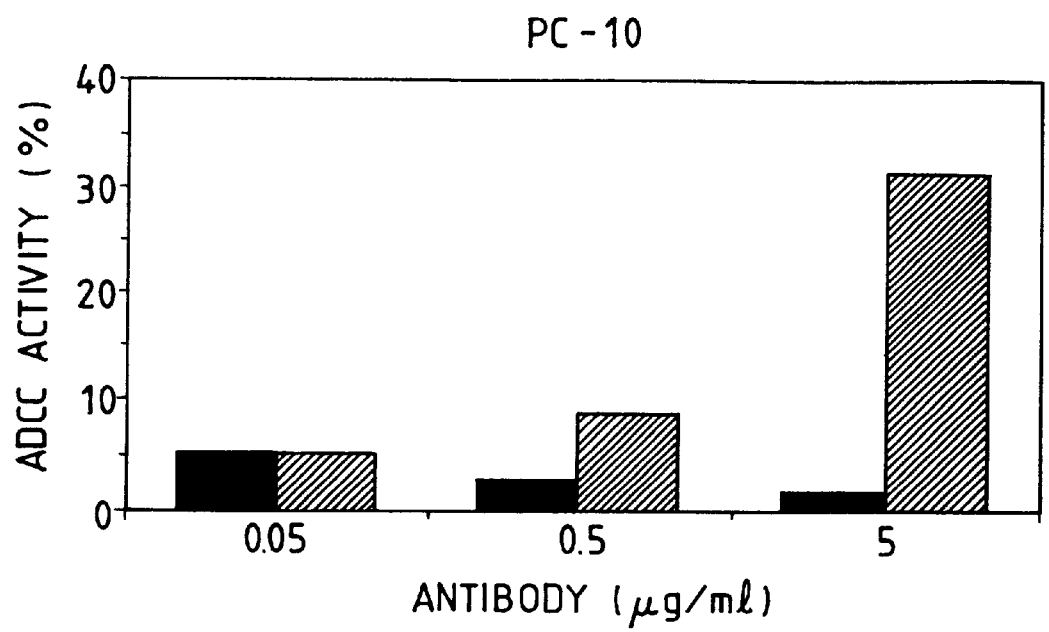
FIG. 25 graphically shows the ADCC activities of KM966 against the human lung squamous carcinoma cell line PC-10 and human lung adenocarcinoma cell line RERF-LC-MS. The ordinate indicates the cytotoxic activity and the abscissa the concentration of the antibody added. The solid bars indicate the ADCC activities of KM-696 and the shaded bars the ADCC activities of KM966.
Figure 25B:
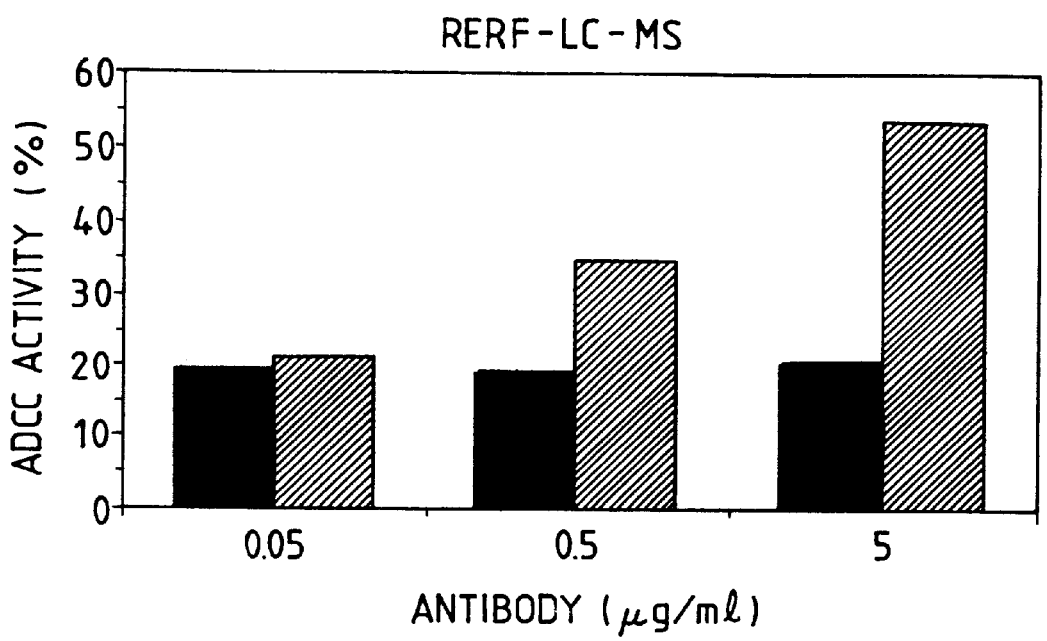

Cells of the transformant KM968 were suspended in GIT medium (Nippon Pharmaceutical) containing 0.5 mg/ml G418 and 500 nM MTX to a concentration of 1 to $2\times10^5$ cells/ml and the suspension was distributed in 100-ml portions into 175 $cm^2$ flasks (Greiner). Cultivation was conducted in a $CO_2$ incubator at 37° C. for 5 to 7 days and, when confluence was attained, the culture fluid was recovered. Treatment of about 3.0 liters of the culture fluid with Affi-Gel Protein A MAPS-II kit (Bio-Rad) gave about 1 mg of a purified chimeric human anti-$GM_2$ antibody. About 2 $\mu$g of this purified chimeric human anti-$GM_2$ antibody KM968 was electrophoresed by the conventional method [Laemmli: Nature, 227, 680 (1970)] for molecular weight checking. The results are shown in FIG. 19. Under reducing conditions, the molecular weight of the antibody H chain was about 50 kilodaltons and the molecular weight of the antibody L chain was about 25 kilodaltons, thus confirming the expression of the H chain and L chain having the correct molecular weight. Under nonreducing conditions, the molecular weight of the chimeric human antibody was about 150 kilodaltons, confirming that the antibody expressed was composed of two H chains and two L chains and was correct in size.

13. Reaction Specificity of the Chimeric Human Anti-$GM_2$ Antibodies

The reactivities of the chimeric anti-$GM_2$ antibodies with ganglioside $GM_1$, N-acetyl-$GM_2$ (Boehringer Mannheim), N-glycolyl-$GM_2$, N-acetyl-$GM_3$, N-glycolyl-$GM_3$, $GD_{1a}$, $GD_{1b}$ (Iatron), $GD_2$, $GD_3$ (Iatron) and $GQ_{1b}$ (Iatron) were examined by the technique of ELISA. The results are shown below in Table 1. $GM_1$ and $GD_{1a}$ were purified from the bovine brain, N-glycolyl-$GM_2$ and N-glycolyl-$GM_3$ from the mouse liver, N-acetyl-$GM_3$ from canine erythrocytes, and $GD_2$ from the cultured cell line IMR32 (ATCC CCL127), by a known method [J. Biol. Chem., 263, 10915 (1988)].

As shown in Table 1, it was confirmed that the chimeric human anti-$GM_2$ antibodies KM966 and KM967 specifically react with $GM_2$. The reactivity of KM966 was greater than that of KM967, however. On the contrary, KM968 (KM-603-derived chimeric human antibody) did not show any reactivity for $GM_2$.

TABLE 1

| Ganglioside | Binding activity of antibody ($OD_{415}$) | |
|---|---|---|
| | KM966 (5 $\mu$g/ml) | KM967 (5 $\mu$g/ml) |
| $GM_1$ | 0.105 | 0.000 |
| N-Acetyl-$GM_2$ | 0.870 | 0.423 |
| N-Glycolyl-$GM_2$ | 0.774 | 0.065 |
| N-Acetyl-$GM_3$ | 0.002 | 0.000 |
| N-Glycolyl-$GM_3$ | 0.122 | 0.001 |
| $GD_{1a}$ | 0.004 | 0.000 |
| $GD_{1b}$ | 0.002 | 0.000 |
| $GD_2$ | 0.095 | 0.001 |
| $GD_3$ | 0.004 | 0.000 |
| $GQ_{1b}$ | 0.005 | 0.000 |

14. Reactivities of the Chimeric Human Anti-$GM_2$ Antibodies KM966 and KM967 With Cancer Cells (Fluorescent Antibody Technique)

Suspended in PBS were $1\times10^6$ cells of cultured human lung small cell carcinoma cell line QC90 [Cancer Res., 49, 2683 (1989)], NCI-H69 (ATCC HTB119), NCI-H128 (ATCC HTB120), SBC-1 (JCRB 0816), SBC-2 (JCRB 0817), SBC-3 (JCRB 0818), SBC-5 (JCRB 0819), RERF-LC-MA (JCRB 0812), Lu-134-A-H (JCRB 0235), Lu-139 (RCB 469), Lu-130 (RCB 465), Lu-135 (RCB 468), Lu-134-B (RCB 467), Lu-140 (RCB 470), PC-6 [Naito et al.: Gann to Kagaku Ryoho (Cancer and Chemotherapy), 5 (suppl.), 89 (1978)], cultured human lung squamous carcinoma cell line PC-1 [Naito et al.: Gann to Kagaku Ryoho, 5 (suppl.), 89 (1978)], PC-10 [Naito et al.: Gann to Kagaku Ryoho, 5 (suppl.), 89 (1978)], Colol6 [Moor et al.: Cancer Res., 35, 2684 (1975)], Calu-1 (ATCC HTB54), SK-LC-4 [Proc. Natl. Acad. Sci. U.S.A., 85, 4441 (1988)], cultured human lung adenocarcinoma cell line PC-7 [Hayata et al.: Hito Gansaibo no Baiyo (Human Cancer Cell Culture), 131 (1975)], PC-9 [Kinjo et al.: Brit. J. Cancer, 39, 15 (1979)], PC-12 (ATCC CRL1721), RERF-LC-MS (JCRB 0081), HLC-1 (RCB 083), cultured human lung large cell carcinoma cell line PC-13 [Oboshi et al.: Tanpakushitsu, Kakusan, Koso (Protein, Nucleic Acid, Enzyme), 23, 697 (1978)], Lu65 (JCRB 0079), CALU-6 (ATCC HTB56), SK-LC-6 [Proc. Natl. Acad. Sci. U.S.A., 85, 4441 (1988)], cultured human neuroblastoma cell line YT-nu [Ishikawa et al.: Acta Path. Jap., 27, 697 (1977)], NAGAI [Ishikawa et al.: Acta Path. Jap., 29, 289 (1979)], NB-1 [Ishikawa et al.: Acta Path. Jap., 27, 697 (1977)], IMR32 (ATCC CCL127), GOTO (JCRB 0612), NB-9 (RCB 477), SK-N-MC (ATCC HTB10), cultured human brain tumor (glioma) cell line SK-MG-4 [EMBO J., 6, 2939 (1987)], A172 (ATCC CRL1620), T98G (ATCC CRL1690), U-118MG (ATCC HTB15), cultured human leukemia cell line HSB-2 (ATCC CCL120.1), ATN-1, U-937 (ATCC CRL1593), HPB-ALL [Oboshi et al.: Tanpakushitsu, Kakusan, Koso, 23, 697 (1978)], CCRF-SB (ATCC CCL120), KOPN-K [Hanei et al.: Haigan (Lung Cancer), 25, 524 (1985)], TYH [Haranaka et al.: Int. J. Cancer, 36, 313 (1985)], MOLT-3 (ATCC CRL1552), CCRF-CEM (ATCC CCL119), TALL-1 (JCRB 0086), NALL-1 [Oboshi et al.: Tanpakushitsu, Kakusan, Koso, 23, 697 (1978), CCRF-SB (JCRB 0032), THP-1 (ATCC TIB202), HEL92-1-7 (ATCC TIB180), cultured human maligant melanoma cell line C24•32 (EP-A-0 493686), KHm-3/P [J. Natl. Cancer Inst., 59, 775 (1977)] or G361 (ATCC CRL1424). The suspension was placed in a microtube (Tref) and centrifuged (3,000 rpm, 2 minutes) to wash the cells, 50 µl of KM966 or KM967 (50 µg/ml) was added, the mixture was stirred, and the reaction was allowed to proceed at 4° C. for 1 hour. Then, the cells were washed three times by centrifugation with PBS, 20 µl of fluorescein isocyanate-labeled protein A (30-fold dilution; Boehringer Mannheim Yamanouchi) was added and, after stirring, the reaction was allowed to proceed at 4° C. for 1 hour. Then, the cells were washed three times by centrifugation with PBS, then suspended in PBS and subjected to analysis using flow cytometer EPICS Elite (Coulter). In a control run, the same procedure as described above was followed without adding the chimeric human antibody. The results thus obtained are shown in Table 2. The chimeric human antibody KM966 reacted with 9 (NCI-H-128, SBC-1, SBC-3, SBC-5, Lu-139, Lu-130, Lu-135, Lu-134-B and Lu-140) of the 14 lung small cell carcinoma cell lines, 2 (PC-10 and Calu-1) of the 5 lung squamous carcinoma cell lines, 2 (PC-9 and RERF-LC-MS) of the 5 lung adenocarcinoma cell lines, 2 (PC-13 and SK-LC-6) of the 4 lung large cell carcinoma cell lines, 7 (YT-nu, NAGAI, NB-1, IMR32, GOTO, NB-9 and SK-N-MC) of the 7 neuroblastoma cell lines and 4 (SK-MG-4, A172, T98G and U-118MG) of the 4 brain tumor (glioma) cell lines. On the other hand, the chimeric human antibody KM967 did not react with any of the cultured cell lines. The above results indicate that the chimeric human antibody KM966 is useful in the diagnosis and treatment of brain tumors, peripheral nervous system tumors and lung cancer, among others.

TABLE 2

| Cell line | KM966 (%) (50 µg/ml) | KM967 (%) (50 µg/ml) |
|---|---|---|
| Lung small cell carcinoma | 9/14 (64) | 0/14 (0) |
| Lung squamous cell carcinoma | 2/5 (40) | 0/5 (0) |
| Lung adenocarcinoma | 2/5 (40) | 0/5 (0) |
| Lung large cell carcinoma | 2/4 (50) | 0/4 (0) |
| Neuroblastoma | 7/7 (100) | 0/7 (0) |
| Brain tumor (glioma) | 4/4 (100) | 0/4 (0) |
| Leukemia | 0/14 (0) | 0/14 (0) |
| Malignant melanoma | 0/3 (0) | 0/3 (0) |

15. In Vitro Antitumor Activity of the Chimeric Human Anti-GM$_2$ Antibody KM966: Complement Dependent Cytotoxicity (CDC)

(1) Preparation of target cells

The target cells SBC-3, Lu-135, PC-10, RERF-LC-MS, PC-13, NAGAI, GOTO or A172, cultured in RPMI1640 medium supplemented with 10% FCS, were adjusted to a cell concentration of $5 \times 10^6$ cells/ml, Na$_2^{51}$CrO$_4$ was added to a concentration of 100 µCi/$5 \times 10^6$ cells, then the reaction was allowed to proceed at 37° C. for 1 hours, and the cells were washed three times with the medium. The cells were then allowed to stand in the medium at 4° C. for 30 minutes for spontaneous dissociation and then, after centrifugation, the medium was added to adjust the cell concentration to $1 \times 10^6$ cells/ml.

(2) Preparation of the complement

Sera from three healthy subjects were combined and used as a complement source.

(3) CDC activity measurement

The chimeric human anti-GM$_2$ antibody KM966 or mouse anti-GM$_2$ antibody KM696 (FERM BP-3337) was added to wells of 96-well U-bottom plates within the final concentration range of 0.5 to 50 µg/ml and then $5 \times 10^4$ cells/well of the target cells prepared in (1) were added. The reaction was allowed to proceed at room temperature for 30 minutes. After centrifugation, the supernatants were discarded, 150 µl of the human serum obtained in (2) was added to each well (final concentration 15% v/v), and the reaction was allowed to proceed at 37° C. for 1 hour. After centrifugation, the amount of $^{51}$Cr in each supernatant was determined using a gamma counter. The amount of spontaneously dissociated $^{51}$Cr was determined by adding to the target cells the medium alone in lieu of the antibody and complement solutions and measuring the amount of $^{51}$Cr in the supernatant in the same manner as mentioned above. The total amount of dissociated $^{51}$Cr was determined by adding to the target cells 5 N sodium hydroxide in lieu of the antibody and complement solutions and measuring the amount of 51Cr in the supernatant in the same manner as mentioned above. The CDC activity was calculated as follows:

$$\text{CDC activity (\%)} = \frac{\text{Amount of }^{51}\text{Cr in sample supernatant} - \text{Amount of }^{51}\text{Cr spontaneously dissociated}}{\text{Total amount of }^{51}\text{Cr dissociated} - \text{Amount of }^{31}\text{Cr spontaneously dissociated}} \times 100$$

The results thus obtained are shown in FIGS. 20 to 23. It was shown that the chimeric human antibody KM966 show CDC activity against all the cells tested.

16. In Vitro Antitumor Activity of the Chimeric Human Anti-GM$_2$ Antibody KM966: Antibody Dependent Cell Mediated Cytotoxicity (ADCC)

(1) Preparation of target cells

The target cells SBC-3, Lu-135, PC-10, RERF-LC-MS, PC-13, NAGAI, GOTO or A172, cultured in RPMI1640 medium supplemented with 10% FCS, were adjusted to a cell concentration of 1×10$^6$ cells/ml, Na$_2$$^{51}$CrO$_4$ was added to a concentration of 50 μCi/1×10$^6$ cells, then the reaction was allowed to proceed at 37° C. for 1 hour, and the cells were washed three times with the medium. The cells were then allowed to stand in the medium at 4° C. for 30 minutes for spontaneous dissociation and then, after centrifugation, the medium was added to adjust the cell concentration to 2×10$^5$ cells/ml.

(2) Preparation of effector cells

Human venous blood (25 ml) was collected, 0.5 ml of heparin sodium (Takeda Chemical Industries; 1,000 units/ml) was added, and the mixture was gently stirred. This mixture was centrifuged (1,500 to 1,800 g, 30 minutes) using Polymorphprep (Nycomed Pharma AS), the lymphocyte layer was separated and washed three times by centrifugation with RPMI1640 medium (15,00 to 1,800 g, 15 minutes), and the cells were suspended in RPMI1640 medium supplemented with 10% FCS (5×10$^6$ cells/ml) for use as effector cells.

(3) ADCC activity measurement

The chimeric human anti-GM$_2$ antibody KM966 or mouse anti-GM$_2$ antibody KM696 were added to wells of 96-well U-bottom plates within the final concentration range of 0.05 to 5 μg/ml and then 50 μl (1×10$^4$ cells/well) of the target cell suspension prepared in (1) and 100 μl (5×10$^5$ cells/well) of the effector cell suspension prepared in (2) were added to each well (the ratio between the effector cells and target cells being 50:1). The reaction was allowed to proceed at 37° C. for 4 hours and, after centrifugation, the amount of $^{51}$Cr in each supernatant was measured using a gamma counter. The amount of spontaneously dissociated $^{51}$Cr was determined by adding to the target cells the medium alone in lieu of the antibody and effector cells and measuring the amount of $^{51}$Cr in the supernatant in the same manner as mentioned above. The total amount of dissociated $^{51}$Cr was determined by adding to the target cells 5N sodium hydroxide in lieu of the antibody and effector cells and measuring the amount of $^{51}$Cr in the supernatant in the same manner as mentioned above. The ADCC activity was calculated as follows:

$$\text{ADCC activity (\%)} = \frac{\text{Amount of }^{51}\text{Cr in sample supernatant} - \text{Amount of }^{51}\text{Cr spontaneously dissociated}}{\text{Total amount of }^{51}\text{Cr dissociated} - \text{Amount of }^{31}\text{Cr spontaneously dissociated}} \times 100$$

The results thus obtained are shown in FIGS. 24 to 27. The chimeric antibody KM966 showed ADCC activity against all the cells whereas the mouse anti-GM$_2$ antibody KM696 showed no or low ADCC activity. The above results indicate that the chimeric human antibody KM966 is more effective in the treatment of human cancer than the mouse antibody KM-696.

REFERENCE EXAMPLE 1

Construction of the Vector pChiIgLA1 for Chimeric Human Antibody L Chain Expression 1. Isolation of the KM50 Cell-Derived Immunoglobulin H Chain Promoter and Enhancer Genes (1) Preparation of chromosomal DNAs from KM50 cells, P3U1 cells and rat kidney Chromosal DNAs were prepared by the conventional method [Maniatis et al. (ed.): Molecular Cloning, 1989, p. 9.16], as follows.

KM50 cells (1.2×10$^8$ cells), P3U1 cells (ATCC CRL1597) (2×10$^8$ cells) and a rat kidney sample (frozen at −80° C. and then smashed to a sufficient extent using a wooden hammer) (1.6 g) were suspended in 2 ml of 10 mM Tris-hydrochloride buffer (pH 7.5) containing 150 mM sodium chloride and 10 mM ethylenediaminetetraacetic acid disodium salt (hereinafter, "EDTA"), 0.8 mg of proteinase K (Sigma) and 10 mg of sodium lauryl sulfate (hereinafter, "SDS"), were added to each suspension, and the suspension was incubated at 37° C. for 10 hours. Then, each mixture was extracted once with an equal volume of phenol, twice with an equal volume of chloroform and then once with an equal volume of ether, and dialyzed for 10 hours against 10 mM Tris-hydrochloride buffer (pH 7.5) containing 1 mM EDTA. The DNA solution was recovered from the dialysis tube and ribonuclease A (Sigma) was added to the solution to a final concentration of 20 μg/ml. Each resultant solution was incubated at 37° C. for 6 hours for sufficient decomposition of RNA, 15 mg of SDS and 1 mg of proteinase K were then added and the mixture was incubated at 37° C. for 10 hours. The mixture was then extracted twice with an equal volume of phenol, twice with an equal volume of chloroform and twice with an equal volume of ether and then dialyzed for 10 hours against 10 mM Tris-hydrochloride buffer (pH 7.5) containing 1 mM EDTA. The DNA solution was recovered from the dialysis tube for use as a chromosomal DNA sample. DNA concentration measurement in terms of the absorbance at 260 nm revealed that the yield of chromosomal DNA from 1.2×10$^8$ KM50 cells was 1.6 mg, that from 2×10$^8$ P3U1 cells 1.5 mg, and that from 1.6 g of rat liver 1.9 mg.

(2) Identification of the active-form immunoglobulin H chain gene in KM50 cells by Southern blotting The KM50 cell, p3U1 cell and rat kidney chromosomal DNAs obtained in (1) (3 μg each) were dissolved in 25 μl of 10 mM Tris-hydrochloride buffer (pH 7.5) containing 6 mM magnesium chloride and 100 mM sodium chloride, 15 units of XbaI (Takara Shuzo; hereinafter the restriction enzymes used were products of Takara Shuzo) was added and incubation was carried out at 37° C. for 2 hours for effecting cleavage at the XbaI sites. Each reaction mixture was subjected to agarose gel electrophoresis, then DNA transfer onto a nitrocellulose filter was effected by the method of Southern et al. [J. Mol. Biol., 98, 503 (1975)] and hybridization was carried out by the conventional method [Kameyama et al.: FEBS Letters, 244, 301–306 (1989)] using the mouse JH probe described in the last-cited reference. The KM50 cell DNA alone gave a band at a site corresponding to about 9.3 kb. Therefore, the immunoglobulin XbaI fragment DNA was considered to code for the active-form immunoglobulin H chain gene in KM50 cells.

(3) Construction of a KM50 cell genomic DNA library A 60-μg portion of the KM50 cell-derived chromosomal DNA obtained in (1) was dissolved in 250 μl of 10 mM Tris-hydrochloride buffer (pH 7.5) containing 6 mM magnesium chloride and 100 mM sodium chloride, 150 units of XbaI was added, and incubation was conducted at 37° C. for 2 hours for causing cleavage at the XbaI sites. The reaction mixture was fractionated by agarose gel electrophoresis and a KM50 cellderived 9.3 kb DNA fraction sample (about 2 μg) was recovered using, for example, the DEAE paper method [Maniatis et al. (ed.): Molecular Cloning, 1989, p.

6.24]. Separately, 3 μg of Lambda ZAP (Stratagene), for use as the vector, was dissolved in 200 μl of 10 mM Tris-hydrochloride buffer (pH 7.5) containing 6 mM magnesium chloride and 100 mM sodium chloride, 50 units of XbaI was added, and the mixture was incubated at 37° C. for 2 hours to effect cleavage at the XbaI sites. The reaction mixture was subjected to phenol-chloroform extraction and then to ethanol precipitation, whereby about 3 μg of DNA was recovered. This DNA was dissolved in 100 μl of 100 mM Tris-hydrochloride buffer (pH 7.5), 1 unit of alkaline phosphatase (Takara Shuzo) was added, dephosphorylation was effected at the restriction enzyme cleavage ends of the vector DNA. The reaction mixture was subjected to phenol-chloroform extraction and then to ethanol precipitation, whereby 2 μg of DNA was recovered. This DNA was dissolved in 10 μl of 10 mM Tris-hydrochloride buffer (pH 7.5) containing 1 mM EDTA for use as a vector sample. Two tenths μg of the vector DNA sample and 0.2 μg of the KM50 cell-derived 9.3 kb DNA sample were dissolved in 5 μl of T4 ligase buffer, 175 units of T4 ligase (Takara Shuzo) was added, and the mixture was incubated at 4° C. for 3 days. A 2-μl portion of this mixture was packaged into the lambda phage by the conventional method [Maniatis et al. (ed.): Molecular Cloning, 1989, p. 2.95] using Giga Pak Gold (Stratagene), and the packaging mixture was used to transfect *Escherichia coli* BB4 to give 200,000 phage clones. Among them, 100,000 clones were fixed on a nitrocellulose filter by the conventional method [Maniatis et al. (ed.): Molecular Cloning, 1989, p. 2.112].

(4) Selection of a recombinant DNA containing the gene for the H chain variable region of an immunoglobulin occurring as an active form in KM50 cells (anti-human serum albumin)

From among the phage library composed of 100,000 clones, as constructed in (3), two clones firmly associable at 65° C. with the $^{32}$P-labeled mouse JH probe [labeled by the method of Kameyama et al. [FEBS Letters, 44, 301–306 (1989)]] were isolated. The phage DNA was recovered from them by the conventional method [Maniatis et al. (ed.): Molecular Cloning, 1989, p. 2.118–2.169], whereupon the 9.3 kb XbaI fragment of the KM50 cell-derived chromosomal DNA was found to have been inserted therein.

(5) Base sequence of the gene for the H chain variable region of the immunoglobulin occurring as an active form in KM50 cells (anti-human serum albumin)

For the two clones obtained in (4), restriction enzyme cleavage maps were prepared by conducting digestion using various restriction enzymes, whereby it was revealed that the same DNA fragment (9.3 kb) had been inserted therein (FIG. 28). Therefore, those portions of this 9.3 kb DNA fragment which were supposed to be coding for the rat immunoglobulin H chain promoter region and variable region were sequenced by the method of Sanger [Sanger et al.: Proc. Natl. Acad. Sci. U.S.A., 74, 5463 (1977); AMERSHAM M13 cloning and sequencing handbook]. In SEQ ID NO:16, the portion containing the octamer sequence such as ATGCAAAT and the TATA box sequence such as TTGAAAA is considered to be the immunoglobulin promoter region.

2. Construction of Heterologous Protein Expression Vectors Using the Promoter and Enhancer For the H Chain Variable Region Gene for an Immunoglobulin Occurring as an Active Form in KM50 cells (anti-human serum albumin)

(1) Construction of pKMB11

A 1-μg portion of the 9.3 kb immunoglobulin H chain variable region gene fragment obtained in Paragraph 1 (5) was dissolved in 30 μl of 10 mM Tris-hydrochloride buffer (pH 7.5) containing 6 mM magnesium chloride and 100 mM sodium chloride, 10 units each of BglII and HindIII were added, and the mixture was incubated at 37° C. for 2 hours for causing cleavage at the BglII and HindIII sites. The reaction mixture was subjected to agarose gel electrophoresis and 0.01 μg of a DNA fragment containing the 0.8 kb immunoglobulin promoter was recovered. Then, 1 μg of the plasmid pBR322-BglII [Kuwana et al.: FEBS Letters, 219, 360 (1987)] was dissolved in 30 μl of 10 mM Tris-hydrochloride buffer (pH 7.5) containing 6 mM magnesium chloride and 100 mM sodium chloride, 10 units of BglII and 10 units of HindIII were added, and the mixture was incubated at 37° C. for 2 hours to effect cleavage at the BglII and HindIII sites. The reaction mixture was subjected to agarose gel electrophoresis and a DNA fragment of about 4.2 kb in size was recovered. The thus-obtained pBR322-BglII-derived DNA fragment (about 4.2 kb, 0.1 μg) and immunoglobulin promoter-containing DNA fragment (0.01 yg) were dissolved in 20 μl of T4 ligase buffer, 175 units of T4 DNA ligase (Takara Shuzo) was added, and the mixture was incubated at 4° C. for 1 day. The reaction mixture was used to transform *Escherichia coli* HB101 [J. Mol. Biol., 41, 459 (1969)] by the method of Scott et al. [Masaru Shigesada: Saibo Kokagu (Cell Engineering), 2, 616 (1983)] to give an Ap-resistant colony. The recombinant plasmid DNA was recovered from this colony. Plasmid pKMB11, shown in FIG. 29, was thus obtained.

(2) Construction of pKMD6

For providing an appropriate restriction enzyme site downstream from the immunoglobulin promoter, the plasmid pKMB11 constructed in (1) was digested at the NcoI site using the nuclease BAL31. Thus, 10 μg of the plasmid pKMB11 was dissolved in 100 μl of 10 mM Tris-hydrochloride buffer (pH 7.5) containing 6 mM magnesium chloride and 50 mM potassium chloride, 30 units of NcoI was added, and the mixture was incubated at 37° C. for 2 hours to effect cleavage at the NcoI site. The reaction mixture was subjected to phenol-chloroform extraction and then to ethanol precipitation, the whole amount of the DNA fragment was dissolved in 100 μl of BAL31 buffer (20 mM Tris-hydrochloride buffer (pH 8.0) containing 600 mM sodium chloride, 12 mM calcium chloride, 12 mM magnesium chloride and 1 mM EDTA], 0.25 unit of BAL31 [Bethesda Research Laboratories (BRL)]] was added, and digestion was carried out at 37° C. for 5 seconds. The reaction was terminated by extraction with phenol and subjected to chloroform extraction and then to ethanol precipitation, and 1 μg of DNA was recovered. A 0.1-μg portion of this DNA and 0.01 μg of a synthetic DNA linker (SalI) were dissolved in 20 μl of T4 ligase buffer, 175 units of T4 DNA ligase was added, and the mixture was incubated at 4° C. for 1 day. The reaction mixture was used to transform *Escherichia coli* HB101 by the method of Scott et al. An Ap-resistant colony was obtained and the recombinant plasmid DNA was recovered from this colony to give the plasmid pKMD6 shown in FIG. 30. For this plasmid, the portion of BAL31 digestion was sequenced by the method of Sanger, whereupon deletion was found to the third base (303rd base in SEQ ID NO:16) toward the upstream of the initiation codon ATG for immunoglobulin.

(3) Construction of pEPKMA1, pEPKMB1 and pAGE501

The original immunoglobulin promoter and enhancer are positionally separated. Therefore, it was necessary to construct a vector containing the promoter and enhancer connected to each other for use of said vector as a heterologous protein expression vector. Accordingly, the following procedure was followed.

Thus, 1 μg of the 9.3 kb immunoglobulin H chain variable region gene obtained in Paragraph 1 (5) was dissolved in 30 μl of 10 mM Tris-hydrochloride buffer (pH 7.5) containing 6 mM magnesium chloride and 100 mM sodium chloride, 10 units of EcoRV and 10 units of XbaI were added, and the mixture was incubated at 37° C. for 2 hours for causing cleavage at the EcoRV and XbaI sites. The reaction mixture was subjected to agarose gel electrophoresis and 0.1 μg of a DNA fragment (about 1 kb) containing the immunoglobulin enhancer region was recovered. Separately, 1 μg of the plasmid pKMD6 obtained in (2) was dissolved in 100 μl of 10 mM Tris-hydrochloride buffer (pH 7.5) containing 6 mM magnesium chloride and 100 mM sodium chloride, 10 units of BglII was added, and the mixture was incubated at 37° C. for 2 hours to effect cleavage at the BglII site. After phenol-chloroform extraction, the DNA was precipitated with ethanol and dissolved in a total of 40 μl of DNA polymerase I buffer, 6 units of *Escherichia coli*-derived DNA polymerase I Klenow fragment was added, and the reaction was allowed to proceed at 16° C. for 90 minutes for rendering the 5' protruding ends formed upon BglII digestion blunt-ended. The reaction was terminated by extraction with phenol, the mixture was extracted with chloroform and then subjected to ethanol precipitation, the DNA obtained was dissolved in 30 μl of 10 mM Tris-hydrochloride buffer (pH 7.5) containing 6 mM magnesium chloride and 50 mM sodium chloride, 10 units of HindIII was added, and the mixture was incubated at 37° C. for 2 hours to effect cleavage at the HindIII site. The reaction mixture was subjected to agarose gel electrophoresis and 0.1 μg of a DNA fragment (about 0.8 kb) containing the immunoglobulin promoter region was recovered. Then, 0.2 μg of the plasmid pUC18 [Messing: Methods in enzymology 101, 20 (1983)] was dissolved in 30 μl of 10 mM Tris-hydrochloride buffer (pH 7.5) containing 6 mM magnesium chloride and 100 mM sodium chloride, 10 units of HindIII and 10 units of XbaI were added, and the mixture was incubated at 37° C. for 2 hours for causing cleavage at the HindIII and XbaI sites. The reaction mixture was subjected agarose gel electrophoresis and 0.1 μg of a DNA fragment of about 2.7 kb in size was recovered. The thus-obtained pPKMD6-derived 0.8 kb DNA fragment (0.1 μg), immunoglobulin enhancer region-containing DNA fragment (0.02 μg) and pUC18 (0.1 μg) were dissolved in 20 μl of T4 ligase buffer, 175 units of T4 DNA ligase was added, and the mixture was incubated at 4° C. for 1 day. The reaction mixture was used to transform *Escherichia coli* HB101 to give an Ap-resistant colony. The recombinant plasmid DNA was recovered from this colony to give pEPKMA1 shown in FIG. 31.

Then, 1 μg of the plasmid pEPKMA1 was dissolved in 100 μl of 10 mM Tris-hydrochloride buffer (pH 7.5) containing 6 mM magnesium chloride and 100 mM sodium chloride, 10 units of XbaI was added, and the mixture was incubated at 37° C. for 2 hours for causing cleavage at the XbaI site. After phenol-chloroform extraction, the resultant DNA fragment was precipitated with ethanol and dissolved in a total of 40 μl of DNA polymerase I buffer, 6 units of *Escherichia coli*-derived DNA polymerase I Klenow fragment was added, and the reaction was allowed to proceed at 16° C. for 90 minutes for rendering the cohesive ends formed upon XbaI digestion blunt-ended. The reaction was terminated by extraction with phenol and, after chloroform extraction, the DNA fragment was recovered by ethanol precipitation. This DNA fragment and a synthetic DNA linker XhoI (Takara Shuzo) (0.01 μg) were dissolved in 20 μl of T4 ligase buffer, 175 units of T4 DNA ligase was added, and the mixture was incubated at 4° C. for 1 day. The reaction mixture was used to transform *Escherichia coli* HB101 to give an Ap-resistant colony. The recombinant plasmid DNA was recovered from this colony to give pEPKMB1 shown in FIG. 32.

Then, the SV40 early gene promoter and enhancer regions (hereinafter abbreviated as $P_{SE}$) of the heterologous gene expression vector pAGE107 for use in animals [Miyaji et al.: Cytotechnology, 3, 133–140 (1990)] were replaced with the KM50-derived immunoglobulin H chain promoter and enhancer (hereinafter abbreviated as $P_{IH}$) of pEPKMB1 in the following manner.

One μg of the plasmid pAGE107 was dissolved in 30 μl of 10 mM Tris-hydrochloride buffer (pH 7.5) containing 6 mM magnesium chloride and 150 mM sodium chloride, 10 units of SalI and 10 units of XhoI were added, and the mixture was incubated at 37° C. for 2 hours to effect cleavage at the SalI and XhoI sites. The reaction mixture was subjected to agarose gel electrophoresis and 0.5 μg of a DNA fragment (about 5.95 kb) containing the G418 resistance gene, among others, was recovered. Then, 1 μg of the plasmid pEPKMB1 was dissolved in 30 μl of 10 mM Tris-hydrochloride buffer (pH 7.5) containing 6 mM magnesium chloride and 150 mM sodium chloride, 10 units of SalI and 10 units of XhoI were added, and the mixture was incubated at 37° C. for 2 hours to effect cleavage at the SalI and XhoI sites. The reaction mixture was subjected to agarose gel electrophoresis and 0.1 μg of a DNA fragment (about 1.7 kb) containing the immunoglobulin promoter and enhancer regions was recovered. The thus-obtained pAGE107-derived 5.95 kb DNA fragment (0.1 μg) and immunoglobulin promoter and enhancer region-containing DNA fragment (0.02 μg) were dissolved in 20 μl of T4 ligase buffer, 175 units of T4 DNA ligase was added, and the mixture was incubated at 4° C. for 1 day. The reaction mixture was used to transform *Escherichia coli* HB101. An Ap-resistant colony was isolated and the recombinant plasmid DNA was recovered therefrom to give pAGE501 shown in FIG. 33.

(4) Construction of pAGE109

A plasmid, pAGE109, derived from pAGE106 by deletion of one of the two EcoRI sites in pAGE106 was constructed as follows.

Thus, 2 μg of the heterologous gene expression vector pAGE106 for use in animal cells as described in EP-A-0 405 285 was added to 100 μl of 10 mM Tris-hydrochloride buffer (pH 7.5) containing 6 mM magnesium chloride and 50 mM sodium chloride; 10 units each of EcoRI and SacI were further added, and digestion was conducted at 37° C. for 4 hours. The reaction mixture was fractionated by agarose gel electrophoresis and about 1.5 μg of a DNA fragment (4.3 kb) resulting from cleavage of pAGE106 with EcoRI and SacI and containing the SV40 early gene promoter and G418 resistance gene was recovered. Then, this DNA fragment was dissolved in a total of 40 μl of DNA polymerase I buffer, 5 units of *Escherichia coli*-derived DNA polymerase I large fragment was added, and the reaction was conducted at 16° C. for 2 hours for rendering the 3' protruding ends formed upon SalI digestion and the 5' protruding ends formed upon EcoRI digestion blunt-ended. The reaction mixture was subjected to phenol-chloroform extraction and then to ethanol precipitation, the precipitate was dissolved in 20 μl of T4 ligase buffer; 350 units of T4 DNA ligase was further added to the mixed solution, and ligation was carried out at 4° C. for 4 hours. The thus-obtained recombinant plasmid DNA was used to transform *Escherichia coli* HB101 to give the plasmid pAGE109 shown in FIG. 34.

(5) Construction of pAGE502

For replacing the SV40 promoter and enhancer of pAGE107 with the immunoglobulin H chain promoter and enhancer, a plasmid named pAGE502 was constructed as follows.

Two μg of pAGE107 described in EP-A-0 405 285 was added to 100 μl of 10 mM Tris-hydrochloride buffer (pH 7.5) containing 6 mM magnesium chloride and 50 mM sodium chloride, 10 units of HindIII was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon HindIII digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 100 mM sodium chloride, 10 units of XhoI was further added, and digestion was effected at 37° C. for 4 hours. The reaction mixture was fractionated by agarose gel electrophoresis and about 1.5 μg of a DNA fragment (about 5.95 kb), resulting from cleavage of pAGE107 with XhoI and HindIII and containing the G418 resistance gene and Ap resistance, was recovered.

Two μg of pAGES01 obtained in (3) was added to 100 μl of 10 mM Tris-hydrochloride buffer (pH 7.5) containing 6 mM magnesium chloride and 175 mM sodium chloride, 10 units of SalI was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon SalI digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 100 mM sodium chloride, 10 units of XhoI was further added, and digestion was effected at 37° C. for 4 hours. The reaction mixture was fractionated by agarose gel electrophoresis and about 0.2 μg of a DNA fragment (1.8 kb) resulting from cleavage of pAGE501 with XhoI and SalI and containing the KM50 cell immunoglobulin H chain promoter and enhancer was recovered.

Then, 0.1 μg of the HindIII-XhoI fragment (about 5.95 kb) of pAGE107 as obtained above and 0.1 μg of the SalI-XhoI fragment (about 1.8 kb) of pAGE501 were dissolved in a total of 20 μl of T4 ligase buffer; 350 units of T4 DNA ligase was added to the solution, and the mixture was incubated at 4° C. for 1 day. The thus-obtained recombinant plasmid DNA was used to transform *Escherichia coli* HB101 to give the plasmid PAGE502 shown in FIG. 35.

(6) Construction of pAGE503

A plasmid named pAGE503 derived from pAGE502 by deletion of one of the two EcoRI sites was constructed as follows.

Two μg of pAGE109 obtained in (4) was added to 30 μl of 10 mM Tris-hydrochloride buffer (pH 7.5) containing 6 mM magnesium chloride and 50 mM sodium chloride; 10 units of HindIII and 10 units of ClaI were further added, and digestion was carried out at 37° C. for 4 hours. The reaction mixture was fractionated by agarose gel electrophoresis and about 0.2 μg of a DNA fragment (about 1 kb) resulting from cleavage of pAGE109 with ClaI and HindIII and containing the poly-A signal gene for the beta globulin and SV40 early genes was recovered.

Then, 2 μg of pAGE502 obtained in (5) was added to 30 μl of 10 mM Tris-hydrochloride buffer (pH 7.5) containing 6 mM magnesium chloride and 50 mM sodium chloride, 10 units of HindIII and 10 units of ClaI were further added, and digestion was conducted at 37° C. for 4 hours. The reaction mixture was fractionated by agarose gel electrophoresis and about 1 μg of a DNA fragment (about 6.1 kb) resulting from cleavage of pAGE502 with HindIII and ClaI and containing the KM50 cell immunoglobulin H chain promoter and enhancer genes, the Ap resistance gene and the G418 resistance gene was recovered by the DEAE paper method.

Then, 0.1 μg of the HindIII-ClaI fragment (about 1 kb) of pAGE109 as obtained above and 0.1 μg of the HindIII-ClaI fragment (about 6.1 kb) of pAGE502 as obtained above were dissolved in a total of 20 μl of T4 ligase buffer, 350 units of T4 DNA ligase was added to the solution, and the mixture was incubated at 4° C. for 1 day. The thus-obtained recombinant plasmid DNA was used to transform *Escherichia coli* HB101 and the plasmid pAGES03 shown in FIG. 36 was obtained.

(7) Construction of pSE1d1

A plasmid named pSEldl was constructed by introducing the dhfr gene into pAGE107, as follows.

Two μg of pAGE107 described in EP-A-0 405 825 was added to 100 μl of 100 mM Tris-hydrochloride buffer (pH 7.5) containing 6 mM magnesium chloride and 50 mM sodium chloride, 10 units of EcoRI was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon EcoRI digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 50 mM sodium chloride; 10 units of HindIII was further added, and digestion was effected at 37° C. for 4 hours. The reaction mixture was fractionated by agarose gel electrophoresis and about 1.5 μg of a DNA fragment (about 5.6 kb) resulting from cleavage of pAGE107 with EcoRI and HindIII and containing the G418 resistance gene and Ap resistance gene was recovered.

Two μg of pSV2-dhfr [Subramani et al.: Mol. Cell. Biol., 1, 854 (1981)] was added to 100 μl of 10 mM Tris-hydrochloride buffer (pH 7.5) containing 6 mM magnesium chloride and 100 mM sodium chloride, 10 units of BglII was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon BglII digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 100 mM sodium chloride, 10 units of HindIII was further added, and digestion was effected at 37° C. for 4 hours. The reaction mixture was fractionated by agarose gel electrophoresis and about 0.2 μg of a pSV2-dhfr DNA fragment (0.76 kb) resulting from cleavage with BglII and HindIII and containing the dehydrofolate reductase (dhfr) gene was recovered.

Then, 0.1 μg of the HindIII-EcoRI fragment (about 5.6 kb) of pAGE107, as obtained above, and 0.1 μg of the BglII-HindIII fragment (about 0.76 kb) of pSV2-dhfr, as obtained above, were dissolved in a total of 20 μl of T4 ligase buffer; 350 units of T4 DNA ligase was added to the solution, and the mixture was incubated at 4° C. for 1 day. The thus-obtained recombinant plasmid DNA was used to transform *Escherichia coli* HB101 and the plasmid pSE1d1 shown in FIG. 37 was obtained.

(8) Construction of pSE1d2

A plasmid named pSE1d2 was constructed by deleting the HindIII cleavage site from pSE1d1, as follows.

Thus, 2 μg of pSE1d1 obtained in (7) was added to 100 μl of 10 mM Tris-hydrochloride buffer (pH 7.5) containing 6 mM magnesium chloride and 50 mM sodium chloride, 10 units of HindIII was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon HindIII digestion blunt-ended. The reaction mixture was subjected to phenol-chloroform extraction and then to ethanol precipitation, the precipitate was dissolved in 20 μl of T4 ligase buffer, 350 units of T4 DNA ligase was added to the solution, and the mixture was incubated at 4° C. for 1 day. The thus-obtained recombinant plasmid DNA was used to transform *Escherichia coli* HB101 and the plasmid pSE1d2 shown in FIG. 38 was obtained.

(9) Construction of pIg1SE1d2

A plasmid named pIg1SE1d2 was constructed by introducing the dhfr gene into pAGE503, as follows.

Two μg of pAGE503 obtained in (6) was added to 100 μl of 10 mM Tris-hydrochloride buffer (pH 7.5) containing 6 mM magnesium chloride and 50 mM sodium chloride, 10 units of ClaI was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon ClaI digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 50 mM sodium chloride; 10 units of MluI was further added, and digestion was effected at 37° C. for 4 hours. The reaction mixture was fractionated by agarose gel electrophoresis and about 1 μg of a DNA fragment (about 5.4 kb) resulting from cleavage of pAGE503 with ClaI and MluI and containing the KM50 immunoglobulin H chain promoter and enhancer was recovered.

Then, 2 μg of pSE1d2 obtained in (8) was added to 100 μl of 10 mM Tris-hydrochloride buffer (pH 7.5) containing 6 mM magnesium chloride and 100 mM sodium chloride, 10 units of XhoI was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon XhoI digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 100 mM sodium chloride, 10 units of MluI was further added, and digestion was effected at 37° C. for 4 hours. The reaction mixture was fractionated by agarose gel electrophoresis and about 1 μg of a DNA fragment (about 3.8 kb) resulting from cleavage of pSE1d2 with XhoI and MluI and containing the dhfr gene was recovered.

Then, 1 μg of the ClaI-MluI fragment (about 5.4 kb) of pAGE503 as obtained above and 1 μg of the XhoI-MluI fragment (about 3.8 kb) of pSE1d2 as obtained above were dissolved in a total of 20 μl of T4 ligase buffer, 350 units of T4 DNA ligase was added to the solution, and the mixture was incubated at 4° C. for 1 day. The thus-obtained recombinant plasmid DNA was used to transform *Escherichia coli* HB101 and the plasmid pIg1SE1d2 shown in FIG. 39 was obtained.

(10) Construction of pIg1SE1d3

A plasmid named pIg1SE1d3 was constructed by deleting the ApaI cleavage site from pIg1SE1d2, as follows.

Two μg of pIg1SE1d2 obtained in (9) was added to 100 μl of 10 mM Tris-hydrochloride buffer (pH 7.5) containing 6 mM magnesium chloride, 10 units of ApaI was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was carried out at 16° C. for 2 hours for rendering the 3' protruding ends formed upon ApaI digestion blunt-ended. The reaction mixture was subjected to phenol-chloroform extraction and then to ethanol precipitation, the precipitate was dissolved in 20 μl of T4 ligase buffer, 350 units of T4 ligase was added to the solution, and ligation was effected at 4° C. for 24 hours. The thus-obtained recombinant plasmid DNA was used to transform *Escherichia coli* HB101 and the plasmid pIg1SE1d3 shown in FIG. 40 was obtained.

(11) Construction of pIg1SE1d4

For providing pIg1SE1d3 with a cloning site between the HindIII cleavage site and EcoRI cleavage site, a plasmid named pIg1SE1d4 was constructed containing the synthetic DNA defined by SEQ ID NO:17 as an insert, as follows.

Two μg of pIg1SE1d3 obtained in (10) was added to 30 μl of 10 mM Tris-hydrochloride buffer (pH 7.5) containing 6 mM magnesium chloride and 50 mM sodium chloride, 10 units each of HindIII and EcoRI were further added, and digestion was carried out at 37° C. for 4 hours. The reaction mixture was fractionated by agarose gel electrophoresis and about 1 μg of a DNA fragment (about 9.2 kb) resulting from cleavage of pIg1SE1d3 with HindIII and EcoRI and containing the KM50 cell immunoglobulin H chain promoter, enhancer, Ap resistance gene, G418 resistance gene and dhfr gene was recovered.

Then, 0.1 μg of the HindIII-EcoRI fragment (about 9.2 kb) of pIg1SE1d3 as obtained above and 10 ng of the synthetic DNA (SEQ ID NO:17) were a total of 20 μl of T4 ligase buffer, 350 units of T4 DNA ligase was added to the solution, and the mixture was incubated at 4° C. for 1 day. The thus-obtained recombinant plasmid DNA was used to transform *Escherichia coli* HB101 and the plasmid pIg1SE1d4 shown in FIG. 41 was obtained.

3. Preparation of the Moloney Mouse Leukemia Virus Long Terminal Repeat (hereinafter abbreviated as "MoLTR")

It is known that MoLTR has promoter and enhancer activity [Kuwana et al.: Biochem. Biophys. Res. Commun., 149, 960 (1987)]. Therefore, for using MoLTR as a promoter and enhancer in vectors for chimeric human antibody expression, a plasmid, pPMOL3, containing MoLTR was constructed as follows.

Three μg of pPMOL1 described in JP-A-1-63394 was added to 30 μl of 10 mM Tris-hydrochloride buffer (pH 7.5) containing 7 mM magnesium chloride and 6 mM 2-mercaptoethanol, 10 units of ClaI was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was carried out at 16° C. for 2 hours for rendering the 5' protruding ends formed upon ClaI digestion blunt-ended. The reaction was terminated by extraction with phenol, the reaction mixture was subjected to chloroform extraction and then to ethanol precipitation, and 2 μg of a DNA fragment was recovered. This DNA fragment and 0.01 μg of a synthetic DNA linker XhoI (Takara Shuzo) were dissolved in 20 μl of T4 ligase buffer, 175 units of T4 DNA ligase was added, and the mixture was incubated at 4° C. for 1 day. The reaction mixture was used to transform *Escherichia coli* HB101 and the plasmid pPMOL2 shown in FIG. 42 was obtained. Then, 3 μg of pPMOL2 was added to 30 μl of 10 mM Tris-hydrochloride buffer (pH 7.5) containing 7 mM magnesium chloride, 10 mM sodium chloride and 6 mM 2-mercaptoethanol, 10 units of SmaI was further added, and digestion was conducted at 37° C. for 4 hours. The reaction mixture was subjected to phenol-chloroform extraction and then to ethanol precipitation, and 2 μg of a DNA fragment was recovered. This DNA fragment and 0.01 μg of a synthetic DNA linker (EcoRI; Takara Shuzo) were dissolved in 20 μl of T4 ligase buffer, 175 units of T4 DNA ligase was added, and the mixture was incubated at 4° C. for 1 day. The reaction mixture was used to transform *Escherichia coli* HB101 and the plasmid pPMOL3 shown in FIG. 43 was obtained.

4. Cloning of the Human Immunoglobulin IgG1 H Chain Constant Region (Cγ1) cDNA and L Chain Constant Region (Cκ) cDNA (1) Isolation of mRNA from the chimeric antibody producer cell line SP2-PC Chimera-1

Using mRNA extraction kit Fast Track (product number K1593-02) manufactured by Invitrogen, MRNA (6.2 μg) was isolated from 1×10⁸ cells of the chimeric antibody producer cell line SP2-PC Chimera-1 described in FEBS Letters, 244, 301–306 (1989) and capable of producing a chimeric antibody having anti-phosphorylcholine activity.

(2) Construction of an SP2-PC Chimera-1 cDNA library and cloning of the human immunoglobulin H chain constant region (Cγ1) cDNA and L chain constant region (Cκ) cDNA Starting with 2 μg of the MRNA obtained in (1) and using cDNA Synthesis Kit (product number 27-9260-01) manufactured by Pharmacia, EcoRI adapter joining was performed, followed by phosphorylation. The cDNA solution obtained was subjected to phenol-chloroform extraction and then to ethanol precipitation, and 4 μg of cDNA was recovered. This cDNA was dissolved in 20 μl of sterilized water and then fractionated by agarose gel electrophoresis, and about 0.3 μg each of two DNA fragments, about 1.8 kb and about 1.0 kb in size, were recovered.

Then, 5 μg of the vector pUC18 was added to 100 μl of 100 mM Tris-hydrochloride buffer (pH 7.5) containing 6 mM magnesium chloride and 100 mM sodium chloride, 50 units of EcoRI was further added, and digestion was carried out at 37° C. for 4 hours for cleaving the pUC18 DNA at the EcoRI site. The reaction mixture was subjected to phenol-chloroform extraction and then to ethanol precipitation, and about 3 μg of a DNA fragment resulting from cleavage of pUC18 at the EcoRI site thereof was recovered.

Then, 0.1 μg of the EcoRI fragment (about 2.7 kb) of pUC18 as obtained above and 0.1 μg each of the 1.8 kb and 1.0 kb cDNA fragments prepared from SP2-PC Chimera-1 cells were dissolved in a total of 20 μl of T4 ligase buffer; 350 units of T4 DNA ligase was added to the solution, and ligation was effected at 4° C. for 24 hours.

The thus-obtained recombinant plasmid DNA was used to transform *Escherichia coli* LE392. About 3,000 colonies obtained were fixed onto a nitrocellulose filter. From among the strains firmly bound at 65° C. to probes prepared by labeling the human immunoglobulin constant region chromosomal genes (IgG1 H chain constant region Cγ1 and L chain constant region Cγ) [Kameyama et al.: FEBS Letters, 244, 301 (1989)] with ³²P, a plasmid (pPCVHhCGI1) associable with Cγ1 and another (pPCVLhCK1) associable with Cκ were isolated.

(3) Introduction of an EcoRV site into the human Igκ chain constant region gene

An EcoRV site was introduced into the human Igκ chain constant region at a site near the 5' end thereof by site-directed mutagenesis using a kit (catalog number Q6210) manufactured by Promega. The plasmid pPCVLhCK1 (2 μg) was added to 30 μl of 10 mM Tris-hydrochloride buffer (pH 7.5) containing 6 mM magnesium chloride and 50 mM sodium chloride, 10 units of EcoRI and 10 units of KpnI were further added, and digestion was conducted at 37° C. for 4 hours. The reaction mixture was fractionated by agarose gel electrophoresis and about 0.2 μg of a DNA fragment (about 0.8 kb) resulting from cleavage of pPCV-LhCK1 with KpnI and EcoRI and containing the human immunoglobulin L chain constant region gene was recovered.

Then, 2 μg of pSELECT1 (a kit manufactured by Promega; catalog number Q6210) was added to 30 μl of 10 mM Tris-hydrochloride buffer (pH 7.5) containing 6 mM magnesium chloride and 50 mM sodium chloride, 10 units each of EcoRI and KpnI were further added, and digestion was carried out at 37° C. for 4 hours. The reaction mixture was fractionated by agarose gel electrophoresis and about 1 μg of a DNA fragment (about 5.7 kb) resulting from cleavage of pSELECT1 with EcoRI and KpnI was recovered.

Then, 0.1 μg of the EcoRI-KpnI fragment (about 0.8 kb) of pPCVLhCK1 as obtained above and 0.1 μg of the EcoRI-KpnI fragment (about 5.7 kb) of pSELECT1 as obtained above were dissolved in a total of 20 μl of T4 ligase buffer; 350 units of T4 DNA ligase was added to the solution, and ligation was effected at 4° C. for 24 hours. The thus-obtained recombinant plasmid DNA was used to transform *Escherichia coli* JM109 and the plasmid pchCKA7 shown in FIG. 44 was obtained.

Then, using pchCKA7 and using the synthetic DNA defined by SEQ ID NO:18 as a mutagenic primer, the sequence covering the 12th base to 14 base from the N terminus of the human immunoglobulin L chain constant region, namely ACC, was converted to GAT and thus an EcoRV site was introduced into that site, to give a plasmid named pchCKB1 (FIG. 45).

Then, the EcoRV site of pchCKB1 was converted to a HindIII cleavage site in the following manner.

Thus, 2 μg of the plasmid pchCKB1 was added to 10 μl of 100 mM Tris-hydrochloride buffer (pH 7.5) containing 6 mM magnesium chloride and 100 mM sodium chloride, 10 units of EcoRI was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived polymerase I Klenow fragment was added, and the reaction was carried out at 37° C. for 30 minutes for rendering the 5' protruding ends formed upon EcoRI digestion blunt-ended. The reaction mixture was subjected to phenol-chloroform extraction and then ethanol precipitation, the precipitate was dissolved, together with 0.1 μg of a HindIII linker (Takara Shuzo), in 20 μl of T4 ligase buffer; 350 units of T4 ligase was added to the solution, and ligation was effected at 4° C. for 24 hours. The thus-obtained recombinant plasmid DNA was used to transform *Escherichia coli* HB101 and the plasmid pchCKC1 shown in FIG. 46 was obtained.

5. Construction of Vectors for Chimeric Human Antibody H Chain Expression (1) Construction of a vector to be used in constructing chimeric human antibody H chain expression vectors (vector for chimeric human antibody H chain expression)

The plasmid pIg1SE1d4 obtained in Paragraph 2 (11) (2 μg) was added to 30 μl of 10 mM Tris-hydrochloride buffer (pH 7.5) containing 6 mM magnesium chloride and 100 mM sodium chloride, 10 units each of EcoRV and ApaI were further added, and digestion was effected at 37° C. for 4 hours. The reaction mixture was fractionated by agarose gel electrophoresis and about 1.5 μg of a DNA fragment (about 9.2 kb) resulting from cleavage of pIg1SE1d4 with EcoRV and ApaI was recovered.

Then, 2 μg of pPCVHhCGI1 obtained in Paragraph 4 (2) was added to 30 μl of 10 mM Tris-hydrochloride buffer (pH 7.5) containing 6 mM magnesium chloride, 10 units of ApaI and 10 units of SmaI were further added, and digestion was conducted at 37° C. for 1 hour. The reaction mixture was fractionated by agarose gel electrophoresis and about 0.2 μg of a DNA fragment (about 1 kb) resulting from cleavage of pPCVHhCGI1 with ApaI and SmaI and containing the human immunoglobulin H chain constant region gene was recovered.

Then, 0.1 μg of the EcoRV-ApaI fragment (about 9.2 kb) of pIg1SE1d4 as obtained above and 0.1 μg of the ApaI-SmaI fragment (about 1 kb) of pPCVHhCGI1 as obtained above were dissolved in a total of 20 μl of T4 ligase buffer; 350 units of T4 DNA ligase was added to the solution, and ligation was conducted at 4° C. for 24 hours. The thus-obtained recombinant plasmid DNA was used to transform *Escherichia coli* HB101 and the vector pCHiIgHB2 for chimeric human antibody H chain expression as shown in FIG. 47 was obtained.

(2) Construction of a vector to be used in constructing chimeric human antibody L chain expression vectors (vector for chimeric human antibody L chain expression)

The plasmid pIg1SE1d4 obtained in Paragraph 2 (11) (2 μg) was added to 30 μl of 10 mM Tris-hydrochloride buffer (pH 7.5) containing 6 mM magnesium chloride and 100 mM sodium chloride, 10 units of EcoRV and 10 units of HindIII were further added, and digestion was effected at 37° C. for 4 hours. The reaction mixture was fractionated by agarose gel electrophoresis and about 1.5 μg of a DNA fragment (about 9.2 kb) resulting from cleavage of pIg1SE1d4 with EcoRV and HindIII was recovered.

Then, 2 μg of pckCKC1 obtained in Paragraph 4 (3) was added to 30 μl of 10 mM Tris-hydrochloride (pH 7.5) containing 6 mM magnesium chloride and 100 mM sodium chloride, 10 units of EcoRV and 10 units of HindIII were further added, and digestion was carried out at 37° C. for 1 hour. The reaction mixture was fractionated by agarose gel electrophoresis and about 0.2 μg of a DNA fragment (about 0.6 kb) resulting from cleavage of pPCVLhCK1 with EcoRV and HindIII and containing the human immunoglobulin L chain constant region gene was recovered.

Then, 0.1 μg of the EcoRV-HindIII fragment (about 9.2 kb) of pIg1SE1d4 as obtained above and 0.1 μg of the EcoRV-HindIII fragment (about 0.6 kb) of pchCKC1 as obtained above were dissolved in a total of 20 μl of T4 ligase buffer, 350 units of T4 DNA ligase was added to the solution, and ligation was carried out at 4° C. for 24 hours. The thus-obtained recombinant plasmid DNA was used to transform *Escherichia coli* HB101 and the vector pChi-IgLA1 for chimeric human antibody L chain expression as shown in FIG. 48 was obtained.

REFERENCE EXAMPLE 2

Construction of a Chimeric Human Antibody H Chain Expression Vector, pChi641HA1

1. Isolation of MRNA from mouse anti-GD$_3$ monoclonal antibody KM-641-producing hybridoma cells Using mRNA extraction kit Fast Track (product number K1593-02) manufactured by Invitrogen, 34 μg of mRNA was isolated from 1×10$^8$ mouse anti-GD$_3$ monoclonal antibody KM-641-producing hybridoma cells obtainable as in Reference Example 1.

2. Construction of a KM-641 H chain cDNA library and a KM-641 L chain cDNA library Using 3 μg of the mRNA obtained in Paragraph 1 and using cDNA synthesis kit ZAP-cDNA Synthesis Kit (product number sc200400) manufactured by Stratagene, cDNA having an EcoRI adapter at the 5' terminus and cDNA having an XhoI adapter at the 3' terminus were synthesized. About 6 μg of each cDNA was dissolved in 10 μl of sterilized water and fractionated by agarose gel electrophoresis. In this way, about 0.1 μg of a cDNA fragment having a size of about 1.8 kb and corresponding to the H chain and a cDNA fragment having a size of about 1.0 kb and corresponding to the L chain were recovered. Then, 0.1 μg of the cDNA fragment of about 1.8 kb in size, 0.1 μg of the cDNA fragment of about 1.0 kb in size and 1 μg of Uni-ZAP XR (Stratagene; derived from the Lambda ZAPII vector by cleavage with EcoRI and XhoI, followed by treatment with calf intestine alkaline phosphatase), to be used as the vector, were dissolved in T4 ligase buffer; 175 units of T4 DNA ligase was added, and the mixture was incubated at 12° C. for 10 hours and further at room temperature for 2 hours. A 4-μl portion of the reaction mixture was packaged into the lambda phage by the conventional method [Maniatis et al. (ed.): Molecular Cloning, 1989, p. 2.95] using Giga Pak Gold (Stratagene), followed by transfection of *Escherichia coli* PLK-F with the packaging mixture by the conventional method [Maniatis et al. (ed.): Molecular Cloning, 1989, p. 2.95–107]. As an H chain cDNA library and as an L chain cDNA library, about 10,000 phage clones were respectively obtained. The phages were then fixed onto nitrocellulose filters by the conventional method [Maniatis et al. (ed.): Molecular Cloning, 1989, p. 2.112].

3. Cloning of the monoclonal antibody KM-641 H chain and L chain cDNAs

Using probes prepared by labeling a mouse Cγ1 gene (mouse immunoglobulin constant region chromosomal gene)-containing EcoRI fragment (about 6.8 kb) [Roeder et al.: Proc. Natl. Acad. Sci. U.S.A., 78, 474 (1981)] and a mouse Cκ gene-containing HindIII-BamHI fragment (about 3 kb) [Sakano et al.: Nature, 280, 288 (1979)] with $^{32}$P, one phage clone strongly associable with the former probe at 65° C. and one phage clone strongly associable with the latter probe at 65° C. were isolated from the H chain cDNA library and L chain cDNA library constructed in Paragraph 2 in accordance with the conventional method [Maniatis et al. (ed.): Molecular Cloning, 1989, p. 2.108]. Then, by converting the phage clones to pBluescript plasmids using cDNA synthesis kit ZAP-cDNA Synthesis Kit (product number sc200400) manufactured by Stratagene, a KM-641 H chain cDNA-containing recombinant plasmid, pKM641HA3, and a KM-641 L chain cDNA-containing recombinant plasmid, pKM641LA2, were obtained. Cleavage of pKM641HA3 and pKM641LA2 with EcoRI and XhoI revealed that a cDNA fragment of about 1.6 kb and a cDNA fragment of about 0.9 kb had been inserted therein, respectively (FIG. 49).

4. Base sequences of the immunoglobulin variable regions in the KM-641 H chain cDNA (pKM641HA3) and KM-641 L chain cDNA (pKM641LA2)

The base sequences of the immunoglobulin regions in pKM641HA3 and pKM641LA2 obtained in Paragraph 3 were determined by the dideoxy method [Maniatis et al. (ed.): Molecular Cloning, 1989, p. 13.42] using Sequnase Version 2.0 DNA Sequencing Kit (United States Biochemical Corporation). The results obtained are shown in SEQ ID NO:19 and SEQ ID NO:20. In pKM641LA2, a methionine codon, presumably the initiation codon ATG, was found in the vicinity of the 5' terminus and the cDNA was a leader sequence-containing full-length one. In pKM641HA3, no methionine initiation codon was found and the leader sequence was partly lacking.

5. Construction of a KM-641-derived chimeric human antibody H chain expression vector A chimeric human antibody H chain expression vector was constructed by joining the H chain variable region gene obtained by cleaving the plasmid pKM641HA3 at the AluI site near the 5' terminus of the variable region gene and at the StyI site near the 3' terminus of the variable region gene to the vector for chimeric human antibody H chain expression as obtained in Reference Example 1 using the synthetic DNAs defined by SEQ ID NO:21 and SEQ ID NO:22 (FIG. 50).

First, the DNA defined by SEQ ID NO:22 composed of the base sequence from the 3' terminus of the immunoglobulin H chain variable region in pKM641HA3 to the StyI cleavage site near said 3'terminus and the base sequence from the 5' terminus of the immunoglobulin H chain constant region in pAGE28 to the ApaI cleavage site near said 5' terminus and having a StyI cleavage site and an ApaI cleavage site on the respective termini (cf. FIG. 50) was synthesized using a DNA synthesizer. This synthetic DNA was then introduced into the plasmid pKM641HA3 in the following manner.

Three μg of pKM641HA3 was added to 30 μl of 50 mM Tris-hydrochloride buffer (pH 7.5) containing 10 mM magnesium chloride, 50 mM sodium chloride and 1 mM DTT, 10 units of EcoRI and 10 units of StyI were further added, and digestion was effected at 37° C. for 4 hours. The reaction mixture was fractionated by agarose gel electrophoresis and about 0.3 μg of a 0.41 kb DNA fragment was recovered. Then, 3 μg of pAGE28 [Mizukami et al.: J. Biochem., 101, 1307–1310 (1987)] was added to 30 μl of 10 mM Tris-hydrochloride buffer (pH 7.5) containing 7 mM magnesium chloride and 6 mM 2-mercaptoethanol, 10 units of EcoRI and 10 units of ApaI were further added, and digestion was carried out at 37° C. for 4 hours. The reaction mixture was fractionated by agarose gel electrophoresis and about 2 μg of a 2.45 kb DNA fragment was recovered. Then, 0.1 μg of the EcoRI-StyI fragment (about 0.41 kb) of pKM641HA3, as obtained above, 0.1 μg of the EcoRI-ApaI fragment (about 2.45 kb) of pAGE28, as obtained above, and 0.3 μg of the synthetic DNA, defined by SEQ ID NO:22, were dissolved in a total of 20 μl of T4 ligase buffer; 350 units of T4 ligase was added to the solution, and ligation was conducted at 4° C. for 24 hours. The thus-obtained recombinant plasmid DNA was used to transform *Escherichia coli* HB101 and the plasmid pKM641HE1 shown in FIG. 51 was obtained.

Since pKM641HE1 had no leader sequence, the following measure was taken to supplement the deficit using the synthetic DNA defined by SEQ ID NO:21.

pKM641HE1 (3 μg) was added to 30 μl of 10 mM Tris-hydrochloride buffer (pH 7.5) containing 7 mM magnesium chloride and 6 mM 2-mercaptoethanol, 10 units of EcoRI and 10 units of ApaI were further added, and digestion was effected at 37° C. for 4 hours. The reaction mixture was fractionated by agarose gel electrophoresis and about 0.4 μg of a DNA fragment of about 0.42 kb in size was recovered. The EcoRI-ApaI fragment (about 0.42 kb; 0.4 μg) of pKM641HE1 was added to 30 μl of 10 mM Tris-hydrochloride buffer (pH 7.5) containing 7 mM magnesium chloride, 50 mM sodium chloride and 6 mM 2-mercaptoethanol, 10 units of AluI was further added, and digestion was effected at 37° C. for 4 hours. The reaction mixture was subjected to phenol-chloroform extraction and then to ethanol precipitation, and about 0.3 μg of a DNA fragment of about 0.4 kb in size was recovered.

Then, 0.1 μg of the AluI-ApaI fragment (about 0.4 kb) of pKM641HE1 as obtained above, 0.1 μg of the EcoRI-ApaI fragment (about 2.45 kb) of pAGE28 as obtained above and 0.3 μg of the synthetic DNA defined by SEQ ID NO:21 were dissolved in a total of 20 μl of T4 ligase buffer; 350 units of T4 ligase was added to the solution, and ligation was carried out at 4° C. for 24 hours. The thus-obtained recombinant plasmid DNA was used to transform *Escherichia coli* HB101 and the plasmid pKM641HF1 shown in FIG. 52 was obtained.

Then, the immunoglobulin H chain variable region of pKM641HF1 was introduced into the vector pChiIgHB2 for chimeric human antibody H chain expression, as follows. pKM641HF1 (3 μg) was added to 30 μl of 10 mM Tris-hydrochloride buffer (pH 7.5) containing 7 mM magnesium chloride and 6 mM 2-mercaptoethanol, 10 units of EcoRI and 10 units of ApaI were further added, and digestion was effected at 37° C. for 4 hours. The reaction mixture was fractionated by agarose gel electrophoresis and about 0.5 μg of a 0.44 kb DNA fragment was recovered. Then, 3 μg of pChiIgHB2 was added to 30 μl of 10 mM Tris-hydrochloride buffer (pH 7.5) containing 7 mM magnesium chloride and 6 mM 2-mercaptoethanol, 10 units of EcoRI and 10 units of ApaI were further added, and digestion was conducted at 37° C. for 4 hours. The reaction mixture was subjected to phenol-chloroform extraction and about 3 μg of DNA was recovered. Then, 0.1 μg of the EcoRI-ApaI fragment (about 0.44 kb) of pKM641HF1 as obtained above and 0.1 μg of the EcoRI-ApaI fragment (about 10.1 kb) of pChiIgHB2 as obtained above were dissolved in a total of 20 μl of T4 ligase buffer; 350 units of T4 ligase was added to the solution, and ligation was carried out at 4° C. for 24 hours. The thus-obtained recombinant plasmid DNA was used to transform

*Escherichia coli* HB101 and the plasmid pChi641HA1 shown in FIG. 53 was obtained.

Then, the KM50-derived immunoglobulin H chain promoter and enhancer region of pChi641HA1 was replaced with MoLTR, as follows.

pChi641HA1 (3 µg) was added to 30 µl of 50 mM Tris-hydrochloride buffer (pH 7.5) containing 10 mM magnesium chloride, 50 mM sodium chloride and 1 mM DTT, 10 units of EcoRI and 10 units of XhoI were further added, and digestion was effected at 37° C. for 4 hours. The reaction mixture was fractionated by agarose gel electrophoresis and about 0.2 µg of a DNA fragment of about 8.8 kb in size was recovered. pPMOL3 (3 µg) obtained in Example 1, Paragraph 2 was added to 30 µl of 50 mM Tris-hydrochloride buffer (pH 7.5) containing 10 mM magnesium chloride, 50 mM sodium chloride and 1 mM DTT; 10 units of EcoRI and 10 units of XhoI were further added, and digestion was carried out at 37° C. for 4 hours. The reaction mixture was fractionated by agarose gel electrophoresis and about 0.3 µg of a MoLTR-containing DNA fragment (0.63 kg) was recovered. Then, 0.1 µg of the EcoRI-XhoI fragment of pChi641HA1 and 0.1 µg of the EcoRI-XhoI fragment of pPMOL3 were dissolved in 20 µl of T4 ligase buffer, 175 units of T4 DNA ligase was added, and the mixture was incubated at 4° C. for 1 day. The reaction mixture was used to transform *Escherichia coli* HB101 and the KM-641-derived chimeric human H chain expression vector pChi641HAM1 shown in FIG. 54 was obtained.

EXAMPLE 2

Production of human CDR-transplanted anti-GM$_2$ antibodies (1)

1. Construction of DNAs Each Coding For Human CDR-Transplanted Anti-GM$_2$ Antibody H Chain Variable Region and Human CDR-transplanted Anti-GM$_2$ Antibody L Chain Variable Region (1) Construction of DNA coding for human CDR-transplanted anti-GM$_2$ antibody H chain variable region A DNA coding for a human CDR-transplanted anti-GM$_2$ antibody H chain variable region, hKM796H, which contains amino acid sequences of SEQ ID NO:94, SEQ ID NO:95 and SEQ ID NO:96, was constructed in the following manner.

NEWM [BIO/TECHNOLOGY, 9, 266 (1991)] was used as human antibody H chain variable region-encoding DNA to which each CDR was to be transplanted. DNAs set forth in SEQ ID NO:23 through NO:29 corresponding to NEWM in which each CDR was replaced with amino acid sequences of SEQ ID NO:94, SEQ ID NO:95 and SEQ ID NO:96 were synthesized using an automatic DNA synthesizer (model 380A manufactured by Applied Biosystems Co., Ltd.). The thus-obtained synthetic DNAs (50 picomoles each) were dissoloved in 20 µl of 50 mM Tris-hydrochloride buffer (pH 7.6) containing 10 mM magnesium chloride, 5 mM DTT, 0.1 mM EDTA and 0.5 mM ATP, 5 units of T4 polynucleotide kinase was added, and 5'-phosphorylation was carried out at 37° C. for 30 minutes. Ten picomoles each of the resulting phosphorylated synthetic DNAs, which had restriction enzyme sites on both ends, were ligated in the order of SEQ ID NO. (SEQ ID NO:23 throuth NO:29) using a DNA ligation kit (Takara Shuzo) in accordance with the manufacturer's instruction attached to the kit to obtain a DNA, hKM796H, shown in FIG. 55. The amino acid sequence corresponding to hKM796H is shown in SEQ ID NO:100.

(2) Construction of DNA coding for human CDR-transplanted anti-GM$_2$ antibody L chain variable region A DNA coding for a human CDR-transplanted anti-GM$_2$ antibody L chain variable region, hKM796L, which contains amino acid sequences of SEQ ID NO:97, SEQ ID NO:98 and SEQ ID NO:99, was constructed in the following manner.

REI [BIO/TECHNOLOGY, 9, 266 (1991)] was used as human antibody L chain variable region-encoding DNA to which each CDR was to be transplanted. DNAs set forth in SEQ ID NO:30 through NO:35 corrresponding to REI in which each CDR was replaced with amino acid sequences of SEQ ID NO:97, SEQ ID NO:98 and SEQ ID NO:99 were synthesized using an automatic DNA synthesizer (model 380A manufactured by Applied Biosystems Co., Ltd.). The thus-obtained synthetic DNAs (50 picomoles each) were dissoloved in 20 µl of 50 mM Tris-hydrochloride buffer (pH 7.6) containing 10 mM magnesium chloride, 5 mM DTT, 0.1 mM EDTA and 0.5 mM ATP, 5 units of T4 polynucleotide kinase was added, and 5'-phosphorylation was carried out at 37° C. for 30 minutes. Ten picomoles each of the resulting phosphorylated synthetic DNAs, which had restriction enzyme sites on both ends, were ligated in the order of SEQ ID NO. (SEQ ID NO:30 through NO:35) using a DNA ligation kit (Takara Shuzo) in accordance with the manufacturer's instruction attached to the kit to obtain a DNA, hKM796L, shown in FIG. 56. The amino acid sequence corresponding to hKM796L is shown in SEQ ID NO:101.

2. Construction of Human CDR-Transplanted Antibody H Chain Expression Vector and Human CDR-Transplanted Antibody L Chain Expression Vector (1) Construction of human CDR-transplanted antibody H chain expression vector A NotI-ApaI fragment of the DNA coding for human CDR-transplanted antibody H chain variable region, obtained in Paragraph 1(1) of Example 2, was ligated to the plasmid pChi796HM1, obtained in Paragraph 7(3) of Example 1, in the following manner (FIG. 57).

Three µg of pChi796HM1, obtained in Paragraph 7(3) of Example 1, were dissolved in 30 µl of 10 mM Tris-hydrochloride buffer (pH 7.5) containing 10 mM magnesium chloride and 1 mM DTT, 10 units of ApaI were added thereto and the mixture was allowed to react at 37° C. for 1 hour. The resulting mixture was subjected to ethanol precipitation and the thus-obtained precipitate was dissolved in 30 µl of 50 mM Tris-hydrochloride buffer (pH 7.5) containing 10 mM magnesium chloride, 100 mM sodium chloride and 1 mM DTT. Ten units of NotI were added thereto to allow the mixture to react at 37° C. for 1 hour. The reaction mixture was fractionated by agarose gel electrophoresis to recover about 2 µg of a DNA fragment of about 9.0 kb. Then, about 0.1 µg of the thus-obtained ApaI-NotI fragment of pChi796HM1 was ligated to 0.5 pmoles of the NotI-ApaI fragment of the DNA coding for human CDR-transplanted antibody H chain variable region, obtained in Paragraph 1(1) of Example 2, using a DNA ligation kit (Takara Shuzo). The resulting recombinant plasmid DNA was used to transform *Escherichia coli* HB101 and the plasmid phKM796HM1 shown in FIG. 57 was obtained.

Then, a human CDR-transplanted antibody H chain expression vector was constructed by introducing β-globin 3' splicing signal into the plasmid phKM796HM1 in the following manner (FIG. 58).

Three µg of phKM796HM1 were added to 30 µl of 10 mM Tris-hydrochloride buffer (pH 7.5) containing 10 mM magnesium chloride and 1 mM DTT, 1 unit of KpnI was added thereto. The mixture was allowed to react at 37° C. for 10 minutes to effect partial digestion. The resulting mixture was subjected to ethanol precipitation and the thus-obtained precipitate was dissolved in 30 µl of 50 mM Tris-hydrochloride buffer (pH 7.5) containing 10 mM magnesium chloride, 100 mM sodium chloride and 1 mM DTT. After adding 1 unit of XhoI, the mixture was allowed to react at 37° C. for 10 minutes to effect partial digestion. The reaction mixture was fractionated by agarose gel electrophoresis to recover about 0.2 μg of a DNA fragment of about 2.1 kb. Separately, 3 μg of pAGE148, obtained in Paragraph 7(2) of Example 1, were added to 30 μl of 10 mM Tris-hydrochloride buffer (pH 7.5) containing 10 mM magnesium chloride and 1 mM DTT. Ten units of KpnI were added thereto to allow the mixture to react at 37° C. for 1 hour. The reaction mixture was subjected to ethanol precipitation and the thus-obtained precipitate was dissloved in 30 μl of 50 mM Tris-hydrochloride buffer (pH 7.5) containing 10 mM magnesium chloride, 100 mM sodium chloride and 1 mM DTT. After adding 10 units of XhoI, the mixture was allowed to react at 37° C. for 1 hour and then fractionated by agarose gel electrophoresis to recover about 1 μg of a DNA fragment of about 8.7 kb. One tenth μg of the thus-obtained XhoI-KpnI fragment of phKM796HM1 was ligated to 0.1 μg of the XhoI-KpnI fragment of pAGE148 using a DNA ligation kit (Takara Shuzo). The thus-obtained recombinant plasmid DNA was used to transform *Escherichia coli* HB101 to obtain the plasmid phKM796HMS1 shown in FIG. 58.

(2) Construction of human CDR-transplanted antibody L chain expression vector

An EcoRI fragment having blunt ends of the DNA coding for human CDR-transplanted antibody L chain variable region, obtained in Paragraph 1 (2) of Example 2, was ligated to the chimeric human antibody L chain expression vector pChiIgLA1 in the following manner (FIG. 59).

Three μg of pChiIgLA1, obtained in Reference Example 1, were added to 30 μl of 50 mM Tris-hydrochloride buffer (pH 7.5) containing 10 mM magnesium chloride, 100 mM sodium chloride and 1 mM DTT, 10 units of EcoRI and 10 units of EcoRV were added thereto and the mixture was allowed to react at 37° C. for 1 hour. The reaction mixture was fractionated by agarose gel electrophoresis to recover about 1 μg of a DNA fragment of about 8.6 kb. Then, about 0.1 μg of the thus-obtained EcoRI-EcoRV fragment of pChiIgLA1 was ligated to 0.5 pmoles of the EcoRI fragment having blunt ends derived from the DNA coding for human CDR-transplanted antibody L chain variable region, obtained in Paragraph 1(2) of Example 2, using a DNA ligation kit (Takara Shuzo). The resulting recombinant plasmid DNA was used to transform *Escherichia coli* HB101 and the plasmid phKM796LI1 shown in FIG. 59 was obtained.

Then, $P_{MO}$ was introduced into the plasmid phKM796LI1 in the following manner (FIG. 60).

Three μg of phKM796LI1 were added to 30 μl of 50 mM Tris-hydrochloride buffer (pH 7.5) containing 10 mM magnesium chloride, 100 mM sodium chloride and 1 mM DTT, 10 units of EcoRI and 10 units of XhoI were added thereto, and the mixture was allowed to react at 37° C. for 1 hour. The reaction mixture was fractionated by agarose gel electrophoresis to recover about 1 μg of a DNA fragment of about 8.2 kb. Separately, 3 μg of the chimeric human antibody H chain expression vector pChi641HAM1, obtained in Reference Example 2, were added to 30 μl of 50 mM Tris-hydrochloride buffer (pH 7.5) containing 10 mM magnesium chloride, 100 mM sodium chloride and 1 mM DTT. Ten units of EcoRI and 10 units of XhoI were added thereto to allow the mixture to react at 37° C. for 1 hour. The reaction mixture was fractionated by agarose gel electrophoresis to recover about 0.3 μg of a DNA fragment of about 0.6 kb. One tenth μg of the thus-obtained EcoRI-XhoI fragment of pChi641HAM1 was ligated to 0.1 μg of the EcoRI-XhoI fragment of phKM796LI1 using a DNA ligation kit (Takara Shuzo). The thus-obtained recombinant plasmid DNA was used to transform *Escherichia coli* HB101 to obtain the plasmid phKM796LM1 shown in FIG. 60.

Then, a human CDR-transplanted antibody L chain expression vector was constructed by introducing β-globin 3' splicing signal into the plasmid phKM796LM1 in the following manner (FIG. 61).

Three μg of phKM796LM1 were added to 30 μl of 10 mM Tris-hydrochloride buffer (pH 7.5) containing 10 mM magnesium chloride and 1 mM DTT, 10 units of KpnI were added thereto, and the mixture was allowed to react at 37° C. for 1 hour. The resulting mixture was subjected to ethanol precipitation and the thus-obtained precipitate was dissolved in 30 μl of 50 mM Tris-hydrochloride buffer (pH 7.5) containing 10 mM magnesium chloride, 100 mM sodium chloride and 1 mM DTT. After adding 10 units of XhoI, the mixture was allowed to react at 37° C. for 1 hour. The reaction mixture was fractionated by agarose gel electrophoresis to recover about 0.3 μg of a DNA fragment of about 1.6 kb. Separately, 3 μg of pAGE148, obtained in Paragraph 7(2) of Example 1, were added to 30 μl of 10 mM Tris-hydrochloride buffer (pH 7.5) containing 10 mm magnesium chloride and 1 mM DTT. Ten units of KpnI were added thereto to allow the mixture to react at 37° C. for 1 hour. The reaction mixture was subjected to ethanol precipitation and the thus-obtained precipitate was dissloved in 30 μl of 50 mM Tris-hydrochloride buffer (pH 7.5) containing 10 mM magnesium chloride, 100 mM sodium chloride and 1 mM DTT. After adding 10 units of XhoI, the mixture was allowed to react at 37° C. for 1 hour and then fractionated by agarose gel electrophoresis to recover about 1 μg of a DNA fragment of about 8.7 kb. One tenth μg of the thus-obtained XhoI-KpnI fragment of phKM796LM1 was ligated to 0.1 μg of the XhoI-KpnI fragment of pAGE148 using a DNA ligation kit (Takara Shuzo). The thus-obtained recombinant plasmid DNA was used to transform *Escherichia coli* HB101 to obtain the plasmid phKM796LMS1 shown in FIG. 61.

3. Construction of Human CDR-Transplanted Antibody H Chain and L Chain Tandem Expression Vector A tandem expression vector containing both of cDNA coding for human CDR-transplanted antibody H chain and cDNA coding for human CDR-transplanted antibody L chain was constructed in the following manner (FIG. 62 and FIG. 63). Three μg of phKM796HMS1, obtained in Paragraph 2(1) of Example 2, were dissolved in 30 μl of 50 mM Tris-hydrochloride buffer (pH 7.5) containing 10 mM magnesium chloride, 100 mM sodium chloride and 1 mM DTT, 1 unit of SalI was added thereto and the mixture was allowed to react at 37° C. for 10 minutes to effect partial digestion. The resulting mixture was subjected to ethanol precipitation and the thus-obtained precipitate was dissolved in 30 μl of 50 mM Tris-hydrochloride buffer (pH 7.5) containing 10 mM magnesium chloride, 100 mM sodium chloride and 1 mM DTT. Ten units of MluI was added thereto to allow the mixture to react at 37° C. for 1 hour. The reaction mixture was fractionated by agarose gel electrophoresis to recover about 0.2 μg of a DNA fragment of about 5.9 kb. Then, about 2 μg of pAGE107 as described in EP-A-0 405 285 was added to 30 μl of 50 mM Tris-hydrochloride buffer (pH 7.5) containing 10 mM magnesium chloride, 100 mM sodium chloride and 1 mM DTT, 10 units of MluI and 10 units of SalI were added thereto, and the mixture was allowed to react at 37° C. for 1 hour. The reaction mixture was fractionated by agarose gel electrophoresis to recover about 0.2 μg of a DNA fragment of about 3.35 kb. Then, 0.1 μg of the thus-obtained MluI-SalI fragment of phKM796HMS1 was ligated to 0.1 μg of the MluI-SalI fragment of pAGE107 using a DNA ligation kit (Takara Shuzo). The thus-obtained recombinant plasmid DNA was used to transform *Escherichia coli* HB101 to obtain the plasmid phKM796H107 shown in FIG. 62.

Then, 3 μg of phKM796H107 were added to 30 μl of 10 mM Tris-hydrochloride (pH 7.5) containing 10 mM magnesium chloride, 100 mM sodium chloride and 1 mM DTT, 10 units of ClaI was added thereto and the mixture was allowed to react at 37° C. for 1 hour. The reaction mixture was subjected to phenol-chloroform extraction and ethanol precipitation. The resulting precipitate was dissolved in 20 μl of DNA polymerase I buffer, 5 units of *Escherichia coli*-derived DNA polymerase I Klenow fragment were added, and the 5' cohesive ends produced by ClaI digestion were rendered blunt by incubation at 22° C. for 30 minutes. The reaction mixture was fractionated by agarose gel electrophoresis to recover about 0.2 μg of a DNA fragment of about 3.35 kb. The reaction mixture was also subjected to phenol-chloroform extraction and then to ethanol precipitation. The resulting precipitate was dissolved in 30 μl of 10 mM Tris-hydrochloride buffer (pH 7.5) containing 10 mM magnesium chloride, 100 mM sodium chloride and 1 mM DTT, 10 units of MluI were added thereto and the mixture was allowed to react at 37° C. for 1 hour. The reaction mixture was fractionated by agarose gel electrophoresis to recover about 0.3 μg of a DNA fragment of about 7.5 kb. Separately, 3 μg of phKM796LMS1 were added to 30 μl of 50 mM Tris-hydrochloride buffer (pH 7.5) containing 10 mM magnesium chloride, 100 mM sodium chloride and 1 mM DTT, 10 units of XhoI were added and the mixture was allowed to react at 37° C. for 1 hour. The reaction mixture was subjected to phenol-chloroform extraction and then to ethanol precipitation. The resulting precipitate was dissloved in 20 μl of DNA polymerase I buffer, 5 units of *Escherichia coli*-derived DNA polymerase I Klenow fragment were added, and the 5' cohesive ends produced by XhoI digestion were rendered blunt by incubation at 22° C. for 30 minutes. The reaction mixture was subjected to phenol-chloroform extraction followed by ethanol precipitation. The resulting precipitate was added to 30 μl of 10 mM Tris-hydrochloride buffer (pH 7.5) containing 10 mM magnesium chloride, 50 mM sodium chloride and 1 mM DTT, 10 units of MluI were added thereto, and the mixture was allowed to react at 37° C. for 1 hour. The reaction mixture was fractionated by agarose gel electrophoresis to recover about 0.3 μg of a DNA fragment of about 9.3 kb. Then, 0.1 μg of the thus-obtained MluI-ClaI fragment of phKM796H107 was ligated to 0.1 μg of the MluI-XhoI fragment of phKM796LMS1 using a DNA ligation kit (Takara Shuzo). The thus-obtained recombinant plasmid DNA was used to transform *Escherichia coli* HB101 to obtain the plasmid phKM796HL1 shown in FIG. 63.

4. Expression of Human CDR-Transplanted Anti-$GM_2$ Antibody in YB2/0 Cells

The plasmids were introduced into YB2/0 cells by the electroporation method of Miyaji et al. [Cytotechnology, 3, 133 (1990)].

After introduction of 4 μg of phKM796HL1 obtained in Paragraph 3 of Example 2 into 4×10⁶ YB2/0 (ATCC CRL1581) cells, the cells were suspended in 40 ml of RPMI1640-FCS(10) [RPMI1640 medium (Nissui Pharmaceutical) containing 10% of FCS, 1/4 volume of 7.5% $NaHCO_3$, 3% of 200 mM L-glutamine solution (Gibco) and 0.5% of penicillin-streptomycin solution (Gibco; containing 5,000 units/ml penicillin and 5,000 μg/ml streptomycin)], and the suspension was distributed in 200-μl portions into wells of 96-well microtiter plates. After 24 hours of incubation at 37° C. in a $CO_2$ incubator, G418 (Gibco) was added to a concentration of 0.5 mg/ml and then incubation was continued for 1 to 2 weeks. Transformant colonies appeared, the culture fluid was recovered from each well in which the cells had grown to confluence and an enzyme-linked immunosorbent assay (ELISA) described in Paragraph 11 of Example 1 was conducted for anti-$GM_2$ human CDR-transplanted antibody activity measurement.

The clone showing the highest activity in ELISA among the clones obtained gave a human CDR-transplanted anti-$GM_2$ antibody content of about 0.1 μg/ml of culture fluid.

Cells of the clone showing the above-mentioned human CDR-transplanted anti-$GM_2$ antibody activity were suspended in RPMI1640-FCS(10) medium containing 0.5 mg/ml G418 and 50 nM MTX to a concentration of 1 to 2×10⁵ cells/ml, and the suspension was distributed in 2-ml portions into wells of 24-well plates. Incubation was performed at 37° C. in a $CO_2$ incubator for 1 to 2 weeks to induce 50 nM MTX-resistant clones. At the time of confluence, the human CDR-transplanted anti-$GM_2$ antibody activity in each culture fluid was determined by ELISA. The 50 nM MTX-resistant clone showing the highest activity among the clones obtained showed a human CDR-transplanted anti-$GM_2$ antibody content of about 1.0 μg/ml.

Cells of the above 50 nM MTX-resistant clone were suspended in RPMI1640-FCS(10) medium containing 0.5 mg/ml G418 and 200 nM MTX to a concentration of 1 to 2×10⁵ cells/ml, and the suspension was distributed in 2-ml portions into wells of 24-well plates. Incubation was carried out at 37° C. in a $CO_2$ incubator for 1 to 2 weeks to induce 200 nM MTX-resistant clones. At the time of confluence, each culture fluid was assayed for human CDR-transplanted anti-$GM_2$ antibody activity by ELISA. The 200 nM MTX-resistant clone showing the highest activity among the clones obtained had a human CDR-transplanted anti-$GM_2$ antibody content of about 5.0 μg/ml.

As described in detail hereinabove, the present invention provides humanized antibodies reacting with the ganglioside $GM_2$.

EXAMPLE 3

Production of Human CDR-Transplanted Anti-$GM_2$ Antibodies (2)

1. Construction of Tandem Cassette Type Humanized Antibody Expression Vector, pKANTEX93

A tandem cassette type humanized antibody expression vector, pKANTEX93, for the expression of a human CDR-transplanted antibody in mammalian cells was constructed based on the plasmid pSE1UK1SEd1-3 described in JP-A-2-257891 by inserting a DNA fragment coding for a human CDR-transplanted anti-$GM_2$ antibody H chain variable region and a DNA fragment coding for a human CDR-transplanted anti-$GM_2$ antibody L chain variable region into said plasmid upstream of the human antibody γ 1H chain constant region cDNA and human antibody κ L chain constant region cDNA, respectively, in the following manner.

(1) Modification of ApaI and EcoRI restriction enzyme sites occurring in rabbit β-globin gene splicing and poly A signals For making it possible to construct a human CDR-transplanted antibody expression vector by inserting human CDR-transplanted antibody variable regions cassette-wise in the form of NotI-ApaI (H chain) and EcoRI-SpII (L chain) restriction fragments into a vector for human CDR-transplanted antibody expression, the ApaI and EcoRI restriction sites occurring in the rabbit β-globin gene splicing and polyA signals of the plasmid pSE1UK1SEd1-3 were modified in the following manner.

Three μg of the plasmid pBluescript SK(-) (Stratagene) was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the digestion reaction was allowed to proceed at 37° C. for 1 hour. The reaction mixture was subjected to ethanol precipitation, and the 3' cohesive ends resulting from ApaI digestion were rendered blunt using DNA Blunting Kit (Takara Shuzo), followed by ligation using DNA Ligation Kit (Takara Shuzo). The thus-obtained recombinant plasmid DNA solution was used to transform Escherichia coli HB101. Thus was obtained a plasmid, pBSA, shown in FIG. 64. Furthermore, 3 μg of the plasmid pBSA thus obtained was added to 10 μl of 50 mM Tris-hydrochloride buffer (pH 7.5) containing 10 mM magnesium chloride, 100 mM sodium chloride and 1 mM DTT, 10 units of the restriction enzyme EcoRI (Takara Shuzo) was further added, and the reaction was allowed to proceed at 37° C. for 1 hour. The reaction mixture was subjected to ethanol precipitation, and the 5' cohesive ends resulting from EcoRI digestion were rendered blunt using DNA Blunting Kit (Takara Shuzo), followed by ligation using DNA Ligation Kit (Takara Shuzo). The thuso-btained recombinant plasmid DNA solution was used to transform Escherichia coli HB101. Thus was obtained the plasmid pBSAE shown in FIG. 65.

Then, 3 μg of the thus-obtained plasmid pBSAE was added to 10 μl of 10 mM Tris-hydrochloride buffer (pH 7.5) containing 10 mM magnesium chloride, 50 mM sodium chloride and 1 mM DTT, 10 units of the restriction enzyme HindIII (Takara Shuzo) was further added, and the reaction was allowed to proceed at 37° C. for 1 hour. The reaction mixture was subjected to ethanol precipitation, the precipitate was dissolved in 20 μl of 10 mM Tris-hydrochloride buffer (pH 7.5) containing 10 mM magnesium chloride and 1 mM DTT, and the solution was divided into two 10-μl portions. To one portion, 10 units of the restriction enzyme SacII (Toyobo) was further added and, to the other, 10 units of the restriction enzyme KpnI (Takara Shuzo) was further added, and the reaction was allowed to proceed at 37° C. for 1 hour. Both the reaction mixtures were fractionated by agarose gel electrophoresis, whereby about 0.3 μg each of a HindIII-SacII fragment (about 2.96 kb) and a KpnI-HindIII fragment (about 2.96 kb) were recovered.

Then, 3 μg of the plasmid pSE1UK1SEd1-3 was added to 10 μl of 10 mM Tris-hydrochloride buffer (pH 7.5) containing 10 mM magnesium chloride and 1 mM DTT, 10 units of the restriction enzyme SacII (Toyobo) and 10 units of the restriction enzyme KonI (Takara Shuzo) were further added, and the reaction was allowed to proceed at 37° C. for 1 hour. The reaction mixture was subjected to ethanol precipitation, the precipitate was dissolved in 10 μl of 10 mM Tris-hydrochloride buffer (pH 7.5) containing 10 mM magnesium chloride, 50 mM sodium chloride and 1 mM DTT, 10 units of the restriction enzyme HindIII (Takara Shuzo) was further added, and the reaction was allowed to proceed at 37° C. for 1 hour. The reaction mixture was fractionated by agarose gel electrophoresis, whereby about 0.2 μg each of a HindIII-SacII fragment (about 2.42 kb) and a KpnI-HindIII fragment (about 1.98 kb) were recovered.

Then, 0.1 μg of the thus-obtained HindIII-SacII fragment of pSE1UK1SEd1-3 and 0.1 μg of the above HindIII-SacII fragment of pBSAE were dissolved in a total of 20 μl of sterilized water and ligated to each other using Ready-To-Go T4 DNA Ligase (Pharmacia Biotech). The thus-obtained recombinant plasmid DNA solution was used to transform Escherichia coli HB101 and, as a result, a plasmid, pBSH-S, shown in FIG. 66 was obtained. Further, 0.1 μg of the above-mentioned KpnI-HindIII fragment of pSE1UK1SEd1-3 and 0.1 μg of the above-mentioned KpnI-HindIII fragment of pBSAE were dissolved in a total of 20 μl of sterilized water and ligated to each other using Ready-To-Go T4 DNA Ligase (Pharmacia Biotech). The thus-obtained recombinant plasmid DNA solution was used to transform Escherichia coli HB101, and the plasmid pBSK-H shown in FIG. 67 was obtained.

Then, 3 μg each of the thus-obtained plasmids pBSH-S and pBSK-H were respectively added to 10-μl portions of 10 mM Tris-hydrochloride buffer (pH 7.5) containing 10 mM magnesium chloride and 1 mM DTT, 10 units of the restriction enzyme ApaI (Takara Shuzo) was further added to each mixture, and the reaction was allowed to proceed at 37° C. for 1 hour. Both the reaction mixtures were subjected to ethanol precipitation. With each precipitate, the 3' cohesive ends resulting from ApaI digestion were rendered blunt using DNA Blunting Kit (Takara Shuzo), followed by ligation using DNA Ligation Kit (Takara Shuzo). The thus-obtained recombinant DNA solution were used to transform Escherichia coli HB101, and the plasmids pBSH-SA and pBSK-HA shown in FIG. 68 were obtained.

Then, 5 μg each of the thus-obtained plasmids pBSH-SA and pBSK-HA were respectively added to 10-μl portions of 50 mM Tris-hydrochloride buffer (pH 7.5) containing 10 mM magnesium chloride, 100 mM sodium chloride and 1 mM DTT, 1 unit of the restriction enzyme EcoRI (Takara Shuzo) was further added to each mixture, and the reaction was allowed to proceed at 37° C. for 10 minutes for partial digestion. Both the reaction mixtures were subjected to ethanol precipitation. With each precipitate, the 5' cohesive ends resulting from EcoRI digestion were rendered blunt using DNA Blunting Kit (Takara Shuzo), followed by fractionation by agarose gel electrophoresis, whereby about 0.5 μg each of a fragment about 5.38 kb in length and a fragment about 4.94 kb in length were recovered. The thus-recovered fragments (0.1 μg each) were each dissolved in a total of 20 μl of sterilized water and subjected to ligation treatment using Ready-To-Go T4 DNA Ligase (Pharmacia Biotech). The thus-obtained recombinant DNA solutions were respectively used to transform Escherichia coli HB101, and the plasmids pBSH-SAE and pBSK-HAE shown in FIG. 69 were obtained.

Then, 3 μg each of the thus-obtained plasmids pBSH-SAE and pBSK-HAE were respectively added to 10-μl portions of 50 mM Tris-hydrochloride buffer (pH 7.5) containing 10 mM magnesium chloride, 100 mM sodium chloride and 1 mM DTT, 10 units of the restriction enzyme EcoRI (Takara Shuzo) was further added to each mixture, and the reaction was allowed to proceed at 37° C. for 1 hour. Both the reaction mixtures were subjected to ethanol precipitation. With each precipitate, the 5' cohesive ends resulting from EcoRI digestion were rendered blunt using DNA Blunting Kit (Takara Shuzo), followed by ligation using DNA Ligation Kit (Takara Shuzo). The thus-obtained recombinant plasmid DNA solutions were each used to transform Escherichia coli HB101, and two plasmids, pBSH-SAEE and pBSK-HAEE, shown in FIG. 70 were obtained. Ten μg each of the thus-obtained plasmids were subjected to sequencing reaction according to the instructions attached to AutoRead Sequencing Kit (Pharmacia Biotech), followed by base sequence determination by electrophoresis on A.L.F. DNA Sequencer (Pharmacia Biotech), whereby it was confirmed that both the ApaI and EcoRI sites had disappeared as a result of the above modification.

(2) SalI restriction site introduction downstream from rabbit β-globin gene splicing and poly A signals and SV40 early gene poly A signal For making it possible to exchange the antibody H chain and L chain expression promoters of the human CDR-transplanted antibody expression vector each for an arbitrary promoter, a SalI restriction site was introduced into the plasmid pSE1UK1SEd1-3 downstream from the rabbit β-globin gene splicing and poly A signals and from the SV40 early gene poly A signal in the following manner.

Three μg of the plasmid pBSK-HAEE obtained in Paragraph 1 (1) of Example 3 was added to 10 μl of 10 mM Tris-hydrochloride buffer (pH 7.5) containing 10 mM magnesium chloride and 1 mM DTT, 10 units of the restriction enzyme NaeI (Takara Shuzo) was further added, and the reaction was allowed to proceed at 37° C. for 1 hour. The reaction mixture was subjected to ethanol precipitation, the precipitate was dissolved in 20 μl of 50 mM Tris-hydrochloride buffer (pH 9.0) containing 1 mM magnesium chloride, 1 unit of alkaline phosphatase (*E. coli* C75, Takara Shuzo) was further added, and the reaction was allowed to proceed at 37° C. for 1 hour for dephosphorylation at the 5' termini. The reaction mixture was further subjected to phenol-chloroform extraction and then to ethanol precipitation, and the precipitate was dissolved in 20 μl of 10 mM Tris-hydrochloride buffer (pH 8.0) containing 1 mM disodium ethylenediaminetetraacetate (hereinafter briefly referred to as TE buffer). One μl of said reaction solution and 0.1 μg of a phosphorylated SalII linker (Takara Shuzo) were added to sterilized water to make a total volume of 20 μl, followed by ligation treatment using Ready-To-Go T4 DNA Ligase (Pharmacia Biotech). The thus-obtained recombinant plasmid DNA solution was used to transform *Escherichia coli* HB101, and a plasmid, pBSK-HAEESal, shown in FIG. 71 was obtained. Ten μg of the plasmid thus obtained was subjected to sequencing reaction according to the instructions attached to AutoRead Sequencing Kit (Pharmacia Biotech), followed by electrophoresis on A.L.F. DNA Sequencer (Pharmacia Biotech) for base sequence determination, whereby it was confirmed that one SalI restriction site had been introduced downstream from the rabbit β-globin gene splicing and poly A signals and from the SV40 early gene poly A signal.

(3) Modification of ApaI restriction site occurring in poly A signal of Herpes simplex virus thymidine kinase (hereinafter referred to as HSVtk) gene The ApaI restriction site occurring in the HSVtk gene poly A signal downstream from the Tn5 kanamycin phosphotransferase gene of the plasmid pSE1UK1SEd1-3 was modified in the following manner.

Three μg of the plasmid pBSA obtained in Paragraph 1 (1) of Example 3 was added to 10 μl of 10 mM Tris-hydrochloride buffer (pH 7.5) containing 10 mM magnesium chloride and 1 mM DTT, 10 units of the restriction enzyme SacII (Toyobo) was further added, and the reaction was allowed to proceed at 37° C. for 1 hour. The reaction mixture was subjected to ethanol precipitation, the precipitate was added to 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was allowed to proceed at 37° C. for 1 hour. The reaction mixture was fractionated by agarose gel electrophoresis, whereby about 1 μg of a SacII-XhoI fragment (about 2.96 kb) was recovered.

Then, 5 μg of the plasmid pSE1UK1SEd1-3 was added to 10 μl of 10 mM Tris-hydrochloride buffer (pH 7.5) containing 10 mM magnesium chloride and 1 mM DTT, 10 units of the restriction enzyme SacII (Toyobo) was further added, and the reaction was allowed to proceed at 37° C. for 1 hour. The reaction mixture was subjected to ethanol precipitation, the precipitate was added to 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was fractionated by agarose gel electrophoresis, whereby about 1 μg of a SacII-XhoI fragment (about 4.25 kb) was recovered.

Then, 0.1 μg of the above SacII-XhoI fragment of pBSA and the above SacII-XhoI fragment of pSE1UK1SEd1-3 were added to a total of 20 gl of sterilized water, followed by ligation using Ready-To-Go T4 DNA Ligase (Pharmacia Biotech). The thus-obtained recombinant plasmid DNA solution was used to transform *Escherichia coli* HB101, and the plasmid pBSX-S shown in FIG. 72 was obtained.

Then, 3 μg of the thus-obtained plasmid pBSX-S was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the 3' cohesive ends resulting from ApaI digestion were rendered blunt using DNA Blunting Kit (Takara Shuzo) and then ligation was carried out using DNA Ligation Kit (Takara Shuzo). The thus-obtained recombinant plasmid DNA solution was used to transform *Escherichia coli* HB101, and a plasmid, pBSX-SA, shown in FIG. 73 was obtained. Ten μg of the thus-obtained plasmid was subjected to sequencing reaction according to the instructions attached to AutoRead Sequencing Kit (Pharmacia Biotech), followed by electrophoresis on A.L.F. DNA Sequencer (Pharmacia Biotech) for base sequence determination, whereby it was confirmed that the ApaI restriction site in the HSVtk gene poly A signal had disappeared.

(4) Construction of human CDR-transplanted antibody L chain expression unit

A plasmid, pMohCκ, containing a human antibody κ L chain constant region cDNA downstream from the promoter/enhancer of the Moloney mouse leukemia virus long terminal repeat and having a human CDR-transplanted antibody L chain expression unit allowing cassette-wise insertion thereinto of a human CDR-transplanted antibody L chain variable region was constructed in the following manner.

Three μg of the plasmid pBluescript SK(–) (Stratagene) was added to 10 μl of 10 mM Tris-hydrochloride buffer (pH 7.5) containing 10 mM magnesium chloride and 1 mM DTT, 10 units of the restriction enzyme SacI (Takara Shuzo) was further added, and the reaction was allowed to proceed at 37° C. for 1 hour. The reaction mixture was subjected to ethanol precipitation, the precipitate was added to 10 μl of 10 mM Tris-hydrochloride buffer (pH 7.5) containing 50 mM sodium chloride, 10 mM magnesium chloride and 1 mM DTT, 10 units of the restriction enzyme ClaI (Takara Shuzo) was further added, and the reaction was allowed to proceed at 37° C. for 1 hour. The reaction mixture was subjected to ethanol precipitation, and the cohesive ends resulting from SacI and ClaI digestion were rendered blunt using DNA Blunting Kit (Takara Shuzo), followed by fractionation by agarose gel electrophoresis, whereby about 1 μg of a DNA fragment about 2.96 kb in length was recovered. A 0.1-μg portion of the DNA fragment recovered was added to a total of 20 μl of sterilized water and subjected to ligation reaction using Ready-To-Go T4 DNA Ligase (Pharmacia Biotech). The thus-obtained recombinant plasmid DNA solution was used to transform *Escherichia coli* HB101, and the plasmid pBSSC shown in FIG. 74 was obtained.

Then, 3 μg of the thus-obtained plasmid pBSSC was added to 10 μl of 10 mM Tris-hydrochloride buffer (pH 7.5) containing 10 mM magnesium chloride and 1 mM DTT, 10 units of the restriction enzyme KpnI (Takara Shuzo) was further added, and the reaction was allowed to proceed at 37° C. for 1 hour. The reaction mixture was subjected to ethanol precipitation, the precipitate was dissolved in 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was allowed to proceed at 37° C. for 1 hour. The reaction mixture was fractionated by agarose gel electrophoresis, whereby about 1 μg of a KpnI-XhoI fragment (about 2.96 kb) was recovered.

Then, 5 μg of the plasmid pAGE147 described in JP-A-6-205694 was added to 10 μl of 10 mM Tris-hydrochloride buffer (pH7.5) containing 10 mM magnesium chloride and 1 mM DTT, 10 units of the restriction enzyme KpnI (Takara Shuzo) was further added, and the reaction was allowed to proceed at 37° C. for 1 hour. The reaction mixture was subjected to ethanol precipitation, the precipitate was dissolved in 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was fractionated by agarose gel electrophoresis, whereby about 0.3 μg of a KpnI-XhoI fragment (about 0.66 kb) containing the Moloney mouse leukemia virus long terminal repeat promoter/enhancer was recovered.

Then, 0.1 μg of the KpnI-XhoI fragment of pBSSC and 0.1 μg of the KpnI-XhoI fragment of pAGE147 each obtained as mentioned above were dissolved in a total of 20 μl of sterilized water and subjected to ligation using Ready-To-Go T4 DNA Ligase (Pharmacia Biotech). The thus-obtained recombinant plasmid DNA solution was used to transform *Escherichia coli* HB101, and the plasmid pBSMo shown in FIG. 75 was obtained.

Then, 3 μg of the above plasmid pBSMo was added to 10 μl of 10 mM Tris-hydrochloride buffer (pH 7.5) containing 10 mM magnesium chloride and 1 mM DTT, 10 units of the restriction enzyme KpnI (Takara Shuzo) was further added, and the reaction was allowed to proceed at 37° C. for 1 hour. The reaction mixture was subjected to ethanol precipitation, the precipitate was dissolved in 10 μl of 10 mM Tris-hydrochloride buffer (pH 7.5) containing 50 mM sodium chloride, 10 mM magnesium chloride and 1 mM DTT, 10 units of the restriction enzyme HindIII (Takara Shuzo) was further added, and the reaction was allowed to proceed at 37° C. for 1 hour. The reaction mixture was fractionated by agarose gel electrophoresis, whereby about 1 μg of a KpnI-HindIII fragment (about 3.62 kb) was recovered.

Then, synthetic DNAs respectively having the base sequences shown in SEQ ID No:38 and SEQ ID No:39 were synthesized using an automatic DNA synthesizer (Applied Biosystems model 380A) To 15 μl of sterilized water were added 0.3 μg each of the thus-obtained synthetic DNAs, and the mixture was heated at 65° C. for 5 minutes. The reaction mixture was allowed to stand at room temperature for 30 minutes and then 2 μl of 10-fold concentrated buffer [500 mM Tris-hydrochloride (pH 7.6), 100 mM magnesium chloride, 50 mM DTT] and 2 μl of 10 mM ATP were added, 10 units of T4 polynucleotide kinase was further added, and the reaction was allowed to proceed at 37° C. for 30 minutes for phosphorylation of the 5' termini. To a total of 20 μl of sterilized water were added 0.1 μg of the above KpnI-HindIII fragment (3.66 kb) derived from the plasmid pBSMo and 0.05 μg of the phsophorylated synthetic DNA pair, and ligation was effected using Ready-To-Go T4 DNA Ligase (Pharmacia Biotech). The thus-obtained recombinant plasmid DNA solution was used to transform *Escherichia coli* HB101, and the plasmid pBSMoS shown in FIG. 76 was obtained. Ten μg of the plasmid thus obtained was subjected to sequencing reaction according to the instructions attached to AutoRead Sequencing Kit (Pharmacia Biotech), followed by electrophoresis on A.L.F. DNA Sequencer (Pharmacia Biotech) for base sequence determination, whereby it was confirmed that the synthetic DNA pair had been introduced as desired.

Then, 3 μg of the plasmid pChiIgLA1 described in JP-A-5-304989 was dissolved in 10 μl of 50 mM Tris-hydrochloride buffer (pH 7.5) containing 100 mM sodium chloride, 10 mM magnesium chloride and 1 mM DTT, 10 units each of the restriction enzymes EcoRI (Takara Shuzo) and EcoRV (Takara Shuzo) were further added, and the reaction was allowed to proceed at 37° C. for 1 hour. The reaction mixture was fractionated by agarose gel electrophoresis, whereby about 1 μg of an EcoRI-EcoRV fragment (about 9.70 kb) was recovered.

Then, synthetic DNAs respectively having the base sequences shown in SEQ ID NO:40 and SEQ ID NO:41 were synthesized using an automatic DNA synthesizer (Applied Biosystems model 380A). To 15 μl of sterilized water were added 0.3 μg each of the thus-obtained synthetic DNAs, and the mixture was heated at 65° C. for 5 minutes. The reaction mixture was allowed to stand at room temperature for 30 minutes. Then, 2 μl of 10-fold concentrated buffer [500 mM Tris-hydrochloride (pH 7.6), 100 mM magnesium chloride, 50 mM DTT] and 2 μl of 10 mM ATP were added, 10 units of T4 polynucleotide kinase was further added, and the reaction was allowed to proceed at 37° C. for 30 minutes for phosphorylation of the 5' termini. To a total of 20 μl of sterilized water were added 0.1 μg of the above EcoRI-EcoRV fragment (9.70 kb) derived from the plasmid pChiIgLA1 and 0.05 μg of the phsophorylated synthetic DNA, and ligation was effected using Ready-To-Go T4 DNA Ligase (Pharmacia Biotech). The thus-obtained recombinant plasmid DNA solution was used to transform *Escherichia coli* HB101, and the plasmid pChiIgLA1S shown in FIG. 77 was obtained.

Then, 3 μg of the plasmid pBSMoS obtained in the above manner was dissolved in 10 μl of 20 mM Tris-hydrochloride buffer (pH 8.5) containing 100 mM potassium chloride, 10 mM magnesium chloride and 1 mM DTT, 10 units of the restriction enzyme HpaI (Takara Shuzo) was further added, and the reaction was allowed to proceed at 37° C. for 1 hour. The reaction mixture was subjected to ethanol precipitation, the precipitate was dissolved in 10 μl of 50 mM Tris-hydrochloride buffer (pH 7.5) containing 100 mM sodium chloride, 10 mM magnesium chloride and 1 mM DTT, 10 units of the restriction enzyme EcoRI (Takara Shuzo) was further added, and the reaction was allowed to proceed at 37° C. for 1 hour. The reaction mixture was fractionated by agarose gel electrophoresis, whereby about 1 μg of an HpaI-EcoRI fragment (about 3.66 kb) was recovered.

Then, 10 μg of the plasmid pChiIgLA1S obtained as mentioned above was dissolved in 10 μl of 20 mM Tris-acetate buffer (pH 7.9) containing 50 mM potassium acetate, 10 mM magnesium acetate, 1 mM DTT and 100 μg/ml BSA, 10 units of the restriction enzyme NlaIV (New England BioLabs) was further added, and the reaction was allowed to proceed at 37° C. for 1 hour. The reaction mixture was subjected to ethanol precipitation, the precipitate was dissolved in 10 μl of 50 mM Tris-hydrochloride buffer (pH 7.5) containing 100 mM sodium chloride, 10 mM magnesium chloride and 1 mM DTT, 10 units of the restriction enzyme EcoRI (Takara Shuzo) was further added, and the reaction was allowed to proceed at 37° C. for 1 hour. The reaction mixture was fractionated by agarose gel electrophoresis, whereby about 0.3 μg of an NlaIV-EcoRI fragment (about 0.41 kb) was recovered.

Then, 0.1 μg of the above HpaI-EcoRI fragment of pBSMoS and 0.1 μg of the above NlaIV-EcoRI fragment of pChiIgLA1S were added to a total of 20 μl of sterilized water, and ligation was effected using Ready-To-Go T4 DNA Ligase (Pharmacia Biotech). The thus-obtained recombinant plasmid DNA solution was used to transform *Escherichia coli* HB101, and the plasmid pMohCκ shown in FIG. 78 was obtained.

(5) Construction of human CDR-transplanted antibody H chain expression unit

A plasmid, pMohCγ1, containing a human antibody γ1 H chain constant region cDNA downstream from the promoter/enhancer of the Moloney mouse leukemia virus long terminal repeat and having a human CDR-transplanted antibody H chain expression unit allowing cassette-wise insertion thereinto of a human CDR-transplanted antibody H chain variable region was constructed in the following manner.

Three μg of the plasmid pBSMo obtained in Paragraph 1 (4) of Example 3 was added to 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was allowed to proceed at 37° C. for 1 hour. The reaction mixture was subjected to ethanol precipitation, the precipitate was dissolved in 10 μl of 30 mM sodium acetate buffer (pH 5.0) containing 100 mM sodium chloride, 1 mM zinc acetate and 10% glycerol, 10 units of Mung bean nuclease (Takara Shuzo) was further added, and the reaction was allowed to proceed at 37° C. for 10 minutes. The reaction mixture was subjected to phenol-chloroform extraction and then to ethanol precipitation, the cohesive ends of the precipitate were rendered blunt using DNA Blunting Kit (Takara Shuzo) and ligation was effected using DNA Ligation Kit (Takara Shuzo). The thus-obtained recombinant plasmid DNA solution was used to transform *Escherichia coli* HB101, and the plasmid pBSMoSal shown in FIG. 79 was obtained. A 10-μg portion of the plasmid obtained was subjected to sequencing reaction according to the instructions attached to AutoRead Sequencing Kit (Pharmacia Biotech), followed by electrophoresis on A.L.F. DNA Sequencer (Pharmacia Biotech) for base sequence determination, whereby it was confirmed that the XhoI restriction site upstream of the Moloney mouse leukemia virus long terminal repeat promoter/enhancer had disappeared.

Then, 3 μg of the plasmid pBSMoSal obtained as mentioned above was added to 10 μl of 10 mM Tris-hydrochloride buffer (pH 7.5) containing 10 mM magnesium chloride and 1 mM DTT, 10 units of the restriction enzyme KpnI (Takara Shuzo) was further added, and the reaction was allowed to proceed at 37° C. for 1 hour. The reaction mixture was subjected to ethanol precipitation, the precipitate was dissolved in 10 μl of 10 mM Tris-hydrochloride buffer (pH 7.5) containing 50 mM sodium chloride, 10 mM magnesium chloride and 1 mM DTT, 10 units of the restriction enzyme HindIII (Takara Shuzo) was further added, and the reaction was allowed to proceed at 37° C. for 1 hour. The reaction mixture was fractionated by agarose gel electrophoresis, whereby about 1 μg of a KpnI-HindIII fragment (about 3.66 kb) was recovered.

Then, synthetic DNAs respectively having the base sequences shown in SEQ ID NO:42 and SEQ ID NO:43 were synthesized using an automatic DNA synthesizer (Applied Biosystems model 380A). To 15 μl of sterilized water were added 0.3 μg each of the thus-obtained synthetic DNAs, and the mixture was heated at 65° C. for 5 minutes. The reaction mixture was allowed to stand at room temperature for 30 minutes. Then, 2 μl of 10-fold concentrated buffer [500 mM Tris-hydrochloride (pH 7.6), 100 mM magnesium chloride, 50 mM DTT] and 2 μl of 10 mM ATP were added, 10 units of T4 polynucleotide kinase was further added, and the reaction was allowed to proceed at 37° C. for 30 minutes for phosphorylation of the 5' termini. To a total of 20 μl of sterilized water were added 0.1 μg of the above KpnI-HindIII fragment (3.66 kb) derived from the plasmid pBSMoSal and 0.05 μg of the phosphorylated synthetic DNA, and ligation was effected using Ready-To-Go T4 DNA Ligase (Pharmacia Biotech). The thus-obtained recombinant plasmid DNA solution was used to transform *Escherichia coli* HB101, and the plasmid pBSMoSa1S shown in FIG. 80 was obtained. A 10-μg portion of the thus-obtained plasmid was subjected to sequencing reaction according to the instructions attached to AutoRead Sequencing Kit (Pharmacia Biotech), followed by electrophoresis on A.L.F. DNA Sequencer (Pharmacia Biotech), for base sequence determination whereby it was confirmed that the synthetic DNA had been introduced as desired.

Then, 10 Ag of the plasmid pChiIgHB2 described in JP-A-5-304989 was dissolved in 10 μl of 50 mM Tris-hydrochloride buffer (pH 7.5) containing 100 mM sodium chloride, 10 mM magnesium chloride and 1 mM DTT, 10 units of the restriction enzyme Eco52I (Toyobo) was further added, and the reaction was allowed to proceed at 37° C. for 1 hour. The reaction mixture was subjected to ethanol precipitation, the precipitate was dissolved in 10 μl of 30 mM sodium acetate buffer (pH 5.0) containing 100 mM sodium chloride, 1 mM zinc acetate and 10% glycerol, 10 units of Mung bean nuclease (Takara Shuzo) was further added, and the reaction was allowed to proceed at 37° C. for 10 minutes. The reaction mixture was subjected to phenolchloroform extraction and then to ethanol precipitation, and the cohesive ends were rendered blunt using DNA Blunting Kit (Takara Shuzo). After ethanol precipitation, the precipitate was dissolved in 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was fractionated by agarose gel electrophoresis, whereby about 0.7 μg of ApaI-blunt end fragment (about 0.99 kb) was recovered.

Then, 3 μg of the plasmid pBluescript SK(−) (Stratagene) was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was dissolved in 10 μl of 33 mM Tris-acetate buffer (pH 7.9) containing 10 mM magnesium acetate, 66 mM potassium acetate, 0.5 mM DTT and 100 μg/ml BSA, 10 units of the restriction enzyme SmaI (Takara Shuzo) was further added, and the reaction was allowed to proceed at 37° C. for 1 hour. The reaction mixture was fractionated by agarose gel electrophoresis, whereby about 1 μg of an ApaI-SmaI fragment (about 3.0 kb) was recovered.

Then, 0.1 μg of the ApaI-blunt end fragment of pChi-IgHB2 and 0.1 μg of the ApaI-SmaI fragment of pbluescript SK(−), each obtained as mentioned above, were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pBShCγ1 shown in FIG. 81 was obtained.

Then, 5 μg of the above plasmid pBShCγ1 was dissolved in 10 μl of 10 mM Tris-hydrochloride buffer (pH 7.5) containing 10 mM magnesium chloride and 1 mM DTT, 10 units of the restriction enzyme ApAI (Takara Shuzo) was further added, and the reaction was allowed to proceed at 37° C. for 1 hour. The reaction mixture was subjected to ethanol precipitation, the precipitate was dissolved in 10 μl of 10 mM Tris-hydrochloride buffer (pH 7.5) containing 50 mM sodium chloride, 10 mM magnesium chloride and 1 mM DTT, 10 units of the restriction enzyme SpeI (Takara Shuzo) was further added, and the reaction was allowed to proceed at 37° C. for 1 hour. The reaction mixture was fractionated by agarose gel electrophoresis, whereby about 1 μg of an ApaI-SpeI fragment (about 1.0 kb) was recovered.

Then, 3 μg of the plasmid pBSMoSalS obtained as mentioned above was dissolved in 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was dissolved in 10 μl of 10 mM Tris-hydrochloride buffer (pH 7.5) containing 50 mM sodium chloride, 10 mM magnesium chloride and 1 mM DTT, 10 units of the restriction enzyme SpeI (Takara Shuzo) was further added, and the reaction was allowed to proceed at 37° C. for 1 hour. The reaction mixture was fractionated by agarose gel electrophoresis, whereby about 1 μg of an ApaI-SpeI fragment (about 3.66 kb) was recovered.

Then, 0.1 μg of the ApaI-SpeI fragment of pBShCγ1 and 0.1 μg of the ApaI-SpeI fragment of pBSMoSa1S, each obtained as mentioned above, were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pMohCγ1 shown in FIG. 82 was obtained.

(6) Construction of tandem cassette type humanized antibody expression vector pKANTEX93

A tandem cassette type humanized antibody expression vector, pKANTEX93, was constructed using the various plasmids obtained in Paragraphs (1) through (5) of Example 3 in the following manner.

Three μg of the plasmid PBSH-SAEE obtained in Paragraph 1 (1) of Example 3 was added to 10 μl of 10 mM Tris-hydrochloride buffer (pH 7.5) containing 50 mM sodium chloride, 10 mM magnesium chloride and 1 mM DTT, 10 units of the restriction enzyme HindIII (Takara Shuzo) was further added, and the reaction was allowed to proceed at 37° C. for 1 hour. The reaction mixture was subjected to ethanol precipitation, the precipitate was dissolved in 10 μl of 50 mM Tris-hydrochloride buffer (pH 7.5) containing 100 mM sodium chloride, 10 mM magnesium chloride and 1 mM DTT, 10 units of the restriction enzyme SalI (Takara Shuzo) was further added, and the reaction was allowed to proceed at 37° C. for 1 hour. The reaction mixture was fractionated by agarose gel electrophoresis, whereby about 1 μg of a HindIII-SalI fragment (about 5.42 kb) was recovered.

Then, 5 μg of the plasmid PBSK-HAEE obtained in Paragraph 1 (1) of Example 3 was added to 10 μl of 10 mM Tris-hydrochloride buffer (ph 7.5) containing 10 mM magnesium chloride and 1 mM DTT, 10 units of the restriction enzyme KpnI (Takara Shuzo) was further added, and the reaction was allowed to proceed at 37° C. for 1 hour. The reaction mixture was subjected to ethanol precipitation, the precipitate was dissolved in 10 μl of 10 mM Tris-hydrochloride buffer (pH 7.5) containing 50 mM sodium chloride, 10 mM magnesium chloride and 1 mM DTT, 10 units of the restriction enzyme HindIII (Takara Shuzo) was further added, and the reaction was allowed to proceed at 37° C. for 1 hour. The reaction mixture was fractionated by agarose gel electrophoresis, whereby about 0.8 μg of a KpnI-HindIII fragment (about 1.98 kb) containing the rabbit β-globin gene splicing and poly A signals, the SV40 early gene poly A signal and the SV40 early gene promoter was recovered.

Then, 5 μg of the plasmid pMohCγ1 obtained in Paragraph 1 (5) of Example 3 was added to 10 μl of 10 mM Tris-hydrochloride buffer (pH 7.5) containing 10 mM magnesium chloride and 1 mM DTT, 10 units of the restriction enzyme KpnI (Takara Shuzo) was further added, and the reaction was allowed to proceed at 37° C. for 1 hour. The reaction mixture was subjected to ethanol precipitation, the precipitate was dissolved in 10 μl of 50 mM Tris-hydrochloride buffer (pH 7.5) containing 100 mM sodium chloride, 10 mM magnesium chloride and 1 mM DTT, 10 units of the restriction enzyme SalI (Takara Shuzo) was further added, and the reaction was allowed to proceed at 37° C. for 1 hour. The reaction mixture was fractionated by agarose gel electrophoresis, whereby about 0.8 μg of a human CDR-transplanted antibody H chain expression unit-containing KpnI-SalI fragment (about 1.66 kb) was recovered.

Then, 0.1 μg of the HindIII-SalI fragment of PBSH-SAEE, 0.1 μg of the KpnI-HindIII fragment of pBSK-HAEE and 0.1 μg of the KpnI-SalI fragment of pMohCγ1, each obtained as mentioned above, were added to a total of 20 μl of sterilized water and ligated together using Ready-To-Go T4 DNA Ligase (Pharmacia Biotech). The thus-obtained recombinant plasmid DNA solution was used to transform *Escherichia coli* HB101, and the plasmid pMoγ1SP shown in FIG. 83 was obtained.

The, 3 μg of the above plasmid pMoγ1SP was added to 10 μl of 50 mM Tris-hydrochloride buffer (pH 7.5) containing 100 mM sodium chloride, 10 mM magnesium chloride and 1 mM DTT, 10 units of the restriction enzyme SalI (Takara Shuzo) and 10 units of the restriction enzyme XhoI were further added, and the reaction was allowed to proceed at 37° C. for 1 hour. The reaction mixture was fractionated by agarose gel electrophoresis, whereby about 1 μg of a SalI-XhoI fragment (about 9.06 kb) was recovered.

Then, 5 μg of the plasmid pBSK-HAEESal obtained in Paragraph 1 (2) of Example 3 was added to 10 μl of 10 mM Tris-hydrochloride buffer (pH 7.5) containing 10 mM magnesium chloride and 1 mM DTT, 10 units of the restriction enzyme KpnI (Takara Shuzo) was further added, and the reaction was allowed to proceed at 37° C. for 1 hour. The reaction mixture was subjected to ethanol precipitation, the precipitate was. dissolved in 10 μl of 50 mM Tris-hydrochloride buffer (pH 7.5) containing 100 mM sodium chloride, 10 mM magnesium chloride and 1 mM DTT, 10 units of the restriction enzyme SalI (Takara Shuzo) was further added, and the reaction was allowed to proceed at 37° C. for 1 hour. The reaction mixture was fractionated by agarose gel electrophoresis, whereby about 0.7 μg of a KpnI-SalI fragment (about 1.37 kb) containing the rabbit β-globin gene splicing and poly A signals and the SV40 early gene poly A signal was recovered.

Then, 5 μg of the plasmid pMohCκ obtained in Paragraph 1 (4) of Example 3 was added to 10 μl of 10 mM Tris-hydrochloride buffer (pH 7.5) containing 10 mM magnesium chloride and 1mM DTT, 10 units of the restriction enzyme KpnI (Takara Shuzo) was further added, and the reaction was allowed to proceed at 37° C. for 1 hour. The reaction mixture was subjected to ethanol precipitation, the precipitate was dissolved in 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was allowed to proceed at 37° C. for 1 hour. The reaction mixture was fractionated by agarose gel electrophoresis, whereby about 0.7 μg of a human CDR-transplanted antibody L chain expression unit-containing KpnI-XhoI fragment (about 1.06 kb) was recovered.

Then, 0.1 μg of the SalI-XhoI fragment of pMoγ1SP, 0.1 μg of the KpnI-SalI fragment of pBSK-HAEESal and 0.1 μg of the KpnI-XhoI fragment of pMohCκ, each obtained as mentioned above, were added to a total of 20 μl of sterilized water and ligated together using Ready-To-Go T4 DNA Ligase (Pharmacia Biotech). The thus-obtained recombinant plasmid DNA solution was used to transform *Escherichia coli* HB101, and the plasmid pMoκγ1SP shown in FIG. 84 was obtained.

Then, 3 μg of the above plasmid pMoκγ1 SP was added to 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was allowed to proceed at 37° C. for 1 hour. The reaction mixture was subjected to ethanol precipitation, the precipitate was added to 10 μl of 10 mM Tris-hydrochloride buffer (pH 7.5) containing 10 mM magnesium chloride and 1 mM DTT, 1 units of the restriction enzyme SacII (Toyobo) was further added, and the reaction was allowed to proceed at 37° C. for 10 minutes for partial digestion. The reaction mixture was fractionated by agarose gel electrophoresis, and about 0.2 μg of a SacII-XhoI fragment (about 8.49 kb) was recovered.

Then, 3 μg of the plasmid pBSX-SA obtained in Paragraph 1 (4) of Example 3 was added to 10 μl of 10 mM Tris-hydrochloride buffer (pH 7.5) containing 10 mM magnesium chloride and 1 mM DTT, 10 units of the restriction enzyme SacII (Toyobo) was further added, and the reaction was allowed to proceed at 37° C. for 1 hour. The reaction mixture was subjected to ethanol precipitation, the precipitate was dissolved in 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was allowed to proceed at 37° C. for 1 hour. The reaction mixture was fractionated by agarose gel electrophoresis, and about 1 μg of a SacII-XhoI fragment (about 4.25 kb) was recovered.

Then, 0.1 μg of the SacII-XhoI fragment of pMoκγ1SP and 0.1 μg of the SacII-XhoI fragment of pBSX-SA, each obtained as mentioned above, were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pKANTEX93 shown in FIG. 85 was obtained.

2. Expression of Human Anti-GM$_2$ Chimera Antibody Using Humanized Antibody Expression Vector pKANTEX93

Human anti-GM$_2$ chimera antibody expression was effected using the humanized antibody expression vector pKANTEX93 mentioned above in Paragraph 1 of Example 3 in the following manner.

(1) Construction of plasmid pBSH3 containing mouse anti-GM$_2$ antibody KM796 H chain variable region cDNA Three μg of the plasmid pBluescript SK(−) (Stratagene) was added to 10 μl of 10 mM Tris-hydrochloride buffer (pH 7.5) containing 10 mM magnesium chloride and 1 mM DTT, 10 units each of the restriction enzymes SacII (Toyobo) and KpnI (Takara Shuzo) were further added, and the reaction was allowed to proceed at 37° C. for 1 hour. The reaction mixture was subjected to ethanol precipitation, and the precipitate was subjected to blunting treatment for rendering blunt the 3' cohesive ends resulting from the restriction enzyme digestion using DNA Blunting Kit (Takara Shuzo) and then to fractionation by agarose gel electrophoresis, and about 1 μg of a DNA fragment about 2.95 kb in size was recovered.

Then, synthetic DNAs respectively having the base sequences shown in SEQ ID NO:44 and SEQ ID NO:45 were synthesized using an automatic DNA synthesizer (Applied Biosystems model 380A). To 15 μl of sterilized water were added 0.3 μg each of the synthetic DNAs obtained, and the mixture was heated at 65° C. for 5 minutes. The reaction mixture was allowed to stand at room temperature for 30 minutes and then 2 μl of 10-fold concentrated buffer [500 mM Tris-hydrochloride (pH 7.6), 100 mM magnesium chloride, 50 mM DTT] and 2 μl of 10 mM ATP were added, 10 units of T4 polynucleotide kinase was further added, and the reaction was allowed to proceed at 37° C. for 30 minutes for phosphorylating the 5' termini. To a total of 20 μl of sterilized water were added 0.1 μg of the DNA fragment (2.95 kb) derived from the plasmid pbluescript SK(−) and 0.05 μg of the phosphorylated synthetic DNA, each obtained as mentioned above, followed by ligation to each other using Ready-To-Go T4 DNA Ligase (Pharmacia Biotech). The thus-obtained recombinant plasmid DNA solution was used to transform *Escherichia coli* HB101, and the plasmid pBSNA shown in FIG. 86 was obtained. Ten μg of the plasmid obtained was subjected to sequencing reaction treatment according to the instructions attached to AutoRead Sequencing Kit (Pharmacia Biotech), followed by electrophoresis on A.L.F. DNA Sequencer (Pharmacia Biotech) for base sequence determination, whereby it was confirmed that the synthetic DNA had been introduced as desired.

Then, 3 μg of the plasmid pBSNA obtained as mentioned above was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was added to 10 μl of 50 mM Tris-hydrochloride buffer (pH 7.5) containing 100 mM sodium chloride, 10 mM magnesium chloride, 1 mM DTT, 100 μg/ml BSA and 0.01% Triton X-100, 10 units of the restriction enzyme NotI (Takara Shuzo) was further added, and the reaction was allowed to proceed at 37° C. for 1 hour. The reaction mixture was fractionated by agarose gel electrophoresis, and about 1 μg of a DNA fragment about 2.95 kb in size was recovered.

Then, 10 μg of the plasmid pChi796HM1 obtained in Paragraph 7 (3) of Example 1 was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was added to 10 μl of 50 mM Tris-hydrochloride buffer (pH 7.5) containing 100 mM sodium chloride, 10 mM magnesium chloride, 1 mM DTT, 100 μg/ml BSA and 0.0% Triton X-100, 10 units of the restriction enzyme NotI (Takara Shuzo) was further added, and the reaction was allowed to proceed at 37° C. for 1 hour. The reaction mixture was fractionated by agarose gel electrophoresis, and about 0.3 μg of a DNA fragment about 0.45 kb in size was recovered.

Then, 0.1 μg of the Apa-NotI fragment of PBSNA and 0.1 μg of the Apa-NotI fragment of pChi796HM1, each obtained as mentioned above, were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pBSH3 shown in FIG. 87 was obtained.

(2) Construction of plasmid pBSL3 containing mouse anti-GM$_2$ antibody KM796 L chain variable region cDNA Three μg of the plasmid pBluescript SK(−) (Stratagene) was added to 10 μl of 10 mM Tris-hydrochloride buffer (pH 7.5) containing 10 mM magnesium chloride and 1 mM DTT, 10 units of the restriction enzyme KpnI (Takara Shuzo) was further added, and the reaction was allowed to proceed at 37° C. for 1 hour. The reaction mixture was subjected to ethanol precipitation, and the precipitate was subjected to blunting treatment for rendering blunt the 3' cohesive ends resulting from KpnI digestion using DNA Blunting Kit (Takara Shuzo) and then to ethanol precipitation, the precipitate was added to 10 μl of 10 mM Tris-hydrochloride buffer (pH 7.5) containing 10 mM magnesium chloride and 1 mM DTT, 10 units of the restriction enzyme SacI (Takara Shuzo) was further added, and the reaction was allowed to proceed at 37° C. for 1 hour. The reaction mixture was fractionated by agarose gel electrophoresis, whereby about 1 μg of a DNA fragment about 2.95 kb in size was recovered.

Then, synthetic DNAs respectively having the base sequences shown in SEQ ID NO:46 and SEQ ID NO:47 were synthesized using an automatic DNA synthesizer (Applied Biosystems model 380A). To 15 μl of sterilized water were added 0.3 μg each of the synthetic DNAs obtained, and the mixture was heated at 65° C. for 5 minutes. The reaction mixture was allowed to stand at room temperature for 30 minutes. Then, 2 μl of 10-fold concentrated buffer [500 mM Tris-hydrochloride (pH 7.5), 100 mM magnesium chloride, 50 mM DTT] and 2 μl of 10 mM ATP were added, 10 units of T4 polynucleotide kinase was further added, and the reaction was allowed to proceed at 37° C. for 30 minutes for phosphorylating the 5' termini The 0.1 μg of the DNA fragment (2.95 kb) derived from the plasmid pbluescript SK(−) and 0.05 μg of the phosphorylated synthetic DNA, each obtained as mentioned above, were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pBSES shown in FIG. 88 was obtained. Ten μg of the plasmid obtained was subjected to sequencing reaction treatment according to the instructions attached to AutoRead Sequencing Kit (Pharmacia Biotech), followed by electrophoresis on A.L.F. DNA Sequencer (Pharmacia Biotech) for base sequence determination, whereby it was confirmed that the synthetic DNA had been introduced as desired.

Then, 3 μg of the plasmid pBSES obtained as mentioned above was added to 10 μl of 50 mM Tris-hydrochloride buffer (pH 7.5) containing 100 mM sodium chloride, 10 mM magnesium chloride, 1 mM DTT and 100 μg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 1 μg of a DNA fragment about 2.95 kb in size was recovered.

The, 5 μg of the plasmid pKM796L1 obtained in Paragraph 4 of Example 1 was added to 10 μl of 50 mM Tris-hydrochloride buffer (pH 7.5) containing 10 mM magnesium chloride and 1 mM DTT, 10 units each of the restriction enzymes EcoRI (Takara Shuzo) and AflIII (Takara Shuzo) were further added, and the reaction was allowed to proceed at 37° C. for 1 hour. The reaction mixture was fractionated by agarose gel electrophoresis, and about 0.3 μg of an EcoRI-AflIII fragment about 0.39 kb in size was recovered.

The, synthetic DNAs respectively having the base sequences shown in SEQ ID NO:48 and SEQ ID NO:49 were synthesized using an automatic DNA synthesizer (Applied Biosystems model 380A). To 15 μl of sterilized water were added 0.3 μg each of the synthetic DNAs obtained, and the mixture was heated at 65° C. for 5 minutes. The reaction mixture was allowed to stand at room temperature for 30 minutes. Then, 2 μl of 10-fold concentrated buffer [500 mM Tris-hydrochloride (pH 7.6), 100 mM magnesium chloride, 50 mM DTT] and 2 μl of 10 mM ATP were added, 10 units of T4 polynucleotide kinase was further added, and the reaction was allowed to proceed at 37° C. for 30 minutes for phosphorylating the 5' termini.

Then, 0.1 μg of the pBSES-derived EcoRI-SplI fragment (2.95 kb), 0.1 μg of the pKM796L1-derived EcoRI-AflIII fragment and 0.05 μg of the phosphorylated synthetic DNA, each obtained as mentioned above, were added to a total of 20 μl of sterilized water and ligated together using Ready-To-Go T4 DNA Ligase (Pharmacia Biotech). The thus-obtained recombinant plasmid DNA solution was used to transform *Escherichia coli* HB101, and the plasmid pBSL3 shown in FIG. 89 was obtained. Ten μg of the plasmid obtained was subjected to sequencing reaction treatment according to the instructions attached to AutoRead Sequencing Kit (Pharmacia Biotech), followed by electrophoresis on A.L.F. DNA Sequencer (Pharmacia Biotech) for base sequence determination, whereby it was confirmed that the synthetic DNA had been introduced as desired.

(3) Construction of human anti-GM$_2$ chimera antibody expression vector pKANTEX796

An human anti-GM$_2$ chimera antibody expression vector, pKANTEX796, was constructed using the plasmid pKANTEX93 obtained in Paragraph 1 of Example 3 and the plasmids pBSH3 and pBSL3 respectively obtained in Paragraph 2 (1) and (2) of Example 3, in the following manner.

Three μg of the plasmid pBSH3 was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was dissolved in 10 µl of 50 mM Tris-hydrochloride buffer (pH 7.5) containing 100 mM sodium chloride, 10 mM magnesium chloride, 1 mM DTT, 100 µg/ml BSA and 0.01% Triton X-100, 10 units of the restriction enzyme NotI (Takara Shuzo) was further added, and the reaction was allowed to proceed at 37° C. for 1 hour. The reaction mixture was fractionated by agarose gel electrophoresis, and about 0.3 µg of an ApaI-NotI fragment about 0.46 kb in size was recovered.

Then, 3 µg of the plasmid pKANTEX93 was added to 10 µl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was dissolved in 10 µl of 50 mM Tris-hydrochloride buffer (pH 7.5) containing 100 mM sodium chloride, 10 mM magnesium chloride, 1 mM DTT, 100 µg/ml BSA and 0.01% Triton X-100, 10 units of the restriction enzyme NotI (Takara Shuzo) was further added, and the reaction was allowed to proceed at 37° C. for 1 hour. The reaction mixture was fractionated by agarose gel electrophoresis, whereby about 1 µg of an ApaI-NotI fragment about 12.75 kb in size was recovered.

Then, 0.1 µg of the pBSH3-derived ApaI-NotI fragment and 0.1 µg of the pKANTEX93-derived ApaI-NotI fragment, each obtained as mentioned above, were added to a total of 20 µl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pKANTEX796H shown in FIG. 90 was obtained.

Then, 3 µg of the plasmid pBSL3 was added to 10 µl of 50 mM Tris-hydrochloride buffer (pH 7.5) containing 100 mM sodium chloride, 10 mM magnesium chloride, 1 mM DTT and 100 µg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 0.3 µg of an EcoRI-SplI fragment about 0.4 kb in size was recovered.

Then, 3 µg of the plasmid pKANTEX796H was added to 10 µl of 50 mM Tris-hydrochloride buffer (pH 7.5) containing 100 mM sodium chloride, 10 mM magnesium chloride, 1 mM DTT and 100 µg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 1 µg of an EcoRI-SplI fragment about 13.20 kb in size was recovered.

Then, 0.1 µg of the pBSL3-derived EcoRI-SplI fragment and 0.1 µg of the pKANTEX796H-derived EcoRI-SplI fragment, each obtained as mentioned above, were added to a total of 20 µl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pKANTEX796 shown in FIG. 91 was obtained.

(4) Expression of human anti-GM$_2$ chimera antibody by pKANTEX796

According to the procedure described in Paragraph 11 of Example 1, pKANTEX796 was introduced into YB2/0 (ATCC CRL 1581) cells and, as a result of selection by means of G418 (0.5 mg/ml) and MTX (200 nM), a cell line capable of producing about 1 to 2 µg/ml of human anti-GM$_2$ chimera antibody was obtained. It was confirmed that efficient and stable humanized antibody expression is possible using expression vector pKANTEX93.

3. Transient Humanized Antibody Expression in COS-7 (ATCC CRL 1651) Cells

For enabling more rapid activity evaluation of various versions of human CDR-transplanted anti-GM$_2$ antibody, transient expression of human anti-GM$_2$ chimera antibody expression was caused in COS-7 cells by the Lipofectamine method using pKANTEX796 and a variant thereof in the following manner.

(1) Construction of variant of pKANTEX796

Since transient antibody expression in animal cells is dependent on the copy number of an expression vector introduced, it was supposed that an expression vector smaller in size would show a higher expression efficiency. Therefore, a smaller humanized antibody expression vector, pT796, was constructed by deleting a region supposedly having no effect on humanized antibody expression from pKANTEX796 in the following manner.

Thus, 3 µg of the plasmid pKANTEX796 was added to 10 µl of 10 mM Tris-hydrochloride buffer (pH 7.5) containing 50 mM sodium chloride, 10 mM magnesium chloride and 1 mM DTT, 10 units of the restriction enzyme HindIII (Takara Shuzo) was further added, and the reaction was allowed to proceed at 37° C. for 1 hour. The reaction mixture was subjected to ethanol precipitation, the precipitate was dissolved in 10 µl of 50 mM Tris-hydrochloride buffer (pH 7.5) containing 100 mM sodium chloride, 10 mM magnesium chloride and 1 mM DTT, 10 units of the restriction enzyme MluI (Takara Shuzo) was further added, and the reaction was allowed to proceed at 37° C. for 1 hour. The reaction mixture was subjected to ethanol precipitation, and the 5' cohesive ends resulting from the restriction enzyme digestion were rendered blunt using DNA Blunting Kit (Takara Shuzo). The reaction mixture was fractionated by agarose gel electrophoresis and about 1 µg of a DNA fragment about 9.60 kb in size was recovered. A 0.1-µg portion of the thus-recovered DNA fragment was added to a total of 20 µl of sterilized water and subjected to ligation treatment using Ready-To-Go T4 DNA Ligase (Pharmacia Biotech). The thus-obtained recombinant plasmid DNA solution was used to transform *Escherichia coli* HB101, and the plasmid pT796 shown in FIG. 92 was obtained.

(2) Transient expression of human anti-GM$_2$ chimera antibody using pKANTEX796 and pT796

A 1×10$^5$ cells/ml suspension of COS-7 cells was distributed in 2-ml portions into wells of a 6-well plate (Falcon) and cultured overnight at 37° C. Two µg of pKANTEX796 or pT796 was added to 100 µl of OPTI-MEM medium (Gibco), a solution prepared by adding 10 µl of LIPOFECTAMINE reagent (Gibco) to 100 µl of OPTI-MEM medium (Gibco) was further added, and the reaction was allowed to proceed at room temperature for 40 minutes to cause DNA-liposome complex formation. The COS-7 cells cultured overnight were washed twice with 2 ml of OPTI-MEM medium (Gibco), the complex-containing solution was added, and the cells were cultured at 37° C. for 7 hours. Then, the solution was removed, 2 ml of DMEM medium (Gibco) containing 10% FCS was added to each well, and the cells were cultured at 37° C. After 24 hours, 48 hours, 72 hours, 96 hours and 120 hours of cultivation, the culture supernatant was recovered and, after concentration procedure as necessary, evaluated for human anti-GM$_2$ chimera antibody activity in the culture supernatant by the ELISA method described in Paragraph 11 of Example 1. The results are shown in FIG. 93. As shown in FIG. 93, higher levels of transient human anti-$GM_2$ chimera antibody expression was observed with pT796 as compared with pKANTEX796. For pT796, the level of expression was highest at 72 to 96 hours, the concentration being about 30 ng/ml (in terms of $GM_2$ binding activity). The above results indicate that construction of a pKANTEX93-derived vector having a reduced size and introduction thereof into COS-7 cells make it possible to make activity evaluation of expression vector-derived humanized antibodies in a transient expression system. Furthermore, for close activity comparison of various versions of human CDR-transplanted anti-$GM_2$ antibody as mentioned hereinafter, the ELISA method described below under (3) was used to determine antibody concentrations in transient expression culture supernatants.

(3) Determination by ELISA of humanized antibody concentrations in transient expression culture supernatants A solution prepared by 400-fold dilution of goat anti-human IgG (γ chain) antibody (Igaku Seibutugaku Kenkyusho) with PBS was distributed in 50-μl portions into wells of a 96-well microtiter plate and allowed to stand overnight at 4° C. for binding to the wells. After removing the antibody solution, blocking was effected with 100 μl of PBS containing 1% BSA at 37° C. for 1 hour. Fifty μl of a transient expression culture supernatant or purified human anti-$GM_2$ chimera antibody was added thereto and allowed to react at room temperature for 1 hour. Thereafter, the solution was removed, the wells were washed with PBS, and 50 μl of a solution prepared by 500-fold dilution of peroxidase-labeled mouse anti-human κ L chain antibody (Zymet) with PBS was added and allowed to react at room temperature for 1 hour. After washing with PBS, 50 μl of an ABTS substrate solution [prepared by dissolving 550 mg of 2,2'-azinobis(3-ethylbenzothiazoline-6-sulfonic acid) diammonium salt in 0.1M citrate buffer (pH 4.2) and adding, just before use, 1 μl/ml of hydrogen peroxide] was added for causing color development, and the $OD_{415}$ was measured.

4. Production of human CDR-transplanted anti-$GM_2$ antibody using humanized antibody expression vector pKANTEX93

A human CDR-transplanted anti-$GM_2$ antibody higher in $GM_2$ binding activity than the human CDR-transplanted anti-$GM_2$ antibody described in Example 2 was produced in the following manner.

(1) Modification of human CDR-transplanted anti-$GM_2$ antibody H chain variable region described in Paragraph 1 (1) of Example 2

DNAs coding for some versions of the human CDR-transplanted anti-$GM_2$ antibody H chain variable region described in Example 2 as derived by replacing several amino acids in regions other than the CDR (framework; hereinafter referred to as FR) with original mouse antibody amino acids were constructed in the following manner. Based on a computer model for the variable region of mouse KM796, those amino acid residues that were expected to contribute to restoration of antigen-binding activity as a result of mutation were selected as the amino acid residues to be mutated.

First, DNAs respectively having the base sequences of SEQ ID NO:50 and SEQ ID NO:51 were synthesized using an automatic DNA synthesize (Applied Biosystems model 380A).

Then, a version (version 2) of human CDR-transplanted antibody H chain variable region shown in SEQ ID NO:52 and having mutation in positions 78 (threonine in lieu of glutamine), 79 (alanine in lieu of phenylalanine) and 80 (tyrosine in lieu of serine) was constructed in the same manner as in Paragraph 1 (1) of Example 2 using a synthetic DNA of SEQ ID NO:50 in lieu of the synthetic DNA of SEQ ID NO:27.

Then, another version (version 4) of human CDR-transplanted antibody H chain variable region shown in SEQ ID NO:53 and having mutations in positions 27 (tyrosine in lieu of phenylalanine), 30 (threonine in lieu of serine), 40 (serine in lieu of proline) and 41 (histidine in lieu of proline) was constructed in the same manner as in Paragraph 1 (1) of Example 2 using a synthetic DNA of SEQ ID NO:51 in lieu of the synthetic DNA of SEQ ID NO:25.

(2) Construction of human CDR-transplanted anti-$GM_2$ antibody H chain variable region using known common human antibody H chain variable region According to Kabat et al. (Kabat E. A. et al., "Sequences of Proteins of Immunological Interest", US Dept. of Health and Human Services, 1991), known human antibody H chain variable regions are classifiable into subgroups I to III (HSG I to III) based on the homology of their FR regions, and common sequences have been identified for respective subgroups. Therefore, a human CDR-transplanted anti-$GM_2$ antibody H chain variable region was constructed based on those common sequences. First, for selecting common sequences to serve as the base, the homology was examined between the FR of the mouse KM796 H chain variable region and the common sequence FR of the human antibody H chain variable region of each subgroup (Table 3).

TABLE 3

Homology (%) between mouse KM796 H chain variable region FR and human antibody H chain variable region common sequence FR

| HSG I | HSG II | HSG III |
|---|---|---|
| 72.1 | 52.9 | 58.6 |

As a result, it was confirmed that subgroup I shows the greatest similarity. Thus, based on the common sequences of subgroup I, a human CDR-transplanted anti-$GM_2$ antibody H chain variable region was constructed by the PCR method in the following manner.

Synthetic DNAs respectively having the base sequences of SEQ ID NO:54 through SEQ ID NO:59 were synthesized using an automatic DNA synthesizer (Applied Systems model 380A). The DNAs synthesized were added, each to a final concentration of 0.1 μM, to 50 μl of 10 mM Tris-hydrochloride buffer (pH 8.3) containing 50 mM potassium chloride, 1.5 mM magnesium chloride, 0.00% gelatin, 200 μM dNTP, 0.5 μM M13 primer RV (Takara Shuzo), 0.5 μM M13 primer M4 (Takara Shuzo) and 2 units of TaKaRa Taq DNA polymerase, the mixture was covered with 50 μl of mineral oil, a DNA thermal cycler (Perkin Elmer model PJ480) was loaded with the mixture, and 30 PCR cycles (2 minutes at 94° C., 2 minutes at 55° C. and 2 minutes at 72° C. per cycle) were conducted. The reaction mixture was purified using QIAquick PCR Purification Kit (Qiagen) and then made into a solution in 30 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was added to 10 μl of 50 mM Tris-hydrochloride (pH 7.5) containing 100 mM sodium chloride, 10 mM magnesium chloride, 1 mM DTT, 100 μg/ml BSA and 0.0% Triton X-100, 10 units of the restriction enzyme NotI (Takara Shuzo) was further added, and the reaction was allowed to proceed at 37° C. for 1 hour. The reaction mixture was fractionated by agarose gel electrophoresis, and about 0.2 μg of an ApaI-NotI fragment about 0.44 kb in size was recovered.

Then, 3 μg of the plasmid pBSH3 obtained in Paragraph 2 (1) of Example 3 was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was added to 10 μl of 50 mM Tris-hydrochloride buffer (pH 7.5) containing 100 mM sodium chloride, 10 mM magnesium chloride, 1 mM DTT, 100 μg/ml BSA and 0.01% Triton X-100, 10 units of the restriction enzyme NotI (Takara Shuzo) was further added, and the reaction was allowed to proceed at 37° C. for 1 hour. The reaction mixture was fractionated by agrose gel electrophoresis, and about 1 μg of an ApaI-NotI fragment about 2.95 kb in size was recovered.

Then, 0.1 μg of the ApaI-NotI fragment of the human CDR-transplanted anti-GM$_2$ antibody H chain variable region and 0.1 μg of the ApaI-NotI fragment of pBSH3, each obtained as mentioned above, were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101. Plasmid DNAs were prepared from 10 transformant clones and their base sequences were determined. As a result, a plasmid, pBSH10, shown in FIG. 94 and having the desired base sequence was obtained. The amino acid sequence and base sequence of the human CDR-transplanted anti-GM$_2$ antibody H chain variable region contained in pBSH10 are shown in SEQ ID NO:60. In the amino acid sequence of the thus-constructed human CDR-transplanted anti-GM$_2$ antibody H chain variable region, the amino acids in positions 67, 72, 84 and 98 in the FR as selected based on a computer model for the variable region are those amino acids found in the mouse KM796 H chain variable region. This is for the purpose of retaining the antigenbinding capacity of mouse KM796.

(3) Modification of human CDR-transplanted anti-GM$_2$ antibody L chain variable region described in Paragraph 1 (2) of Example 2

First, a DNA having the base sequence of SEQ ID NO:61 was synthesized using an automatic DNA synthesizer (Applied Biosystems model 380A), and a human CDR-transplanted anti-GM$_2$ antibody L chain variable region cDNA with a 3' terminus capable of pairing with the restriction enzyme SplI was constructed by following the same reaction procedure as in Paragraph 1 (2) of Example 2 using the synthetic DNA in lieu of the synthetic DNA of SEQ ID NO:35.

Then, 3 μg of the plasmid pBSL3 obtained in Paragraph 2 (2) of Example 3 was added to 10 μl of 50 mM Tris-hydrochloride buffer (pH 7.5) containing 100 mM sodium chloride, 10 mM magnesium chloride, 1 mM DTT and 100 μg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 1 μg of an EcoRI-SplI fragment about 2.95 kb in size was recovered.

Then, 0.1 μg of the EcoRI-SplI fragment of the human CDR-transplanted anti-GM$_2$ antibody L chain variable region obtained as mentioned above and 0.1 μg of the above EcoRI-SplI fragment of pBSL3 were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pBSL16 shown in FIG. 95 was obtained.

Then, DNAs coding for certain versions of the human CDR-transplanted anti-GM$_2$ antibody L chain variable region contained in the above plasmid pBSL16 were constructed by replacing a certain number of amino acids in the FR with original mouse antibody amino acids by mutagenesis by means of PCR in the following manner (FIG. 96). Based on a computer model for the variable region of mouse KM796, those amino acid residues that were expected to contribute to restoration of antigen-binding activity as a result of mutation were selected as the amino acid residues to be mutated.

Antisense and sense DNA primers for introducing mutations were synthesized using an automatic DNA synthesizer (Applied Biosystems model 380A). A first PCR reaction was conducted in the same manner as in Paragraph 4 (2) of Example 3 using a final concentration each of 0.5 μM of M13 primer RV (Takara Shuzo) and the antisense DNA primer and of M13 primer M4 (Takara Shuzo) and the sense DNA primer, with 1 ng of pBSL16 as the template. Each reaction mixture was purified using QIAquick PCR Purification Kit (Qiagen) with elution with 20 μl of 10 mM Tris-hydrochloride (pH 8.0). Using 5 μl of each eluate, a second PCR reaction was conducted in the same manner as in Paragraph 4 (2) of Example 3. The reaction mixture was purified using QIAaquick PCR Purification Kit (Qiagen) and then made into a solution in 30 μl of 50 mM Tris-hydrochloride buffer (pH 7.5) containing 100 mM sodium chloride, 10 mM magnesium chloride, 1 mM DTT and 100 μg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 0.2 μg of an EcoRI-SplI fragment (about 0.39 kb) of each mutant version of the human CDR-transplanted anti-GM$_2$ antibody L chain variable region was recovered.

Then, 0.1 μg of the above EcoRI-SplI fragment of each mutant version of the human CDR-transplanted anti-GM$_2$ antibody L chain variable region and 0.1 μg of the EcoRI-SplI fragment of pBSL3 were added to a total of 20 μl of sterilized water and ligated to each other using Ready-To-Go T4 DNA ligase (Pharmacia Biotech). The thus-obtained recombinant plasmid DNA solution was used to transform *Escherichia coli* HB101, and a plasmid DNA was prepared from a transformant clone, and the base sequence of said plasmid was determined. In this way, plasmids respectively containing a base sequence having a desired mutation or mutations were obtained.

Thus, a plasmid, pBSLV1, containing version 1, shown in SEQ ID NO:64, of the human CDR-transplanted anti-GM$_2$ antibody L chain variable region was obtained following the above procedure using the synthetic DNA of SEQ ID NO:62 as the mutant antisense primer and the synthetic DNA of SEQ ID NO:63 as the mutant sense primer. In the amino acid sequence of the version 1 human CDR-transplanted anti-GM$_2$ antibody L chain variable region, the amino acid in position 15 in the FR is that amino acid found in the mouse KM796 L chain variable region. This is for the purpose of retaining the antigen-binding capacity of mouse KM796.

A plasmid, pBSLV2, containing version 2, shown in SEQ ID NO:67, of the human CDR-transplanted anti-GM$_2$ antibody L chain variable region was obtained following the above procedure using the synthetic DNA of SEQ ID NO:65 as the mutant antisense primer and the synthetic DNA of SEQ ID NO:66 as the mutant sense primer. In the amino acid sequence of the version 2 human CDR-transplanted anti-GM$_2$ antibody L chain variable region, the amino acid in positions 46 in the FR is that amino acid found in the mouse KM796 L chain variable region. This is for the purpose of retaining the antigen-binding capacity of mouse KM796.

A plasmid, pBSLV3, containing version 3, shown in SEQ ID NO:70, of the human CDR-transplanted anti-GM$_2$ antibody L chain variable region was obtained following the above procedure using the synthetic DNA of SEQ ID NO:68 as the mutant antisense primer and the synthetic DNA of SEQ ID NO:69 as the mutant sense primer. In the amino acid sequence of the version 3 human CDR-transplanted anti-GM$_2$ antibody L chain variable region, the amino acids in position 79 and 82 in the FR are those amino acids found in the mouse KM796 L chain variable region. This is for the purpose of retaining the antigen-binding capacity of mouse KM796.

Then, a plasmid, pBSLV1+2, containing a human CDR-transplanted anti-GM$_2$ antibody L chain variable region having both the version 1 and version 2 mutations was constructed in the following manner.

Three μg of the plasmid pBSLV1 obtained as mentioned above was added to 10 μl of 10 mM Tris-hydrochloride buffer (pH 7.5) containing 50 mM sodium chloride, 10 mM magnesium chloride and 1 mM DTT, 10 units each of the restriction enzymes EcoRI (Takara Shuzo) and HindIII (Takara Shuzo) were further added, and the reaction was allowed to proceed at 37° C. for 1 hour. The reaction mixture was fractionated by agarose gel electrophoresis, and about 0.2 μg of an EcoRI-HindIII fragment about 0.20 kb in size was recovered.

Then, 3 μg of the plasmid pBSLV2 obtained as mentioned above was added to 10 μl of 10 mM Tris-hydrochloride buffer (pH 7.5) containing 50 mM sodium chloride, 10 mM magnesium chloride and 1 mM DTT, 10 units each of the restriction enzymes EcoRI (Takara Shuzo) and HindIII (Takara Shuzo) were further added, and the reaction was allowed to proceed at 37° C. for 1 hour. The reaction mixture was fractionated by agarose gel electrophoresis, and about 1 μg of an EcoRI-HindIII fragment about 3.2 kb in size was recovered.

Then, 0.1 μg of the EcoRI-HindIII fragment of pBSLV1 and 0.1 μg of the EcoRI-HindIII fragment of pBSLV2, each obtained as mentioned above, were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pBSLV1+2 shown in FIG. 97 was obtained.

Then, the PCR reaction procedure mentioned above was followed using 1 ng of the plasmid pBSLV1+2 obtained as mentioned above as the template, a synthetic DNA having the base sequence of SEQ ID NO:71 as the mutant antisense primer and a synthetic DNA having the base sequence of SEQ ID NO:72 as the mutant sense primer, whereby a plasmid, pBSLV4, containing a version 4 human CDR-transplanted anti-GM$_2$ antibody L chain variable region set forth in SEQ ID NO:73 was obtained. In the amino acid sequence of the version 4 human CDR-transplanted anti-GM$_2$ antibody L chain variable region, the amino acids in positions 15, 46, 69, 70 and 71 in the FR are those amino acids that are found in the mouse KM796 L chain variable region. This is for the purpose of retaining the antigen-binding capacity of mouse KM796.

Then, the PCR reaction procedure mentioned above was followed using 1 ng of the plasmid pBSLV1+2 obtained as mentioned above as the template, a synthetic DNA having the base sequence of SEQ ID NO:74 as the mutant antisense primer and a synthetic DNA having the base sequence of SEQ ID NO:75 as the mutant sense primer, whereby a plasmid, pBSLV8, containing a version 8 human CDR-transplanted anti-GM$_2$ antibody L chain variable region set forth in SEQ ID NO:76 was obtained. In the amino acid sequence of the version 8 human CDR-transplanted anti-GM$_2$ antibody L chain variable region, the amino acids in positions 15, 46, 69, 70, 71, 76, 77 and 78 in the FR are those amino acids that are found in the mouse KM796 L chain variable region. This is for the purpose of retaining the antigen-binding capacity of mouse KM796.

Then, the PCR reaction procedure mentioned above was followed using 1 ng of the plasmid pBSLV4 obtained as mentioned above as the template, a synthetic DNA having the base sequence of SEQ ID NO:77 as the mutant antisense primer and a synthetic DNA having the base sequence of SEQ ID NO:78 as the mutant sense primer, whereby a plasmid, pBSLm-2, containing a version Lm-2 human CDR-transplanted anti-GM$_2$ antibody L chain variable region set forth in SEQ ID NO:79 was obtained. In the amino acid sequence of the version Lm-2 human CDR-transplanted anti-GM$_2$ antibody L chain variable region, the amino acids in positions 15, 35, 46, 69, 70 and 71 in the FR are those amino acids that are found in the mouse KM796 L chain variable region. This is for the purpose of retaining the antigen-binding capacity of mouse KM796.

Then, the PCR reaction procedure mentioned above was followed using 1 ng of the plasmid pBSLV4 obtained as mentioned above as the template, a synthetic DNA having the base sequence of SEQ ID NO:80 as the mutant antisense primer and a synthetic DNA having the base sequence of SEQ ID NO:81 as the mutant sense primer, whereby a plasmid, pBSLm-8, containing a version Lm-8 human CDR-transplanted anti-GM$_2$ antibody L chain variable region set forth in SEQ ID NO:82 was obtained. In the amino acid sequence of the version Lm-8 human CDR-transplanted anti-GM$_2$ antibody L chain variable region, the amino acids in positions 15, 46, 69, 70, 71, 72 and 77 in the FR are those amino acids that are found in the mouse KM796 L chain variable region. This is for the purpose of retaining the antigen-binding capacity of mouse KM796.

Then, a plasmid, pBSLm-28, containing a human CDR-transplanted anti-GM$_2$ antibody L chain variable region having both the version Lm-2 and version Lm-8 mutations was constructed in the following manner.

Three μg of the plasmid pBSLm-2 obtained as mentioned above was added to 10 μl of 50 mM Tris-hydrochloride buffer (pH 7.5) containing 100 mM sodium chloride, 10 mM magnesium chloride and 1 mM DTT, 10 units of the restriction enzyme EcoRI (Takara Shuzo) was further added, and the reaction was allowed to proceed at 37° C. for 1 hour. The reaction mixture was subjected to ethanol precipitation, the precipitate was added to 10 μl of 10 mM Tris-hydrochloride buffer (pH 7.5) containing 50 mM sodium chloride, 10 mM magnesium chloride, 1 mM DTT and 100 μg/ml BSA, 10 units of the restriction enzyme XbaI (Takara Shuzo) was further added, and the reaction as allowed to proceed at 37° C. for 1 hour. The reaction mixture was fractionated by agarose gel electrophoresis, and about 0.2 μg of an EcoRI-XbaI fragment about 0.24 kb in size was recovered.

Then, 3 μg of the plasmid pBSLm-8 obtained as mentioned above was added to 10 μl of 50 mM Tris-hydrochloride buffer (pH 7.5) containing 100 mM sodium chloride, 10 mM magnesium chloride and 1 mM DTT, 10 units of the restriction enzyme EcoRI (Takara Shuzo) was further added, and the reaction was allowed to proceed at 37° C. for 1 hour. The reaction mixture was subjected to ethanol precipitation, the precipitate was added to 10 µl of 10 mM Tris-hydrochloride buffer (pH 7.5) containing 50 mM sodium chloride, 10 mM magnesium chloride, 1 mM DTT and 100 µg/ml BSA, 10 units of the restriction enzyme XbaI (Takara Shuzo) was further added, and the reaction was allowed to proceed at 37° C. for 1 hour. The reaction mixture was fractionated by agarose gel electrophoresis, and about 1 µg of an EcoRI-XbaI fragment about 3.16 kb in size was recovered.

Then, 0.1 µg of the EcoRI-XbaI fragment of pBSLm-2 and 0.1 µg of the EcoRI-XbaI fragment of pBSLm-8, each obtained as mentioned above, were added to a total of 20 µl of sterilized water and ligated to each other using Ready-To-go T4 DNA Ligase (Pharmacia Biotech). The thus-obtained recombinant plasmid DNA solution was used to transform *Escherichia coli* HB101, and the plasmid pBSLm-28 shown in FIG. 98 was obtained. The version Lm-28 human CDR-transplanted anti-GM$_2$ antibody L chain variable region contained in the plasmid pBSLm-28 is shown in SEQ ID NO:83. In the amino acid sequence of the version Lm-28 human CDR-transplanted anti-GM$_2$ antibody L chain variable region thus constructed, the amino acids in positions 15, 35, 46, 69, 70, 71, 72 and 77 are those amino acids that are found in the mouse KM796 L chain variable region. This is for the intended purpose of retaining the antigen-binding capacity of mouse KM796.

(4) Construction of human CDR-transplanted anti-GM$_2$ antibody L chain variable region using known common human antibody L chain variable region According to Kabat et al. (Kabat E. A. et al., "Sequences of Proteins of Immunological Interest", US Dept. of Health and Human Services, 1991), known human antibody L chain variable regions are classifiable into subgroups I to IV based on the homology of their FR regions, and common sequences have been identified for respective subgroups. Therefore, a human CDR-transplanted anti-GM$_2$ antibody L chain variable region was constructed based on those common sequences. First, for selecting common sequences to serve as the base, the homology was examined between the FR of the mouse KM796 L chain variable region and the common sequence FR of the human antibody L chain variable region of each subgroup (Table 4).

TABLE 4

Homology (%) between mouse KM796 L chain variable region FR and human antibody L chain variable region common sequence FR

| HSG I | HSG II | HSG III | HSG IV |
|---|---|---|---|
| 70.0 | 65.0 | 68.8 | 67.5 |

As a result, it was confirmed that subgroup I shows the greatest similarity. Thus based on the common sequence of subgroup I, a human CDR-transplanted anti-GM$_2$ antibody L chain variable region was constructed by the PCR method in the following manner.

Synthetic DNAs respectively having the base sequences of SEQ ID NO:84 through SEQ ID NO:89 were synthesized using an automatic DNA synthesizer (Applied Systems model 380A). The DNAs synthesized were added, each to a final concentration of 0.1 µM, to 50 µl of 10 mM Tris-hydrochloride buffer (pH 8.3) containing 50 mM potassium chloride, 1.5 mM magnesium chloride, 0.001% gelatin, 200 µM dNTP, 0.5 µM M13 primer RV (Takara Shuzo), 0.5 µM M13 primer M4 (Takara Shuzo) and 2 units of TaKaRa Taq DNA polymerase. The mixture was covered with 50 µl of mineral oil, a DNA thermal cycler (Perkin Elmer model PJ480) was loaded with the mixture, and 30 PCR cycles (2 minutes at 94° C., 2 minutes at 55° C. and 2 minutes at 72° C. per cycle) were conducted. The reaction mixture was purified using QIAquick PCR Purification Kit (Qiagen) and then made into a solution in 30 µl of 50 mM Tris-hydrochloride buffer (pH 7.5) containing 100 mM sodium chloride, 10 mM magnesium chloride, 1 mM DTT and 100 µg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electro-phoresis, and about 0.2 µg of an EcoRI-SplI fragment about 0.39 kb in size was recovered.

Then, 0.1 µg of the above EcoRI-SplI fragment of the human CDR-transplanted anti-GM$_2$ antibody L chain variable region and 0.1 µg of the EcoRI-SplI fragment of pBSL3 were added to a total of 20 µl of sterilized water and ligated to each other using Ready-To-Go T4 DNA Ligase (Pharmacia Biotech). The thus-obtained recombinant plasmid DNA solution was used to transform *Escherichia coli* HB101. Plasmid DNAs were prepared from 10 transformant clones and their base sequences were determined. As a result, a plasmid, PBSHSGL, shown in FIG. 99 and having the desired base sequence was obtained. The amino acid sequence and base sequence of the human CDR-transplanted anti-GM$_2$ antibody L chain variable region contained in pBSHSGL are shown in SEQ ID NO:90. In the amino acid sequence of the thus-constructed human CDR-transplanted anti-GM$_2$ antibody L chain variable region, the amino acids in positions 4, 11, 15, 35, 42, 46, 69, 70, 71, 77 and 103 in the FR as selected based on a computer model for the variable region are those amino acids found in the mouse KM796 L chain variable region. This is for the intended purpose of retaining the antigen-binding capacity of mouse MK796.

(5) Activity evaluation of mutant versions of human CDR-transplanted anti-GM$_2$ antibody in terms of transient expression Various mutant version human CDR-transplanted anti-GM$_2$ antibodies composed of the human CDR-transplanted anti-GM$_2$ antibody H chain and L chain variable regions constructed in Paragraphs (1) through (4) of Example 3 and having varying mutations were evaluated for activity in terms of transient expression in the following manner.

First, for evaluating the human CDR-transplanted anti-GM$_2$ antibody H chain variable regions having varying mutations, expression vectors, pT796HCDRHV2, pT796HCDRHV4 and pT796HCDRH10, were constructed by replacing the mouse H chain variable region of the human anti-GM$_2$ chimera antibody transient expression vector pT796 obtained in Paragraph 3 (1) of Example 3 with the human CDR-transplanted anti-GM$_2$ antibody H chain variable regions having varying mutations, in the following manner. For comparison, an expression vector, pT796HCDR was constructed by replacing the mouse H chain variable region of pT796 with the human CDR-transplanted anti-GM$_2$ antibody H chain variable region obtained in Paragraph 1 (1) of Example 1.

Three µg of the plasmid pT796 was added to 10 µl of 50 mM Tris-hydrochloride buffer (pH 7.5) containing 100 mM sodium chloride, 10 mM magnesium chloride, lmM DTT and 100 µg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 1 μg of an EcoRI-SplI fragment about 9.20 kb in size was recovered.

Then, 3 μg of the plasmid pBSL16 obtained in Paragraph 4 (3) of Example 3 was added to 10 μl of 50 mM Tris-hydrochloride buffer (pH 7.5) containing 100 mM sodium chloride, 10 mM magnesium chloride, 1 mM DTT and 100 μg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 0.3 μg of an EcoRI-SplI fragment about 0.39 kb in size was recovered.

Then, 0.1 μg of the EcoRI-SplI fragment of pT796 and 0.1 μg of the EcoRI-SplI fragment of pBSL16, each obtained as mentioned above, were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pT796LCDR shown in FIG. 100 was obtained.

Then, 3 μg of the above plasmid pT796LCDR was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the reaction was allowed to proceed at 37° C. for 1 hour. The reaction mixture was subjected to ethanol precipitation, the precipitate was added to 10 μl of 50 mM Tris-hydrochloride buffer (pH 7.5) containing 100 mM sodium chloride, 10 mM magnesium chloride, 1 mM DTT, 100 μg/ml BSA and 0.01% Triton X-100, 10 units of the restriction enzyme NotI (Takara Shuzo) was further added, and the reaction was allowed to proceed at 37° C. for 1 hour. The reaction mixture was fractionated by agarose gel electrophoresis, and about 1 μg of an ApaI-NotI fragment about 9.11 kb in size was recovered.

Then, 0.1 μg of the human CDR-transplanted anti-GM$_2$ antibody H chain variable region obtained in Paragraph 1 (1) of Example 2 or the mutant version 2 or 4 human CDR-transplanted anti-GM$_2$ antibody H chain variable region obtained in Paragraph 4 (1) of Example 3 and 0.1 μg of the ApaI-NotI fragment of pT796LCDR were added to a total of 20 μl of sterilized water and ligated to each other using Ready-To-Go T4 DNA Ligase (Pharmacia Biotech). Each recombinant plasmid DNA solution thus obtained was used to transform *Escherichia coli* HB101. The plasmids pT796HLCDR, pT796HLCDRHV2 and pT796HLCDRHV4 shown in FIG. 101 were obtained.

Then, 3 μg of the plasmid pBSH10 obtained in Paragraph 4 (2) of Example 3 was added to 10 μl of 10 mM Tris-hydrochloride buffer (pH 7.5) containing 10 mM magnesium chloride and 1 mM DTT, 10 units of the restriction enzyme ApaI (Takara Shuzo) was further added, and the restriction was allowed to proceed at 37° C. for 1 hour. The reaction mixture was subjected to ethanol precipitation, the precipitate was added to 10 μl of 50 mM Tris-hydrochloride buffer (pH 7.5) containing 100 mM sodium chloride, 10 mM magnesium chloride, 1 mM DTT, 100 μg/ml BSA and 0.01% Triton X-100, 10 units of the restriction enzyme NotI (Takara Shuzo) was further added, and the reaction was allowed to proceed at 37° C. for 1 hour. The reaction mixture was fractionated by agarose gel electrophoresis, and about 0.3 μg of an ApaI-NotI fragment about 0.44 kb in size was recovered.

Then, 0.1 μg of the ApaI-NotI fragment of pBSM10 and 0.1 μg of the ApaI-NotI fragment of pT796LCDR were added to a total of 20 μl of sterilized water and ligated to each other using Ready-To-Go T4 DNA Ligase (Pharmacia Biotech). The thus-obtained recombinant plasmid DNA solution was used to transform *Escherichia coli* HB101, and the plasmid pT796HLCDRH10 shown in FIG. 102 was obtained.

Then, 3 μg each of the plasmids pT796HLCDR, pT796HLCDRHV2, pT796HLCDRHV4 and pT796HLCDRH10 were respectively added to 10 μl of 50 mM Tris-hydrochloride buffer (pH 7.5) containing 100 mM sodium chloride, 10 mM magnesium chloride, 1 mM DTT and 100 μg/ml BSA, 10 units each of the restriction enzymes EcoRI (Takara Shuzo) and SplI (Takara Shuzo) were further added, and the reaction was allowed to proceed at 37° C. for 1 hour. Each reaction mixture was fractionated by agarose gel electrophoresis, and about 1 μg of an EcoRI-SplI fragment about 9.15 kb in size was recovered.

Then, 5 μg of the plasmid pBSL3 obtained in Paragraph 2 (2) of Example 3 was added to 10 μl of 50 mM Tris-hydrochloride buffer (pH 7.5) containing 100 mM sodium chloride, 10 mM magnesium chloride, 1 mM DTT and 100 μg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 0.4 μg of an EcoRI-SplI fragment about 0.39 kb in size was recovered.

Then, 0.1 μg of the EcoRI-SplI fragment of each of pT796HLCDR, pT796HLCDRHV2, pT796HLCDRHV4 and pT796HLCDRH10 and 0.1 μg of the EcoRI-SplI fragment of pBSL3 were added to a total of 20 μl of sterilized water and ligated to each other using Ready-To-Go DNA Ligase (Pharmacia Biotech). Each recombinant plasmid DNA solution thus obtained was used to transform *Escherichia coli* HB101. In this way, the plasmids pT796HCDR, pT796HCDRHV2, pT796HCDRHV4 and pT796HCDRH10 shown in FIG. 103 were obtained.

Then, 2 μg each of the plasmids pT796HCDR, pT796HCDRHV2, pT796HCDRHV4 and pT796HCDRH10 thus obtained were used for transient human CDR-transplanted anti-GM$_2$ antibody expression and for culture supernatant human CDR-transplanted anti-GM$_2$ antibody activity evaluation by the procedures described in Paragraph 3 (2) and (3) of Example 3, respectively. After introduction of each plasmid, the culture supernatant was recovered at 72 hours, and the GM$_2$-binding activity and antibody concentration in the culture supernatant were determined by ELISA and the relative activity was calculated with the activity of the positive control chimera antibody taken as 100%. The results are shown in FIG. 104.

The results revealed that the amino acid mutations alone in mutant versions 2 and 4 have little influence on the restoration of the antigen-binding activity of the human CDR-transplanted anti-GM$_2$ antibody but that the use of the pBSH10-derived human CDR-transplanted antibody H chain variable region constructed based on the known human antibody H chain variable region common sequence, contributes to the restoration of the antigen-binding activity.

In view of the above results, the human CDR-transplanted anti-GM$_2$ antibody H chain variable region constructed based on the known human antibody H chain variable region common sequence as shown in SEQ ID NO:60 was selected as a novel human CDR-transplanted anti-GM$_2$ antibody H chain variable region.

Then, for evaluating the human CDR-transplanted anti-GM$_2$ antibody L chain variable regions having varying variations, expression vectors, pT796HLCDRLV1, pT796HLCDRLV2, pT796HLCDRLV3, pT796HLCDRLV4, pT796HLCDRLV8, pT796HLCDRLm-2, pT796HLCDRLm-8, pT796HLCDRLm-28 and pT796HLCDRHSGL, were constructed in the following manner by replacing the mouse L chain variable region of the vector pT796HCDRH10 for transient human CDR-transplanted anti-GM$_2$ antibody expression obtained as mentioned above with the human CDR-transplanted anti-GM$_2$ antibody L chain variable regions having varying mutations.

Thus, 3 μg of the plasmid pT796HCDRH10 was added to 10 μl of 50 mM Tris-hydrochloride buffer (pH 7.5) containing 100 mM sodium chloride, 10 mM magnesium chloride, 1 mM DTT and 100 μg/ml BSA, 10 units each of the restriction enzymes EcoRI (Takara Shuzo) and SplI (Takara Shuzo) were further added, and the reaction was allowed to proceed at 37° C. for 1 hour. The reaction mixture was fractionated by agarose gel electrophoresis, and about 1 μg of an EcoRI-SplI fragment about 9.15 kb in size was recovered.

Then, 3 μg of the plasmid pBSLV1, pBSLV2, pBSLV3, pBSLV4, pBSLV8, pBSLm-2, pBSLm-8, pBSLm-28 or PBSHSGL obtained in Paragraph (3) or (4) of Example 3 was added to 10 μl of 50 mM Tris-hydrochloride buffer (pH 7.5) containing 100 mM sodium chloride, 10 mM magnesium chloride, 1 mM DTT and 100 μg/ml BSA, 10 units each of the restriction enzymes EcoRI (Takara Shuzo) and SplI (Takara Shuzo) were further added, and the reaction was allowed to proceed at 37° C. for 1 hour. Each reaction mixture was fractionated by agarose gel electrophoresis, and about 0.3 μg of an EcoRI-SplI fragment about 0.39 kb in size was recovered.

Then, 0.1 μg of the EcoRI-SplI fragment of the pT796HCDRH10 and 0.1 μg of the EcoRI-SplI fragment of each mutant version human CDR-transplanted anti-GM$_2$ antibody L chain variable region were added to a total of 20 μl of sterilized water and ligated to each other using Ready-To-Go T4 DNA Ligase (Pharmacia Biotech). Each recombinant plasmid DNA solution thus obtained was used to transform *Escherichia coli* HB101. In this way, the plasmids pT796HLCDRLV1, pT796HLCDRLV2, pT796HLCDRLV3, pT796HLCDRLV4, pT796HLCDRLV8, pT796HLCDRLm-2, pT796HLCDRLm-8, pT796HLCDRLm-28 and pT796HLCDRHSGL were obtained as shown in FIG. 105.

Then, 2 μg each of the thus-obtained plasmids pT796HLCDRLV1, pT796HLCDRLV2, pT796HLCDRLV3, pT796HLCDRLV4, pT796HLCDRLV8, pT796HLCDRLm-2, pT796HLCDRLm-8, pT796HLCDRLm-28 and pT796HLCDRHSGL and of the plasmid pT796HLCDR described in Example 2 and capable of expressing human CDR-transplanted anti-GM$_2$ antibody were used for transient human CDR-transplanted anti-GM$_2$ antibody expression and for culture supernatant human CDR-transplanted anti-GM$_2$ antibody activity evaluation by the procedures described in Paragraph 3 (2) and (3) of Example 3, respectively. After introduction of each plasmid, the culture supernatant was recovered at 72 hours, and the GM$_2$-binding activity and antibody concentration in the culture supernatant were determined by ELISA and the relative activity was calculated with the activity of the positive control chimera antibody taken as 100%. The results are shown in FIG. 106.

The results revealed that the amino acid mutations alone in mutant versions 1, 2, 3, 4 and 8 have little influence on the restoration of the antigen-binding activity of the human CDR-transplanted anti-GM$_2$ antibody but that the amino acid mutations in mutant versions Lm-2 and Lm-8 contributes to the restoration of the antigen-binding activity. Furthermore, version Lm-28 having both the amino acid mutations of Lm-2 and Lm-8 showed a high level of antigen-biding activity almost comparable to that of the chimera antibody, revealing that those amino acids mutated in producing Lm-28 were very important from the antigen-binding activity viewpoint.

In view of the above results, the version Lm-28 human CDR-transplanted anti-GM$_2$ antibody L chain variable region shown in SEQ ID NO:83 was selected as a first novel human CDR-transplanted anti-GM$_2$ antibody L chain variable region.

It was further revealed that the antigen-binding activity can be restored when the pBSHSGL-derived human CDR-transplanted anti-GM$_2$ antibody L chain variable region, namely the human CDR-transplanted anti-GM$_2$ antibody L chain variable region constructed based on the known human antibody L chain variable region common sequence, is used.

In view of the above result, the human CDR-transplanted anti-GM$_2$ antibody L chain variable region constructed based on the known human antibody L chain variable region common sequence as set forth in SEQ ID NO:90 was selected as a second novel human CDR-transplanted anti-GM$_2$ antibody L chain variable region.

It is to be noted that in those human CDR-transplanted anti-GM$_2$ antibody L chain variable regions that showed high binding activity against GM$_2$, certain amino acid residues which cannot be specified by deduction from known human CDR-transplanted antibody production examples have been replaced with amino acids found in the mouse L chain variable region. Thus, obviously, it was very important, in human CDR-transplanted anti-GM$_2$ antibody production, to identify these amino acid residues.

Furthermore, the fact that the human CDR-transplanted anti-GM$_2$ antibodies having those human CDR-transplanted anti-GM$_2$ antibody H chain and L chain variable regions based on the known human antibody variable region common sequences showed high antigen binding activity is proof of the usefulness of the present process in human CDR-transplanted antibody production.

(6) Acquisition of cell lines for stable production of human CDR-transplanted anti-GM$_2$ antibodies Based on the results of Paragraph 4 (5) of Example 3, two cell lines, KM8966 and KM8967, capable of stably expressing KM8966, which has the amino acid sequence set forth in SEQ ID NO:60 as the H chain variable region and the amino acid sequence set forth in SEQ ID NO:83 as the L chain variable region, and KM8967, which has the amino acid sequence set forth in SEQ ID NO:60 as the H chain variable region and the amino acid sequence set forth in SEQ ID NO:90 as the L chain variable region, respectively as human CDR-transplanted anti-GM$_2$ antibodies having higher antigen-binding activity than the human CDR-transplanted anti-GM$_2$ antibody described in Example 2 were obtained in the following manner.

Three μg each of the plasmids pT796HLCDRLm-28 and pT796HLCDRHSGL obtained in Paragraph 4 (5) of Example 3 were respectively added to 10 μl of 20 mM Tris-hydrochloride buffer (pH 8.5) containing 100 mM potassium chloride, 10 mM magnesium chloride and 1 mM DTT, 10 units of the restriction enzyme BamHI (Takara Shuzo) was further added, and the reaction was allowed to proceed at 37° C. for 1 hour. Each reaction mixture was subjected to ethanol precipitation, the precipitate was added to 10 μl of 50 mM Tris-hydrochloride buffer (pH 7.5)

containing 100 mM sodium chloride, 10 mM magnesium chloride and 1 mM DTT, 10 units of the restriction enzyme XhoI (Takara Shuzo) was further added, and the reaction was allowed to proceed at 37° C. for 1 hour. Each reaction mixture was fractionated by agarose gel electrophoresis, and about 1 μg of a BamHI-XhoI fragment about 4.93 kb in size was recovered.

Then, 3 μg of the plasmid pKANTEX93 obtained in Paragraph 1 of Example 3 was added to 10 μl of 20 mM Tris-hydrochloride buffer (pH 8.5) containing 100 mM potassium chloride, 10 mM magnesium chloride and 1 mM DTT, 10 units of the restriction enzyme BamHI (Takara Shuzo) was further added, and the reaction was allowed to proceed at 37° C. for 1 hour. The reaction mixture was subjected to ethanol precipitation, the precipitate was added to 10 μl of 50 mM Tris-hydrochloride buffer (pH 7.5) containing 100 mM sodium chloride, 10 mM magnesium chloride and 1 mM DTT, 10 units of the restriction enzyme XhoI (Takara Shuzo) was further added, and the reaction was allowed to proceed at 37° C. for 1 hour. The reaction mixture was fractionated by agarose gel electrophoresis, and about 1 μg of a BamHI-XhoI fragment about 8.68 kb in size was recovered.

Then, 0.1 μg of the BamHI-XhoI fragment of pT796HLCDRLm-28 or pT796HLCDRHSGL and 0.1 μg of the BamHI-XhoI fragment of pKANTEX93, each obtained as mentioned above, were added to a total of 20 μl of sterilized water and ligated to each other using Ready-To-Go T4 DNA Ligase (Pharmacia Biotech). Each recombinant plasmid DNA solution thus obtained was used to transform *Escherichia coli* HB101. In this way, the plasmids pKANTEX796HLCDRLm-28 and pKANTEX796HLCDRHSGL shown in FIG. 107 were obtained.

Then, 4 μg each of the above plasmids pKANTEX796HLCDRLm-28 and pKANTEX796HLCDRHSGL were respectively used to transform YB2/0 (ATCC CRL 1581) cells according to the procedure described in Paragraph 1 of Example 1 and, after final selection using G418 (0.5 mg/ml) and MTX (200 nM), a transformant cell line, KM8966, capable of producing about 40 μg/ml of KM8966, i.e. the pKANTEX796HLCDRLm-28-derived human CDR-transplanted anti-$GM_2$ antibody, and a transformant cell line, KM8967, capable of producing about 30 μg/ml of KM8966, i.e. the pKANTEX796HLCDRHSGL-derived human CDR-transplanted anti-$GM_2$ antibody, were obtained.

(7) Purification of human CDR-transplanted anti-$GM_2$ antibodies KM8966 and KM8967

The transformant cell lines KM8966 and 8967 obtained in Paragraph 4 (6) of Example 3 were respectively suspended in GIT medium (Nippon Pharmaceutical) containing 0.5 mg/ml G418 and 200 nM MTX and, according to the procedure of Paragraph 11 of Example 1, 18 mg of purified human CDR-transplanted anti-$GM_2$ antibody KM8966 and 12 mg of purified KM8967 were obtained each from about 0.5 liter of culture fluid. Three μg each of the purified human CDR-transplanted anti-$GM_2$ antibodies obtained and the human anti-$GM_2$ chimera antibody KM966 were subjected to electrophoresis by the known method [Laemli, Nature, 227, 680 (1979)] for molecular weight determination. The results are shown in FIG. 108. As shown, under reducing conditions, both antibody H chains showed a molecular weight of about 50 kilodaltons and both antibody L chains showed a molecular weight of about 25 kilodaltons. Expression of H and L chains of correct molecular weights was thus confirmed. Under non-reducing conditions, both human CDR-transplanted anti-$GM_2$ antibodies showed a molecular weight of about 150 kilodaltons and it was thus confirmed that antibodies each composed of two H chains and two L chains and having a correct size had been expressed. Furthermore, the H and L chains of each human CDR-transplanted anti-$GM_2$ antibody were analyzed for N-terminal amino acid sequence by automatic Edman degradation using a protein sequencer (Applied Biosystems model 470A), whereby an amino acid sequence deducible from the base sequence of the variable region DNA constructed was revealed.

5. In vitro reactivity of human CDR-transplanted anti-$GM_2$ antibodies KM8966 and KM8967 against $GM_2$ The human anti-$GM_2$ chimera antibody KM966 and the purified human CDR-transplanted anti-$GM_2$ antibodies KM8966 and KM8967 were tested for reactivity against $GM_2$ by ELISA as described in Paragraph 11 of Example 1. The results are shown in FIG. 109. $GM_2$ (N-acetyl-$GM_2$) used was purified from cultured cell line HPB-ALL [Oboshi et al., Tanpakushitsu, Kakusan & Koso (Protein, Nucleic acid & Enzyme), 23, 697 (1978) ] in accordance with the known method [J. Biol. Chem., 263, 10915 (1988)]. As shown, it was found that the purified human CDR-transplanted anti-$GM_2$ antibody KM8966 exerted the binding activity comparable to that of the human anti-$GM_2$ chimera antibody KM966. On the other hand, the binding activity of purified human CDR-transplanted anti-$GM_2$ antibody KM8967 was about ¼ to ⅕ of that of the human anti-$GM_2$ chimera antibody KM966.

6. Reaction specificity of human CDR-transplanted anti-$GM_2$ antibodies KM8966 and KM8967

The human anti-$GM_2$ chimera antibody KM966 and the human CDR-transplanted anti-$GM_2$ antibodies KM8966 and KM8967 were tested for reactivity against the gangliosides $GM_1$, N-acetyl-$GM_2$, N-glycolyl-$GM_2$, N-acetyl-$GM_3$, N-glycolyl-$GM_3$, $GD_{1a}$, $GD_{1b}$ (Iatron), $GD_2$, $GD_3$ (Iatron) and $GQ_{1b}$ (Iatron) by ELISA as described in Paragraph 11 of Example 1. The results are shown in FIG. 110. $GM_1$ and $GD_{1a}$ were purified from bovine brain, N-acetyl-$GM_2$ from cultured cell line HPB-ALL [Oboshi et al., Tanpakushitsu, Kakusan & Koso (Protein, Nucleic acid & Enzyme), 23, 697 (1978)], N-glycolyl-$GM_2$ and N-glycolyl-$GM_3$ from mouse liver, N-acetyl-$GM_3$ canine erythrocytes, and $GD_2$ from cultured cell line IMR32 (ATCC CCL127), respectively by the per se known method [J. Biol. Chem., 263, 10915 (1988)]. Each antibody was used in a concentration of 10 μg/ml.

As shown in FIG. 110, it was confirmed that the human CDR-transplanted anti-$GM_2$ antibodies KM8966 and KM8967 react specifically with $GM_2$ (N-acetyl-$GM_2$ and N-glycolyl-$GM_2$) like the human anti-$GM_2$ chimera antibody KM966.

7. Reactivity of human CDR-transplanted anti-$GM_2$ antibodies KM8966 and KM8967 against cancer cells The human lung small cell carcinoma culture cell line SBC-3 (JCRB 0818) (1×10⁶ cells) was suspended in PBS, the suspension was placed in a microtube (TREF) and centrifuged (1200 rpm, 2 minutes). To the thus-washed cells was added 50 μl (50 μg/ml) of the human anti-$GM_2$ chimera antibody KM966 or the purified human CDR-transplanted anti-$GM_2$ antibody KM8966 or KM8967, followed by stirring and 1 hour of standing at 4° C. After the above reaction step, the cells were washed three times with PBS, each time followed by centrifugation. Then, 20 μl of fluorescein isocyanate-labeled protein A (30-fold dilution, Boehringer Mannheim) was added and, after stirring, the reaction was allowed to proceed at 4° C. for 1 hour. Thereafter, the cells were washed three times with PBS, each time followed by centrifugation, then further suspended in PBS and subjected to analysis using a flow cytometer, EPICS Elite (Coulter). In a control run, the above procedure was followed without addition of the human CDR-transplanted anti-$GM_2$ antibody and analyzed. The results are shown in FIG. 111. It was found that the purified human CDR-transplanted anti-$GM_2$ antibodies KM8966 and KM8967 strongly reacted with the human lung small cell carcinoma culture cell line SBC-3 like the human anti-$GM_2$ chimera antibody KM966.

The results shown indicate that, like the human chimera antibodies, the human CDR-transplanted anti-$GM_2$ antibodies are useful in the diagnosis and treatment of human cancer, among others.

While the invention has been described in detail and with reference to specific examples thereof, it will be apparent to one skilled in the art that various changes and modifications can be made therein without departing from the spirit and scope thereof.

What is claimed is:

1. A CDR-grafted antibody wherein said antibody is KM8966 (Accession No. FERM BP-5105).

2. A CDR-grafted antibody wherein said antibody is KM8967 (Accession No. FERM BP-5106).

* * * * *